US012215366B2

(12) United States Patent
Gersbach et al.

(10) Patent No.: US 12,215,366 B2
(45) Date of Patent: *Feb. 4, 2025

(54) COMPOSITIONS AND METHODS FOR EPIGENOME EDITING

(71) Applicant: Duke University, Durham, NC (US)

(72) Inventors: Charles A. Gersbach, Chapel Hill, NC (US); Isaac Hilton, Houston, TX (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/471,935

(22) Filed: Sep. 10, 2021

(65) Prior Publication Data

US 2022/0098561 A1 Mar. 31, 2022

Related U.S. Application Data

(62) Division of application No. 16/865,151, filed on May 1, 2020, now Pat. No. 11,155,796, which is a division of application No. 15/549,842, filed as application No. PCT/US2016/017221 on Feb. 9, 2016, now Pat. No. 10,676,726.

(60) Provisional application No. 62/113,569, filed on Feb. 9, 2015.

(51) Int. Cl.
*C12N 9/22* (2006.01)
*C12N 9/10* (2006.01)
*C12N 15/11* (2006.01)
*C12N 15/63* (2006.01)
*C12N 15/85* (2006.01)

(52) U.S. Cl.
CPC ............. *C12N 9/22* (2013.01); *C12N 9/1029* (2013.01); *C12N 15/11* (2013.01); *C12N 15/63* (2013.01); *C12N 15/85* (2013.01); *C12Y 203/01048* (2013.01); *C07K 2319/80* (2013.01); *C12N 2310/20* (2017.05)

(58) Field of Classification Search
CPC ........ C12N 9/22; C12N 9/1029; C12N 15/11; C12N 15/63; C12N 15/85; C12N 2310/20; C12Y 203/01048; C07K 2319/80
See application file for complete search history.

(56) References Cited

U.S. PATENT DOCUMENTS

| | | | |
|---|---|---|---|
| 3,687,808 A | 8/1972 | Merigan, Jr. |
| 4,469,863 A | 9/1984 | Ts'o et al. |
| 4,476,301 A | 10/1984 | Imbach et al. |
| 4,501,729 A | 2/1985 | Boucher et al. |
| 4,554,101 A | 11/1985 | Hopp |
| 4,587,044 A | 5/1986 | Miller et al. |
| 4,605,735 A | 8/1986 | Miyoshi et al. |
| 4,667,025 A | 5/1987 | Miyoshi et al. |
| 4,737,323 A | 4/1988 | Martin et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 5,013,830 A | 5/1991 | Ohsuka et al. |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,139,941 A | 8/1992 | Muzyczka et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,219,740 A | 6/1993 | Miller et al. |
| 5,220,007 A | 6/1993 | Pederson et al. |

(Continued)

FOREIGN PATENT DOCUMENTS

| | | |
|---|---|---|
| AU | 2022318664 A1 | 2/2024 |
| CA | 2749305 A1 | 7/2010 |

(Continued)

OTHER PUBLICATIONS

Whisstock et al., Prediction of protein function from protein sequence. Q. Rev. Biophysics., 2003, vol. 36 (3): 307-340. (Year: 2003).*

Ifuku et al., "Restoration of Dystrophin Protein Expression by Exon Skipping Utilizing CRISPR-Cas9 in Myoblasts Derived from DMD Patient iPS Cells," Methods Mol Biol, 2018, Chapter 12, pp. 191-217.

Min et al., "CRISPR Correction of Duchene Muscular Dystrophy Exon 44 Deletion Mutations in Mice and Human Cells," Science Advances, 2019, 5: eaav4324.

(Continued)

*Primary Examiner* — Ganapathirama Raghu
(74) *Attorney, Agent, or Firm* — Michael Best & Friedrich LLP

(57) ABSTRACT

Disclosed herein are CRISPR/Cas9-based gene activation systems that include a fusion protein of a Cas9 protein and a protein having histone acetyltransferase activity, and methods of using said systems.

12 Claims, 44 Drawing Sheets

Specification includes a Sequence Listing.

(56) References Cited

U.S. PATENT DOCUMENTS

| | | |
|---|---|---|
| 5,235,033 A | 8/1993 | Summerton et al. |
| 5,245,022 A | 9/1993 | Weis et al. |
| 5,254,469 A | 10/1993 | Warren, III |
| 5,256,775 A | 10/1993 | Froehler |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,321,131 A | 6/1994 | Agrawal et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,478,745 A | 12/1995 | Samulski et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,473 A | 4/1996 | Camerini-otero et al. |
| 5,510,475 A | 4/1996 | Agrawal et al. |
| 5,512,439 A | 4/1996 | Horner et al. |
| 5,512,667 A | 4/1996 | Reed et al. |
| 5,514,785 A | 5/1996 | Van Ness et al. |
| 5,519,126 A | 5/1996 | Hecht |
| 5,525,465 A | 6/1996 | Haralambidis et al. |
| 5,525,711 A | 6/1996 | Hawkins et al. |
| 5,536,821 A | 7/1996 | Agrawal et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,567,810 A | 10/1996 | Weis et al. |
| 5,571,799 A | 11/1996 | Tkachuk et al. |
| 5,574,142 A | 11/1996 | Meyer et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,593,972 A | 1/1997 | Weiner et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,633,360 A | 5/1997 | Bischofberger et al. |
| 5,652,355 A | 7/1997 | Metelev et al. |
| 5,652,356 A | 7/1997 | Agrawal |
| 5,658,784 A | 8/1997 | Eckner et al. |
| 5,663,312 A | 9/1997 | Chaturvedula et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,922 A | 12/1997 | Cook et al. |
| 5,714,331 A | 2/1998 | Buchardt et al. |
| 5,719,262 A | 2/1998 | Buchardt et al. |
| 5,741,683 A | 4/1998 | Zhou et al. |
| 5,750,692 A | 5/1998 | Cook et al. |
| 5,773,700 A | 6/1998 | Van Grinsven et al. |
| 5,962,428 A | 10/1999 | Carrano et al. |
| 6,057,152 A | 5/2000 | Samulski et al. |
| 6,140,081 A | 10/2000 | Barbas |
| 6,204,059 B1 | 3/2001 | Samulski et al. |
| 6,207,453 B1 | 3/2001 | Maass et al. |
| 6,268,213 B1 | 7/2001 | Samulski et al. |
| 6,268,490 B1 | 7/2001 | Imanishi et al. |
| 6,287,860 B1 | 9/2001 | Monia et al. |
| 6,453,242 B1 | 9/2002 | Eisenberg et al. |
| 6,462,254 B1 | 10/2002 | Vernachio et al. |
| 6,491,907 B1 | 12/2002 | Rabinowitz et al. |
| 6,534,261 B1 | 3/2003 | Cox, III et al. |
| 6,596,535 B1 | 7/2003 | Carter |
| 6,660,514 B1 | 12/2003 | Zolotukhin et al. |
| 6,734,291 B2 | 5/2004 | Kochkine et al. |
| 6,770,748 B2 | 8/2004 | Imanishi et al. |
| 6,794,499 B2 | 9/2004 | Wengel et al. |
| 6,951,753 B2 | 10/2005 | Shenk et al. |
| 7,034,133 B2 | 4/2006 | Wengel et al. |
| 7,053,207 B2 | 5/2006 | Wengel |
| 7,060,809 B2 | 6/2006 | Wengel et al. |
| 7,074,596 B2 | 7/2006 | Darzynkiewicz et al. |
| 7,084,125 B2 | 8/2006 | Wengel |
| 7,094,604 B2 | 8/2006 | Snyder et al. |
| 7,125,717 B2 | 10/2006 | Carter |
| 7,172,893 B2 | 2/2007 | Rabinowitz et al. |
| 7,201,898 B2 | 4/2007 | Monahan et al. |
| 7,229,823 B2 | 6/2007 | Samulski et al. |
| 7,282,199 B2 | 10/2007 | Gao et al. |
| 7,439,065 B2 | 10/2008 | Ferrari et al. |
| 7,449,561 B1 | 11/2008 | Sommer et al. |
| 7,456,683 B2 | 11/2008 | Takano et al. |
| 7,572,582 B2 | 8/2009 | Wengel et al. |
| 7,588,772 B2 | 9/2009 | Kay et al. |
| 7,728,118 B2 | 6/2010 | Wood et al. |
| 7,745,651 B2 | 6/2010 | Heyes et al. |
| 7,790,449 B2 | 9/2010 | Gao et al. |
| 7,799,565 B2 | 9/2010 | Maclachlan et al. |
| 7,906,111 B2 | 3/2011 | Wilson et al. |
| 8,278,036 B2 | 10/2012 | Kariko et al. |
| 8,450,107 B1 | 5/2013 | Zhang et al. |
| 8,586,526 B2 | 11/2013 | Gregory et al. |
| 8,697,359 B1 | 4/2014 | Zhang et al. |
| 8,889,356 B2 | 11/2014 | Zhang |
| 8,993,233 B2 | 3/2015 | Zhang et al. |
| 9,139,554 B2 | 9/2015 | Hope et al. |
| 9,458,205 B2 | 10/2016 | Gregory et al. |
| 9,738,879 B2 | 8/2017 | Gersbach et al. |
| 9,828,582 B2 | 11/2017 | Perez-Pinera et al. |
| 9,834,791 B2 | 12/2017 | Zhang et al. |
| 9,890,364 B2 | 2/2018 | Joung et al. |

(56) References Cited

U.S. PATENT DOCUMENTS

| | | |
|---|---|---|
| 10,011,850 B2 | 7/2018 | Joung et al. |
| 10,190,106 B2 | 1/2019 | Wolfe et al. |
| 10,266,850 B2 | 4/2019 | Doudna et al. |
| 10,676,726 B2 | 6/2020 | Gersbach et al. |
| 10,676,735 B2 | 6/2020 | Gersbach et al. |
| 10,704,060 B2 | 7/2020 | Gersbach et al. |
| 10,711,256 B2 | 7/2020 | Gersbach et al. |
| 10,745,714 B2 | 8/2020 | Gersbach et al. |
| 11,155,796 B2 | 10/2021 | Gersbach et al. |
| 11,421,251 B2 | 8/2022 | Gersbach et al. |
| 11,427,817 B2 | 8/2022 | Josephs et al. |
| 2002/0160940 A1 | 10/2002 | Case et al. |
| 2004/0142025 A1 | 7/2004 | Maclachlan et al. |
| 2004/0175727 A1 | 9/2004 | Draghia-Akli et al. |
| 2004/0192593 A1 | 9/2004 | Draghia-Akli et al. |
| 2004/0204345 A1 | 10/2004 | Case et al. |
| 2006/0068395 A1 | 3/2006 | Wood et al. |
| 2006/0211647 A1 | 9/2006 | Khan |
| 2007/0042031 A1 | 2/2007 | Maclachlan et al. |
| 2007/0042462 A1 | 2/2007 | Hildinger |
| 2007/0059795 A1 | 3/2007 | Moore et al. |
| 2007/0185042 A1 | 8/2007 | Tsai et al. |
| 2007/0192880 A1 | 8/2007 | Muyan et al. |
| 2008/0070299 A1 | 3/2008 | Wood et al. |
| 2008/0090291 A1 | 4/2008 | Wood et al. |
| 2008/0200409 A1 | 8/2008 | Wilson et al. |
| 2009/0018031 A1 | 1/2009 | Trinklein et al. |
| 2010/0035968 A1 | 2/2010 | Rasmussen et al. |
| 2010/0076057 A1 | 3/2010 | Sontheimer et al. |
| 2010/0261175 A1 | 10/2010 | Rasmussen et al. |
| 2010/0267018 A1 | 10/2010 | Wengel et al. |
| 2011/0145940 A1 | 6/2011 | Voytas et al. |
| 2011/0197290 A1 | 8/2011 | Fahrenkrug et al. |
| 2011/0236353 A1 | 9/2011 | Wilson et al. |
| 2011/0263682 A1 | 10/2011 | De Kimpe et al. |
| 2011/0286957 A1 | 11/2011 | Prieve et al. |
| 2011/0301073 A1 | 12/2011 | Gregory et al. |
| 2011/0301218 A1 | 12/2011 | Bozzoni et al. |
| 2012/0195917 A1 | 8/2012 | Sahin et al. |
| 2012/0207744 A1 | 8/2012 | Mendlein et al. |
| 2013/0274129 A1 | 10/2013 | Katzen et al. |
| 2013/0323001 A1 | 12/2013 | Ueki et al. |
| 2014/0068797 A1 | 3/2014 | Doudna et al. |
| 2014/0140969 A1 | 5/2014 | Beausejour et al. |
| 2014/0170753 A1 | 6/2014 | Zhang |
| 2014/0179006 A1 | 6/2014 | Zhang |
| 2014/0186958 A1 | 7/2014 | Zhang et al. |
| 2014/0234975 A1 | 8/2014 | Silva et al. |
| 2014/0295557 A1 | 10/2014 | Joung et al. |
| 2014/0309177 A1 | 10/2014 | Perez-Pinera et al. |
| 2014/0315862 A1 | 10/2014 | Kaye |
| 2014/0356956 A1 | 12/2014 | Church et al. |
| 2014/0357530 A1 | 12/2014 | Zhang et al. |
| 2014/0377868 A1 | 12/2014 | Joung et al. |
| 2015/0024499 A1 | 1/2015 | Brouns et al. |
| 2015/0031089 A1 | 1/2015 | Lindstrom |
| 2015/0044772 A1 | 2/2015 | Zhao |
| 2015/0045413 A1 | 2/2015 | De Visser et al. |
| 2015/0056705 A1 | 2/2015 | Conway et al. |
| 2015/0079064 A1 | 3/2015 | Gersbach et al. |
| 2015/0159178 A1 | 6/2015 | Green et al. |
| 2015/0166980 A1 | 6/2015 | Liu et al. |
| 2015/0225717 A1 | 8/2015 | Lee et al. |
| 2015/0252358 A1 | 9/2015 | Maeder et al. |
| 2016/0002634 A1 | 1/2016 | Sazani et al. |
| 2016/0040189 A1 | 2/2016 | Kennedy et al. |
| 2016/0058889 A1 | 3/2016 | Olson et al. |
| 2016/0177278 A1 | 6/2016 | Wolfe et al. |
| 2016/0199419 A1 | 7/2016 | Miura |
| 2016/0201089 A1 | 7/2016 | Gersbach et al. |
| 2016/0281166 A1 | 9/2016 | Bhattacharjee et al. |
| 2016/0354487 A1 | 12/2016 | Zhang et al. |
| 2017/0002316 A1 | 1/2017 | Gascón Jiménez et al. |
| 2017/0198308 A1 | 7/2017 | Qi et al. |
| 2017/0204407 A1 | 7/2017 | Gilbert et al. |
| 2017/0283831 A1 | 10/2017 | Zhang et al. |
| 2017/0298331 A1 | 10/2017 | Gersbach et al. |
| 2017/0327806 A1 | 11/2017 | Joung et al. |
| 2017/0362635 A1 | 12/2017 | Chamberlain et al. |
| 2018/0023064 A1 | 1/2018 | Gersbach et al. |
| 2018/0073012 A1 | 3/2018 | Liu et al. |
| 2018/0094238 A1 | 4/2018 | Perez-Pinera et al. |
| 2018/0127780 A1 | 5/2018 | Liu et al. |
| 2018/0135109 A1 | 5/2018 | Jayaram et al. |
| 2018/0201951 A1 | 7/2018 | Guilak et al. |
| 2018/0237771 A1 | 8/2018 | Kim et al. |
| 2018/0251735 A1 | 9/2018 | Ko |
| 2018/0271069 A1 | 9/2018 | Min et al. |
| 2018/0280539 A1 | 10/2018 | Debs et al. |
| 2018/0291370 A1 | 10/2018 | Gersbach et al. |
| 2018/0305689 A1 | 10/2018 | Sætrom et al. |
| 2018/0305704 A1 | 10/2018 | Zhang |
| 2018/0305719 A1 | 10/2018 | Perez-Pinera et al. |
| 2018/0319850 A1 | 11/2018 | Payne et al. |
| 2018/0320197 A1 | 11/2018 | Gersbach et al. |
| 2018/0327740 A1 | 11/2018 | Gifford et al. |
| 2018/0334685 A1 | 11/2018 | Yeo et al. |
| 2018/0334688 A1 | 11/2018 | Gersbach et al. |
| 2018/0353615 A1 | 12/2018 | Gersbach et al. |
| 2019/0032049 A1 | 1/2019 | Naldini et al. |
| 2019/0038776 A1 | 2/2019 | Pyle et al. |
| 2019/0048337 A1 | 2/2019 | Hsu et al. |
| 2019/0062790 A1 | 2/2019 | Doudna et al. |
| 2019/0078119 A1 | 3/2019 | Wilson et al. |
| 2019/0106710 A1 | 4/2019 | Zhang et al. |
| 2019/0127713 A1 | 5/2019 | Gersbach et al. |
| 2019/0134221 A1 | 5/2019 | Bumcrot et al. |
| 2019/0136229 A1 | 5/2019 | Josephs et al. |
| 2019/0151476 A1 | 5/2019 | Gersbach et al. |
| 2019/0183932 A1 | 6/2019 | Mackall et al. |
| 2019/0194633 A1 | 6/2019 | Gersbach et al. |
| 2019/0201402 A1 | 7/2019 | Jiang et al. |
| 2019/0248854 A1 | 8/2019 | Tremblay et al. |
| 2019/0264232 A1 | 8/2019 | Hou et al. |
| 2019/0351074 A1 | 11/2019 | Ahituv et al. |
| 2019/0359959 A1 | 11/2019 | Jaenisch et al. |
| 2019/0374655 A1 | 12/2019 | Kabadi et al. |
| 2020/0002731 A1 | 1/2020 | Frendewey et al. |
| 2020/0056206 A1 | 2/2020 | Tremblay et al. |
| 2020/0080108 A1 | 3/2020 | Jaskula-Ranga et al. |
| 2020/0109406 A1 | 4/2020 | Miller et al. |
| 2020/0123533 A1 | 4/2020 | Wang et al. |
| 2020/0216549 A1 | 7/2020 | Fukumura et al. |
| 2020/0216810 A1 | 7/2020 | Metelitsa et al. |
| 2020/0260698 A1 | 8/2020 | Kyrychenko et al. |
| 2020/0275641 A1 | 9/2020 | Min et al. |
| 2020/0318139 A1 | 10/2020 | Gersbach et al. |
| 2020/0332307 A1 | 10/2020 | Hummel et al. |
| 2020/0347105 A1 | 11/2020 | Gersbach et al. |
| 2020/0385695 A1 | 12/2020 | Gersbach et al. |
| 2021/0002665 A1 | 1/2021 | Gersbach et al. |
| 2021/0032654 A1 | 2/2021 | Gersbach et al. |
| 2021/0040460 A1 | 2/2021 | Gersbach et al. |
| 2021/0322577 A1 | 10/2021 | Lande et al. |
| 2022/0177879 A1 | 6/2022 | Gersbach et al. |
| 2022/0184229 A1 | 6/2022 | Gersbach et al. |
| 2022/0195406 A1 | 6/2022 | Gersbach et al. |
| 2022/0305141 A1 | 9/2022 | Gersbach et al. |
| 2022/0307015 A1 | 9/2022 | Gersbach et al. |
| 2022/0364124 A1 | 11/2022 | Gersbach et al. |
| 2022/0396790 A1 | 12/2022 | Gersbach et al. |
| 2023/0032846 A1 | 2/2023 | Gersbach et al. |
| 2023/0047669 A1 | 2/2023 | Josephs et al. |
| 2024/0052328 A1 | 2/2024 | Kwon et al. |
| 2024/0058425 A1 | 2/2024 | Gersbach et al. |
| 2024/0067968 A1 | 2/2024 | Cosgrove et al. |

FOREIGN PATENT DOCUMENTS

| | | |
|---|---|---|
| CA | 2981508 A1 | 10/2016 |
| CA | 3086885 A1 | 7/2019 |
| CA | 3101477 A1 | 12/2019 |
| EP | 2620161 A1 | 7/2013 |
| EP | 3009511 A2 | 4/2016 |

(56) References Cited

FOREIGN PATENT DOCUMENTS

| | | |
|---|---|---|
| EP | 3199632 A1 | 8/2017 |
| EP | 3712272 A1 | 9/2020 |
| EP | 3209783 B1 | 11/2021 |
| EP | 3995584 A1 | 5/2022 |
| JP | 2013-509159 A | 3/2013 |
| JP | 2015-534817 A | 12/2015 |
| JP | 2016-521452 A | 7/2016 |
| JP | 2016-521452 A2 | 7/2016 |
| JP | 2016-521975 A | 7/2016 |
| JP | 2016-523082 A | 8/2016 |
| KR | 20190134673 A | 12/2019 |
| WO | WO1991/18114 A1 | 11/1991 |
| WO | WO1992/000387 A1 | 1/1992 |
| WO | WO1993/007883 A1 | 4/1993 |
| WO | WO1993/024640 A2 | 12/1993 |
| WO | WO1994/016737 A1 | 8/1994 |
| WO | WO1998/053058 A1 | 11/1998 |
| WO | WO1998/053059 A1 | 11/1998 |
| WO | WO1998/053060 A1 | 11/1998 |
| WO | WO 2000/028004 A1 | 5/2000 |
| WO | 2001/083793 A2 | 11/2001 |
| WO | WO2001/083783 A2 | 11/2001 |
| WO | WO 2001/092551 A2 | 12/2001 |
| WO | WO2002/016536 A1 | 2/2002 |
| WO | WO2003/016496 A2 | 2/2003 |
| WO | WO2003/042397 A2 | 5/2003 |
| WO | 2003/072788 A1 | 9/2003 |
| WO | WO2005/033321 A2 | 4/2005 |
| WO | WO2006/110689 A2 | 10/2006 |
| WO | WO2007/019301 A2 | 2/2007 |
| WO | WO2008/006028 A2 | 1/2008 |
| WO | WO2008/070859 A2 | 6/2008 |
| WO | WO2010/053572 A2 | 5/2010 |
| WO | WO2010/075424 A2 | 7/2010 |
| WO | 2010/144740 A1 | 12/2010 |
| WO | WO2011/036640 A2 | 3/2011 |
| WO | WO2011/126808 A2 | 10/2011 |
| WO | WO2011/141820 A1 | 11/2011 |
| WO | WO2011/154427 A1 | 12/2011 |
| WO | WO2012/136476 A1 | 10/2012 |
| WO | WO2012/170930 A1 | 12/2012 |
| WO | WO2013/049493 A1 | 4/2013 |
| WO | WO2013/098244 A1 | 7/2013 |
| WO | WO2013/143555 A1 | 10/2013 |
| WO | WO2013/163628 A2 | 10/2013 |
| WO | WO2013/176772 A1 | 11/2013 |
| WO | WO2013/182683 A1 | 12/2013 |
| WO | WO2014/018423 A2 | 1/2014 |
| WO | WO2014/059255 A1 | 4/2014 |
| WO | WO2014/065596 A1 | 5/2014 |
| WO | WO2014/081855 A1 | 5/2014 |
| WO | 2014/093622 A2 | 6/2014 |
| WO | 2014/093712 A1 | 6/2014 |
| WO | 2014/099744 A1 | 6/2014 |
| WO | 2014089290 A1 | 6/2014 |
| WO | WO2014/093479 A1 | 6/2014 |
| WO | WO2014/093595 A1 | 6/2014 |
| WO | WO2014/093655 A2 | 6/2014 |
| WO | WO2014/093661 A2 | 6/2014 |
| WO | WO2014/093709 A1 | 6/2014 |
| WO | WO2014/144288 A1 | 9/2014 |
| WO | WO2014/144592 A2 | 9/2014 |
| WO | WO2014/152432 A2 | 9/2014 |
| WO | WO2014/172470 A2 | 10/2014 |
| WO | WO2014/186585 A2 | 11/2014 |
| WO | 2014/197568 A2 | 12/2014 |
| WO | WO2014/191128 A1 | 12/2014 |
| WO | WO2014/197748 A2 | 12/2014 |
| WO | WO2014/204726 A1 | 12/2014 |
| WO | WO2014/204728 A1 | 12/2014 |
| WO | WO2015/006747 A2 | 1/2015 |
| WO | 2015/021457 A2 | 2/2015 |
| WO | WO2015/017519 A1 | 2/2015 |
| WO | 2015/035136 A2 | 3/2015 |
| WO | 2015/035139 A2 | 3/2015 |
| WO | WO2015/048690 A1 | 4/2015 |
| WO | WO2015/070083 A1 | 5/2015 |
| WO | 2015/089427 A1 | 6/2015 |
| WO | 2015/089462 A1 | 6/2015 |
| WO | WO2015/089419 A2 | 6/2015 |
| WO | WO2015/089465 A1 | 6/2015 |
| WO | WO2015/089486 A2 | 6/2015 |
| WO | WO2015/126927 A2 | 8/2015 |
| WO | 2015/161276 A2 | 10/2015 |
| WO | WO2015/155686 A2 | 10/2015 |
| WO | 2015/195621 A1 | 12/2015 |
| WO | 2016/011070 A2 | 1/2016 |
| WO | 2016/011080 A2 | 1/2016 |
| WO | 2016/049258 A2 | 3/2016 |
| WO | WO2016/063264 A1 | 4/2016 |
| WO | WO2016/070070 A1 | 5/2016 |
| WO | WO2016/081924 A1 | 5/2016 |
| WO | WO2016/094880 A1 | 6/2016 |
| WO | 2016/114972 A1 | 7/2016 |
| WO | 2016/123578 A1 | 8/2016 |
| WO | WO2016/130600 A2 | 8/2016 |
| WO | WO2016/161380 A1 | 10/2016 |
| WO | 2016/205613 A1 | 12/2016 |
| WO | WO2016/187717 A1 | 12/2016 |
| WO | WO2017/015637 A1 | 1/2017 |
| WO | 2017/016915 A1 | 2/2017 |
| WO | 2017/049407 A1 | 3/2017 |
| WO | WO2017/035416 A2 | 3/2017 |
| WO | WO2017/049266 A2 | 3/2017 |
| WO | WO2017/066497 A2 | 4/2017 |
| WO | WO2017/070632 A2 | 4/2017 |
| WO | WO2017/072590 A1 | 5/2017 |
| WO | WO2017/075478 A2 | 5/2017 |
| WO | WO2017/095967 A2 | 6/2017 |
| WO | WO2017/139505 A2 | 8/2017 |
| WO | WO2017/165859 A1 | 9/2017 |
| WO | 2017/180976 A1 | 10/2017 |
| WO | WO2017/180915 A2 | 10/2017 |
| WO | WO2017/193029 A1 | 11/2017 |
| WO | 2018/002812 A1 | 1/2018 |
| WO | 2018/005805 A1 | 1/2018 |
| WO | 2018/017483 A1 | 1/2018 |
| WO | WO 2018/013932 A1 | 1/2018 |
| WO | WO2018/017751 A1 | 1/2018 |
| WO | WO2018/017754 A1 | 1/2018 |
| WO | WO2018/031762 A1 | 2/2018 |
| WO | WO2018/035388 A1 | 2/2018 |
| WO | WO2018/035495 A1 | 2/2018 |
| WO | 2018/039145 A1 | 3/2018 |
| WO | WO2018/081504 A1 | 5/2018 |
| WO | WO2018/098480 A1 | 5/2018 |
| WO | 2018/107003 A1 | 6/2018 |
| WO | WO2018/129296 A1 | 7/2018 |
| WO | 2018/162702 A1 | 9/2018 |
| WO | 2018/179578 A1 | 10/2018 |
| WO | WO2018/191388 A1 | 10/2018 |
| WO | 2019/009682 A2 | 1/2019 |
| WO | 2019/023291 A1 | 1/2019 |
| WO | WO2019/002590 A1 | 1/2019 |
| WO | WO 2019/036599 A1 | 2/2019 |
| WO | 2019/046755 A1 | 3/2019 |
| WO | WO2019/067786 A1 | 4/2019 |
| WO | WO2019/077001 A1 | 4/2019 |
| WO | WO2019/079514 A1 | 4/2019 |
| WO | 2019/084050 A1 | 5/2019 |
| WO | WO2019/092505 A1 | 5/2019 |
| WO | 2019/113472 A1 | 6/2019 |
| WO | 2019/123014 A1 | 6/2019 |
| WO | 2019/136216 A1 | 7/2019 |
| WO | WO2019/144061 A1 | 7/2019 |
| WO | 2019/204750 A1 | 10/2019 |
| WO | 2019/213626 A1 | 11/2019 |
| WO | WO2019/232069 A1 | 12/2019 |
| WO | 2020/018918 A1 | 1/2020 |
| WO | WO2020/124257 A1 | 6/2020 |
| WO | WO 2020/132226 A1 | 6/2020 |
| WO | 2020/168133 A1 | 8/2020 |
| WO | WO2020/163396 A1 | 8/2020 |
| WO | WO2020/210776 A1 | 10/2020 |

(56) References Cited

FOREIGN PATENT DOCUMENTS

| WO | WO2020/214609 A1 | 10/2020 |
|---|---|---|
| WO | WO2020/214613 A1 | 10/2020 |
| WO | WO2020/257665 A1 | 12/2020 |
| WO | WO2021/026516 A1 | 2/2021 |
| WO | WO2021/034984 A2 | 2/2021 |
| WO | WO2021/034987 A1 | 2/2021 |
| WO | WO2021/055956 A1 | 3/2021 |
| WO | WO2021/067878 A1 | 4/2021 |
| WO | WO2021/113536 A1 | 6/2021 |
| WO | PCT/US2021/054292 | 10/2021 |
| WO | PCT/US2021/054636 | 10/2021 |
| WO | PCT/US2021/056122 | 10/2021 |
| WO | PCT/US2021/059270 | 11/2021 |
| WO | WO2021/222268 A1 | 11/2021 |
| WO | WO2021/222314 A1 | 11/2021 |
| WO | WO2021/222327 A1 | 11/2021 |
| WO | WO2021/222328 A1 | 11/2021 |
| WO | WO2021/226555 A2 | 11/2021 |
| WO | 2022/038264 A1 | 2/2022 |
| WO | PCT/US2022/018400 | 3/2022 |
| WO | WO2022/087321 A1 | 4/2022 |
| WO | WO 2022/103935 A1 | 5/2022 |
| WO | WO2022/104159 A1 | 5/2022 |
| WO | 2022/133062 A1 | 6/2022 |
| WO | WO2022/187288 A2 | 9/2022 |
| WO | PCT/US2023/063296 | 2/2023 |
| WO | PCT/US2023/063297 | 2/2023 |
| WO | WO 2023/010133 A2 | 2/2023 |
| WO | PCT/US2023/018559 | 4/2023 |
| WO | WO 2023/137471 A1 | 7/2023 |
| WO | WO 2023/137472 A2 | 7/2023 |
| WO | WO 2024/015881 A2 | 1/2024 |
| WO | 2024/040253 A1 | 2/2024 |
| WO | WO 2024/064642 A2 | 3/2024 |
| WO | 2024/081937 A1 | 4/2024 |
| WO | WO 2024/040254 A3 | 5/2024 |

OTHER PUBLICATIONS

Robinson-Hamm et al., "Gene therapies that restore dystrophin expression for the treatment of Duchenne muscular dystrophy," Human Genetics, 2016, 135(9): 1029-1040.
NCBI Reference Sequence NG_028016.2 (2013).
NCBI Reference Sequence NM_004020.2 (2010).
NCBI Reference Sequence XM011532698.1 (2015).
United States Patent Office Action for U.S. Appl. No. 16/322,234 dated Apr. 19, 2023 (25 pages).
United States Patent Office Action for U.S. Appl. No. 16/093,272 dated Mar. 14, 2023 (9 pages).
U.S. Appl. No. 17/879,506, filed Aug. 2, 2022, by Josephs et al.
U.S. Appl. No. 17/922,751, filed Nov. 1, 2022, by Iglesias et al.
Adamson et al., "A Multiplexed Single-Cell CRISPR Screening Platform Enables Systematic Dissection of the Unfolded Protein Response," Cell, 2016, 167: 1867-1882.e21.
Chen et al., "Genome-wide CRISPR screen in a mouse model of tumor growth and metastasis," Cell, 2015, 160: 1246-1260.
Chen et al., "Vitamin D receptor suppresses proliferation and metastasis in renal cell carcinoma cell lines via regulating the expression of the epithelial Ca2+ channel TRPV5," PLoS One, 2018, 13: e0195844.
Corces et al., "The chromatin accessibility landscape of primary human cancers, " Science, 2018, 362(6413): eaav1898.
Datlinger et al., "Pooled CRISPR screening with single-cell transcriptome readout," Nat. Methods, 2017, 14: 297-301.
Dempster et al., "Extracting Biological Insights from the Project Achilles Genome-Scale CRISPR Screens in Cancer Cell Lines," Cold Spring Harbor Laboratory, 2019, 35 pages.
Dixit et al., "Perturb-Seq: Dissecting Molecular Circuits with Scalable Single-Cell RNA Profiling of Pooled Genetic Screens," Cell, 2016, 167: 1853-1866.e17.

Encode Project Consortium, "Expanded encyclopaedias of DNA elements in the human and mouse genomes," Nature, 2020, 583: 699-710.
Eraslan et al., "Deep learning: new computational modelling techniques for genomics," Nat. Rev. Genet., 2019, 20: 389-403.
Ernst et al., "ChromHMM: automating chromatin-state discovery and characterization," Nat. Methods, 2012, 9: 215-216.
Frank et al., "HDAC inhibitors cause site-specific chromatin remodeling at PU.1-bound enhancers in K562 cells," Epigenetics Chromatin, 2016, 9: 15.
Fulco et al., "Activity-by-contact model of enhancer-promoter regulation from thousands of CRISPR perturbations," Nature Genetics, 2019, 51: 1664-1669.
Gasperini et al., "A Genome-wide Framework for Mapping Gene Regulation via Cellular Genetic Screens," Cell, 2018, 176(1-2); 377-390.e19.
Ghisletti et al., "Identification and characterization of enhancers controlling the inflammatory gene expression program in macrophages," Immunity, 2010, 32: 317-328.
Gray et al., "G quadruplexes are genomewide targets of transcriptional helicases XPB and XPD," Nat. Chem. Biol, 2014, 10: 313-318.
Hacein-Bey-Abina et al., "LMO2-associated clonal T cell proliferation in two patients after gene therapy for SCID-X1," Science, 2003, 302: 415-419.
Harrow et al., "Gencode: the reference human genome annotation for The Encode Project," Genome Res., 2012, 22: 1760-1774.
Hart et al., "High-Resolution CRISPR Screens Reveal Fitness Genes and Genotype-Specific Cancer Liabilities," Cell, 2015, 163: 1515-1526.
Hayward et al., "Whole-genome landscapes of major melanoma subtypes," Nature, 2017, 545: 175-180.
He et al., "Molecular Genetic Mechanisms of Hereditary Spherocytosis: Current Perspectives," Acta Haematol., 2018, 139: 60-66.
Horlbeck et al., "Compact and highly active next-generation libraries for CRISPR-mediated gene repression and activation," eLife, 2016, 5: e19760.
Jimenez et al., "Activation of the beta-globin locus control region precedes commitment to the erythroid lineage," Proceedings of the National Academy of Sciences, 1992, 89: 10618-10622.
Kempfer et al., "Methods for mapping 3D chromosome architecture," Nat. Rev. Genet., 2020, 21: 207-226.
Khurana et al., "Role of non-coding sequence variants in cancer," Nat. Rev. Genet., 2016, 17: 93-108.
Kim et al., "Epigenetic therapy of Prader-Willi Syndrome," Transl Res, 2019, 208: 105-118.
Klann et al., "Genome-wide annotation of gene regulatory elements linked to cell fitness," bioRxiv doi: 10.1101/2021.03.08.434470. Preprint posted Mar. 9, 2021, 42 pages.
Landry et al., "Expression of the leukemia oncogene Lmo2 is controlled by an array of tissue-specific elements dispersed over 100 kb and bound by Tal1/Lmo2, Ets, and Gata factors," Blood, 2009, 113: 5783-5792.
Laumont et al., "Noncoding regions are the main source of targetable tumor-specific antigens," Sci. Transl. Med., 2018, 10(470): eaau5516, 11 pages.
Lawrence et al., "Discovery and saturation analysis of cancer genes across 21 tumour types," Nature, 2014, 505: 495-501.
Lenoir et al., "Pickles: the database of pooled in-vitro CRISPR knockout library essentiality screens," Nucleic Acids Res, 2018, 46: D776-D780.
Li et al., "RSEM: accurate transcript quantification from RNA-Seq data with or without a reference genome," BMC Bioinformatics, 2011, 12: 323.
Maurano et al., "Systematic localization of common disease-associated variation in regulatory DNA," Science, 2012, 337: 1190-1195.
Maxwell et al., "A detailed cell-free transcription-translation-based assay to decipher CRISPR protospacer-adjacent motifs," Methods, 2018, 143: 48-57.
Meyers et al., "Computational correction of copy number effect improves specificity of CRISPR-Cas9 essentiality screens in cancer cells," Nat. Genet., 2017, 49: 1779-1784.

(56) References Cited

OTHER PUBLICATIONS

Montalbano et al., "High-Throughput Approaches to Pinpoint Function within the Noncoding Genome," Mol. Cell, 2017, 68: 44-59.
Nguyen et al., "Transcriptional Enhancers in the Regulation of T Cell Differentiation," Front. Immunol., 2015, 6: 462.
O'Brien et al., "GT-Scan: identifying unique genomic targets," Bioinformatics, 2014, 30: 2673-2675.
Orlando et al., "Promoter capture Hi-C-based identification of recurrent noncoding mutations in colorectal cancer," Nat. Genet., 2018, 50: 1375-1380.
Rajagopal et al., "High-throughput mapping of regulatory DNA," Nat. Biotechnol, 2016, 34: 167-174.
Rauscher et al., "GenomeCRISPR—a database for high-throughput CRISPR/Cas9 screens," Nucleic Acids Res, 2017, 45: D679-D686.
Rheinbay et al., "Analyses of non-coding somatic drivers in 2,658 cancer whole genomes," Nature, 2020, 578: 102-111.
Rhodes et al., "G-quadruplexes and their regulatory roles in biology," Nucleic Acids Res, 2015, 43: 8627-8637.
Schmidt et al., "GenomeRNAi: a database for cell-based and in vivo RNAi phenotypes, 2013 update," Nucleic Acids Res, 2013, 41: D1021-6.
Sengupta et al., "Super-Enhancer-Driven Transcriptional Dependencies in Cancer," Trends Cancer Res, 2017, 3: 269-281.
Shalem et al., "Genome-scale CRISPR-Cas9 knockout screening in human cells," Science, 2014, 343: 84-87.
Stephens, "False discovery rates: a new deal," Biostatistics, 2017, 18: 275-294.
Sur et al., "The role of enhancers in cancer," Nat. Rev. Cancer., 2016, 16: 483-493.
Tam et al., "Benefits and limitations of genome-wide association studies," Nat. Rev. Genet., 2019, 20: 467-484.
Tan et al., "Rationally engineered *Staphylococcus aureus* Cas9 nucleases with high genome-wide specificity," Proc. Nat. Acad. Sci. USA, 2019, 116(46): 20969-20976.
Wang et al., "Gene Essentiality Profiling Reveals Gene Networks and Synthetic Lethal Interactions with Oncogenic Ras," Cell, 2017, 168: 890-903.e15.
Wang et al., "Genetic screens in human cells using the CRISPR-Cas9 system," Science, 2014, 343: 80-84.
Wang et al., "Identification and characterization of essential genes in the human genome," Science, 2015, 350: 1096-1101.
Wei et al., "Targeting Regnase-1 programs long-lived effector T cells for cancer therapy," Nature, 2019, 576(7787): 471-476.
Wu et al., "Induction of anion exchanger-1 translation and its opposite roles in the carcinogenesis of gastric cancer cells and differentiation of K562 cells," Oncogene, 2010, 29: 1987-1996.
Xie et al., "Multiplexed Engineering and Analysis of Combinatorial Enhancer Activity in Single Cells," Mol. Cell, 2017, 66: 285-299.e5.
Zhu et al., "The role of histone deacetylase 7 (HDAC7) in cancer cell proliferation: regulation on c-Myc," J. Mol. Med, 2011, 89: 279-289.
Mevissen et al., "Molecular basis of Lys11-polyubiquitin specificity in the deubiquitinase Cezanne," Nature, 2016, 538(7625): 402-405.
Lin et al., "Essential Role of the 58-kDa Microspherule Protein in the Modulation of Daxx-dependent Transcriptional Repression as Revealed by Nucleolar Sequestration," J Biol Chem, 2002, 277: 25446-25456.
International Search Report and Written Opinion for Application No. PCT/US2021/054292 dated Mar. 17, 2022.
International Search Report and Written Opinion for Application No. PCT/US2021/054636 dated Mar. 22, 2022 (18 pages).
International Search Report and Witten Opinion for Application No. PCT/US2021/059270 dated Apr. 19, 2022 (20 pages).
United States Patent Office Action for U.S. Appl. No. 16/322,234 dated Mar. 1, 2022 (24 pages).
United States Patent Office Action for U.S. Appl. No. 16/093,272 dated Jun. 9, 2022 (10 pages).
U.S. Appl. No. 17/603,243, filed Oct. 12, 2021.
U.S. Appl. No. 17/603,329, filed Oct. 12, 2021.
U.S. Appl. No. 17/603,330, filed Oct. 12, 2021.
Aloia, "Epigenetic Regulation of Cell-Fate Changes That Determine Adult Liver Regeneration After Injury," Front. Cell Dev. Biol., 2021, 9: 643055.
Asrani et al., "Burden of liver diseases in the world," J Hepatol, 2019, 70(1): 151-171.
Baratta et al., "Cellular organization of normal mouse liver: a histological, quantitative immunocytochemical, and fine structural analysis," Histochem Cell Biol, 2009, 131(6): 713-726.
Gemberling et al., "Transgenic mice for in vivo epigenome editing with CRISPR-based systems," Nat Methods, 2021, 18(8): 965-974.
Hori et al., "Simple and reproducible hepatectomy in the mouse using the clip technique," World J Gastroenterol, 2012, 18(22): 2767-2774.
Keys et al., "A genome-wide screen in the mouse liver reveals sex-specific and cell non-autonomous regulation of cell fitness," bioRxiv preprint doi: https://doi.org/10.1101/2021.01.30.428976, posted Feb. 1, 2021.
Mastellos et al., "Inducing and characterizing liver regeneration in mice: Reliable models, essential "readouts" and critical perspectives," Curr Protoc Mouse Biol., 2013, 3(3): 141-170.
Nikfarjam et al., "A Model of Partial Hepatectomy in Mice," Journal of Investigative Surgery, 2004, 17(5): 291-294.
Nuñez et al., "Genome-wide programmable transcriptional memory by CRISPR-based epigenome editing," Cell, 2021, 184(9): P2503-2519.
Povero et al., "Lipid-induced toxicity stimulates hepatocytes to release angiogenic microparticles that require Vanin-1 for uptake by endothelial cells," Sci Signal, 2013, 6(296): ra88.
Rmilah et al., "Understanding the marvels behind liver regeneration," Wiley Interdiscip Rev Dev Biol., 2019, 8(3): e340.
Tracy, "Human DNA sequence from clone RP11-34D15 on chromosome 10, complete sequence," Genbank entry, National Center for Biotechnology Information, <https://www.ncbi.nlm.nih.gov/nucleotide/AL139819.8> 2012.
Yang et al., "Gene Reactivation by 5-Aza-2'-Deoxycytidine-Induced Demethylation Requires SRCAP-Mediated HZA.Z Insertion to Establish Nucleosome Depleted Regions", PLoS Genetics, 2012, vol. 8, Issue 3, e1002604, 12 pages.
Younossi et al., "Epidemiology of chronic liver diseases in the USA in the past three decades," Gut, 2020, 69(3): 564-568.
Amabile et al., "Inheritable Silencing of Endogenous Genes by Hit-and-Run Targeted Epigenetic Editing," Cell, 2016, 167(1): 219-232.e14.
Amabile et al., "Permanent Epigenetic Silencing of Human Genes With Artificial Transcriptional Repressors,", Molecular Therapy, 2015, 23(Suppl. 1): S275.
Blancafort et al., "Writing and rewriting the epigenetic code of cancer cells: from engineered proteins to small molecules," Mol. Pharmacol., 2013, 83(3): 563-576.
Jeltsch et al., "Application of DNA methyltransferases in targeted DNA methylation," Appl. Microbiol. Biotechnol., 2007, 75(6): 1233-1240.
Jurkowska and Jeltsch, "Silencing of Gene Expression by Targeted DNA Methylation: Concepts and Approaches," Methods Mol. Biol. 649, 2010, Chapter 9: 149-161.
Kabadi et al., "Engineering Synthetic TALE and CRISPR/Cas9 Transcription Factors for Regulating Gene Expression," Methods, 2014, 69(2): 188-197.
Kocak, "Synthetic Transcription Factors and their Effects on Endogenous DNA Methylation in Human Cells," Thesis submitted in partial fulfillment of the requirements for the degree of Master of Science in the Department of Biomedical Engineering in the Graduate School of Duke University, 2013, p. 1-29.
Kuhnel et al., "Tumor-specific adenoviral gene therapy: Transcriptional repression of gene expression by utilizing p53-signal transduction pathways," Cancer Gene Ther., 2004, 11: 28-40.
Li et al., "Chimeric DNA methyltransferases target DNA methylation to specific DNA sequences and repress expression of target genes," Nucleic Acids Res., 2007, 35(1): 100-112.
Ma et al., "Targeted gene suppression by inducing de novo DNA methylation in the gene promoter," Epigenetics Chromatin, 2014, 7: 20.

(56) References Cited

OTHER PUBLICATIONS

Segal and Meckler, "Genome Engineering at the Dawn of the Golden Age," Annu. Rev. Genomics Hum. Genet., 2013, 14: 135-158.
Siddique et al., "Targeted methylation and gene silencing of VEGF-A in human cells by using a designed Dnmt3a-Dnmt3L single-chain fusion protein with increased DNA methylation activity," J. Mol. Biol., 2013, 425(3): 479-491.
Stepper et al., "Efficient targeted DNA methylation with chimeric dCas9-Dnmt3a-Dnmt3L methyltransferase," Nucleic Acids Res., 2017, 45(4): 1703-1713.
Stolzenburg et al., "Targeted silencing of the oncogenic transcription factor SOX2 in breast cancer," Nucleic Acids Res., 2012, 40(14): 6725-6740.
Urrutia, "KRAB-containing zinc-finger repressor proteins," Genome Biol., 2003, 4(10): 231.
Zhao et al., "Intracellular delivery of artificial transcription factors fused to the protein transduction domain of HIV-1 Tat," Protein Expr Purif, 2013, 90(1): 27-33.
U.S. Appl. No. 17/636,750, filed Feb. 18, 2022, by Gersbach et al.
U.S. Appl. No. 17/636,754, filed Feb. 18, 2022, by Gersbach et al.
'T Hoen et al., "Generation and characterization of transgenic mice with the full-length human DMD gene," J. Biol. Chem., 2008, 283: 5899-5907.
Acosta et al., "Use of two gRNAs for CRISPR/Cas9 improves bi-allelic homologous recombination efficiency in mouse embryonic stem cells, " Genesis, 2018, 56(5): 1-8.
Adamson et al., "A Multiplexed Single-Cell CRISPR Screening Platform Enables Systematic Dissection of the Unfolded Protein Response," Cell, 2016, 167: 1867-1882 e1821.
Ahlenius et al., "FoxO3 regulates neuronal reprogramming of cells from postnatal and aging mice," Proc Natl Acad Sci U S A, 2016, 113: 8514-8519.
Albuquerque et al., "Mammalian nicotinic acetylcholine receptors: from structure to function," Physiol Rev, 2009, 89: 73-120.
Arechavala-Gomeza et al., "Comparative analysis of antisense oligonucleotide sequences for targeted skipping of exon 51 during dystrophin pre-mRNA splicing in human muscle, " Human Gene Therapy, 2007, 18: 798-810.
Asokan et al., "Reengineering a receptor footprint of adeno-associated virus enables selective and systemic gene transfer to muscle," Nat Biotechnol, 2010, 28: 79-82.
Bae et al., "Cas-OFFinder: a fast and versatile algorithm that searches for potential off-target sites of Cas9 RNA-guided endonucleases," Bioinformatics, 2014, 30: 1473-1475.
Barrangou et al., "CRISPR provides acquired resistance against viruses in prokaryotes," Science, 2007, 315(5819): 1709-1712.
Bauer et al., "An erythroid enhancer of BCL11A subject to genetic variation determines fetal hemoglobin level," Science 342, 2013, 253-257.
Bernstein et al., "An integrated encyclopedia of DNA elements in the human genome," Nature, 2012, 489: 57-74.
Bladen et al., "The Treat-NMD DMD Global Database: analysis of more than 7,000 Duchenne muscular dystrophy mutations," Human Mutation, 2015, 36(4):395-402.
Blakemore et al., "Editing of Human Genes May Begin by Year's End in the U.S." Smithsonian.com, <https://www.smithsonianmag.com/smart-news/editing-human-genes-may-begin-years-end-us-180959532/?no-ist> 2016.
Briguet et al., "Histological parameters for the quantitative assessment of muscular dystrophy in the mdx-mouse," Neuromuscul. Disord., 2004, 14: 675-682.
Briner et al., "Guide RNA Functional Modules Direct Cas9 Activity and Orthogonality," Molecular Cell, 2014, 56(2): 333-339.
Briner et al., "Lactobacillus buchneri genotyping on the basis of clustered regularly interspaced short palindromic repeat (CRISPR) locus diversity," Appl. Environ. Microbiol., 2014, 80: 994-1001.
Brunger et al., "CRISPR/Cas9 Editing of Murine Induced Pluripotent Stem Cells for Engineering Inflammation-Resistant Tissues," Arthritis Rheumatol, 2017, 69: 1111-1121.

Brunger et al., "Genome Engineering of Stem Cells for Autonomously Regulated, Closed-Loop Delivery of Biologic Drugs," Stem Cell Reports, 2017, 8: 1202-1213.
Buenrostro et al., "Transposition of native chromatin for fast and sensitive epigenomic profiling of open chromatin, DNA-binding proteins and nucleosome position," Nat Methods, 2013, 10: 1213-1218.
Busskamp et al., "Rapid neurogenesis through transcriptional activation in human stem cells," Mol Syst Biol, 2014, 10: 760.
Carroll, "A CRISPR approach to gene targeting," Molecular Therapy, 2012, 20: 1658-1660.
Cencic et al., "Protospacer adjacent motif (PAM)-distal sequences engage CRISPR Cas9 DNA target cleavage," PLoS one, 2014, 9, e109213, 13 pages.
Chamberlain et al., "Progress toward Gene Therapy for Duchenne Muscular Dystrophy," Mol. Ther., 2017, 25: 1125-1131.
Chanda et al., "Generation of induced neuronal cells by the single reprogramming factor ASCL1," Stem Cell Reports, 2014, 3: 282-296.
Cheloufi et al., "The histone chaperone CAF-1 safeguards somatic cell identity," Nature, 2015, 528: 218-224.
Chen et al., "Targeted activation of diverse CRISPR-Cas systems for mammalian genome editing via proximal CRISPR targeting," Nature Communications, 2017, 8: 14958.
Childers et al., "Gene therapy prolongs survival and restores function in murine and canine models of myotubular myopathy," Sci Transl Med, 2014, 6: 220ra210.
Chronis et al., "Cooperative Binding of Transcription Factors Orchestrates Reprogramming," Cell, 2017, 168: 442-459 e420.
Cooper et al., "Improved induction of immune tolerance to factor IX by hepatic AAV-8 gene transfer," Hum Gene Ther, 2009, 20: 767-776.
Cordier et al., "Muscle-specific promoters may be necessary for adeno-associated virus-mediated gene transfer in the treatment of muscular dystrophies," Hum. Gene Ther., 2001, 12: 205-215.
D'Alessio et al., "A Systematic Approach to Identify Candidate Transcription Factors that Control Cell Identity," Stem Cell Reports, 2015, 5: 763-775.
Daley et al., "CRISPhieRmix: a hierarchical mixture model for CRISPR pooled screens," Genome Biol, 2018, 19: 159.
Darmanis et al., "A survey of human brain transcriptome diversity at the single cell level," Proc Natl Acad Sci U S A, 2015, 112: 7285-7290.
Deconinck et al., "Utrophin-Dystrophin-Deficient Mice as a Model for Duchenne Muscular Dystrophy," Cell, 1997, 90(4): 717-727.
Dirks et al., "Triggered amplification by hybridization chain reaction," Proceedings of the National Academy of Sciences of the United States of America, 2004, 101(43): 15275-15278.
Du et al., "Genetic interaction mapping in mammalian cells using CRISPR interference," Nat Methods, 2017, 14: 577-580.
Duan et al., "Expanding AAV packaging capacity with transsplicing or overlapping vectors: a quantitative comparison, " Molecular Therapy, 2001, 4: 383-391.
Duan et al., "Genome-wide identification of CRISPR/Cas9 off-targets in human genome," Cell research, 2014, 24(8): 1009-12.
Duan, "Systemic AAV Micro-dystrophin Gene Therapy for Duchenne Muscular Dystrophy," Molecular Therapy, 2018, 26(10): 2337-2356.
Dykeman, "An implementation of the Gillespie algorithm for RNA kinetics with logarithmic time update," Nucleic Acids Research, 2015, 45(12): 5708-5715.
Eguchi et al., "Reprogramming cell fate with a genome-scale library of artificial transcription factors," Proc Natl Acad Sci U S A, 2016, 113: E8257-E8266.
Ernsberger, "Role of neurotrophin signalling in the differentiation of neurons from dorsal root ganglia and sympathetic ganglia," Cell Tissue Res, 2009, 336: 349-384.
Erwin et al., "Synthetic transcription elongation factors license transcription across repressive chromatin," Science, 2017, 358: 1617-1622.
Fagerlund et al., "The Cpf1 CRISPR-Cas protein expands genome-editing tools," Genome Biology, 2015, 16:251.

(56) References Cited

OTHER PUBLICATIONS

Farasat et al., "A Biophysical Model of CRISPR/Cas9 Activity for Rational Design of Genome Editing and Gene Regulation," PLOS Computational Biology, 2016, 12(1):e1004724.
Farasat, "Sequence-to-Function Models for Efficient Optimization of Metabolic Pathways and Genetic Circuits," Ph. D. Thesis, 2015, 254 pages.
FDA approval brings first gene therapy to the United States, <https://www.fda.gov/newsevents/newsroom/pressannouncements/ucm574058.htm> (Aug. 30, 2017).
FDA approves first drug for spinal muscular atrophy, <https://www.fda.gov/newsevents/newsroom/pressannouncements/ucm534611.htm> (Dec. 23, 2016).
FDA approves first-of-its kind targeted RNA-based therapy to treat a rare disease, <https://www.fda.gov/newsevents/newsroom/pressannouncements/ucm616518.htm> (Aug. 10, 2018).
FDA approves novel gene therapy to treat patients with a rare form of inherited vision loss, <https://www.fda.gov/newsevents/newsroom/pressannouncements/ucm589467.htm> (Dec. 18, 2017).
FDA grants accelerated approval to first drug for Duchenne muscular dystrophy, <https://www.fda.gov/newsevents/newsroom/pressannouncements/ucm521263.htm> (Sep. 19, 2016).
Flamm et al., "RNA folding at elementary step resolution," Rna, 2000, 6: 325-338.
Flandin et al., "Lhx6 and Lhx8 coordinately induce neuronal expression of Shh that controls the generation of interneuron progenitors," Neuron, 2011, 70: 939-950.
Forget, "Molecular basis of hereditary persistence of fetal hemoglobin," Ann N Y Acad Sci, 1998, 850, 38-44.
Friedland et al., "Characterization of *Staphylococcus aureus* Cas9: a smaller Cas9 for all-in-one adeno-associated virus delivery and paired nickase applications," Genome Biology, 2015, 16(16):257, 10 pages.
Friedland et al., "*Staphyloccocus aureus* Cas9: An Alternative Cas9 for Genome Editing Applications," Molecular Therapy, 2015, 23(Suppl. 1):S224.
Friedland et al., "*Staphyloccocus aureus* Cas9: An Alternative Cas9 for Genome Editing Applications," Retrieved from the Internet: <http://www.editasmedicine.com/data/documents/ASGCT%20poster 2015 Ari.pdf> Retrieved on Feb. 28, 2018.
Fu et al., "Landscape of target: guide homology effects on Cas9-mediated cleavage," Nucleic Acids Research, 2014, 42(22): 13778-13787.
Gaj et al., "Structure-Guided Reprogramming of Serine Recombinase DNA Sequence Specificity," Proc Natl Acad Sci U S A, 2011, 108(2): 498-503.
Gao et al., "Complex transcriptional modulation with orthogonal and inducible dCas9 regulators," Nat Methods, 2016, 13: 1043-1049.
Gascon et al., "Direct Neuronal Reprogramming: Achievements, Hurdles, and New Roads to Success," Cell Stem Cell, 2017, 21: 18-34.
Gasiunas et al., "Cas9-crRNA ribonucleoprotein complex mediates specific DNA cleavage for adaptive immunity in bacteria," Proc. Natl. Acad. Sci., 2012, 109: E2579-E2586.
Gee et al., "Cellular Reprogramming Genome Editing, and Alternative CRISPR Cas9 Technologies for Precise Gene Therapy of Duchenne Muscular Dystrophy," Stem Cells International, 2017, pp. 1-11.
Genbank Accenssion AP006627.1 (2016).
Genbank Accenssion BA000004.3 (2016).
Genbank Accenssion BAB04055.1 (2016).
GenBank Accession AF214528.1 (2000).
GenBank Accession No. AAC75803.1 (2018).
GenBank Accession No. AIN33136.1 (2014).
GenBank Accession No. BAB04055.1 (2017).
GenBank Accession No. EOT14076.1 (2013).
GenBank Accession No. AK019325 (2010).
GenBank Accession No. BB730912 (2001).
GenBank Accession No. BC010291 (2006).
GenBank Accession No. BC026642.1 (2007).
GenBank Accession No. BI143915 (2011).
GenBank Accession No. NM_020562.1 (2004).
GenBank Accession X51934.1 (1997).
GenBank P38036.2 (2013).
Gersbach et al., "Targeted plasmid integration into the human genome by an engineered zinc-finger recombinase," Nucleic Acids Res, 2011, 39: 7868-7878.
Gilbert et al., "CRISPR-mediated modular RNA-guided regulation of transcription in eukaryotes," Cell, 2013, 154: 442-451.
Gillespie, "A general method for numerically simulating the stochastic time evolution of coupled chemical reactions," Journal of computational physics, 1976, 22: 403-434.
Gilman et al., "Distal CCAAT box deletion in the A gamma globin gene of two black adolescents with elevated fetal A gamma globin," Nucleic Acids Res 16, 1988, 10635-10642.
Gomaa et al., "Programmable Removal of Bacterial Strains by Use of Genome-Targeting CRISPR-Cas Systems," 2014, mBio 5(1): e00928-13.
Gonda "Aerosols for delivery of therapeutic and diagnostic agents to the respiratory tract," Critical Reviews in Therapeutic Drug Carrier Systems, 1990 6:273-313.
Gong et al., "Molecular insights into DNA interference by CRISPR-associated nuclease-helicase Cas3," Proc Natl Acad Sci U S A, 2014, 111(46): 16359-64.
Gregorevic et al., "Systemic microdystrophin gene delivery improves skeletal muscle structure and function in old dystrophic mdx mice," Mol Ther, 2008, 16: 657-664.
Grissa et al., "CRISPRFinder: a web tool to identify clustered regularly interspaced short palindromic repeats," Nucleic Acids Res., 2007, 35(Web Server issue):W52-57.
Guo et al., "Harnessing accurate non-homologous end joining for efficient prease deletion in CRISPR/Cas9-mediated genome editing," Genome Biology, 2018, 19: 170, 20 pages.
Guo, J. et al., "Directed evolution of an enhanced and highly efficient Fokl cleavage domain for zinc finger nucleases," J Mol Biol, 2010, 400(1): 96-107.
Hakim et al., "Evaluation of Muscle Function of the Extensor Digitorum Longus Muscle Ex vivo and Tibialis Anterior Muscle In situ in Mice," J. Vis. Exp., 2013, 1-8.
Hakim et al., "Systemic gene transfer reveals distinctive muscle transduction profile of tyrosine mutant AAV-1, -6, and -9 in neonatal dogs," Mol. Ther. Methods Clin. Dev., 2014, 1:14002.
Harper et al., "Modular flexibility of dystrophin: implications for gene therapy of Duchenne muscular dystrophy," Nat. Med., 2002, 8: 253-261.
Henikoff et al., "Amino acid substitution matrices from protein blocks, " Proc. Natl. Acad. Sci. USA, 1992, 89: 10915-9.
Hilton et al., "Enabling functional genomics with genome engineering," Genome Research, 2015, 25(10):1442-1455.
Howarth et al., "A monovalent streptavidin with a single femtomolar biotin binding site," Nature methods, 2006, 3(4): 267-273.
Hsu et al., "Development and applications of CRISPR-Cas9 for genome engineering," Cell, 2014, 157: 1262-1278.
Huang et al., "Impaired respiratory function in mdx and mdx/utrn+/− mice," Muscle & Nerve, 2011, 43(2): 263-267.
Inoue et al., "Runx transcription factors in neuronal development," Neural Dev, 2008, 3: 20.
Isaac et al., "Dystrophin and utrophin "double knockout" dystrophic mice exhibit a spectrum of degenerative musculoskeletal abnormalities," Journal of Orthopaedic Research, 2013, 31(3): 343-349.
Iyombe-Engembe et al., "Efficient Restoration of the Dystrophin Gene Reading Frame and Protein Structure in DMD Myoblasts Using the CinDel Method," Molecular Therapy—Nucleic Acids, 2016, 5:e283.
Jiang et al., "A Cas9-guide RNA complex preorganized for target DNA recognition," Science, 2015, 348, 1477-1481.
Jiang et al., "RNA-guided editing of bacterial genomes using CRISPR-Cas systems," Nat. Biotechnol., 2013, 31:233-239.
Jooss et al., "Transduction of dendritic cells by DNA viral vectors directs the immune response to transgene products in muscle fibers," J. Virol., 1998, 72: 4212-4223.

(56) References Cited

OTHER PUBLICATIONS

Josephs et al., "Structure and specificity of the RNA-guided endonuclease Cas9 during DNA interrogation, target binding and cleavage," Nucleic Acids Research, 2015, 43(18): 8924-8941.
Karlin et al., "Applications and statistics for multiple high-scoring segments in molecular sequences," Proc. Natl. Acad. Sci. USA, 1993, 90: 5873-77.
Keil et al., "Brain transcriptome databases: a user's guide," J Neurosci, 2018, 38(10): 2399-2412.
Khambata-Ford et al., "Identification of Promoter Regions in the Human Genome by Using a Retroviral Plasmid Library-Based Functional Reporter Gene Assay," Genome Research, 2003, 13: 1765-1774.
Khodakov et al., "Protected DNA strand displacement for enhanced single nucleotide discrimination in double-stranded DNA," Scientific reports, 2015, 5: 8721.
Kim et al., "A Histone acetylation contributes to chromatin looping between the locus control region and globin gene by influencing hypersensitive site formation," Biochim Biophys Acta, 2013, 1829: 963-969.
Kleinstiver et al., "Genome-wide specificities of CRISPR-Cas Cpf1 nucleases in human cells," Nature Biotechnology, 2016, 34(8):869-874.
Koerber et al., "DNA shuffling of adeno-associated virus yields functionally diverse viral progeny," Mol Ther, 2008, 16: 1703-1709.
Koo et al., "Functional Rescue of Dystrophin Deficiency in Mice Caused by Frameshift Mutations Using Campylobacter jejuni Cas9," Molecular Therapy, 2018 26(6): 1529-1538.
Koopmans et al., "SynGO: An Evidence-Based, Expert-Curated Knowledge Base for the Synapse," Neuron, 2019, 103: 217-234 e214.
Koppanati et al., "Improvement of the mdx mouse dystrophic phenotype by systemic in utero AAV8 delivery of a minidystrophin gene," Gene Ther, 2010, 17: 1355-1362.
Kreis et al., "The Multifaceted p21 (Cip1/Waf1/CDKN1A) in Cell Differentiation, Migration and Cancer Therapy," Cancers (Basel), 2019, 11(9): 1220.
Kwon et al., "Myogenic Progenitor Cell Lineage Specification by CRISPR/Cas9-Based Transcriptional Activators," Stem cell reports, 2020, 14: 755-769.
Lai et al., "Partial restoration of cardiac function with ΔPDZ nNOS in aged mdx model of Duchenne cardiomyopathy," Hum Mol Genet., 2014, 23(12): 3189-3199.
Lake et al., "Integrative single-cell analysis of transcriptional and epigenetic states in the human adult brain," Nat Biotechnol, 2018, 36: 70-80.
Lambert et al., "The Human Transcription Factors," Cell, 2018, 172: 650-665.
Lesnik et al., "Relative thermodynamic stability of DNA, RNA, and DNA: RNA hybrid duplexes: relationship with base composition and structure," Biochemistry, 1995, 34(34): 10807-10815.
Levskaya et al., "Synthetic biology: engineering *Escherichia coli* to see light," Nature, 2005, 438:441-442.
Li et al., "Engineering and selection of shuffled AAV genomes: a new strategy for producing targeted biological nanoparticles," Mol Ther, 2008, 16: 1252-1260.
Li et al., "Ex vivo cell-based CRISPR/Cas9 genome editing for therapeutic applications," Biomaterials, 2020, 234: 119711.
Li et al., "Precise correction of the dystrophin gene in duchenne muscular dystrophy patient induced pluripotent stem cells by TALEN and CRISPR-Cas9," Stem Cell Reports, 2015, 4: 143-154.
Li et al., "Preservation of muscle force in Mdx3cv mice correlates with low-level expression of a near full-length dystrophin protein," Am. J. Pathol., 2008, 172: 1332-1341.
Lim et al., "Application of CRISPR/Cas9 for the Treatment of Duchenne Muscular Dystrophy," Journal of Personalized Medicine, 2018, 8(4): 1-20.
Liu et al., "Adeno-associated virus-mediated microdystrophin expression protects young mdx muscle from contraction-induced injury," Mol. Ther., 2005, 11: 245-256.

Liu et al., "Monte Carlo simulation for single RNA unfolding by force," Biophysical journal, 2005, 88(1): 76-84.
Luo et al., "Repurposing endogenous type I CRISPR-Cas systems for programmable gene repression," Nucleic Acids Research, 2014, 43(1): 674-681.
Machinek et al., "Programmable energy landscapes for kinetic control of DNA strand displacement," Nature communications, 2014, 5: 5324, 9 pages.
MacPherson et al., "Flexible guide-RNA design for CRISPR applications using Protospacer Workbench," Nature biotechnology, 2015, 33(8): 805-806.
Mader et al., "CRISPR RNA-guided activation of endogenous human genes," Nature Methods, 2013, 10(10): 977-979.
Maeder et al., "Robust, synergistic regulation of human gene expression using TALE activators," Nat Methods, 2013, 10(3): 243-245.
Maheshri et al., "Directed evolution of adeno-associated virus yields enhanced gene delivery vectors," Nat Biotechnol, 2006, 24: 198-204.
Makarova et al., "An updated evolutionary classification of CRISPR-Cas systems," Nature Reviews Microbiology, 2015, 13:722-736.
Makarova et al., "Evolution and classification of the CRISPR-Cas systems," Nature Reviews Microbiology, 2011, pp. 467-477.
Mann et al., "Improved antisense oligonucleotide induced exon skipping in the mdx mouse model of muscular dystrophy," J. Gene Med., 2002, 4: 644-654.
Manning et al., "What has the mdx mouse model of duchenne muscular dystrophy contributed to our understanding of this disease?," Journal of Muscle Research and Cell Motility, 2015, 36: 155-167.
Maruyama et al., "Epigenetic Regulation of Cell Type-Specific Expression Patterns in the Human Mammary Epithelium," PLoS Genetics, 2011, 7(4): e1001369, 15 pages.
Mathews et al., "Expanded sequence dependence of thermodynamic parameters improves prediction of RNA secondary structure," Journal of Molecular Biology, 1999, 288(5): 911-940.
McGreevy et al., "Animal models of Duchenne muscular dystrophy: from basic mechanisms to gene therapy," Disease Models Mechanisms, 2015, 8(3): 195-213.
Mertens et al., "Evaluating cell reprogramming, differentiation and conversion technologies in neuroscience," Nat Rev Neurosci, 2016, 17: 424-437.
Miller et al., "Transcriptional landscape of the prenatal human brain," Nature, 2014, 508: 199-206.
Mojica et al., "Short motif sequences determine the targets of the prokaryotic CRISPR defence system," Microbiology, 2009, 155: 733-740.
Morris et al., "Dissecting engineered cell types and enhancing cell fate conversion via CellNet," Cell, 2014, 158: 889-902.
Muir et al., "Engraftment potential of dermal fibroblasts following in vivo myogenic conversion in immunocompetent dystrophic skeletal muscle," Mol. Ther. Methods Clin. Dev., 2014, 1:14025.
Murray et al., "Codon usage in plant genes," Nucl. Acids Res., 1989, 17:477-498.
Najm et al., "Orthologous CRISPR-Cas9 enzymes for combinatorial genetic screens, " Nat Biotechnol, 2018, 36: 179-189.
Naldini, "Gene therapy returns to centre stage," Nature, 2015, 526: 351-360.
Nam et al., "Cas5d protein processes pre-crRNA and assembles into a Cascade-like interference complex in Subtype I-C/Dvulg CRISPR-Cas system," Structure, 2012, 20:1574-1584.
Nelson et al., "Local and Systemic Gene Editing in a Mouse Model of Duchenne Muscular Dystrophy," Molecular Therapy, 2016, 24(Supp 1):S191.
O'Connell et al., "Programmable RNA recognition and cleavage by CRISPR/Cas9," Nature, 2014, 516: 263-266.
Odom et al., "Microutrophin Delivery Through rAAV6 Increases Lifespan and Improves Muscle Function in Dystrophic Dystrophin/Utrophin-deficient Mice," Molecular Therapy, 2008, 16(9): 1539-1545.
O'Geen et al., "Ezh2-dCas9 and KRAB-dCas9 enable engineering of epigenetic memory in a context-dependent manner," Epigenetics Chromatin, 2019, 12: 26.

(56) References Cited

OTHER PUBLICATIONS

Ousterout et al., "Correction of dystrophin expression in cells from duchenne muscular dystrophy patients through genomic excision of exon 51 by zinc finger nucleases," Molecular Therapy 23, 2015, 523-532.
Ousterout et al., "Multiplex CRISPR/Cas9-based genome editing for correction of dystrophin mutations that cause Duchenne muscular dystrophy," Nature Communications, 2015, 6:6244.
Ousterout, "Genetic Correction of Duchenne Muscular Dystrophy using Engineered Nucleases," Dept. of Biomedical Engineering Duke University (Dissertation), 2014, pp. 1-204.
Paez-Espino et al., "CRISPR immunity drives rapid phage genome evolution in *Streptococcus thermophilus*," mBio, 2015, 6(2): e00262-15.
Pang et al., "Induction of human neuronal cells by defined transcription factors," Nature, 2011, 476: 220-223.
Parekh et al., "Mapping Cellular Reprogramming via Pooled Overexpression Screens with Paired Fitness and Single-Cell RNA-Sequencing Readout," Cell Systems, 2018, 7: 548-555.e548.
Park et al., "Multi-Parametric MRI at 14T for Muscular Dystrophy Mice Treated with AAV Vector-Mediated Gene Therapy," PLoS One, 2015, 10(4): e0124914.
Penczek et al., "Three-dimensional reconstruction of single particles embedded in ice," Ultramicroscopy, 1992, 40, 33-53.
Perez-Pinera et al., "Synergistic and tunable human gene activation by combinations of synthetic transcription factors," Nat Methods, 2013, 10: 239-242.
Pinello et al., "Analyzing CRISPR genome-editing experiments with CRISPResso," Nat Biotechnol, 2016, 34(7):695-697.
Polstein et al., "A light-inducible CRISPR-Cas9 system for control of endogenous gene activation," Nature Chemical Biology, 2015, 11: 198-200.
Prykhozhij et al., "CRISPR MultiTargeter: A Web Tool to Find Common and Unique CRISPR Single Guide RNA Targets in a Set of Similar Sequences," PLoS One, 2015, 10(3): e0119372.
Rackham et al., "A predictive computational framework for direct reprogramming between human cell types," Nature Genetics, 2016, 48: 331-335.
Raeburn et al., "Techniques for drug delivery to the airways, and the assessment of lung function in animal models," J. Pharmacol. Toxicol. Meth., 1992, 27:143-159.
Ramachandran et al., "Nitric Oxide Signaling Pathway in Duchenne Muscular Dystrophy Mice: Upregulation of L-arginine Transport," Biochem. J., 2012, 449: 133-142.
Ran et al., "Genome engineering using the CRISPR-Cas9 system," Nature Protocols, 2013, 8(11): 2281-2308.
Ratcliff et al., "A novel single-molecule study to determine protein-protein association constants," Journal of the American Chemical Society, 2001, 123(24): 5632-5635.
Riordan et al., "Application of CRISPR/Cas9 for biomedical discoveries," Cell & Bioscience, 2015, 5(1):11 pages.
Roadmap Epigenomics Consortium, "Integrative analysis of 111 reference human epigenomes," Nature, 2015, 518: 317-330.
Rodriguez et al., "Clustering by fast search and find of density peaks," Science, 2014, 344(6191): 1492-1496.
Roudaut et al., "Restriction of calpain3 expression to the skeletal muscle prevents cardiac toxicity and corrects pathology in a murine model of limb-girdle muscular dystrophy," Circulation, 2013, 128: 1094-1104.
Russa et al. "The New State of the Art: Cas9 for Gene Activation and Repression," Molecular and Cellular Biology, 2015, 35(22):3800-3809.
Rutkauskas et al., "Directional R-loop formation by the CRISPR-Cas surveillance complex cascade provides efficient off-target site rejection," Cell reports, 2015, 10, 1534-1543.
Sagal et al., "Proneural transcription factor Atoh1 drives highly efficient differentiation of human pluripotent stem cells into dopaminergic neurons," Stem Cells Transl Med, 2014, 3: 888-898.
Sanson et al., "Optimized libraries for CRISPR-Cas9 genetic screens with multiple modalities," Nat Commun, 2018, 9: 5416.
SantaLucia et al., "Improved nearest-neighbor parameters for predicting DNA duplex stability," Biochemistry, 1996, 35(11): 3555-3562.
Schreck et al., "DNA hairpins destabilize duplexes primarily by promoting melting rather than by inhibiting hybridization," Nucleic Acids Research, 2015, 43(13): 6181-6190.
Schreck et al., "DNA hairpins primarily promote duplex melting rather than inhibiting hybridization," 2014, arXiv preprint arXiv:1408.4401.
Schultz et al., "Recombinant adeno-associated virus transduction and integration," Molecular Therapy, 2008, 16: 1189-1199.
Schultz et al., "SETDBI: a novel KAP-I-associated histone H3, lysine 9-specific methyltransferase that contributes to HPI-mediated silencing of euchromatic genes by KRAB zinc-finger proteins," Genes & Development, 2002, 16: 919-932.
Semenova et al., "The Case ribonuclease is not required for interference and adaptation by the *E. coli* type I-E CRISPR-Cas system," Nucleic Acids Res, 2015, 43(12):6049-61.
Sequence alignment: SEQ ID No. 102920 (2019).
Sequence alignment: SEQ ID No. 102921 (2019).
Sequence alignment: SEQ ID No. 103735 (2019).
Sequence alignment: SEQ ID No. 103736 (2019).
Serra et al., "Predicting thermodynamic properties of RNA," Methods in Enzymology, 1995, 259: 242-261.
Sharma et al., "In vivo genome editing of the albumin locus as a platform for protein replacement therapy," Blood, 2015, 126: 1777-1784.
Shen et al., "Combinatorial CRISPR-Cas9 screens for de novo mapping of genetic interactions," Nat Methods, 2017, 14: 573-576.
Shin et al., "Microdystrophin Ameliorates Muscular Dystrophy in the Canine Model of Duchenne Muscular Dystrophy," Mol. Ther., 2013, 21: 750-757.
Shlyakhtenko et al., "Silatrane-based surface chemistry for immobilization of DNA, protein-DNA complexes and other biological materials, " Ultramicroscopy, 2003, 97: 279-287.
Simpson, "Contacts between *Escherichia coli* RNA polymerase and thymines in the lac UV5 promoter," Proc. Natl. Acad. Sci. USA, 1979, 76: 3233-3237.
Singh et al. "Protein Engineering Approaches in the Post-Genomic Era," Current Protein and Peptide Science, 2017, 18: 1-11.
Skene et al., "Genetic identification of brain cell types underlying schizophrenia," Nat Genet, 2018, 50: 825-833.
Song et al., "Non-immunogenic utrophin gene therapy for the treatment of muscular dystrophy animal models," Nature Medicine, 2019, 25(10): 1505-1511.
Stemmer et al., "CCTop: An Intuitive, Flexible and Reliable CRISPR/Cas9 Target Prediction Tool," PLoS One, 2015, 10(4): e0124633.
Sugimoto et al., "Thermodynamic parameters to predict stability of RNA/DNA hybrid duplexes," Biochemistry, 1995, 34: 11211-11216.
Sugimoto et al., "Thermodynamics-structure relationship of single mismatches in RNA/DNA duplexes," Biochemistry, 2000, 39: 11270-11281.
Sun et al., "Phage mutations in response to CRISPR diversification in a bacterial population," Environmental microbiology, 2013, 15(2): 463-470.
Suzuki et al., "In vivo genome editing via CRISPR/Cas9 mediated homology-independent targeted integration," Nature, 2016, 540: 144-149.
Szczelkun et al., "Direct observation of R-loop formation by single RNA-guided Cas9 and Cascade effector complexes," Proceedings of the National Academy of Sciences, 2014, 6 pages.
Szymczak et al., "Correction of multi-gene deficiency in vivo using a single 'self-cleaving' 2A peptide-based retroviral vector," Nature Biotechnology, 2004, 22(5): 589-594.
Takahashi et al., "A decade of transcription factor-mediated reprogramming to pluripotency," Nature Reviews, 2016, 17: 183-193.
Takahashi et al., "Induction of pluripotent stem cells from mouse embryonic and adult fibroblast cultures by defined factors," Cell, 2006, 126: 663-676.

(56) References Cited

OTHER PUBLICATIONS

Takami et al., "Complete Genome Sequence of the Alkaliphilic Bacterium Bacillus halodurans and Genomic Sequence Comparison with Bacillus subtilis," Nucleic Acids Research, 2000, 28(21): 4317-4331.
Teratani-Ota et al., "Induction of specific neuron types by overexpression of single transcription factors," In Vitro Cell Dev Biol Anim, 2016, 52(9): 961-973.
Theodorou et al., "A high throughput embryonic stem cell screen identifies Oct-2 as a bifunctional regulator of neuronal differentiation," Genes Dev, 2009, 23: 575-588.
Thorgeirsson et al., "A variant associated with nicotine dependence, lung cancer and peripheral arterial disease," Nature, 2008, 452: 638-642.
Tian et al., "CRISPR Interference-Based Platform for Multimodal Genetic Screens in Human iPSC-Derived Neurons," Neuron, 2019, 104: 239-255 e212.
Tinsley et al., "Amelioration of the dystrophic phenotype of mdx mice using a truncated utrophin transgene," Nature, 1996, 384(6607): 349-353.
Tsai et al., "GUIDE-seq enables genome-wide profiling of off-target cleavage by CRISPR-Cas nucleases," Nature biotechnology, 2015, 33(2): 187-197.
Tsuchiya et al., "The "Spanning Protocol": A new DNA extraction method for efficient single-cell genetic diagnosis," Journal of Assisted Reproduction Genetics, 2005, 22(11-12):407-14.
Tsunemoto et al., "Diverse reprogramming codes for neuronal identity," Nature, 2018, 557: 375-380.
Tycko et al., "Screening S. aureus CRISPR-Cas9 Paired Guide RNAs for Efficient Targeted Deletion in Duchenne Muscular Dystrophy," Editas, Poster presented on May 5, 2016.
Tyle, "Iontophoretic Devices for Drug Delivery," Pharm. Res., 1986, 3: 318-326.
Van Arensbergen et al., "Genome-wide mapping autonomous promoter activity in human cells," Nature Biotechnology, 2017, 35(2): 145-153.
Van der Oost et al., "Unravelling the structural and mechanistic basis of CRISPR-Cas systems," Nature Reviews Microbiology, 2014, 12: 479-492.
Van Deutekom et al., "Advances in Duchenne muscular dystrophy gene therapy," Nat. Rev. Genet., 2003, 4: 774-783.
Vaquerizas et al., "A census of human transcription factors: function, expression and evolution," Nat Rev Genet, 2009, 10: 252-263.
Veltrop et al., "A dystrophic Duchenne mouse model for testing human antisense oligonucleotides," PLoS One, 2018, 13(2): e0193289, 18 pages.
Verkhusha et al., "GFP-like flourescent proteins and chromoproteins of the class Anthozoa," Protein Structures: Kaleidoscope of Structural Properties and Functions, 2003, 405-439.
Vierbuchen et al., "Direct lineage conversions: unnatural but useful?," Nat Biotechnol, 2011, 29: 892-907.
Vierbuchen et al., "Molecular roadblocks for cellular reprogramming," Mol Cell, 2012, 47: 827-838.
Wada et al., "Codon usage tabulated from the GenBank genetic sequence data," Nucl. Acids Res., 1990, 18: 2367-2411.
Wang et al., "Construction and analysis of compact muscle-specific promoters for AAV vectors," Gene Ther, 2008, 15: 1489-1499.
Wang et al., "Systemic human minidystrophin gene transfer improves functions and life span of dystrophin and dystrophin/utrophin-deficient mice," J. Orthop. Res., 2009, 27: 421-426.
Wang et al., "Unbiased detection of off-target cleavage by CRISPR-Cas9 and TALENs using integrase-defective lentiviral vectors," Nature biotechnology, 2015, 33(2): 175-8.
Wapinski et al., "Hierarchical mechanisms for direct reprogramming of fibroblasts to neurons," Cell, 2013, 155: 621-635.
Watkins et al., "Thermodynamic contributions of single internal rA.dA, rC.dC, rG.dG and rU.dT mismatches in RNA/DNA duplexes," Nucleic acids research, 2011, 39(5): 1894-1902.
Westendorp et al., "E2F7 represses a network of oscillating cell cycle genes to control S-phase progression," Nucleic Acids Res, 2012, 40: 3511-3523.
Wherry, "T cell exhaustion," Nat. Immunology, 2011, 12: 492-499.
Wienert et al., "Editing the genome to introduce a beneficial naturally occurring mutation associated with increased fetal globin," Nat Commun 6, 2015, 7085.
Wiggins et al., "High flexibility of DNA on short length scales probed by atomic force microscopy," Nature nanotechnology, 2006, 1(2): 137-141.
Wiles et al., "CRISPR-Cas9_mediated genome editing and guide RNA design," Mammalian Genome, 2015, 26(9): 501-510.
Willmann et al., "Mammalian animal models for Duchenne muscular dystrophy," Neuromuscular Disorders, 2009, 19(4): 241-249.
Wood, "Neuromuscular disease: CRISPR/Cas9 gene-editing platform corrects mutations associated with Duchenne muscular dystrophy," Nature Reviews Neurology, 2015, 11(4):184.
Wu et al., "Genome-wide binding of the CRISPR endonuclease Cas9 in mammalian cells," Nat Biotechnol, 2014, 32: 670-676.
Wylie et al., "Distinct transcriptomes define rostral and caudal serotonin neurons," J Neurosci, 2010, 30: 670-684.
Xie et al., "sgRNAcas9: a software package for designing CRISPR sgRNA and evaluating potential off-target cleavage sites," PLoS One, 2014, 9(6): e100448.
Xu et al., "Direct lineage reprogramming: strategies, mechanisms, and applications," Cell Stem Cell, 2015, 16: 119-134.
Xu et al., "Recent advances in neuroepigenetic editing," Curr Opin Neurobiol, 2019, 59: 26-33.
Xue et al., "Synthetic mRNAs Drive Highly Efficient iPS Cell Differentiation to Dopaminergic Neurons," Stem Cells Transl Med, 2019, 8: 112-123.
Yang et al., "Determination of protein-DNA binding constants and specificities from statistical analyses of single molecules: MutS-DNA interactions," Nucleic acids research, 2005, 33(13): 4322-4334.
Yang et al., "Generation of pure GABAergic neurons by transcription factor programming," Nat Methods, 2017, 14: 621-628.
Yin et al., "Programming biomolecular self-assembly pathways," Nature, 2008, 451(7176): 318-323.
Young et al., "A Single CRISPR-Cas9 Deletion Strategy that Targets the Majority of DMD Patients Restores Dystrophin Function in hiPSC-Derived Muscle Cells," Cell Stem Cell, 2016, 18: 533-540.
Young et al., "Creation of a Novel Humanized Dystrophic Mouse Model of Duchenne Muscular Dystrophy and Application of a CRISPR/Cas9 Gene Editing Therapy," Journal of Neuromuscular Diseases, 2017, 4(2): 139-145.
Zenser et al., "A new TAP system for isolation of plant protein complexes and subsequent mass-spec analysis," <https://www.sigmaaldrich.com/deepweb/assets/sigmaaldrich/product/documents/388/028/flag_ha_tap_poster.pdf> published 2008, printed as pp. 1/4-4/4.
Zetsche et al., "Cpf1 Is a Single RNA-Guided Endonuclease of a Class 2 CRISPR-Cas System," Cell, 2015, 163(3):759-71.
Zhang et al., "Comprehensive Structure-Function Study of Neurogenin3 Disease-Causing Alleles during Human Pancreas and Intestinal Organoid Development," Dev Cell, 2019, 50(3): 367-380.e7.
Zhang et al., "Efficient precise knockin with a double cute HDR donor after CRISPR/Cas9-mediated double-stranded DNA cleavage," Genome Biol, 2017 18(35): 18 pages.
Zhang et al., "Myoediting: Toward Prevention of Muscular Dystrophy by Therapeutic Genome Editing," Physiological Reviews, 2018, 98(3): 1205-1240.
Zhang et al., "Propagated Perturbations from a Peripheral Mutation Show Interactions Supporting WWW Domain Thermostability," Structure, 2018, 26: 1474-1485.
Zhang et al., "Rapid single-step induction of functional neurons from human pluripotent stem cells," Neuron, 2013, 78: 785-798.
Zhao et al., "High-efficiency transfection of primary human and mouse T lymphocytes using RNA electroporation," Mol. Ther., 2006, 13: 151-159.
Zhao et al., "The LIM-homeobox gene Lhx8 is required for the development of many cholinergic neurons in the mouse forebrain," Proc Natl Acad Sci U S A, 2003, 100: 9005-9010.

(56) References Cited

OTHER PUBLICATIONS

Zhou et al., "Haploinsufficiency of utrophin gene worsens skeletal muscle inflammation and fibrosis in mdx mice," Journal of the Neurological Sciences, 2008, 264(1): 106-111.
International Search Report and Written Opinion for Application No. PCT/US2022/018400 dated Sep. 1, 2022 (18 pages).
Japanese Patent Office Action for Application No. 2021-102533 dated Aug. 8, 2022 (2 pages, English translation included).
United States Patent Office Action for U.S. Appl. No. 16/322,234 dated Nov. 7, 2022 (26 pages).
European Patent Office Action for Application No. 16749752.8 dated Jul. 25, 2022 (4 pages).
U.S. Appl. No. 18/180,718, filed Mar. 8, 2023.
U.S. Appl. No. 18/030,745, filed Apr. 6, 2023.
U.S. Appl. No. 18/031,313, filed Apr. 11, 2023.
U.S. Appl. No. 18/033,049, filed Apr. 20, 2023.
Aartsma-Rus et al., "Antisense-mediated exon skipping: a versatile tool with therapeutic and research applications," RNA 13, 2007, 1609-1624.
Aartsma-Rus et al., "Exploring the frontiers of therapeutic exon skipping for Duchenne muscular dystrophy by double targeting within one or multiple exons," Mol Ther, 2006, 14:401-407.
Aartsma-Rus et al., "Theoretic applicability of antisense-mediated exon skipping for Duchenne muscular dystrophy mutations," Hum Mutat, 2009, 30:293-299.
Adler et al., "Nonviral direct conversion of primary mouse embryonic fibroblasts to neuronal cells," Molecular therapy, 2012 Nucleic acids 1, e32.
Aiuti et al., "Lentiviral hematopoietic stem cell gene therapy in patients with Wiskott-Aldrich syndrome," Science, 2013, 341(6148): p. 1233151.
Anders et al., "Differential expression analysis for sequence count data," Genome biology 11, 2010, R106.
Anders et al., "Structural basis of PAM-dependent target DNA recognition by the Cas9 endonuclease," Nature (2014) 513: 569-73.
Anguela et al., "Robust ZFN-mediated genome editing in adult hemophilic mice," Blood, 2013, 122:3283-3287.
Aoki et al., "Bodywide skipping of exons 45-55 in dystrophic mdx52 mice by systemic antisense delivery," Proc Natl Acad Sci USA, 2012, 109:13763-13768.
Arnold et al., "Genome-wide quantitative enhancer activity maps identified by STARR-seq," Science, 2013, 339(6123):1074-7.
Asokan et al., "The AAV Vector Toolkit: Poised at the Clinical Crossroads, " Mol Ther, 2012, 20, 699-708.
Ayyanathan et al., "Regulated recruitment of HP1 to a euchromatic gene induces mitotically heritable, epigenetic gene silencing: a mammalian cell culture model of gene variegation," Genes Dev, 2003, 17, 1855-1869.
Bartel et al., "Isolation of new ribozymes from a large pool of random sequences, " Science, 1993, 261(5127): 1411-1418.
Bartsevich et al., "Engineered zinc finger proteins for controlling stem cell fate," Stem Cells 21, 2003, 632-637.
Beaudry et al., "Directed evolution of an RNA enzyme," Science, 1992, 257(5070): 635-641.
Beerli et al., "Chemically regulated zinc finger transcription factors," J Biol Chem, 2000, 275(42):32617-27.
Beerli et al., "Engineering polydactyl zinc-finger transcription factors," Nat Biotechnol 20, 2002, 135-141.
Beerli et al., "Positive and negative regulation of endogenous genes by designed transcription factors," Proc Natl Acad Sci U S A 97, 2000, 1495-1500.
Beerli et al., "Toward controlling gene expression at will: specific regulation of the erbB-2/HER-2 promoter by using polydactyl zinc finger proteins constructed from modular building blocks," Proc Natl Acad Sci U S A 95, 1998, 14628-14633.
Beltran et al., "Re-activation of a dormant tumor suppressor gene maspin by designed transcription factors, " Oncogene 26, 2007, 2791-2798.

Bender et al., "Independent formation of DnaseI hypersensitive sites in the murine beta-globin locus control region," Blood, 2000, 95, 3600-3604.
Benedetti et al., "Repair or Replace? Exploiting Novel Gene and Cell Therapy Strategies for Muscular Dystrophies," FEBS Journal, 2013, 280:4263-4280.
Berghella et al., "Reversible immortalization of human myogenic cells by site-specific excision of a retrovirally transferred oncogene," Human gene therapy 10, 1999, 1607-1617.
Bernstein et al., "The NIH Roadmap Epigenomics Mapping Consortium," Nat Biotechnol, 2010, 28, 1045-1048.
Beverley, "Primer: making sense of T-cell memory," Nat. Clin. Pract. Rheumatol. 2008, 4, 43-49.
Bhakta et al., "Highly active zinc-finger nucleases by extended modular assembly," Genome Res, 2013, 530-538.
Bidou et al., "Sense from nonsense: therapies for premature stop codon diseases," Trends in Molecular Medicine 18, 2012, 679-688.
Bieth et al., "Highly restricted deletion of the SNORD116 region is implicated in Prader-Willi Syndrome," Eur J Hum Genet, 2015, 23: 252-255.
Bittel et al., "Prader-Willi syndrome: clinical genetics, cytogenetics and molecular biology," Expert Rev Mol Med, 2005, 7(14): 1-20.
Blancafort et al., "Scanning the human genome with combinatorial transcription factor libraries," Nat Biotechnol 21, 2003, 269-274.
Boch et al., "Breaking the code of DNA binding specificity of TAL-type III effectors," Science 326, 2009, 1509.
Boshart et al., "A very strong enhancer is located upstream of an immediate early gene of human cytomegalovirus," Cell, 1985, 41:521-530.
Bowles et al., "Phase 1 Gene Therapy for Duchenne Muscular Dystrophy Using a Translation Optimized AAV Vector," Molecular Therapy 20, 2012, 443-455.
Boyle et al., "High-resolution mapping and characterization of open chromatin across the genome," Cell, 2008. 132(2):311-22.
Braasch et al., "Novel Antisense and Peptide Nucleic Acid Strategies for Controlling Gene Expression," Biochemistry, 2002, 41: 4503-4510.
Breaker et al., "Inventing and improving ribozyme function rational design versus iterative selection methods," TIBTECH, 1994, 12: 268-274.
Breaker, "Are engineered proteins getting competition from RNA?," Curr. Op. Biotech., 1996, 7(4): 442-448.
Brummelkamp et al., "A system for stable expression of short interfering RNAs in mammalian cells," Science, 2002, 296(5567): 550-553.
Brunet et al., "Chromosomal translocations induced at specific loci in human stem cells," Proc Natl Acad Sci USA, 2009, 106:10620-10625.
Buiting, "Prader-Willi syndrome and Angelman syndrome," Am J Med Genet C Semin Med Genet, 2010, 154C(3): 365-376.
Buler et al., "Energy-sensing factors coactivator peroxisome proliferator-activated receptor gamma coactivator 1-alpha (PGC-1 alpha) and AMP-activated protein kinase control expression of inflammatory mediators in liver," The Journal of Biological Chemistry, Jan. 13, 2012, vol. 287, No. 3, pp. 1847-1860.
Bultmann et al., "Targeted transcriptional activation of silent oct4 pluripotency gene by combining designer TALEs and inhibition of epigenetic modifiers," Nucleic Acids Res 40, 2012, 5368-5377.
Burnett et al., "Deficiency in prohormone convertase PC1 impairs prohormone processing in Prader-Willi syndrome," J Clin Invest, 2017, 127: 293-305.
Cano-Rodriguez et al., "Writing of H3K4Me3 overcomes epigenetic silencing in a sustained but context-dependent manner," Nat Commun, 2016, 7: 12284.
Canver et al., "BCL11A enhancer dissection by Cas9-mediated in situ saturating mutagenesis," Nature, 2015, 527: 192-197.
Carrillo et al., "The Multiple Sequence Alignment Problem in Biology" Siam J. Applied Math., 1988, 48, 1073.
Carter et al., "Long-range chromatin regulatory interactions in vivo," Nat Genet, 2002, 32, 623-626.
Cassidy et al., "Prader-Willi syndrome," Eur J Hum Genet, 2009, 17(1): 3-13.

(56) References Cited

OTHER PUBLICATIONS

Cassidy et al., "Prader-Willi syndrome," Genet Med, 2012, 14: 10-26.
Cerletti et al., "Highly efficient, functional engraftment of skeletal muscle stem cells in dystrophic muscles," Cell 134, 2008, 37-47.
Cermak et al., "Efficient design and assembly of custom TALEN and other TAL effector-based constructs for DNA targeting," Nucleic Acids Res 30, 2011, pp. 1-11.
Chakraborty et al., "A CRISPR/Cas9-Based System for Reprogramming Cell Lineage Specification," Stem cell reports 3, 2014, 940-947.
Chang et al., "Integrating Combinatorial Lipid Nanoparticle and Chemically Modified Protein for Intracellular Delivery and Genome Editing," Acc. Chem. Res., 2019, 52: 665-675.
Chapdelaine et al., "Meganucleases can restore the reading frame of a mutual dystrophin," Gene therapy 17, 2010, 846-858.
Chavez et al., "Comparison of Cas9 activators in multiple species," Nat Methods, 2016, 13: 563-67.
Chavez et al., "Highly efficient Cas9-mediated transcriptional programming," Nat Methods 12, 2015, 326-328.
Chen et al., "Acetylation of RelA at discrete sites regulates distinct nuclear functions of NF-kB," The EMBO Journal, 2002, 21(23): 6539-6548.
Chen et al., "Dynamic imaging of genomic loci in living human cells by an optimized CRISPR/Cas system," Cell, 2013, 155: 1479-1491.
Chen et al., "Expanding the CRISPR imaging toolset with *Staphylococcus aureus* Cas9 for simultaneous imaging of multiple genomic loci," Nucleic Acids Research, 2016, 44(8): e75, 13 pages.
Chen et al., "Life and death of transcriptional co-activator p300," Epigenetics 6, 2011, 957-961.
Chen et al., "Two upstream enhancers collaborate to regulate the spatial patterning and timing of MyoD transcription during mouse development," Dev Dyn, 2001, 221, 274-288.
Cheng et al., "Multiplexed activation of endogenous genes by CRISPR-on, an RNA-guided transcriptional activator system," Cell Res, 2013, 23(10):1163-1171.
Chew et al., "A multifunctional AAV-CRISPR-Cas9 and its host response," Nat Methods, 2016;13:868-74.
Cho et al., "Analysis of off-target effects of CRISPR/Cas-derived RNA-guided endonucleases and nickases," Genome Res, 2014, 24:132-141.
Cho et al., "Targeted genome engineering in human cells with the Cas9 RNA-guided endonuclease," Nat Biotechnol 31, 2013, 230-232.
Choy et al., "Eukaryotic activators function during multiple steps of preinitiation complex assembly," Nature 366, 1993, 531-536.
Christian et al., "Targeting DNA double-strand breaks with TAL effector nucleases," Genetics 186, 2010, 757-761.
Christoffersen et al., "Ribozymes as human therapeutic agents," J. Med. Chem., 1995, 38(12): 2023-2037.
Chu et al., "SV40 DNA transfection of cells in suspension: analysis of efficiency of transcription and translation of T-antigen," Gene, 1981, 13:197.
Cirak et al., "Exon skipping and dystrophin restoration in patients with Duchenne muscular dystrophy after systemic phosphorodiamidate morpholino oligomer treatment: an open-label, phase 2, dose-escalation study," Lancet 378, 2011, 595-605.
Concise Encyclopedia of Polymer Science And Engineering, 1990, pp. 858-859.
Cong et al., "Comprehensive interrogation of natural TALE DNA-binding modules and transcriptional repressor domains," Nat Commun 3, 2012, 968.
Cong et al., "Multiplex Genome Engineering Using CRISPR/Cas Systems," Science 339, 2013, 819-823.
Consortium, "An integrated encyclopedia of DNA elements in the human genome," Nature 489, 2012, 57-74.
Cornu et al., "DNA-binding specificity is a major determinant of the activity and toxicity of zinc-finger nucleases," Mol Ther, 2008, 16:352-358.
Cornu et al., "Quantification of zinc finger nuclease-associated toxicity," Meth Mol Biol, 2010, 649:237-245.
Cradick et al., "CRISPR/Cas9 systems targeting beta-globin and CCR5 genes have substantial off-target activity," Nucleic Acids Res, 2013, 41(20):9584-92.
Crawford et al., "Genome-wide mapping of DNase hypersensitive sites using massively parallel signature sequencing (MPSS)," Genome Res. 2006, 16, 123-131.
Crocker et al., "TALE-mediated modulation of transcriptional enhancers in vivo," Nature methods 10, 2013, 762-767.
Crooke et al., "Pharmacokinetic properties of several novel oligonucleotide analogs in mice," J. Pharmacol. Exp. Ther., 1996, 277(2): 923-937.
Cruvinel et al., "Reactivation of maternal SNORD116 cluster via SETDB1 knockdown in Prader-Willi syndrome iPSCs," Hum Mol Genet, 2014, 23: 4674-4685.
Dahlman et al., "Orthogonal gene knockout and activation with a catalytically active Cas9 nuclease," Nat Biotechnol, 2015, 33(11): 1159-1161, correction in Nat Biotechnol, Apr. 2016, 34(4): 441.
Darabi et al., "Human ES-and iPS-derived myogenic progenitors restore dystrophin and improve contractility upon transplantation in dystrophic mice," Cell Stem Cell 10, 2012, 610-619.
De Groote et al., "Epigenetic Editing: targeted rewriting of epigenetic marks to modulate expression of selected target genes," Nucleic Acids Res, 2012, vol. 40, No. 21, pp. 10596-10613.
De Mesmaeker et al., "Antisense Oligonucleotides," Ace. Chem. Res., 1995, 28: 366-374.
De Smith et al., "A deletion of the HBII-85 class of small nucleolar RNAs (snoRNAs) is associated with hyperphagia, obesity and hypogonadism," Hum Mol Genet, 2009, 18: 3257-3265.
Dean et al., "Inducible transcription of five globin genes in K562 human leukemia cells," Proceedings of the National Academy of Sciences of the United States of America 80, 1983, 5515-5519.
Deltcheva et al., "CRISPR RNA maturation by trans-encoded small RNA and host factor RNase III," Nature, 2011, 471(7340):602-7.
Delvecchio et al., "Structure of the p300 catalytic core and implications for chromatin targeting and HAT regulation," Nat Struct Mol Biol 20, 2013, 1040-1046.
Deng et al., "Reactivation of developmentally silenced globin genes by forced chromatin looping," Cell 158, 2014, 849-860.
Dezawa et al., "Bone marrow stromal cells generate muscle cells and repair muscle degeneration," Science Signaling 309, 2005, 314-317.
Diao et al., "A new class of temporarily phenotypic enhancers identified by CRISPR/Cas9-mediated genetic screening," Genome Res, 2016, 26: 397-405.
Dijkema et al., "Cloning and expression of the chromosomal immune interferon gene of the rat," EMBO J., 1985, 4:761.
Ding et al., "A TALEN Genome-Editing System for Generating Human Stem Cell-Based Disease Models," 2013, Cell Stem Cell 12, 238-251.
Ding et al., "Enhanced efficiency of human pluripotent stem cell genome editing through replacing TALENs with CRISPRs," Cell Stem Cell, 2013, 12:393-394.
Ding et al., "Permanent Alteration of PCSK9 With In Vivo CRISPR-Cas9 Genome Editing," Circulation Research, 2014, vol. 115, No. 5, pp. 488-492.
Doench et al., "Optimized sgRNA design to maximize activity and minimize off-target effects of CRISPR-Cas9," Nat Biotechnol. (2016) 34:184-91.
Doench et al., "Rational design of highly active sgRNAs for CRISPR-Cas9-mediated gene inactivation," Nat Biotechnol. (2014) 32:1262-7.
Dostie et al., "Chromosome Conformation Capture Carbon Copy (5C): a massively parallel solution for mapping interactions between genomic elements," Genome research 16, 2006, 1299-1309.
Doudna et al., "Genome editing. The new frontier of genome engineering with CRISPR-Cas9," Science 346, 2014, 1258096.
Doyle et al., "TAL Effector-Nucleotide Targeter (TALE-NT) 2.0: tools for TAL effector design and target prediction," Nucleic Acids Res 40, 2012, W117-122.
Doyon et al., "Enhancing zinc-finger-nuclease activity with improved obligate heterodimeric architectures," Nat Methods 8, 2010, 74-79.

(56) References Cited

OTHER PUBLICATIONS

Duker et al., "Paternally inherited microdeletion at 15q11.2 confirms a significant role for the SNORD116 C/D box snoRNA cluster in Prader-Willi syndrome," Eur J Hum Genet, 2010, 18: 1196-1201.
EBI Accession No. GSP: BCJ39961 (2016).
Edelstein et al., "Gene therapy clinical trials worldwide 1989-2004—an overview," J. Gene Med., 2004, vol. 6, pp. 597-602.
Egger et al., "Epigenetics in human disease and prospects for epigenetic therapy," Nature 429, 2004, 457-463.
Englisch et al., Chemically Modified Oligonucleotides as Probes and Inhibitors, Angewandle Chemie, International Edition, 1991, 30(6): 613-629.
Esvelt et al., "Orthogonal Cas9 proteins for RNA-guided gene regulation and editing," Nature Methods 2013, 10(11):1116-21.
Farinelli et al., "Lentiviral vectors for the treatment of primary immunodeficiencies," J Inherit Metab Dis, 2014, 37:525-533.
Farzadfard et al., "Tunable and Multifunctional Eukaryotic Transcription Factors Based on CRISPR/Cas," ACS Synth Biol, 2013, 604-613.
Ferretti et al., "Complete genome sequence of an M1 strain of *Streptococcus pyogenes*," Proc Natl Acad Sci U S A, 2001, 98(8): 4658-63.
Fine et al., "Trans-spliced Cas9 allows cleavage of HBB and CCR5 genes in human cells using compact expression cassettes," Sci Rep. 2015;5:10777.
Flanigan et al., "Mutational spectrum of DMD mutations in dystrophinopathy patients: application of modern diagnostic techniques to a large cohort," Human mutation 30, 2009, 1657-1666.
Fluiter et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Mol. Biosyst., 2009, 5: 838-843.
Fonfara et al., "Phylogeny of Cas9 determines functional exchangeability of dual-RNA and Cas9 among orthologous type II CRISPR-Cas systems," Nucleic Acids Res, 2013, 42(4):2577-2590.
Fontenot et al., "Regulatory T cell lineage specification by the forkhead transcription factor foxp3," Immunity, 2005, 22, 329-341.
Fu et al., "High-frequency off-target mutagenesis induced by CRISPR-Cas nucleases in human cells," Nat Biotechnol, 2013, 31(9):822-6.
Fu et al., "Improving CRISPR-Cas nuclease specificity using truncated guide RNAs," Nat Biotechnol 32, 2014, 279-284.
Fulco et al., "Systematic mapping of functional enhancer-promoter connections with CRISPR interference," Science, 2016, 354: 769-773.
Fulmer-Smentek et al., "Association of acetylated histones with paternally expressed genes in the Prader-Willi deletion region," Hum Mol Genet, 2001, 10: 645-652.
Gait, "Oligoribonucleotides," Antisense Research and Applications, 1993, Chapter 16, pp. 290-299.
Gaj et al., "Targeted gene knockout by direct delivery of zinc-finger nuclease proteins," Nature Methods, 2012, 9(8):805-807.
Gaj et al., "ZFN, TALEN, and CRISPR/Cas-based methods for genome engineering," Trends Biotechnol, 2013, 31:397-405.
Gao et al., "Comparison of TALE designer transcription factors and the CRISPR/dCas9 in regulation of gene expression by targeting enhancers," Nucleic Acids Res 42, 2014, e155.
Gao et al., "Reprogramming to Pluripotency Using Designer TALE Transcription Factors Targeting Enhancers," Stem Cell Reports, 2013, 1(2):183-97.
Garg et al., "Engineering synthetic TAL effectors with orthogonal target sites," Nucleic Acids Res 40, 2012, 7584-7595.
Garriga-Canut et al., "Synthetic zinc finger repressors reduce mutant huntingtin expression in the brain of R6/2 mice," Proceedings of the National Academy of Sciences of the United States of America 109, 2012, E3136-3145.
Gaudelli et al., "Directed evolution of adenine base editors with increased activity and therapeutic application," Nat Biotechnol, Jul. 2020, 38(7): 892-900.

Gaudelli et al., "Programmable base editing of A•T to G•C in genomic DNA without DNA cleavage," Nature, Nov. 2017, 551(7681): 464-471.
Gebeyehu et al., "Novel biotinylated nucleotide—analogs for labeling and colorimetric detection of DNA," Nucl. Acids Res., 1987, 15(11): 4513-4534.
Gersbach et al., "Activating human genes with zinc finger proteins, transcription activator-like effectors and CRISPR/Cas9 for gene therapy and regenerative medicine," Expert Opin Ther Targets, 2014, 18(8):835-9.
Gersbach, "Genome engineering: the next genomic revolution," Nat Methods 11, 2014, 1009-1011.
Gerstein et al., "Architecture of the human regulatory network derived from ENCODE data," Nature 489, 2012, 91-100.
Gertz et al., "Transposase mediated construction of RNA-seq libraries," Genome Res 22, 2012, 134-141.
Gibson et al., "Enzymatic assembly of DNA molecules up to several hundred kilobases," Nature Methods, 2009, 6(5): 343-345.
Gilbert et al., "CRISPR-mediated modular RNA-guided regulation of transcription in eukaryotes," Cell 154, 2013, 442-451.
Gilbert et al., "Genome-Scale CRISPR-Mediated Control of Gene Repression and Activation," Cell 159, 2014, 647-661.
Goemans et al., "Systemic administration of PRO051 in Duchenne's muscular dystrophy," The New England journal of medicine 364, 2011, 1513-1522.
Gorman et al., "The Rous sarcoma virus long terminal repeat is a strong promoter when introduced into a variety of eukaryotic cells by DNA-mediated transfection," Proc. Natl. Acad. Sci. U.S.A., 1982, 79:6777.
Gou et al., "A novel approach for the construction of multiple shRNA expression vectors," J Gene Med, 2007, 9(9):751-63.
Graham et al., "A new technique for the assay of infectivity of human adenovirus 5 DNA, " Virol., 1973, 52:456-467.
Graslund et al., "Exploring strategies for the design of artificial transcription factors: targeting sites proximal to known regulatory regions for the induction of gamma-globin expression and the treatment of sickle cell disease," J Biol Chem 280, 2005, 3707-3714.
Gregorevic et al., "Systemic delivery of genes to striated muscles using adeno-associated viral vectors," Nat Med, 2004, 10:828-834.
Grimmer et al., "Analysis of an artificial zinc finger epigenetic modulator: widespread binding but limited regulation," Nucleic acids research 42, 2014, 10856-10868.
Groner et al., "KRAB-zinc finger proteins and KAP1 can mediate long-range transcriptional repression through heterochromatin spreading," PLoS Genet 6, 2010, e1000869.
Guo et al., "Directed evolution of an enhanced and highly efficient FokI cleavage domain for zinc finger nucleases," J Mol Biol, 2010, 400:96-107.
Guschin et al., "A rapid and general assay for monitoring endogenous gene modification," Methods Mol Biol 649, 2010, 247-256.
Hamar et al., "Small interfering RNA targeting Fas protects mice against renal ischemia-reperfusion injury," PNAS, 2004, 101:14883-8.
Hardison et al., "Locus control regions of mammalian beta-globin gene clusters: combining phylogenetic analyses and experimental results to gain functional insights," Gene 205, 1997, 73-94.
Hathaway et al., "Dynamics and memory of heterochromatin in living cells," Cell 149, 2012, 1447-1460.
Heagerty et al., "Time-dependent ROC curves for censored survival data and a diagnostic marker," Biometrics, 2000, 56(2): 337-344.
Heasman, "Morpholino oligos: making sense of antisense?," Dev. Biol., 2002, 243(2): 209-214.
Heintzman et al., "Distinct and predictive chromatin signatures of transcriptional promoters and enhancers in the human genome," Nat Genet 39, 2007, 311-318.
Henning et al., "Epigenetic control of CD8 + T cell differentiation," Nat Rev Immunol, 2018, 18(5): 340-356.
Hilton et al., "Epigenome editing by a CRISPR-Cas9-based acetyltransferase activates genes from promoters and enhancers," Nature biotechnology, 2015, vol. 33, No. 5, pp. 510-519.

(56) References Cited

OTHER PUBLICATIONS

Hockemeyer et al., "Efficient targeting of expressed and silent genes in human ESCs and iPSCs using zinc-finger nucleases," Nat Biotechnol, 2009, 27(9):851-7.
Hockemeyer et al., "Genetic engineering of human pluripotent cells using TALE nucleases," Nat Biotechnol 29, 2011, 731-734.
Hoffman et al., "Dystrophin: the protein product of the Duchenne muscular dystrophy locus," Cell, 1987, 51:919.
Hotta et al., "Isolation of human iPS cells using EOS lentiviral vectors to select for pluripotency," Nat Methods 6, 2009, 370-376.
Hou et al., "Efficient genome engineering in human pluripotent stem cells using Cas9 from Neisseria meningitidis," Proc Natl Acad Sci USA, 2013, 110:15644-15649.
Hsu et al., "Dissecting Neural Function Using Targeted Genome Engineering Technologies," ACS Chem. Neurosci., 2012, pp. 603-610.
Hsu et al., "DNA targeting specificity of RNA-guided Cas9 nucleases," Nature Biotechnology 31, 2013, 827-832.
Hu et al., "Direct activation of human and mouse Oct4 genes using engineered TALE and Cas9 transcription factors," Nucleic Acids Res 42, 2014, 4375-4390.
Huang et al., "Generation and comparison of CRISPR-Cas9 and Cre-mediated genetically engineered mouse models of sarcoma," Nature Communications, 2017, 8(15999): 1-11.
Humbert et al., "Targeted gene therapies: tools, applications, optimization", Critical Reviews in Biochemistry and Molecular Biology, CRC Press, vol. 47, No. 3, Apr. 2012, pp. 264-281.
Huntriss et al., "Imprinted expression of SNRPN in human preimplantation embryos," Am J Hum Genet, 1998, 63: 1009-1014.
Hwang et al., "Efficient genome editing in zebrafish using CRISPR-Cas system," Nat Biotechnol, 2013, 31(3):227-9.
Ikonomi et al., "Levels of GATA-1/GATA-2 transcription factors modulate expression of embryonic and fetal hemoglobins," Gene 261, 2000, 277-287.
Jansen et al., "Identification of genes that are associated with DNA repeats in prokaryotes," Mol Microbiol, 2002, 43(6): 1565-1575.
Jepsen et al., "Locked nucleic acid: a potent nucleic acid analog in therapeutics and biotechnology," Oligonucleotides, 2004, 14(2): 130-146.
Ji et al., "Engineered zinc-finger transcription factors activate OCT4 (POU5F1), SOX2, KLF4, c-MYC (MYC) and miR302/367," Nucleic Acids Res 42, 2014, 6158-6167.
Jinek et al., "A programmable dual-RNA-guided DNA endonuclease in adaptive bacterial immunity," Science 337, 2012, 816-821.
Jinek et al., "RNA-programmed genome editing in human cells," eLife 2, 2013, e00471.
Jinek et al., "Structures of Cas9 endonucleases reveal RNA-mediated conformational activation," Science, 2014, 343: 1247997.
Jobling et al., "Chitayat-Hall and Schaaf-Yang syndromes:a common aetiology: expanding the phenotype of MAGEL2-related disorders," J Med Genet, 2018, 55: 316-321.
Jorg, "Engineering of the epigenome: synthetic biology to define functional causality and develop innovative therapies," Epigenomics, 2016, 8(2):153-156.
Joung et al., "TALENs: a widely applicable technology for targeted genome editing," Nature Reviews Molecular Cell Biology 14, 2013, 49-55.
Joyce, "Amplification, mutation and selection of catalytic RNA," Gene, 1989, 82(1): 83-87.
Joyce, "Directed molecular evolution," Scientific American, 1992, 267(6): 90-97.
Kabadi et al., "Multiplex CRISPR/Cas9-based genome engineering from a single lentiviral vector," Nucleic Acids Res, 2014, 42(19):e147.
Kabanov et al., "A new class of antivirals: antisense oligonucleotides combined with a hydrophobic substituent effectively inhibit influenza virus reproduction and synthesis of virus-specific proteins in MDCK cells," FEBS Lett., 1990, 259: 327-330.
Kauppinen et al., "Locked nucleic acid (LNA): High affinity targeting of RNA for diagnostics and therapeutics," Drug Discov Today Technol, 2005, 2(3): 287-290.
Kayali et al., "Site-directed gene repair of the dystrophin gene mediated by PNA-ssODNs," Human Molecular Genetics, vol. 19, No. 16, Aug. 15, 2010, pp. 3266-3281.
Kearns et al., "Cas9 effector-mediated regulation of transcription and differentiation in human pluripotent stem cells," Development, 2014, 141(1):219-23.
Kearns et al., "Functional annotation of native enhancers with a Cas9-histone demethylase fusion," Nat Methods, 2015, 12(5):401-403.
Keung et al., "Using targeted chromatin regulators to engineer combinatorial and spatial transcriptional regulation," Cell 158, 2014, 110-120.
Khoury et al., "Efficient new cationic liposome formulation for systemic delivery of small interfering RNA silencing tumor necrosis factor $\alpha$ in experimental arthritis," Arthritis Rheumatol, 2006, 54: 1867-77.
Kim et al., "Histone acetylation contributes to chromatin looping between the locus control region and g]obin gene by influencing hypersensitive site formation," Biochim Biophys Acta, 2013, 1829: 963-969.
Kim et al., "Surrogate reporters for enrichment of cells with nuclease-induced mutations," Nat Methods, 2011, 8:941-943.
Kim et al., "TALENs and ZFNs are associated with different mutation signatures," Nat Methods, 2013, 10(3):185.
Kim et al., "Targeting the histone methyltransferase G9a activates imprinted genes and improves survival of a mouse model of Prader-Willi syndrome," Nat Med, 2017, 23: 213-222.
Kim et al., "Use of the human elongation factor $1\alpha$ promoter as a versatile and efficient expression system," Gene, 1990, 91:217.
Kim et al., "Engineering and Application of Zinc Finger Proteins and TALEs for Biomedical Research," Mol Cells, 2017, 40(8): 533-541.
Kimura et al., "Cell-lineage regulated myogenesis for dystrophin replacement: a novel therapeutic approach for treatment of muscular dystrophy," Hum Mol Genet 17, 2008, 2507-2517.
Klann et al., "CRISPR-based methods for high-throughput annotation of regulatory DNA," Curr Opin Biotechnol, 2018, 52: 32-41.
Klann et al., "CRISPR-Cas9 epigenome editing enables high-throughput screening for functional regulatory elements in the human genome," Nat Biotechnol, 2017, 35: 561-568.
Kleinstiver et al., "Broadening the targeting range of *Staphylococcus aureus* CRISPR-Cas9 by modifying PAM recognition," Nature Biotechnology, 2015, 33(12): 1293-1298.
Kleinstiver et al., "Engineered CRISPR-Cas9 nucleases with altered PAM specificities," Nature, 2015, 523(7561): 481-485.
Koblan et al., "Improving cytidine and adenine base editors by expression optimization and ancestral reconstruction," Oct. 2018, 36(9): 843-846.
Kocher et al., "Phylogenetic Analysis of the SNORD116 Locus," Genes, 2017, 8(12): 358.
Komor et al., "Programmable editing of a target base in genomic DNA without double-stranded DNA cleavage," Nature, 2016, 533(7603): 420-424.
Konermann et al., "Genome-scale transcriptional activation by an engineered CRISPRCas9 complex," Nature, 2015, 517: 583-588.
Konermann et al., "Optical control of mammalian endogenous transcription and epigenetic states," Nature, 2013, 500(7463): 472-6.
Konieczny et al., "Gene and cell-mediated therapies for muscular dystrophy," Muscle Nerve, 2013, 47:649-663.
Korkmaz et al., "Functional genetic screens for enhancer elements in the human genome using CRISPR-Cas9," Nat Biotechnol, 2016, 34: 192-198.
Kornberg et al., "DNA Replication," 1980, pp. 75-77.
Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron, 1998, 54(14): 3607-3630.
Kotin, "Prospects for the use of adeno-associated virus as a vector for human gene therapy," Hum. Gene Ther., 1994, 5:793-801.
Kubokawa et al., "Molecular characterization of the 5'-UTR of retinal dystrophin reveals a cryptic intron that regulates translational activity," Molecular Vision, 2010, vol. 16, pp. 2590-2597.

(56) References Cited

OTHER PUBLICATIONS

Kumar et al., "Artificial evolution and natural ribozymes," FASEB Journal, 1995, 9: 1183-1195.
Kurreck, "Antisense technologies. Improvement through novel chemical modifications," European Journal of Biochemistry, 2003, 270(8): 1628-1644.
Kuscu et al., "Genome-wide analysis reveals characteristics of off-target sites bound by the Cas9 endonuclease," Nat Biotechnol, 2014, 32(7): 677-83.
Kwa et al., "Chromatin modifying agents—the cutting edge of anticancer therapy," Drug Discovery Today, 2011, 16(13/14):543-547.
Kyte et al., "A Simple Method for Displaying the Hydropathic Character of a Protein," J. Mol. Biol., 1982, 157:105-132.
La Russa et al., "The New State of the Art: Cas9 for Gene Activation and Repression," Molecular and Cellular Biology, 2015, 35(22):3800-3809.
Lacerra et al., "Restoration of hemoglobin A synthesis in erythroid cells from peripheral blood of thalassemic patients," Proc. Natl. Acad. Sci., 2000, 97(17): 9591-9596.
Landen et al., "Intraperitoneal delivery of liposomal siRNA for therapy of advanced ovarian cancer," Cancer Biol. Ther, 2006, 5(12):1708-13.
Langmead et al., "Fast gapped-read alignment with Bowtie 2," Nature methods, 2012, 9: 357-359.
Langmead et al., "Ultrafast and memory-efficient alignment of short DNA sequences to the human genome," Genome biology 10, 2009, R25.
Langouet et al., "Zinc finger protein 274 regulates imprinted expression of transcripts in Prader-Willi syndrome neurons," Hum Mol Genet, 2018, 27: 505-515.
Larson et al., "CRISPR interference (CRISPRi) for sequence-editing control of gene expression," Nat Protoc, 2013, 8(11): 2180-96.
Latta-Mahieu et al., "Gene transfer of a chimeric trans-activator is immunogenic and results in short-lived transgene expression," Human Gene Therapy, Sep. 2002, vol. 13, No. 13, pp. 1611-1620.
Lattanzi et al., "High efficiency myogenic conversion of human fibroblasts by adenoviral vector-mediated MyoD gene transfer. An alternative strategy for ex vivo gene therapy of primary myopathies," The Journal of clinical investigation 101, 1998, 2119-2128.
Lee et al., "Activation of innate immunity is required for efficient nuclear reprogramming," Cell, 2012, 151: 547-558.
Lee et al., "Expression of small interfering RNAs targeted against HIV-1 rev transcripts in human cells," Nature Biotechnol, 2002, 20(5): 500-505.
Lee et al., "Role of satellite cells versus myofibers in muscle hypertrophy induced by inhibition of the myostatin/activin signaling pathway," Proc Natl Acad Sci U S A, 2012, 109(35):E2353-60.
Lee et al., "Targeted chromosomal deletions in human cells using zinc finger nucleases," Genome research 20, 2010, 81-89.
Lee, "Regulation of muscle mass by myostatin," Annu Rev Cell Dev Biol, 2004, 20: 61-86.
Letsinger et al., "Cholesteryl-conjugated oligonucleotides: synthesis, properties, and activity as inhibitors of replication of human immunodeficiency virus in cell culture," Proc. Natl. Acad. Sci. USA, 1989, 86(17): 6553-6556.
Levin et al., "Position-dependent effects of locked nucleic acid (LNA) on DNA sequencing and PCR primers," Nuc. Acids. Res., 2006, 34: e142.
Li et al, "In vivo genome editing restores haemostasis in a mouse model of haemophilia," Nature 475, 2011, 217-221.
Li et al., "Extensive promoter-centered chromatin interactions provide a topological basis for transcription regulation, " Cell, 2012, 148: 84-98.
Li et al., "Locus control regions," Blood, 2002, 100: 3077-3086.
Li et al., "Marginal level dystrophin expression improves clinical outcome in a strain of dystrophin/utrophin double knockout mice," PLoS One, 2010, 5:e15286.
Li et al., "Modularly assembled designer TAL effector nucleases for targeted gene knockout and gene replacement in eukaryotes," Nucleic Acids Research, 2011, vol. 39, No. 14, pp. 6315-6325.
Li et al., "The autism-related gene SNRPN regulates cortical and spine development via controlling nuclear receptor Nr4a1," Sci Rep, 2016, 6: 29878.
Li et al., "The role of chromatin during transcription," Cell, 2007, 128: 707-719.
Li et al., "The Sequence Alignment/Map format and SAMtools," Bioinformatics, 2009, 25: 2078-2079.
Li et al., "Transcription activator-like effector hybrids for conditional control and rewiring of chromosomal transgene expression," Scientific reports 2, 2012, 897.
Liang et al., "Engineering biological systems with synthetic RNA molecules," Mol Cell 43, 2011, 915-926.
Liao et al., "In Vivo Target Gene Activation via CRISPR/Cas9-Mediated Trans-epigenetic Modulation," Cell, 2017, 171: 1495-1507.
Liu et al., "Editing DNA Methylation in the Mammalian Genome," Cell, Sep. 2016, 167(1): 233-247.
Lohmueller et al., "A tunable zinc finger-based framework for Boolean logic computation in mammalian cells," Nucleic Acids Res 40, 2012, 5180-5187.
Love et al., "Moderated estimation of fold change and dispersion for RNA-seq data with DESeq2," Genome biology, 2014, 15: 550.
Lovric et al., "Terminal Differentiation of Cardiac and Skeletal Myocytes Induces Permissivity to AAV Transduction by Relieving Inhibition Imposed by DNA Damage Response Proteins," Molecular Therapy, 2012, 2087-2097.
Lu et al., "The status of exon skipping as a therapeutic approach to duchenne muscular dystrophy," Molecular Therapy 19, 2011, 9-15.
Lund et al., "Promoter-targeted phage display selections with preassembled synthetic zinc finger libraries for endogenous gene regulation," Journal of Molecular Biology, 2004, vol. 340, pp. 599-613.
Luo et al., "Synthetic DNA delivery systems," Nature Biotechnology, 2000, vol. 18, pp. 33-37.
Maeder et al., "CRISPR RNA-guided activation of endogenous human genes," Nat Methods, 2013, 10: 977-979.
Maeder et al., "Robust, synergistic regulation of human gene expression using TALE activators," Nature Methods, vol. 10, No. 3, pp. 243-246, Feb. 10, 2013, including pp. 1/14-14/14 of Supplementary Material.
Maeder, "Targeted DNA demethylation and activation of endogenous genes using programmable TALE-TET1 fusion proteins," Nat Biotechnol, 2013, 31(12): 1137-42.
Magnenat et al., "In vivo selection of combinatorial libraries and designed affinity maturation of polydactyl zinc finger transcription factors for ICAM-1 provides new insights into gene regulation," J Mol Biol, 2004, 341: 635-649.
Majzner et al., "Clinical lessons learned from the first leg of the CAR T cell journey," Nature Medicine, 2019, 25(9): 1341-1355.
Mali et al., "Cas9 as a versatile tool for engineering biology," Nat Methods, 2013, 10(10): 957-63.
Mali et al., "CAS9 transcriptional activators for target specificity screening and paired nickases for cooperative genome engineering," Nat Biotechnol, 2013, 31(9): 833-8.
Mali et al., "RNA-Guided Human Genome Engineering via Cas9," Science 339, 2013, 823-826.
Mamchaoui et al., "Immortalized pathological human myoblasts: towards a universal tool for the study of neuromuscular disorders," Skelet Muscle 1, 2011, 1-11.
Maniatis et al., "Regulation of inducible and tissue-specific gene expression," Science, 1987, 236:1237.
Manoharan et al., "Chemical Modifications to Improve Uptake and Bioavailability of Antisense Oligonucleotides," Ann. N. Y. Acad. Sci., 1992, 660: 306-309.
Manoharan et al., "Cholic acid-oligonucleotide conjugates for antisense applications," Bioorg. Med. Chem. Let., 1994, 4(8): 1053-1060.
Manoharan et al., "Introduction of a lipophilic thioether tether in the minor groove of nucleic acids for antisense applications," Bioorg. Med. Chem. Let., 1993, 3(12): 2765-2770.

(56) References Cited

OTHER PUBLICATIONS

Manoharan et al., "Lipidic Nucleic Acids," Tetrahedron Lett, 1995, 36: 3651-3654.
Manoharan et al., "Oligonucleotide Conjugates: Alteration of the Pharmacokinetic Properties of Antisense Agents," Nucleosides & Nucleotides, 1995, 14: 969-973.
Martin et al., "A New Access to 2'-O-Alkylated Ribonucleosides and Properties of 2'-O-Alkylated Oligoribonucleotides," Helv. Chim. Acta, 1995, 78: 486-504.
Matsushita et al., "Adeno-associated virus vectors can be efficiently produced without helper virus," Gene Therapy, 1998, 5:938.
McCarthy et al., "Schaaf-Yang syndrome overview: Report of 78 individuals," Am J Med Genet A, 2018, 176(12): 2564-2574.
McCarty et al., "Self-complementary recombinant adeno-associated virus (scAAV) vectors promote efficient transduction independently of DNA synthesis," Gene Ther. 2001, 8:1248-54.
McDowell et al., "Structural and functional cross-talk between a distant enhancer and the epsilon-globin gene promoter shows interdependence of the two elements in chromatin," Molecular and cellular biology, 1999, 19: 7600-7609.
McTigue et al., "Sequence-dependent thermodynamic parameters for locked nucleic acid (LNA)-DNA duplex formation," Biochemistry, 2004, 43(18): 5388-5405.
Memedula et al., "Sequential recruitment of HAT and SWI/SNF components to condensed chromatin by VP16," Curr Biol, 2003, 13, 241-246.
Mendell et al., "Dystrophin immunity in Duchenne's muscular dystrophy," New England Journal of Medicine 363, 2010, 1429-1437.
Mendenhall et al., "Locus-specific editing of histone modification at endogenous enhancers," Nat Biotechnol, 2013, 31(12): 1133-6.
Mercer et al., "Regulation of Endogenous Human Gene Expression by Ligand-Inducible TALE Transcription Factors," ACS Synth Biol, 2013.
Miller et al., "A TALE nuclease architecture for efficient genome editing," Nat Biotechnol 29, 2011, 143-148.
Min et al., "CRISPR Correction of Duchene Muscular Dystrophy," Annual Review of Medicine, Epub Oct. 2018, 70: 239-255.
Mishra et al., "Improved leishmanicidal effect of phosphorotioate antisense oligonucleotides by LDL-mediated delivery," Biochim. Biophys. Acta, 1995, 1264(2): 229-237.
Mittler et al., "A novel docking site on Mediator is critical for activation by VP 16 in mammalian cells," EMBO J, 2003, 22: 6494-6504.
Miyagishi et al., "U6 promoter-driven siRNAs with four uridine 3' overhangs efficiently suppress targeted gene expression in mammalian cells," Nature Biotechnol, 2002, 20(5): 497-500.
Mizushima et al., "pEF-BOS, a powerful mammalian expression vector," Nucl. Acids. Res., 1990, 18:5322.
Mojica et al., "Intervening sequences of regularly spaced prokaryotic repeats derive from foreign genetic elements," J Molec Evolution, 2005, 60(2): 174-182.
Moore et al., "Transcription Activator-like Effectors: A Toolkit for Synthetic Biology," ACS Synth Biol, 2014, 3(10): 708-716.
Morrissey et al., "Activity of stabilized short interfering RNA in a mouse model of hepatitis B virus replication," Hepatol. (2005) 41: 1349-56.
Moscou et al., "A simple cipher governs DNA recognition by TAL effectors," Science 326, 2009, 1501.
Murphy et al., "The in vitro transcription of the 7SK RNA gene by RNA polymerase III is dependable only on the presence of an upstream promoter," Cell, 1987, 51:81-87.
Mussolino et al., "A novel TALE nuclease scaffold enables high genome editing activity in combination with low toxicity," Nucleic Acids Res 39, 2011, 9283-9293.
Muzycka, "Use of adeno-associated virus as a general transduction vector for mammalian cells," Curr. Top. Microbiol. Immunol., 1992, 158:97-129.
Myslinski et al., "An unusually compact external promoter for RNA polymerase III transcription of the human H1RNA gene," Nucleic Acids Res, 2001, 29:2502-2509.
Naguibneva et al., "An LNA-based loss-of-function assay for micro-RNAs," Biomed Pharmacother, 2006, 60: 633-638.
Nasevicius et al., "Effective targeted gene 'knockdown' in zebrafish," Nat. Genet., 2000, 26(2): 216-220.
Negroni et al., "In Vivo Myogenic Potential of Human CD133+ Muscle-derived Stem Cells: A Quantitative Study," Molecular Therapy 17, 2009, 1771-1778.
Nelson et al., "In vivo genome editing improves muscle function in a mouse model of Duchenne muscular dystrophy," Science, 2016, 351, 403-7.
Nelson et al., "Long-term evaluation of AAV-CRISPR genome editing for Duchenne muscular dystrophy," Nature Medicine, 2019, 25(3): 427-432.
Nielsen et al., "Sequence-selective recognition of DNA by strand displacement with a thymine-substituted polyamide," Science, 1991, 254: 1497-1500.
Nishimasu et al., "Crystal structure of Cas9 in complex with guide RNA and target DNA," Cell, 2014, 156:935-49.
Nissim et al., "Multiplexed and Programmable Regulation of Gene Networks with an Integrated RNA and CRISPR/Cas Toolkit in Human Cells," Mol Cell, 2014, 54: 698-710.
Nordhoff et al., "Comparative analysis of human, bovine, and murine Oct-4 upstream promoter sequences," Mamm Genome, 2001, 12: 309-317.
Nowotny et al., "Crystal structures of RNase H bound to an RNA/DNA hybrid: substrate specificity and metal-dependent catalysis," Cell, 2005, 121(7): 1005-1016.
Oberhauser et al., "Effective incorporation of 2'-O-methyloligoribonucleotides into liposomes and enhanced cell association through modification with thiocholesterol," Nucl. Acids Res., 1992, 20(3): 533-538.
Obika et al., "Stability and structural features of the duplexes containing nucleoside analogues with a fixed N-type conformation, 2'-0,4'-C-methyleneribonucleosides," Tetrahedron Lett. 1998, 39(30): 5401-5404.
O'Geen et al., "dCas9-based epigenome editing suggests acquisition of histone methylation is not sufficient for target gene repression," Nucleic Acids Res, 2017, 45: 9901-9916.
Ogryzko et al., "The transcriptional coactivators p300 and CBP are histone acetyltransferases," Cell, 1996, 87: 953-959.
Ohshima et al., "Nucleotide sequence of mouse genomic loci including a gene or pseudogene for U6 (4.85) nuclear RNA," Nucleic Acids Res, 1981, 9:5145-5158.
Okkenhaug et al., "PI3K in lymphocyte development, differentiation and activation," Nat. Rev. Immunol., 2003, 3(4): 317-330.
Ong et al., "Enhancer function: new insights into the regulation of tissuespecific gene expression," Nature reviews. Genetics, 2011, 12: 283-293.
Orgel, "Selection in vitro," Proc. R. Soc. B, 1979, 205: 435-442.
Orom et al., "LNA-modified oligonucleotides mediate specific inhibition of microRNA function," Gene, 2006, 372: 137-141.
Osakabe et al., "FLAG-NLS-SpCas9-2A-GFBSD2 [Binary vector pEgP526-2A-GFBSD2]," National Center for Biotechnology Information, Genbank Entry, Retrieved from the Internet on Sep. 18, 2017 <https://www.ncbi.nlm.nih.gov/protein/BAV01234>.
Ousterout et al., "Reading frame correction by targeted genome editing restores dystrophin expression in cells from Duchenne muscular dystrophy patients," Mol Ther, 2013, 21:1718-1726.
Paddison et al., "Short hairpin RNAs (shRNAs) induce sequence-specific silencing in mammalian cells," Genes & Dev, 2002, 16(8): 948-958.
Palu et al., "In pursuit of new developments for gene therapy of human diseases," J. Biotechnol, 1999, vol. 68, pp. 1-13.
Papayannakos et al., "Understanding lentiviral vector chromatin targeting: working to reduce insertional mutagenic potential for gene therapy," Gene Ther, 2013, 20(6): 581-8.
Park et al., "Phenotypic alteration of eukaryotic cells using randomized libraries of artificial transcription factors," Nat Biotechnol 21, 2003, 1208-1214.

(56) References Cited

OTHER PUBLICATIONS

Pattanayak et al., "High-throughput profiling of off-target DNA cleavage reveals RNA-programmed Cas9 nuclease specificity," Nat Biotechnol, 2013, 31(9): 839-43.
Paul et al., "Effective expression of small interfering RNA in human cells," Nature Biotechnol, 2002, 20(5): 505-508.
Peault et al., "Stem and progenitor cells in skeletal muscle development, maintenance, and therapy," Molecular Therapy 15, 2007, 867-877.
Perez et al., "Establishment of HIV-1 resistance in CD4+ T cells by genome editing using zinc-finger nucleases," Nature biotechnology 26, 2008, 808-816.
Perez-Pinera et al., "Advances in targeted genome editing," Current Opinion in Chemical Biology 16, 2012, 268-277.
Perez-Pinera et al., "Gene targeting to the ROSA26 locus directed by engineered zinc finger nucleases," Nucleic Acids Research, 2012, 40:3741-3752.
Perez-Pinera et al., "RNA-guided gene activation by CRISPR-Cas9-based transcription factors," Nat Methods, 2013, 10:973-976.
Perez-Pinera et al., "Synergistic and tunable human gene activation by combinations of synthetic transcription factors," Nature Methods, vol. 10, No. 3, pp. 239-244, Feb. 3, 2013, including pp. 1/12-12-12 of Supplementary Material.
Perez-Pinera et al., "Synergistic Transcriptional Activation by Combinations of Engineered TALEs" was publicly presented at the American Society of Gene & Cell Therapy's 15th Annual Meeting in Philadelphia, Pennsylvania during the Late Abstracts Poster Session III: Saturday, May 19, 2012. Abstract 855.
Persons, "Lentiviral vector gene therapy: effective and safe?" Mol Ther, 2010, 18(5): 861-2.
Piacentino et al., "X-Linked Inhibitor of Apoptosis Protein-Mediated Attenuation of Apoptosis, Using a Novel Cardiac-Enhanced Adeno-Associated Viral Vector," Human Gene Therapy, 2012, 23:635-646.
Pichavant et al., "Current status of pharmaceutical and genetic therapeutic approaches to treat DMD," Molecular Therapy 19, 2011, 830-840.
Polstein et al., "Genome-wide specificity of DNA-binding, gene regulation, and chromatin remodeling by TALE- and CRISPR/Cas9-based transcriptional activators," Genome Res, 2015, 25:1158-1169.
Polstein et al., "Light-inducible spatiotemporal control of gene activation by customizable zinc finger transcription factors," J Am Chem Soc, 2012, 134(40): 16480-3.
Ponting et al., "Evolution and functions of long noncoding RNAs," Cell, 2009, 136(4): 629-641.
Popplewell et al., "Gene correction of a duchenne muscular dystrophy mutation by meganuclease-enhanced exon knock-in," Hum Gene Ther, 2013, 24:692-701.
Powell et al., "A Prader-Willi locus lncRNA cloud modulates diurnal genes and energy expenditure," Hum Molec Genet, 2013, 22: 4318-4328.
Puccini et al., "Colorectal cancer: epigenetic alterations and their clinical implications", Biochim Biophys Acta, 2017, vol. 1868, No. 2, pp. 439-448.
Qi et al., "Repurposing CRISPR as an RNA-guided platform for sequence-specific control of gene expression," Cell 152, 2013, 1173-1183.
Quinlan et al., "BEDTools: a flexible suite of utilities for comparing genomic features," Bioinformatics 26, 2010, 841-842.
Rada-Iglesias et al., "A unique chromatin signature uncovers early developmental enhancers in humans," Nature 470, 2011, 279-283.
Rahdar et al., "Synthetic CRISPR RNA-Cas9-Guided Genome Editing in Human Cells," Proceedings to the National Academy of Sciences of USA, 2015, vol. 112, No. 51, pp. E7110-E7117.
Ran et al., "Double nicking by RNA-guided CRISPR Cas9 for enhanced genome editing specificity," Cell, 2013, 154(6): 1380-9.
Ran et al., "In vivo genome editing using *Staphylococcus aureus* Cas9," Nature 520, 2015, 186-91.
Rebar et al., "Induction of angiogenesis in a mouse model using engineered transcription factors," Nat Med 8, 2002, 1427-1432.
Reynolds et al., "NuRD-mediated deacetylation of H3K27 facilitates recruitment of Polycomb Repressive Complex 2 to direct gene repression," The EMBO Journal 31, 2012, 593-605.
Reyon et al., "FLASH assembly of TALENs for high-throughput genome editing," Nat Biotechnol 30, 2012, 460-465.
Richter et al., "Phage-assisted evolution of an adenine base editor with improved Cas domain compatibility and activity," Nat Biotechnol, Jul. 2020, 38(7): 883-891.
Riley, "PD-1 signaling in primary T cells," Immunological Reviews, 2009, 229: 114-125.
Rivenbark et al., "Epigenetic reprogramming of cancer cells via targeted DNA methylation," Epigenetics 7, 2012, 350-360.
Rousseau et al., "Endonucleases: tools to correct the dystrophin gene" The Journal of Gene Medicine, 2011, vol. 13, pp. 522-537.
Sahoo et al., "Prader-Willi phenotype caused by paternal deficiency for the HBII-85 C/D box small nucleolar RNA cluster," Nat Genet, 2008, 40: 719-721.
Saito et al., "Specific activation of microRNA-127 with downregulation of the proto-oncogene BCL6 by chromatin-modifying drugs in human cancer cells," Cancer Cell, 2006, vol. 9, pp. 435-443.
Saitoh et al., "Parent-of-Origin Histone Acetylation and Reactivation of a Key Imprinted Gene Locus in Prader-Willi Syndrome," Am J Hum Genet, 2000, 66: 1958-1962.
Salmon et al., "Production and titration of lentiviral vectors," Curr Protoc Neurosci, 2006, Chapter 4: Unit 4 21.
Salmon et al., "Production and titration of lentiviral vectors," Curr Protoc Hum Genet Chapter, 2007, 12: Unit 12 10, 24 pages.
Sambrook et al., Molecular Cloning and Laboratory manual, Second Ed., Cold Spring Harbor, 1989, pp. 16.7-16.8.
Sanghvi et al., "Heterocyclic Base Modifications in Nucleic Acids and their Applications in Antisense Oligonucleotides," 1993, Antisense Research and Applications, Chapter 15, pp. 274-285.
Sanjana et al., "High-resolution interrogation of functional elements in the noncoding genome," Science, 2016, 353: 1545-1549.
Schaaf et al., "Truncating mutations of MAGEL2 cause Prader-Willi phenotypes and autism," Nat Genet, 2013, 45(11): 1405-1408.
Schifrut et al., "Genome-wide CRISPR Screens in Primary Human T Cells Reveal Key Regulators of Immune Function," Cell, 2018, 175(7): 1958-1971.e15.
Schmid-Burgk et al., "A ligation-independent cloning technique for high-throughput of transcription activator-like effector genes," Nat Biotechnol 31, 2012, 76-81.
Schmittgen et al., "Analyzing real-time PCR data by the comparative CT method," Nature Protocols, 2008, 3(6): 1101-1108.
Scholze et al., "TAL effectors are remote controls for gene activation," Current Opinion in Microbiology, Jan. 2011, vol. 14, pp. 47-53.
Schultz et al., "Recombinant adeno-associated virus transduction and integration," Molecular Therapy 16, 2008, 1189-1199.
Schultz et al., "SETDB1: a novel KAP-1-associated histone H3, lysine 9-specific methyltransferase that contributes to HP1-mediated silencing of euchromatic genes by KRAB zinc-finger proteins," Genes & development 16, 2002, 919-932.
Sebastiano et al., "In Situ Genetic Correction of the Sickle Cell Anemia Mutation in Human Induced Pluripotent Stem Cells Using Engineered Zinc Finger Nucleases," Stem Cells 29, 2011, 1717-1726.
Seidel et al., "Chromatin-modifygin agents in anti-cancer therapy," Biochimie, 2012, vol. 94, pp. 2264-2279.
Sentmanat et al., "A Survey of Validation Strategies for CRISPR-Cas9 Editing," Scientific Reports, 2018, 8: 888.
Seto et al., "Gene Replacement Therapies for Duchenne Muscular Dystrophy Using Adeno-Associated Viral Vectors," Current Gene Therapy, 2012, 12:139-151.
Sharma et al., "Efficiency of nonhomologous DNA and joining varies among somatic tissues, despite similarity in mechanism," Cellular and Molecular Life Science 68, 2011, 661-676.
Shea et al., "Synthesis, hybridization properties and antiviral activity of lipid-oligodeoxynucleotide conjugates," Nucl. Acids Res, 1990, 18: 3777-3783.

(56) References Cited

OTHER PUBLICATIONS

Shen et al., "Engraftment of a galactose receptor footprint onto adeno-associated viral capsids improves transduction efficiency," J Biol Chem, 2013, 288(40): 28814-28823.
Silva et al., "Meganucleases and other tools for targeted genome engineering: perspective and challenges for gene therapy," Current gene therapy, 2011, 11:11-27.
Smith et al., "Myostatin inhibitors as therapies for muscle wasting associated with cancer and other disorders," Curr Opin Support Palliat Care, 2013, 7, 352-60.
Snowden et al., "Gene-specific targeting of H3K9 methylation is sufficient for initiating repression in vivo," Curr Biol 12, 2002, 2159-2166.
Soejima et al., "Imprinting centers, chromatin structure, and disease," J Cell Biochem, 2005, 95(2): 226-233.
Şöllü et al., "Autonomous zinc-finger nuclease pairs for targeted chromosomal deletion," Nucleic acids research 38, 2010, 8269-8276.
Song et al., "Dnase-seq: a high-resolution technique for mapping active gene regulatory elements across the genome from mammalian cells," Cold Spring Harbor protocols 2010, 2010(2):11.
Song et al., "Open chromatin defined by DNaseI and FAIRE identifies regulatory elements that shape cell-type identify," Genome Res 21, 2011, 1757-1767.
Soutschek et al., "Therapeutic silencing of an endogenous gene by systemic administration of modified siRNAs," Nature (2004) 432: 173-8.
Spitz et al., "Transcription factors: from enhancer binding to developmental control," Nat. Rev. Genet. 2012, 13, 613-626.
Sripathy et al., "The KAP1 corepressor functions to coordinate the assembly of de novo HP1-demarcated microenvironments of heterochromatin required for KRAB zinc finger protein-mediated transcriptional repression," Molecular and cellular biology 26, 2006, 8623-8638.
Stanton et al., "Chemical modification study of antisense gapmers," Nucleic Acid Ther., 2012, 22(5): 344-359.
Sternberg et al., "Conformational Control of DNA Target Cleavage by CRISPR-Cas9," Nature, 2015, vol. 527, No. 7576, pp. 110-113.
Sternberg et al., "DNA interrogation by the CRISPR RNA-guided endonuclease Cas9," Nature, 2014, 507, 62-67.
Su et al., "Identification of biologically relevant enhancers in human erythroid cells," J Biol Chem 288, 2013, 8433-8444.
Su et al., "In vitro and in vivo mRNA delivery using lipid-enveloped pH-responsive polymer nanoparticles," Mol. Pharmaceutics, 2011, 8, 774-787.
Sui et al., "A DNA vector-based RNAi technology to suppress gene expression in mammalian cells," PNAS, 2002, 99(8): 5515-5520.
Sun et al., "Optimized TAL effector nucleases (TALENs) for use in treatment of sickle cell disease," Molecular bioSystems 8, 2012, 1255-1263.
Sutcliffe et al., "Deletions of a differentially methylated CpG island at the SNRPN gene define a putative imprinting control region," Nature Genetics, 1994, 8: 52-58.
Svinarchuk et al., "Inhibition of HIV proliferation in MT-4 cells by antisense oligonucleotide conjugated to lipophilic groups," Biochimie, 1993, 75: 49-54.
Szostak, "in Vitro Genes," TIBS, 1993, 17: 89-93.
Szyf, "Epigenetics, DNA methylation, and chromatin modifying drugs," Annual Review of Pharmacology and Toxicology, 2009, vol. 49, pp. 243-263.
Tabebordbar et al., "In vivo gene editing in dystrophic mouse muscle and muscle stem cells," Science, 2016, 351, 407-11.
Takahashi et al., "Induction of pluripotent stem cells from adult human fibroblasts by defined factors," Cell 1131, 2007, 861-872.
Takeshima et al., "Mutation spectrum of the dystrophin gene in 442 Duchene/Becker muscular dystrophy cases from one Japanese referral center," Journal of Human Genetics, 2010, 55: 379-388.
Tanenbaum et al., "A Protein-Tagging System for Signal Amplification in Gene Expression and Fluorescence Imaging," Cell, 2014, pp. 635-646.
Taniguchi-Ikeda et al., "Pathogenic exon-trapping by SVA retrotransposon and rescue in Fukuyama muscular dystrophy," Nature 478, 2011, 127-131.
Tebas et al., "Gene editing of CCR5 in autologous CD4 T cells of persons infected with HIV," N Engl J Med, 2014, 370:901-910.
Tedesco et al., "Repairing skeletal muscle: regenerative potential of skeletal muscle stem cells," J Clin Invest, 2010, 120:11-19.
Tedesco et al., "Stem Cell-Mediated Transfer of a Human Artificial Chromosome Ameliorates Musculat Dystrophy," Science Translational Medicine 3, 2011, 96ra78-96ra78.
Tedesco et al., "Transplantation of Genetically Corrected Human iPSC-Derived Progenitors in Mice with Limb-Girdle Muscular Dystrophy," Science Translational Medicine 4, 2012, 140ra189.
Thakore et al., "Editing the epigenome: technologies for programmable transcription and epigenetic modulation," Nat Methods. 2016, 13:127-37.
Thakore et al., "Highly specific epigenome editing by CRISPR-Cas9 repressors for silencing of distal regulatory elements," Nat Methods, 2015, 12, 1143-9.
Thakore et al., "RNA-guided transcriptional silencing in vivo with S. aureus CRISPR-Cas9 repressors," Nature Communications, 2018, 9(1):1674, 9 pages.
Thomson et al., "Human herpesvirus 6 (HHV-6) is a helper virus for adeno-associated virus type 2 (AAV-2) and the AAV-2 rep gene homologue in HHV-6 can mediate AAV-2 DNA replication and regulate gene expression," Virol., 1994, 204:304-311.
Thurman et al., "The accessible chromatin landscape of the human genome," Nature 489, 2012, 75-82.
Tone et al., "Smad3 and NFAT cooperate to induce Foxp3 expression through its enhancer," Nat. Immunol., 2008, 9, 194-202.
Truong et al., "Development of an intein-mediated split-Cas9 system for gene therapy, " Nucleic Acids Res. 2015; 43: 6450-6458.
Tuan et al., "Transcription of the hypersensitive site HS2 enhancer in erythroid cells," Proceedings of the National Academy of Sciences of the United States of America 89, 1992, 11219-11223.
U.S. Appl. No. 17/471,935, filed Sep. 10, 2021, by Gersbach et al.
Uchida et al., "In Vivo Messenger RNA Introduction into the Central Nervous System Using Polyplex Nanomicelle," PLoS One, 2013, 8: e56220.
Uetsuki et al., "Isolation and characterization of the human chromosomal gene for polypeptide chain elongation factor-1 alpha," J. Biol. Chem., 1989, 264:5791.
Urnov et al., "Highly efficient endogenous human gene correction using designed zinc-finger nucleases," Nature 435, 2005, 646-651.
Usman et al., "Catalytic RNA (Ribozymes) as Drugs," Ann. Rep. Med. Chem., 1995, Chapter 30, pp. 285-294.
Vakoc et al., "Proximity among distant regulatory elements at the beta-globin locus requires GATA-1 and FOG-1," Molecular cell 17, 2005, 453-462.
Van Putten et al., "Low dystrophin levels in heart can delay heart failure in mdx mice," J Mol Cell Cardiol, 2014, 69C:17-23.
Van Putten et al., "Low dystrophin levels increase survival and improve muscle pathology and function in dystrophin/utrophin double-knockout mice," FASEB J, 2013, 27:2484-2495.
Verma et al., "Gene Therapy: Twenty-first century medicine," Annual Review of Biochemistry, 2005, vol. 74, pp. 711-738.
Verma et al., "Gene therapy—promises, problems and prospects," Nature, 1997, vol. 389, pp. 239-242.
Vierbuchen et al., "Direct conversion of fibroblasts to functional neurons by defined factors," Nature 463, 2010, 1035-1041.
Visel et al., "ChIP-seq accurately predicts tissue-specific activity of enhancers," Nature 457, 2009, 854-858.
Voss et al., "The role of enhancers in the regulation of cell-type-specific transcriptional control," Trends Biochem. Sci., 1986, 11:287.
Wagner et al., "A phase I/IItrial of MYO-029 in adult subjects with muscular dystrophy," Ann Neurol 63, 2008, 561-71.
Wang et al., "Adeno-associated virus vector carrying human minidystrophin genes effectively ameliorates muscular dystrophy in mdx mouse model," Proc Natl Acad Sci US A., 2000, 97(25):13714-13719.

(56) References Cited

OTHER PUBLICATIONS

Wang et al., "Cyclohexene Nucleic Acids (CeNA): Serum Stable Oligonucleotides that Activate RNase H and Increase Duplex Stability with Complementary RNA," J. Am. Chem. Soc., 2000, 122: 8595-8602.
Wang et al., "Efficient delivery of genome-editing proteins using bioreducible lipid nanoparticles," Proc Natl Acad Sci USA, 2016, 113(11): 2868-2873.
Wang et al., "Epstein-Barr virus nuclear protein 2 interacts with p300, CBP, and PCAF histone acetyltransferases in activation of the LMPI promoter," Proc Natl Acad Sci U S A 97, 2000, 430-435.
Wang et al., "Genome-wide mapping of HATs and HDACs reveals distinct functions in active and inactive genes," Cell 138, 2009, 1019-1031.
Wang et al., "One-Step Generation of Mice Carrying Mutations in Multiple Genes by CRISPR- Cas-Mediated Genome Engineering," Cell, 2013, 153(4): 910-8.
Wang et al., "Potential of Epigenetic Therapy for Pader-Willi Syndrome," Trends in Pharmacological Sciences, 2019, 40(9): 605-608.
Wein et al., "Efficient bypass of mutations in dysferlin deficient patient cells by antisense-induced exon skipping," Hum Mutat 31, 2010, 136-142.
Welch et al., "PTC124 targets genetic disorders caused by nonsense mutations," Nature 447, 2007, 87-91.
Whisstock et al., "Prediction of protein function from protein sequence," Q. Rev. Biophysics., 2003, 36(3): 307-340.
Wilbie et al., "Delivery Aspects of CRISPR/Cas for in Vivo Genome Editing," Acc Chem Res, 2019, 52(6): 1555-1564.
Wu et al., "Genome-wide binding of the CRISPR endonuclease Cas9 in mammalian cells," Nat Biotechnol 32, 2014, 670-676.
Wu et al., "Unusual Processing Generates SPA LncRNAs that Sequester Multiple RNA Binding Proteins," Mol Cell, 2016, 64: 534-548.
Yan et al., "Drugging the undruggable: Transcription therapy for cancer," Biochimica et Biophysica Acta (BBA)—Reviews on Cancer, Jan. 2013, vol. 1835, No. 1, pp. 76-85.
Yang, "Optimization of scarless human stem cell genome editing," Nucleic Acids Res, 2013, 41:9049-9061.
Yin et al., "Long noncoding RNAs with snoRNA ends," Mol Cell, 2012, 48(2): 219-230.
You et al., "Design of LNA probes that improve mismatch discrimination," Nuc. Acids. Res., 2006, 34(8): e60.
Youngblood et al., "Chronic virus infection enforces demethylation of the locus that encodes PD-1 in antigen-specific CD8+ T cells," Immunity, 2011, 35: 400-412.
Yu et al., "RNA interference by expression of short-interfering RNAs and hairpin RNAs in mammalian cells," PNAS, 2002, 99(9): 6047-6052.
Yusa et al., "Targeted gene correction of α1-antitrypsin deficiency in induced pluripotent stem cells," Nature 478, 2011, 391-394.
Zhang et al. "Efficient construction of sequence-specific TAL effectors for modulating mammalian transcription," Nat Biotechnol 29, 2011, 149-153.
Zhang et al., "Adenovirus-Adeno-Associated Virus Hybrid for Large-Scale Recombinant Adeno-Associated Virus Production," Hum Gene Ther. 2009, 20:922-9.
Zhang et al., "Gene activation in human cells using CRISPR/Cpf1-p300 and CRISPR/Cpf1-SunTag systems," Protein Cell, 2018, 9: 380-383.
Zhang et al., "Model-based analysis of ChIP-Seq (MACS)," Genome biology 9, 2008, R137.
Zheng et al., "Foxp3 in control of the regulatory T cell lineage," Nat. Immunol. 2007, 8, 457-462.
Zheng et al., "Role of conserved non-coding DNA elements in the Foxp3 gene in regulatory T-cell fate," Nature, 2010, 463, 808-812.
Zhou et al., "High-throughput screening of a CRISPR/Cas9 library for functional genomics in human cells," Nature, 2014, 509(7501): 487-491.
Zhu et al., "Cellular senescence in human telomerase reverse transcriptase and cyclin-dependent kinase 4: consequences in aging muscle and therapeutic strategies for muscular dystrophies," Aging cell 6, 2007, 515-523.
Zincarelli et al., "Analysis of AAV serotypes 1-9 mediated gene expression and tropism in mice after systemic injection," Mol Ther 16, 1073-80 (2008).
Zou et al., "Site-specific gene correction of a point mutation in human iPS cells derived from an adult patient with sickle cell disease," Blood 118, 2011, 4599-4608.
International Search Report and Written Opinion for Application No. PCT/US14/41190 dated Dec. 17, 2014 (14 pages).
International Search Report and Written Opinion for Application No. PCT/US14/17221 dated Oct. 26, 2016 (11 pages).
International Search Report and Written Opinion for Application No. PCT/US2017/027490 dated Sep. 28, 2017 (34 pages).
International Search Report and Written Opinion for Application No. PCT/US2017/046282 dated Jan. 12, 2018 (20 pages).
International Search Report and Written Opinion for Application No. PCT/US2020/027867 dated Jul. 27, 2020 (18 pages).
International Search Report and Written Opinion for Application No. PCT/US2020/054160 dated Mar. 8, 2021 (21 pages).
International Search Report and Written Opinion for Application No. PCT/US2021/029500 dated Sep. 2, 2021 (10 pages).
International Search Report and Written Opinion for Application No. PCT/US2021/031436 dated Nov. 5, 2021 (11 pages).
European Patent Office Extended Search Report for Patent Application No. 16749752.8 dated Jun. 20, 2018 (8 pages).
European Patent Office Action for Patent Application No. 16749752.8 dated Apr. 12, 2019 (3 pages).
European Patent Office Action for Application No. 16749752.8 dated Sep. 30, 2019 (4 pages).
European Patent Office Action for Application No. 16749752.8 dated Apr. 23, 2020 (3 pages).
Japanese Patent Office Action for Application No. 2017-560481 dated Apr. 6, 2020 (4 pages, English translation included).
Japanese Patent Office Action for Application No. 2017-560481 dated Dec. 21, 2020 (3 pages, English translation included).
United States Patent Office Action for U.S. Appl. No. 15/549,842 dated May 17, 2019 (29 pages).
United States Patent Office Action for U.S. Appl. No. 15/549,842 dated Oct. 10, 2019 (14 pages).
United States Patent Office Notice of Allowance for U.S. Appl. No. 15/549,842 dated Jan. 30, 2020 (7 pages).
United States Patent Office Action for U.S. Appl. No. 15/746,653 dated Jun. 28, 2019 (22 pages).
United States Patent Office Notice of Allowance for U.S. Appl. No. 15/746,653 dated Jan. 10, 2020 (5 pages).
United States Patent Office Action for U.S. Appl. No. 14/895,316 dated Dec. 15, 2016 (13 pages).
United States Patent Office Action for U.S. Appl. No. 14/895,316 dated Mar. 21, 2018 (8 pages).
United States Patent Office Action for U.S. Appl. No. 14/895,316 dated Oct. 22, 2018 (11 pages).
United States Patent Office Action for U.S. Appl. No. 14/895,316 dated Apr. 19, 2019 (11 pages).
United States Patent Office Notice of Allowance for U.S. Appl. No. 14/895,316 dated Sep. 30, 2019 (9 pages).
United States Patent Office Notice of Allowance for U.S. Appl. No. 14/895,316 dated Jan. 27, 2020 (7 pages).
United States Patent Office Action for U.S. Appl. No. 15/991,333 dated Apr. 19, 2019 (12 pages).
United States Patent Office Action for U.S. Appl. No. 15/991,333 dated Oct. 4, 2019 (6 pages).
United State Patent Office Notice of Allowance for U.S. Appl. No. 15/991,333 dated Apr. 13, 2020 (8 pages).
United States Patent Office Notice of Allowance for U.S. Appl. No. 16/865,151 dated Mar. 18, 2021 (7 pages).
United States Patent Office Notice of Allowance for U.S. Appl. No. 16/865,151 dated Jun. 10, 2021 (7 pages).
United States Patent Office Action for U.S. Appl. No. 16/093,272 dated Nov. 22, 2021 (11 pages).

(56) References Cited

OTHER PUBLICATIONS

Aguilar et al., "Transcriptional and Chromatin Dynamics of Muscle Regeneration after Severe Trauma," Stem Cell Rep, 2016, 7: 983-997.
Amoasii et al., "Gene editing restores dystrophin expression in a canine model of Duchenne muscular dystrophy," Science, 2018, 362: 86-91.
Amoasii et al., "Single-cut genome editing restores dystrophin expression in a new mouse model of muscular dystrophy," Sci Transl Med, Nov. 2017, 9(418): eaan8081.
Andersen et al., "Dual role of delta-like 1 homolog (DLK1) in skeletal muscle development and adult muscle regeneration," Development, 2013, 140: 3743-3753.
Arnett et al., "Adeno-associated viral vectors do not efficiently target muscle satellite cells," Molecular Therapy Methods & Clinical Development, 2014, 1: 14038.
Balboa et al., "Conditionally Stabilized dCas9 Activator for Controlling Gene Expression in Human Cell Reprogramming and Differentiation," Stem Cell Rep, 2015, 5: 448-459.
Barberi et al., "Derivation of engraftable skeletal myoblasts from human embryonic stem cells," Nat Med, 2007, 13: 642-648.
Barr et al., "Predominant Expression of Alternative PAX3 and PAX7 Forms in Myogenic and Neural Tumor Cell Lines," Cancer Res, 1999, 59: 5443-5448.
Bengtsson et al., "Muscle-specific CRISPR/Cas9 dystrophin gene editing ameliorates pathophysiology in a mouse model for Duchenne muscular dystrophy," Nat Commun, 2017, 8: 1-10.
Black et al., "Targeted Epigenetic Remodeling of Endogenous Loci by CRISPR/Cas9-Based Transcriptional Activators Directly Converts Fibroblasts to Neuronal Cells," Cell Stem Cell, 2016, 19: 406-414.
Boldrin et al., "Donor satellite cell engraftment is significantly augmented when the host niche is preserved and endogenous satellite cells are incapacitated," Stem Cells, 2012, 30: 1971-1984.
Bolger et al., "Trimmomatic: a flexible trimmer for Illumina sequence data," Bioinformatics, 2014, 30: 2114-2120.
Chal et al., "Differentiation of pluripotent stem cells to muscle fiber to model Duchenne muscular dystrophy," Nat Biotechnol, 2015, 33: 962-969.
Chen et al., "Enrichr: interactive and collaborative HTML5 gene list enrichment analysis tool," BMC Bioinformatics, 2013, 14: 128.
Chen et al., "microRNA-1 and microRNA-206 regulate skeletal muscle satellite cell proliferation and differentiation by repressing Pax7," J Cell Biol, 2010, 190: 867-879.
Darabi et al., "Functional skeletal muscle regeneration from differentiating embryonic stem cells," Nat Med, 2008, 14: 134-143.
Dobin et al., "STAR: ultrafast universal RNA-seq aligner," Bioinformatics, 2013, 29: 15-21.
Dumont et al., "Dystrophin expression in muscle stem cells regulates their polarity and asymmetric division," Nat Med, 2015, 21: 1455-1463.
Dumont et al., "Intrinsic and extrinsic mechanisms regulating satellite cell function," Development, 2015, 142: 1572-1581.
Dunbar et al., "Gene therapy comes of age," Science, 2018, 359: eaan4672.
Fairclough et al., "Therapy for Duchenne muscular dystrophy: renewed optimism from genetic approaches," Nat. Rev. Genet., 2013, 14: 373-378.
Goldstein et al., "In Situ Modification of Tissue Stem and Progenitor Cell Genomes," Cell Reports, 2019, 27: 1254-1264.e7.
Hall et al., "Prevention of Muscle Aging by Myofiber-Associated Satellite Cell Transplantation," Sci Transl Med, 2010, 2: 57ra83.
Hardy et al., "Comparative Study of Injury Models for Studying Muscle Regeneration in Mice," PLoS One, 2016, 11: e0147198.
Himeda et al., "Design and Testing of Regulatory Cassettes for Optimal Activity in Skeletal and Cardiac Muscles," Methods Mol Biol, 2011, 709: 3-19 (Published Online Dec. 2010).
Jiang et al., "Notch signaling deficiency underlies age-dependent depletion of satellite cells in muscular dystrophy," Disease Models & Mechanisms, 2014, 7: 997-1004.
Jiwlawat et al., "Current Progress and Challenges for Skeletal Muscle Differentiation from Human Pluripotent Stem Cells Using Transgene-Free Approaches," Stem Cells Int, Apr. 2018, Article ID 6241681, 18 pages.
Keefe et al., "Muscle stem cells contribute to myofibers in sedentary adult mice," Nat Commun, 2015, 6: 7087.
Kim et al., "Expansion and Purification Are Critical for the Therapeutic Application of Pluripotent Stem Cell-Derived Myogenic Progenitors," Stem Cell Rep, 2017, 9: 12-22.
Kodaka et al., "Skeletal Muscle Cell Induction from Pluripotent Stem Cells," Stem Cells Int, Apr. 2017, Article ID 1376151, 16 pages.
Lam et al., "Rapid and Efficient Differentiation of Human Pluripotent Stem Cells into Intermediate Mesoderm That Forms Tubules Expressing Kidney Proximal Tubular Markers," J Am Soc Nephrol JASN, 2014, 25: 1211-1225.
Lamey et al., "Pax genes in myogenesis: alternate transcripts add complexity," Histol Histopathol, 2004, 19: 1289-1300.
Lee et al., "Nanoparticle delivery of Cas9 ribonucleoprotein and donor DNA in vivo induces homology-directed DNA repair," Nat Biomed Eng, 2017, 1: 889-901.
Li et al., "Synthetic muscle promoters: activities exceeding naturally occurring regulatory sequences," Nature Biotechnology, 1999, 17: 241-245.
Lian et al., "Robust cardiomyocyte differentiation from human pluripotent stem cells via temporal modulation of canonical Wnt signaling, " Proc Natl Acad Sci, 2012, 109: E1848-E1857.
Liao et al., "The Subread aligner: fast, accurate and scalable read mapping by seed-and-vote," Nucleic Acids Res, 2013, 41: e108.
Limberis et al., "Transduction efficiencies of novel AAV vectors in mouse airway epithelium in vivo and human ciliated airway epithelium in vitro, " Molecular therapy: the journal of the American Society of Gene Therapy, 2009, 17: 294-301.
Liu et al., "CRISPR Activation Screens Systematically Identify Factors that Drive Neuronal Fate and Reprogramming," Cell Stem Cell, 2018, 23: 758-771 e758.
Liu et al., "CRISPR-Based Chromatin Remodeling of the Endogenous Oct4 or Sox2 Locus Enables Reprogramming to Pluripotency," Cell Stem Cell, 2018, 22: 252-261 e254.
Long et al., "Postnatal genome editing partially restores dystrophin expression in a mouse model of muscular dystrophy," Science, 2016, 351(6271):400-403.
Madigan et al., "Engineering AAV receptor footprints for gene therapy," Curr Opin Virol, 2016, 18: 89-96.
Madisen et al., "A robust and high-throughput Cre reporting and characterization system for the whole mouse brain," Nat Neurosci, 2010, 13: 133-140.
Magli et al., "PAX7 Targets, CD54, Integrin a9B1, and SDC2, Allow Isolation of Human ESC/iPSC-Derived Myogenic Progenitors," Cell Rep, 2017, 19: 2867-2877.
McFadden et al., "The Hand1 and Hand2 transcription factors regulate expansion of the embryonic cardiac ventricles in a gene dosage-dependent manner," Development, 2005, 132: 189-201.
Montarras, "Direct Isolation of Satellite Cells for Skeletal Muscle Regeneration," Science, 2005, 309: 2064-2067.
Nance et al., "AAV9 Edits Muscle Stem Cells in Normal and Dystrophic Adult Mice," Molecular Therapy, 2019, 27: 1568-1585.
Nelson et al., "Engineering Delivery Vehicles for Genome Editing," Annual review of chemical and biomolecular engineering, 2016, 7: 637-662.
Nelson et al., "Genome engineering: a new approach to gene therapy for neuromuscular disorders," Nat Rev Neurol, 2017, 13: 647-661.
Olguin et al., "Pax-7 up-regulation inhibits myogenesis and cell cycle progression in satellite cells: a potential mechanism for self-renewal," Dev Biol, 2004, 275: 375-388.
Papapetrou, "Induced pluripotent stem cells, past and future," Science, 2016, 353: 991-992.
Pawlikowski et al., "Regulation of skeletal muscle stem cells by fibroblast growth factors," Dev Dyn, 2017, 246: 359-367.
Pigozzo et al., "Revertant Fibers in the mdx Murine Model of Duchenne Muscular Dystrophy: An Age- and Muscle-Related Reappraisal," PLoS One, 2013, 8(8): e72147.

(56) References Cited

OTHER PUBLICATIONS

Rao et al., "Engineering human pluripotent stem cells into a functional skeletal muscle tissue," Nat Commun, 2018, 9: 126.
Sacco et al., "Short Telomeres and Stem Cell Exhaustion Model Duchenne Muscular Dystrophy in mdx/mTR Mice," Cell, 2010, 143: 1059-1071.
Salva et al., "Design of tissue-specific regulatory cassettes for high-level rAAV-mediated expression in skeletal and cardiac muscle," Mol. Ther., 2007, 15:320-329.
Sambasivan et al., "Embryonic founders of adult muscle stem cells are primed by the determination gene Mrf4," Developmental Biology, 2013, 381: 241-255.
Shelton et al., "Derivation and Expansion of PAX7-Positive Muscle Progenitors from Human and Mouse Embryonic Stem Cells," Stem Cell Rep, 2014, 3: 516-529.
Stuelsatz et al., "A Contemporary Atlas of the Mouse Diaphragm: Myogenicity, Vascularity, and the Pax3 Connection" J Histochem Cytochem, 2012, 60(9): 638-657.
Tan et al., "Efficient derivation of lateral plate and paraxial mesoderm subtypes from human embryonic stem cells through GSKi-mediated differentiation," Stem Cells Dev, 2013, 22: 1893-1906.
Vorobyov et al., "Expression of two protein isoforms of PAX7 is controlled by competing cleavage-polyadenylation and splicing," Gene, 2004, 342: 107-112.
Waddell et al., "Dlk1 Is Necessary for Proper Skeletal Muscle Development and Regeneration," PLoS One, 2010, 5(11): e15055.
Waldrop et al., "Update in Duchenne and Becker muscular dystrophy," Current Opinion in Neurology, 2019, 32: 722-727.
Wang et al., "Adeno-associated virus serotype 8 efficiently delivers genes to muscle and heart," Nat. Biotechnol., 2005, 23: 321-328.
Weltner et al., "Human pluripotent reprogramming with CRISPR activators," Nat Commun Lond, 2018, 9: 1-12.
Wu et al., "A Myogenic Double-Reporter Human Pluripotent Stem Cell Line Allows Prospective Isolation of Skeletal Muscle Progenitors," Cell Rep, 2018, 25: 1966-1981.e4.
Wüst et al., "Metabolic Maturation during Muscle Stem Cell Differentiation Is Achieved by miR-1/133a-Mediated Inhibition of the Dlk1-Dio3 Mega Gene Cluster," Cell Metab, 2018, 27: 1026-1039.e6.
Xu et al., "CRISPR-mediated Genome Editing Restores Dystrophin Expression and Function in mdx Mice," Molecular Therapy: The Journal of the American Society of Gene Therapy, 2016, 24(3):564-569.
Xu et al., "Human Satellite Cell Transplantation and Regeneration from Diverse Skeletal Muscles," Stem Cell Rep, 2015, 5: 419-434.
International Search Report and Written Opinion for Application No. PCT/US2020/047080 dated Feb. 12, 2021 (14 pages).
Park et al., "Cas-Designer: a web-based tool for choice of CRISPR-Cas9 target sites," Bioinformatics, 2015, 31(24): 4014-4016.
Shen et al., "Massively parallel cis-regulatory analysis in the mammalian central nervous system," Genome Research, 2015, 26(2): 238-255.
Chhatwal et al., "Identification of cell-type-specific promoters within the brain using lentiviral vectors," Gene Therapy, 2007, 14(7): 575-583.
Trinklein et al., "Identification and functional analysis of human transcriptional promoters," Genome Research, 2003, 13(2): 308-312.
Yu et al., "Dystrophin-deficient large animal models: translational research and exon skipping," Am J Transl Res, 2015, 7(8): 1314-1331.
Japanese Patent Office Action for Application No. 2021-102533 dated Mar. 20, 2023 (7 pages, English translation included).
U.S. Appl. No. 18/036,862, filed May 12, 2023.
U.S. Appl. No. 17/636,750, filed Feb. 18, 2022.
U.S. Appl. No. 17/636,754, filed Feb. 18, 2022.
U.S. Appl. No. 17/766,003, filed Apr. 1, 2022.
U.S. Appl. No. 63/314,183, filed Feb. 25, 2022.
U.S. Appl. No. 63/314,256, filed Feb. 25, 2022.
U.S. Appl. No. 63/317,847, filed Mar. 8, 2022.
U.S. Appl. No. 63/325,037, filed Mar. 29, 2022.
U.S. Appl. No. 63/325,039, filed Mar. 29, 2022.
U.S. Appl. No. 63/330,679, filed Apr. 13, 2022.
U.S. Appl. No. 63/372,373, filed Aug. 8, 2022.
U.S. Appl. No. 63/330,691, filed Apr. 13, 2022.
U.S. Appl. No. 17/471,935, filed Sep. 10, 2021, 2022/0098561, Mar. 31, 2022.
U.S. Appl. No. 17/633,467, filed Feb. 7, 2022.
U.S. Appl. No. 63/335,122, filed Apr. 26, 2022.
U.S. Appl. No. 63/342,027, filed May 13, 2022.
Adikusuma et al., "Versatile single-step-assembly CRISPR/Cas9 vectors for dual gRNA expression," 2017, 12(12): e0187236.
Carcagno et al., "Neurogenin3 Restricts Serotonergic Neuron Differentiation to the Hindbrain," The Journal of Neuroscience, 2014, 34(46): 15223-15233.
Kalsner et al., "Prader-Willi, Angelman, and 15q11-q13 Duplication Syndromes," Pediatric Clinics of North America United States, 2015, 62(3): 587-606.
Ohta et al., "Imprinting-Mutation Mechanisms in Prader-Willi Syndrome," The American Journal of Human Genetics, 1999, 64(2): 397-413.
Yang et al., "A dual AAV system enables the Cas9-mediated correction of a metabolic liver disease in newborn mice," Nature Biotechnology, 2016, 34(3): 334-338.
International Search Report and Written Opinion for Application No. PCT/US2023/018559 dated Sep. 29, 2023 (11 pages).
International Search Report and Written Opinion for Application No. PCT/US2023/063296 dated Oct. 19, 2023 (12 pages).
International Search Report and Written Opinion for Application No. PCT/US2023/063297 dated Oct. 18, 2023 (12 pages).
Abaandou et al., "Affecting HEK293 Cell Growth and Production Performance by Modifying the Expression of Specific Genes," Cells, 2021, 10: 1667, 21 pages.
Alerasool et al., "An efficient KRAB domain for CRISPRi applications in human cells," Nat Methods, 2020, 17: 1093-1096.
Alonso-Camino et al., "CARbodies: Human Antibodies Against Cell Surface Tumor Antigens Selected From Repertoires Displayed on T Cell Chimeric Antigen Receptors," Mol Ther Nucl Acids, 2013, 2: e93, 11 pages.
Azuma et al., "Robust expansion of human hepatocytes in Fah-/-/Rag2-/-/Il2rg-/- mice" Nat Biotechnol., 2007, 25(8): 903-910.
Bhakta et al., "The generation of zinc finger proteins by modular assembly," Methods Mol. Biol., 2010, 649: 3-30.
Bloomfield, "Quasi-Elastic Light Scattering Applications in Biochemistry and Biology," Ann. Rev. Biophys. Bioeng., 1981, 10: 421-450.
Boris-Lawrie et al., "Recent advances in retrovirus vector technology," Cur. Opin. Genet. Develop., 1993, 3: 102-109.
Bouhairie et al., "Familial hypercholesterolemia," Cardiol. Clin., 2015, 33(2): 169-179.
Braliou et al., "The v-ErbA oncoprotein quenches the activity of an erythroid-specific enhancer," Oncogene, 2001, 20(7): 775-87.
Brash et al., "Strontium phosphate transfection of human cells in primary culture: stable expression of the simian virus 40 large-T-antigen gene in primary human bronchial epithelial cells," Mol. Cell Biol., 1987, 7(5): 2031-2034.
Broude et al., "p21 (CDKN1A) is a negative regulator of p53 stability," Cell Cycle, 2007, 6(12): 1468-1471.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA, 1993, 90: 8033-8037.
Cano-Rodriguez et al., "Epigenetic Editing: On the Verge of Reprogramming Gene Expression at Will," Curr Genet Med Rep, 2016, 4: 170-179.
Carlens et al., "Ex vivo T lymphocyte expansion for retroviral transduction: influence of serum-free media on variations in cell expansion rates and lymphocyte subset distribution," Exp Hematol, 2000, 28(10): 1137-46.
Cavalieri et al., "Human T lymphocytes transduced by lentiviral vectors in the absence of TCR activation maintain an intact immune competence," Blood, 2003, 102(2): 497-505.

(56) References Cited

OTHER PUBLICATIONS

Chakraborty et al. "553. AAV-fVlediated Delivery of HSV-•Specific Homing Endonucleases To Neurons of the Trigeminal Ganglia for HSV-1 Inhibition." Molecular Therapy 22 (2014).

Chen et al., "Fusion protein linkers: property, design and functionality," Adv. Drug Deliv. Rev., 2013, 65(10): 1357-1369.

Chicaybam et al., "An efficient low cost method for gene transfer to T lymphocytes, " PLoS One, 2013, 8(3): e60298, 11 pages.

Chylinski et al., "The tracrRNA and Cas9 families of type II CRISPR-Cas immunity systems," RNA Biol., 2013, 10(5): 726-737.

Cooper et al., "T-cell clones can be rendered specific for CD19: toward the selective augmentation of the graft-versus-B-lineage leukemia effect," Blood, 2003, 101(4): 1637-1644.

Cortes-Mancera et al., "Gene-Targeted DNA Methylation: Towards Long-Lasting Reprogramming of Gene Expression?" Adv Exp Med Biol., 2022, 1389: 515-533.

Das et al., "Tet-On Systems For Doxycycline-inducible Gene Expression," Current Gene Therapy, 2016, 16: 156-167.

Defesche et al., "Familial hypercholesterolaemia," Nat. Rev. Dis. Primers, 2017, 3: 17093, 20 pages.

Deng et al., "Highly sensitive electrochemical methyltransferase activity assay," Anal Chem., 2014, 86: 2117-2123.

Fuks, "DNA methylation and histone modifications: teaming up to silence genes," Current Opinion in Genetics & Development, 2005, 15(5): 490-495.

Gersbach et al., "Synthetic zinc finger proteins: the advent of targeted gene regulation and genome modification technologies," Acc. Chem. Res., 2014, 47(8): 2309-18.

Gowher et al., "Molecular enzymology of the catalytic domains of the Dnmt3a and Dnmt3b DNA methyltransferases," J. Biol. Chem., 2002, 277(23): 20409-20414.

Gowher et al., "Mechanism of stimulation of catalytic activity of Dnmt3A and Dnmt3B DNA-(cytosine-C5)-methyltransferases by Dnmt3L," J. Biol. Chem., 2005, 280(14): 13341-13348.

Hochstrasser et al., "CasA mediates Cas3-catalyzed target degradation during CRISPR RNA-guided interference," PNAS, 2014, 111(18): 6618-23.

Huang et al., "Ch 9: DNA transposons for modification of human primary T lymphocytes," Methods Mol Biol, 2009, 506: 115-126.

Jia et al., "Structure of Dnmt3a bound to Dnmt3L suggests a model for de novo DNA methylation, " Nature, 2007, 449(7159): 248-251.

Johnston, "Biolistic transformation: microbes to mice," Nature, 1990, 346: 776-777.

Kao et al., "Ectopic DNMT3L triggers assembly of a repressive complex for retroviral silencing in somatic cells," J Virol., 2014, 88(18): 10680-95.

Kim et al., "Zinc-fingers and homeoboxes 1 (ZHX1) binds DNA methyltransferase (DNMT) 3B to enhance DNMT3B-mediated transcriptional repression," Biochemical and Biophysical Research Communications, 2007, 355(2): 318-323.

Koste et al., "T-cell receptor transfer into human T cells with ectotropic retroviral vectors," Gene Ther, 2014, 21(5): 533-538.

Lagace, "PCSK9 and LDLR degradation: regulatory mechanisms in circulation and in cells," Curr. Opin. Lipidol., 2014, 25(5): 387-393.

Lei et al., "Targeted DNA methylation in vivo using an engineered dCas9-MQ1 fusion protein," Nat. Commun, 2017, 8: 16026, 10 pages.

Li et al., "The histone methyltransferase SETDB1 and the DNA methyltransferase DNMT3A interact directly and localize to promoters silenced in cancer cells," J. Biol. Chem., 2006, 281(28): 19489-19500.

Li et al., "Development of fluorescent methods for DNA methyltransferase assay," Methods Appl. Fluoresc., 2017, 5: 012002, 8 pages.

Liu et al., "Design of polydactyl zinc-finger proteins for unique addressing within complex genomes," PNAS, 1997, 94(11): 5525-5530.

Ma et al., "Pol III Promoters to Express Small RNAs: Delineation of Transcription Initiation," Molecular Therapy—Nucleic Acids, 2014, 3: e161, 11 pages.

Makarova et al., "Annotation and Classification of CRISPR-Cas Systems," Methods Mol. Biol, 2015, 1311: 47-75.

Manuri et al., "piggyBac transposon/transposase system to generate CD19-specific T cells for the treatment of B-lineage malignancies," Hum Gene Ther, 2010, 21(4): 427-437.

Mavrothalassitis et al., "Proteins of the ETS family with transcriptional repressor activity," Oncogene, 2000, 19: 6524-6532.

Miller et al., "Improved retroviral vectors for gene transfer and expression," BioTechniques, 1989, 7(9): 980-990.

Miller, "Retrovirus packaging cells," Human Gene Therapy, 1990, 1: 5-14.

Milone et al., "Clinical use of lentiviral vectors," Leukemia, 2018, 32(7): 1529-1541.

Mok et al., "Stabilized plasmid-lipid particles: factors influencing plasmid entrapment and transfection properties," Biochimica et Biophysica Acta, 1999, 1419(2): 137-150.

Moon et al., "Recent advances in the CRISPR genome editing tool set," Exp. Mol. Med. 2019, 51(11): 130, 11 pages.

Moussa et al., "Here to stay: Writing lasting epigenetic memories," Cell, 2021, 184(9): 2281-2283.

Murphy et al., "The Transcriptional Repressive Activity of KRAB Zinc Finger Proteins Does Not Correlate with Their Ability to Recruit TRIM28," PLoS ONE, 2016, 11(9): e0163555, 19 pages.

O'Geen et al., "Determinants of heritable gene silencing for KRAB-dCas9 + DNMT3 and Ezh2-dCas9 + DNMT3 hit-and-run epigenome editing," Nucleic Acids Res, 2022, 50(6): 3239-3253.

Orth et al., "Structural basis of gene regulation by the tetracycline inducible Tet repressor-operator system," natural structural biology, 2000, 7(3): 215-219.

Park et al., "Treating cancer with genetically engineered T cells," Trends Biotechnol, 2011, 29(11): 550-557.

Peterson et al., "PCSK9 function and physiology," J. Lipid Res., 2008, 49(6): 1152-1156.

Pickar-Oliver et al., "The next generation of CRISPR-Cas technologies and applications," Nature Reviews Molecular Cell Biology, 2019, 20(8): 490-507.

Poh et al., "DNA Methyltransferase Activity Assays: Advances and Challenges," Theranostics, 2016, 6(3): 369-391.

Poirier et al., "The proprotein convertase PCSK9 induces the degradation of low density lipoprotein receptor (LDLR) and its closest family members VLDLR and ApoER2" J. Biol. Chem., 2008, 283: 2363-2372.

Policarpi et al., "Epigenetic editing: Dissecting chromatin function in context," Bioessays, 2021, 43(5): e2000316, 16 pages.

Saha et al., "The NIH Somatic Cell Genome Editing program," Nature, 2021, 592: 195-204.

Scarpa et al., "Characterization of recombinant helper retroviruses from moloney-based vectors in ecotropic and amphotropic packaging cell lines," Virology, 1991, 180: 849-852.

Schellenberger et al., "A recombinant polypeptide extends the in vivo half-life of peptides and proteins in a tunable manner," Nature Biotechnology, 2009, 27(12): 1186-1190.

Sharma et al., "Efficient Sleeping Beauty DNA Transposition From DNA Minicircles," Molec Ther Nucl Acids, 2013, 2(2): e74, 10 pages.

Stepper, "Dissertation: CRISPR-Cas9 fusions for synthetic epigenetics," Von der Fakultät 4: Energie-, Verfahrens-und Biotechnik, Institut für Biochemie und Technische Biochemie der Universität Stuttgart, 2020, 148 pages.

Thakore et al., "385. Inhibiting the Myostatin Signaling Pathway using CRISPR/Cas9-Based Repressors." Molecular Therapy 2016, 24: S153.

Tycko et al., "High-Throughput Discovery and Characterization of Human Transcriptional Effectors," Cell, 2020, 183(7): 2020-2035.

Van Tedeloo et al., "High-level transgene expression in primary human T lymphocytes and adult bone marrow CD34+ cells via electroporation-mediated gene delivery," Gene Therapy, 2000, 7(16): 1431-1437.

Verhoeyen et al., "Ch 8: Lentiviral vector gene transfer into human T cells," Methods Mol Biol, 2009, 506: 97-114.

(56) References Cited

OTHER PUBLICATIONS

Wang et al., "Phenotypic and functional attributes of lentivirus modified CD19-specific human CD8+ central memory T cells manufactured at clinical scale," J. Immunother, 2012, 35(9): 689-701.
Wright et al., "Standardized reagents and protocols for engineering zinc finger nucleases by modular assembly," Nat. Protoc., 2006, 1(3): 1637-1652.
Wright et al., "Rational design of a split-Cas9 enzyme complex," PNAS, 2015, 112(10): 2984-2989.
Zetsche et al., "A split-Cas9 architecture for inducible genome editing and transcription modulation," Nat. Biotechnol, 2015, 33(2): 139-142.
Ryu et al., "Adenine base editing in mouse embryos and an adult mouse model of Duchenne muscular dystrophy," Nature Biotechnology, 2018, 36(6): 536-539.
Rees et al., "Base editing: precision chemistry on the genome and transcriptome of living cells, " Nature Reviews Genetics, 2018, 19(12): 770-788.
Nelson et al., "Long-term evaluation of genome editing for Duchenne muscular dystrophy," Duke Presentation, 2019, 123 pages. Retrieved from the Internet: <https://static.seekingalpha.com/uploads/sa_presentations/453/41453/original.pdf>.
Young, "Development of a Therapeutic CRISPR/Cas9 Plataform for Duchenne Muscular Dystrophy," UCLA Electronic Theses and Dissertations, Jan. 1, 2018, 136 pages.
Kwon et al., "In Vivo Gene Editing of Muscle Stem Cells with Adeno-Associated Viral Vectors in a Mouse Model of Duchenne Muscular Dystrophy," Molecular Therapy, 2020, 19: 320-329.
International Search Report and Written Opinion for Application No. PCT/US2023/072524 dated Jan. 12, 2024 (10 pages).
Japanese Patent Office Action for Application No. 2021-102533 dated Dec. 7, 2023 (9 pages, English translation included).
Echevarria et al., "Exon-skipping advances for Duchenne muscular dystrophy," Human Molecular Genetics, 2018, 27 (R2): R163-R172.
Miller, "Non-viral CRISPR/Cas gene editing in vitro and in vivo enabled by synthetic nanoparticle co-delivery of Cas9 mRNA and sgRNA," Angew Chem Int Engl, 2017, 56(4): 1059-1063.
Buckingham, M et al. "The role of Pax genes in the development of tissues and organs: Pax3 and Pax7 regulate muscle progenitor cell functions." Annu. Rev. Cell Dev. Biol. 23 (2007): 645-673. (29 pages).
United States Patent Office Action for U.S. Appl. No. 16/322,234 dated Dec. 1, 2023 (29 pages).
United States Patent Office Action for U.S. Appl. No. 16/093,272 dated Dec. 29, 2023 (11 pages).
Chao et al., "Several log increase in therapeutic transgene delivery by distinct adeno-associated viral serotype vectors," (2000) Molecular Therapy 2:619.
Chen et al., "In vivo CD8+ T cell CRISPR screening reveals control by Fli1 in infection and cancer," Cell, 2021, 184(5): 1262-1280.
Corces et al., "An improved ATAC-seq protocol reduces background and enables interrogation of frozen tissues," Nature Methods. 2017, 14: 959-962.
Galletti et al., "Two subsets of stem-like CD8+ memory T cell progenitors with distinct fate commitments in humans," Nature Immunology, 2020, 21: 1552-1562.
Gao et al., "Clades of Adeno-Associated Viruses Are Widely Disseminated in Human Tissues," (2004) J. Virology 78:6381-6388.
GenBank Accession No. AF028704.1, (1998).
GenBank Accession No. AF028705.1, (1998).
GenBank Accession No. AF043303.1, (2010).
GenBank Accession No. AF063497.1, (1999).
GenBank Accession No. AF288061.1, (2001).
GenBank Accession No. AF513851.1, (2002).
GenBank Accession No. AFS13852.1, (2015).
GenBank Accession No. AH009962.2, (2016).
GenBank Accession No. AY028223.1, (2001).
GenBank Accession No. AY028226.1, (2001).
GenBank Accession No. AY530579.1, (2004).
GenBank Accession No. J01901.1, (1993).
GenBank Accession No. J02275.1, (1995).
GenBank Accession No. NC_000883.2, (2018).
GenBank Accession No. NC_001358.1, (2015).
GenBank Accession No. NC_001401, (2018).
GenBank Accession No. NC_001510.1, (2018).
GenBank Accession No. NC_001540.1, (2018).
GenBank Accession No. NC_001701.1, (2018).
GenBank Accession No. NC_001729, (2018).
GenBank Accession No. NC_001829.1, (2018).
GenBank Accession No. NC_001862.1, (2004).
GenBank Accession No. NC_001863.1, (2004).
GenBank Accession No. NC_002077, (2018).
GenBank Accession No. NC_006152.1, (2018).
GenBank Accession No. NC_006261.1, (2018).
GenBank Accession No. U89790.1, (1997).
GenBank Accession No. X01457.1, (2005).
Hao et al., "Integrated analysis of multimodal single-cell data," Cell, 2021, 184: 3573-3587.e29.
Hart et al., "Kruppel-like factors in lymphocyte biology," J Immunol, 2012, 188(2): 521-526.
Joung et al., "Transcription Factor Atlas of Directed Differentiation," Cell, 2023, 186(1): 209-229.e26.
Jung et al. "BLIMP1 and NR4A3 transcription factors reciprocally regulate antitumor CAR T cell stemness and exhaustion," Cancer Immunotherapy, 2022, 14: eabn7336.
Kaminskiy et al., "Neglected, yet significant role of FOXP1 in T-cell quiescence, differentiation and exhaustion," Front. Immunol, 2022, 13: 971045.
Krishna et al., "Stem-like CD8 T cells mediate response of adoptive cell immunotherapy against human cancer," Science, 2020, 370: 1328-1334.
Kuleshov et al., "Enrichr: a comprehensive gene set enrichment analysis web server 2016 update," Nucleic Acids Research, 2016, 44: 90-97.
Liao et al., "featureCounts: an efficient general purpose program for assigning sequence reads to genomic features," Bioinformatics, 2013, 30(7): 923-30.
Martin et al., "CCR7 Deficiency in NOD Mice Leads to Thyroiditis and Primary Hyperthyroidism," The Journal of Immunology, 2009, 183(5): 3073-3080.
Mimitou et al., "Expanding the CITE-seq tool-kit: Detection of proteins, transcriptomes, clonotypes and CRISPR perturbations with multiplexing, in a single assay," Nat. Methods, 2019, 16: 409-412.
Mori et al., "Two novel adeno-associated viruses from cynomolgus monkey: pseudotyping characterization of capsid protein," (2004) Virology 330: 375-383.
Muzyczka, "Use of adeno-associated virus as a general transduction vector for mammalian cells," (1992) Curr. Topics Microbial. Immunol. 158: 97-129.
Philip et al., "Chromatin states define tumour-specific T cell dysfunction and reprogramming," Nature, 2017, 545: 452-456.
Pritykin et al., "A unified atlas of CD8 T cell dysfunctional states in cancer and infection," Mol. Cell 2021, 81: 2477-2493.
Ramirez et al., "deepTools: a flexible platform for exploring deep-sequencing data," Nucleic Acids Research, 2014, 42:W187-91.
Schubert et al., "Autosomal dominant immune dysregulation syndrome in humans with CTLA4 mutations," Nature Medicine, 2014, 20(2): 1410-1416.
Sen et al., "The epigenetic landscape of T cell exhaustion," Science, 2016, 354(6316): 1165-1169.
Vojta et al., "Repurposing the CRISPR-Cas9 system for targeted DNA methylation," Nucleic Acids Research, 2016, 44(12): 5615-5628.
Wherry et al., "Molecular Signature of CD8+ T Cell Exhaustion during Chronic Viral Infection," Immunity, 2007, 27(4): 670-684.
Woolf et al., "Runx3 and Runx1 are required for CD8 T cell development during thymopoiesis," PNAS, 2003, 100(13): 7731-7736.

(56) References Cited

OTHER PUBLICATIONS

Yang et al., "The transcriptional regulators Id2 and Id3 control the formation of distinct memory CD8+ T cell subsets," Nat Immunol, 2011, 12: 1221-1229.

Yu et al., "ChIPseeker: an R/Bioconductor package for ChIP peak annotation, comparison and visualization," Bioinformatics, 2015, 31(14): 2382-2383.

Yuan et al., "Genetic Modulation of RNA Splicing with a CRISPR-Guided Cytidine Deaminase," Molecular Cell, 2018, 72(2): 380-394.

Zhang et al., "Model-based analysis of ChIP-Seq (MACS)," Genome Biology, 2008, 9(9): R137.

Zheng et al., "Landscape of Infiltrating T Cells in Liver Cancer Revealed by Single-Cell Sequencing," Cell, 2017, 169: 1342-1356.

International Search Report and Written Opinion for Application No. PCT/US2023/078124 dated May 29, 2024 (15 pages).

United States Patent Office Action for U.S. Appl. No. 16/322,234 dated Apr. 22, 2024 (23 pages).

United States Patent Office Action for U.S. Appl. No. 18/405,995 dated Jun. 13, 2024 (12 pages).

Bulcha et al., "Viral vector platforms within the gene therapy landscape," Signal Transduction and Targeted Therapy, 2021, 6: 53.

Duchêne et al., "CRISPR-Induced Deletion with SaCas Restores Dystrophin Expression in Dystrophic Models In Vitro and In Vivo," Molecular Therapy: The Journal of the American Society of Gene Therapy, 2018, 26(11): 2604-2616.

Hideki et al., Geneseq Accession No. BFK30060, 2018. U.S. Appl. No. 16/963,034, U.S. Patent Office Action dated Jun. 27, 2024.

Kotterman et al., "Engineering adeno-associated viruses for clinical gene therapy," Nature Reviews, 2014, 15(7): 445-451.

Lenzi et al., "Oversight and Review of Clinical Gene Transfer Protocols: Assessing the Role of the Recombinant DNA Advisory Committee," NCBI Bookshelf, A Service of the National Library of Medicine, National Institute of Health, Washington, DC, National Academies Press, US, 2014, pp. 1-16.

Liao, "Targeted disruption of DNMT1, DNMT3A and DNMT3B in human embryonic stem cells," Nature Genetics, 2015, 47(5): 469-478.

Long et al., "Correction of Diverse Muscular Dystrohpy Mutations in Human Engineered Heart Muscle by Single-Site Genome Editing," Sci Adv, 2018, 4(1): eaap9004.

Maggio et al., "Adenoviral vectors encoding CRISPR/Cas9 multiplexes rescue dystrophin synthesis in unselected populations of DMD muscle cells," Scientific Reports, 2016, 6: 37051.

Shim et al., "Nonviral Delivery Systems for Cancer Gene Therapy: Strategies and Challenges," Current Gene Therapy, 2017, 17(5): 1-18.

Swiech et al., "In vivo interrogation of gene function in the mammalian brain using CRISPR-Cas9," Nature Biotechnology, 2014, 33(1): 102-106 (Supplementary Information included).

Thule et al., "Engineered Insulin Secretion in Human Primary Thyroid Cells," Molecular Therapy, 2012, 20(Supplement 1): S164, Article 421.

Liu et al., "A CRISPR-Cas9 Strategy for Activating the Saccharopolyspora erythraea Erythromyscin Biosynthetic Gene Cluster with Knock-in Bidirectional Promoters," ACS Synth. Biol. 2019, 8(5): 1134-1143.

Miyazaki et al., "Characterization of deletion breakpoints in patients with dystrophinopathy carrying a deletion of exons 45-55 of the Duchenne muscular dystrophy (DMD) gene," Journal of Human Genetics, 2009, 54: 127-130.

Razzouk, "CRISPR-Cas9: A cornerstone for the evolution of precision medicine," Annal of Human Genetics, 2018, 82(6): 331-357.

Simeonov et al., "Discovery of stimulation-responsive immune enhancers with CRISPR activation," Nature, 2018, 549(7670): 111-115.

United State Patent Office Action for U.S. Appl. No. 18/405,995 dated Sep. 24, 2024 (12 pages).

United States Patent Office Action for U.S. Appl. No. 16/322,234 dated Oct. 15, 2024 (23 pages).

\* cited by examiner

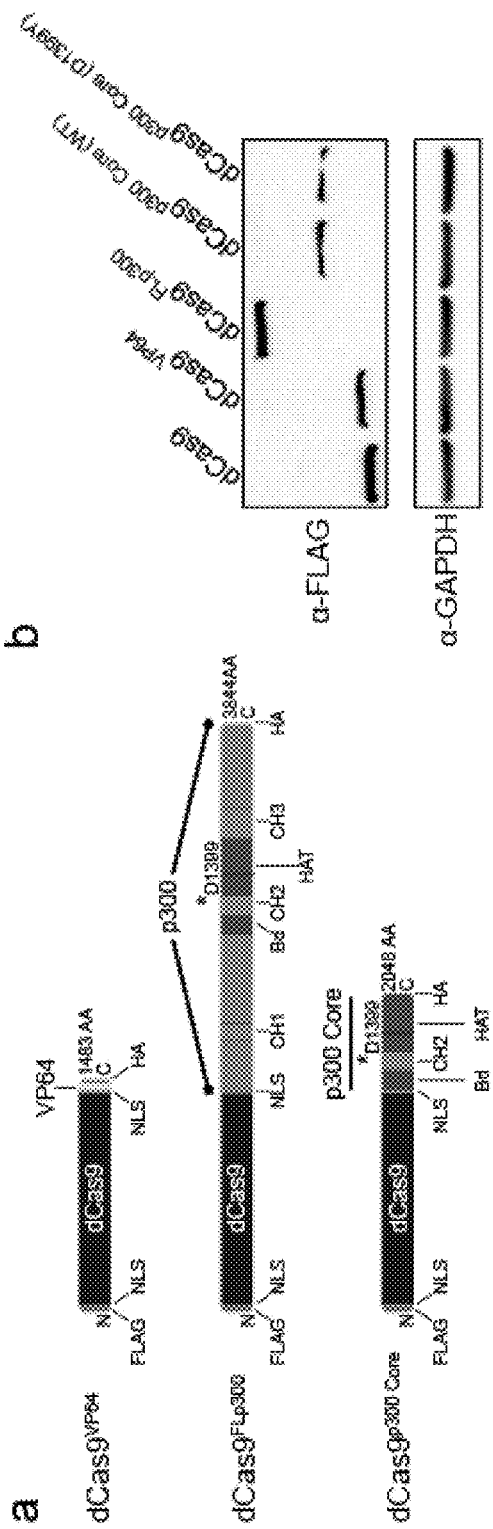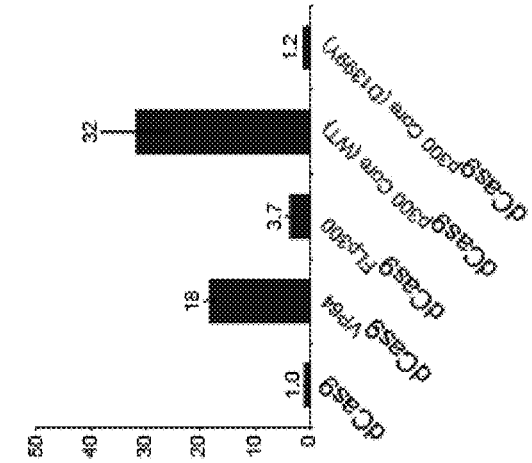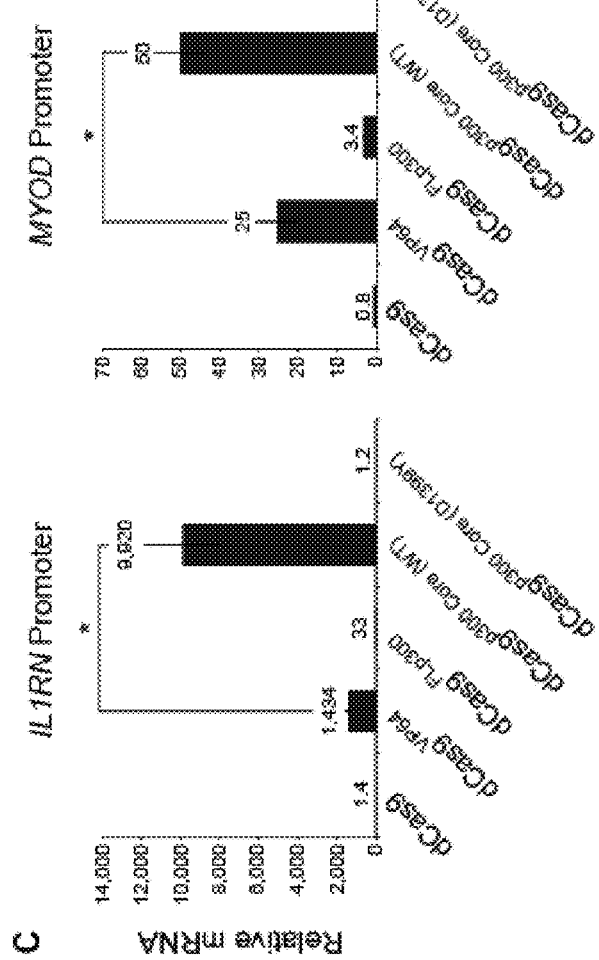
FIG. 1A
FIG. 1B
FIG. 1C

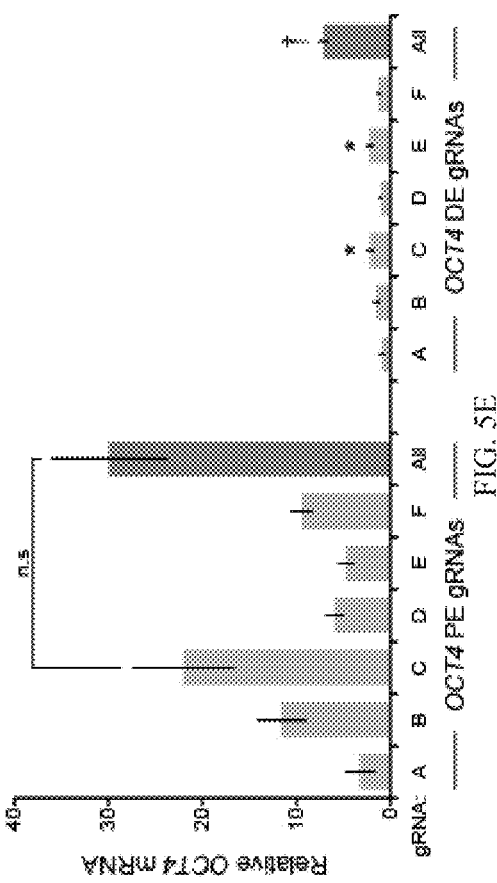
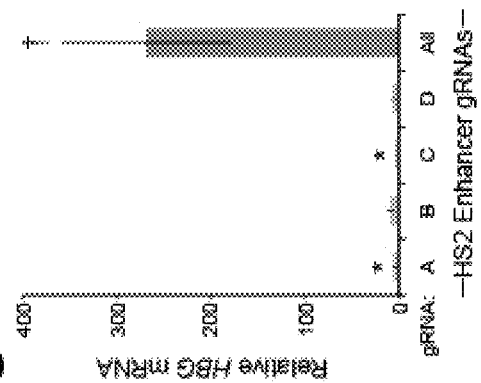
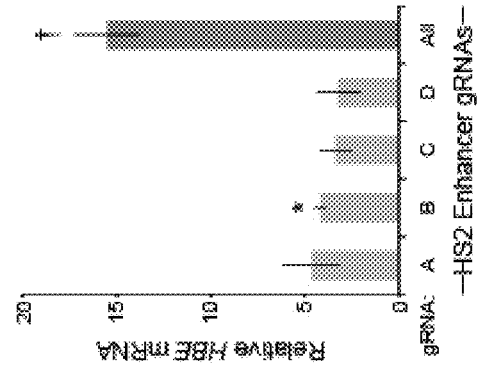
FIG. 5E
FIG. 5F
FIG. 5G

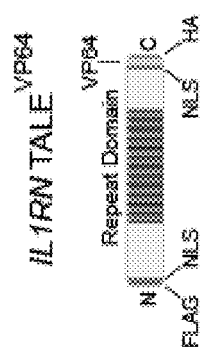
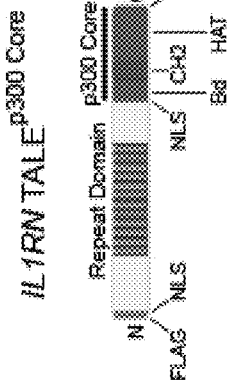
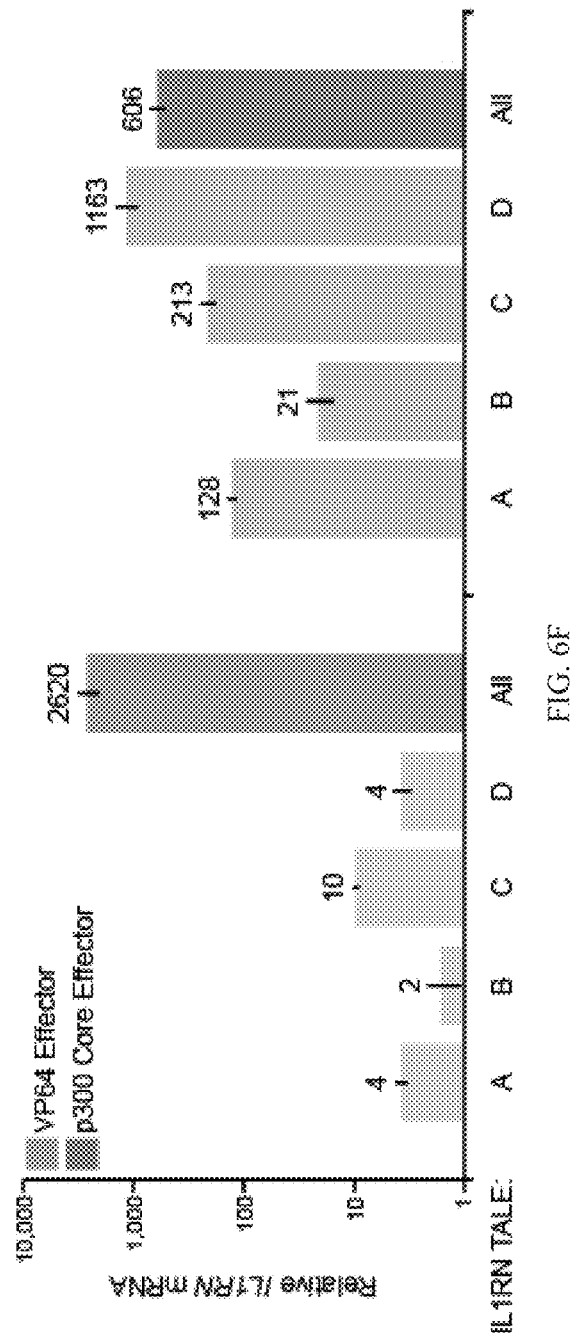
FIG. 6E
FIG. 6F

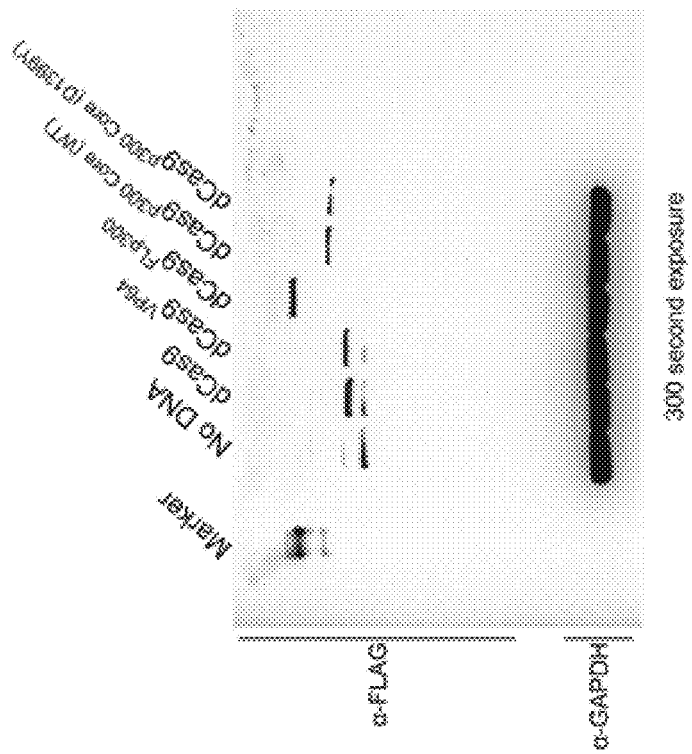
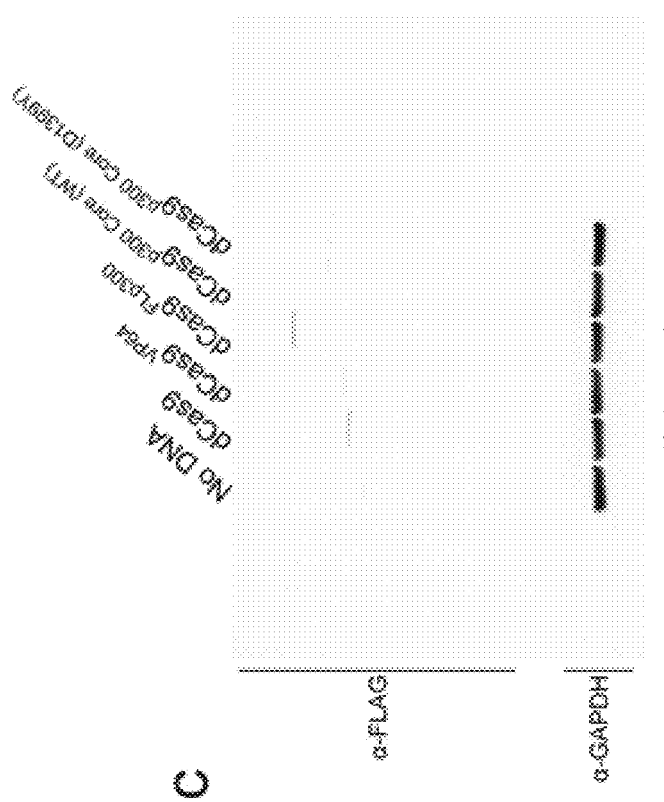
FIG. 7C

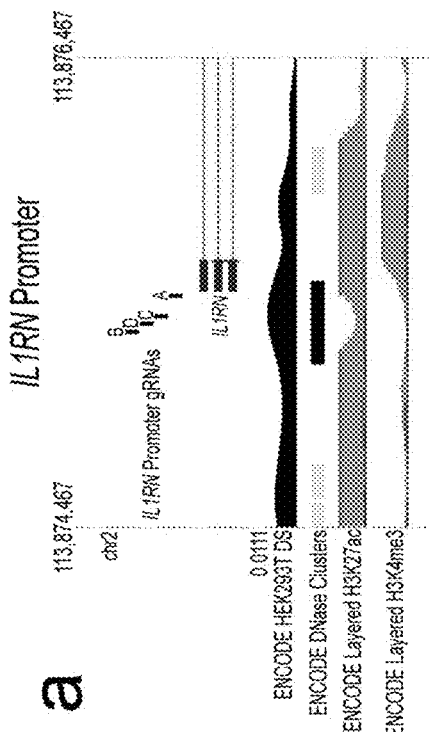
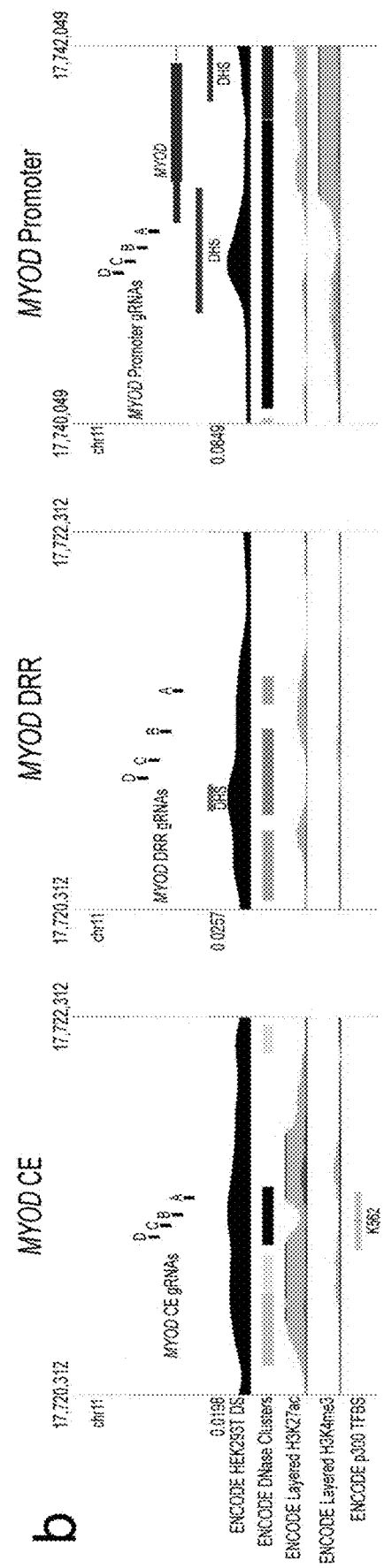
FIG. 14A
FIG. 14B

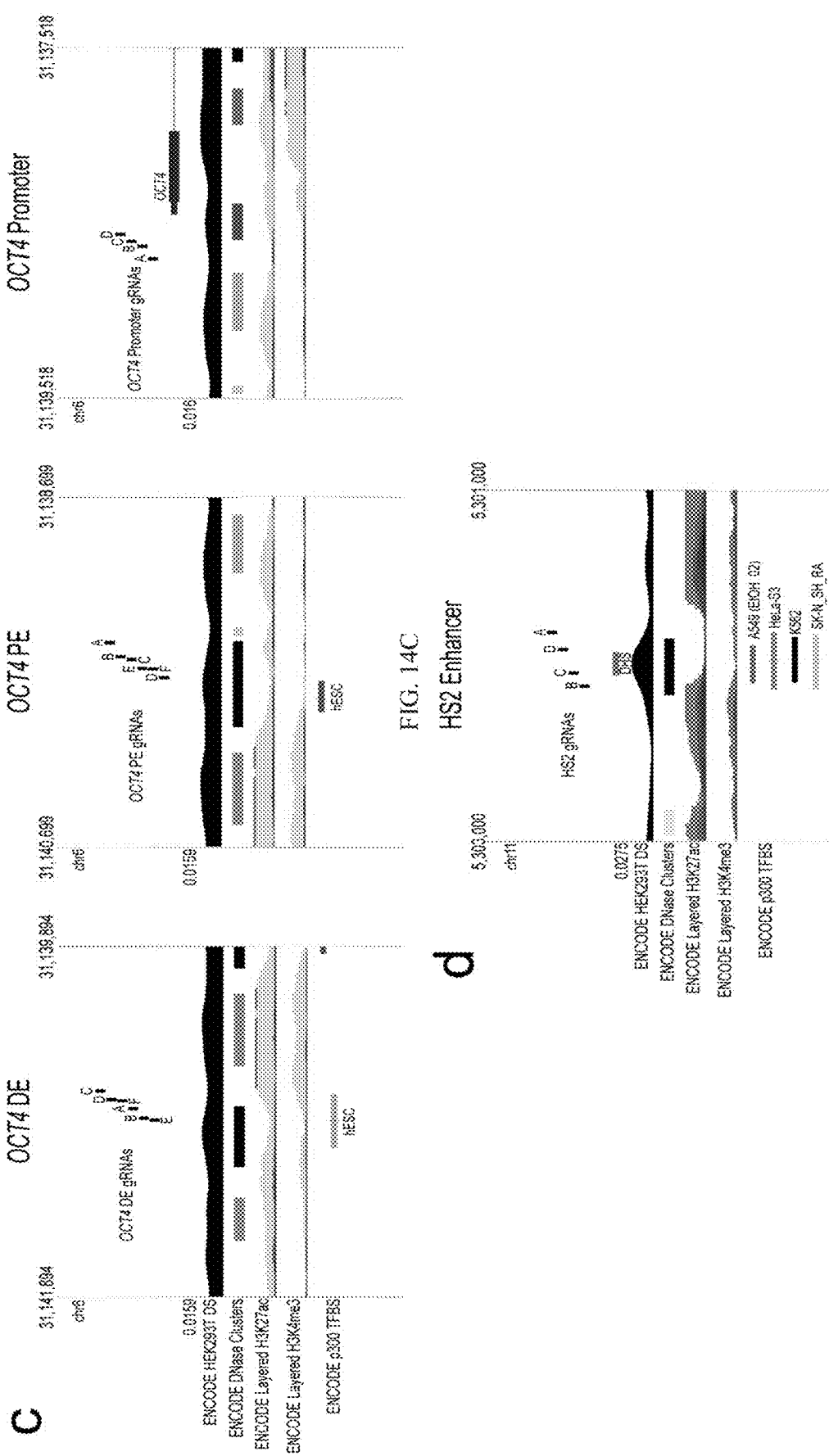

| gRNA-Targeted Locus | Overlap DHS in HEK293T | Overlap DHS in Other ENCODE Lines | Multiple gRNAs Required for Maximal dCas9$^{SunTag\ Core}$ Target Activation | Overlap Endogenous p300 in ENCODE Lines |
|---|---|---|---|---|
| IL1RN Promoter | N | Y | N | N |
| MYOD CE | N | Y | N | Y |
| MYOD DRR | Marginal | Y | N | N |
| MYOD Promoter | N | Y | N | N |
| OCT4 DE | N | Y | Y | Y |
| OCT4 PE | N | Y | N | Marginal |
| OCT4 Promoter | N | Y | N | N |
| HS2 Enhancer | Y | Y | Y | Y |

FIG. 14E dCas9 HA: (Addgene plasmid 61355) amino acid sequence:  Nuclear Localization Sequence, *Streptococcus pyogenes* Cas9 (D10A, H840A), "HA" Epitope (SEQ ID NO: 138)

MAPKKKRKVGRGMDKKYSIGLAIDTNSVGWAVITDEYKVPSKKFKVLGNTDRHSIKKNLIGALLFDSGETAEATRLKRTARRR
YTRRKNRICYLQEIFSNEMAKVDDSFFHRLEESFLVEEDKKHERHPIFGNIVDEVAYHEKYPTIYHLRKKLVDSTDKADLRLIYLALAHMIKFRGHFLIEGDLNPDNSDV
DKLFIQLVQTYNQLFEENPINASGVDAKAILSARLSKSRRLENLIAQLPGEKKNGLFGNLIALSLGLTPNFKSNFDLAEDAKLQLSKDTYDDDLDNLLAQIGDQYADL
FLAAKNLSDAILLSDILRVNTEITKAPLSASMIKRYDEHHQDLTLLKALVRQQLPEKYKEIFFDQSKNGYAGYIDGGASQEEFYKFIKPILEKMDGTEELLVKLNREDLL
RKQRTFDNGSIPHQIHLGELHAILRRQEDFYPFLKDNREKIEKILTFRIPYYVGPLARGNSRFAWMTRKSEETITPWNFEEVVDKGASAQSFIERMTNFDKNLPNEKVL
PKHSLLYEYFTVYNELTKVKYVTEGMRKPAFLSGEQKKAIVDLLFKTNRKVTVKQLKEDYFKKIECFDSVEISGVEDRFNASLGTYHDLLKIIKDKDFLDNEENEDILE
DIVLTLTLFEDREMIEERLKTYAHLFDDKVMKQLKRRRYTGWGRLSRKLINGIRDKQSGKTILDFLKSDGFANRNFMQLIHDDSLTFKEDIQKAQVSGQGDSLHEHIA
NLAGSPAIKKGILQTVKVVDELVKVMGRHKPENIVIEMARENQTTQKGQKNSRERMKRIEEGIKELGSQILKEHPVENTQLQNEKLYLYYLQNGRDMYVDQELDINR
LSDYDVDAIVPQSFLKDDSIDNKVLTRSDKNRGKSDNVPSEEVVKKMKNYWRQLLNAKLITQRKFDNLTKAERGGLSELDKAGFIKRQLVETRQITKHVAQILDSRM
NTKYDENDKLIREVKVITLKSKLVSDFRKDFQFYKVREINNYHHAHDAYLNAVVGTALIKKYPKLESEFVYGDYKVYDVRKMIAKSEQEIGKATAKYFFYSNIMNFFKT
EITLANGEIRKRPLIETNGETGEIVWDKGRDFATVRKVLSMPQVNIVKKTEVQTGGFSKESILPKRNSDKLIARKKDWDPKKYGGFDSPTVAYSVLVVAKVEKGKSK
KLKSVKELLGITIMERSSFEKNPIDFLEAGKYGYKEVKKDLIIKLPKYSLFELENGRKRMLASAGELQKGNELALPSKYVNFLYLASHYEKLKGSPEDNEQKQLFVEQHK
HYLDEIIEQISEFSKRVILADANLDKVLSAYNKHRDKPIREQAENIIHLFTLTNLGAPAAFKYFDTTIDRKRYTSTKEVLDATLIHQSITGLYETRIDLSQLGGDPIAGSKAS
PKKKRKVGRALINYPYDVPDYAS dCas9VP64: (Addgene Plasmid 47107)4 amino acid sequence:  Nuclear Localization Sequence, *Streptococcus pyogenes* Cas9 (D10A, H840A), "HA" Epitope (SEQ ID NO: 139)

MAPKKKRKVGRGMDKKYSIGLAIDTNSVGWAVITDEYKVPSKKFKVLGNTDRHSIKKNLIGALLFDSGETAEATRLKRTARRR
YTRRKNRICYLQEIFSNEMAKVDDSFFHRLEESFLVEEDKKHERHPIFGNIVDEVAYHEKYPTIYHLRKKLVDSTDKADLRLIYLALAHMIKFRGHFLIEGDLNPDNSDV
DKLFIQLVQTYNQLFEENPINASGVDAKAILSARLSKSRRLENLIAQLPGEKKNGLFGNLIALSLGLTPNFKSNFDLAEDAKLQLSKDTYDDDLDNLLAQIGDQYADL
FLAAKNLSDAILLSDILRVNTEITKAPLSASMIKRYDEHHQDLTLLKALVRQQLPEKYKEIFFDQSKNGYAGYIDGGASQEEFYKFIKPILEKMDGTEELLVKLNREDLL
RKQRTFDNGSIPHQIHLGELHAILRRQEDFYPFLKDNREKIEKILTFRIPYYVGPLARGNSRFAWMTRKSEETITPWNFEEVVDKGASAQSFIERMTNFDKNLPNEKVL
PKHSLLYEYFTVYNELTKVKYVTEGMRKPAFLSGEQKKAIVDLLFKTNRKVTVKQLKEDYFKKIECFDSVEISGVEDRFNASLGTYHDLLKIIKDKDFLDNEENEDILE
DIVLTLTLFEDREMIEERLKTYAHLFDDKVMKQLKRRRYTGWGRLSRKLINGIRDKQSGKTILDFLKSDGFANRNFMQLIHDDSLTFKEDIQKAQVSGQGDSLHEHIA
NLAGSPAIKKGILQTVKVVDELVKVMGRHKPENIVIEMARENQTTQKGQKNSRERMKRIEEGIKELGSQILKEHPVENTQLQNEKLYLYYLQNGRDMYVDQELDINR
LSDYDVDAIVPQSFLKDDSIDNKVLTRSDKNRGKSDNVPSEEVVKKMKNYWRQLLNAKLITQRKFDNLTKAERGGLSELDKAGFIKRQLVETRQITKHVAQILDSRM
NTKYDENDKLIREVKVITLKSKLVSDFRKDFQFYKVREINNYHHAHDAYLNAVVGTALIKKYPKLESEFVYGDYKVYDVRKMIAKSEQEIGKATAKYFFYSNIMNFFKT
EITLANGEIRKRPLIETNGETGEIVWDKGRDFATVRKVLSMPQVNIVKKTEVQTGGFSKESILPKRNSDKLIARKKDWDPKKYGGFDSPTVAYSVLVVAKVEKGKSK
KLKSVKELLGITIMERSSFEKNPIDFLEAGKYGYKEVKKDLIIKLPKYSLFELENGRKRMLASAGELQKGNELALPSKYVNFLYLASHYEKLKGSPEDNEQKQLFVEQHK
HYLDEIIEQISEFSKRVILADANLDKVLSAYNKHRDKPIREQAENIIHLFTLTNLGAPAAFKYFDTTIDRKRYTSTKEVLDATLIHQSITGLYETRIDLSQLGGDPIAGSKAS
PKKKRKVGRAINYPYDVPDYAS

FIG. 15A

FIG. 15B dCas9p300 Core: (Addgene Plasmid 61357) amino acid sequence; Nuclear Localization Sequence, *Streptococcus pyogenes* Cas9 (D10A, H840A), "HA" Epitope (SEQ ID NO: 141)

MAPKKKRKVGMDKKYSIGLAIGTNSVGWAVITDEYKVPSKKFKVLGNTDRHSIKKNLIGALLFDSGETAEATRLKRTARRRY
TRRKNRICYLQEIFSNEMAKVDDSFFHRLEESFLVEEDKKHERHPIFGNIVDEVAYHEKYPTIYHLRKKLVDSTDKADLRLIYLALAHMIKFRGHFLIEGDLNPDNSDVD
KLFIQLVQTYNQLFEENPINASGVDAKAILSARLSKSRRLENLIAQLPGEKKNGLFGNLIALSLGLTPNFKSNFDLAEDAKLQLSKDTYDDDLDNLLAQIGDQYADLFL
AAKNLSDAILLSDILRVNTEITKAPLSASMIKRYDEHHQDLTLLKALVRQQLPEKYKEIFFDQSKNGYAGYIDGGASQEEFYKFIKPILEKMDGTEELLVKLNREDLLRK
QRTFDNGSIPHQIHLGELHAILRRQEDFYPFLKDNREKIEKILTFRIPYYVGPLARGNSRFAWMTRKSEETITPWNFEEVVDKGASAQSFIERMTNFDKNLPNEKVLPK
HSLLYEYFTVYNELTKVKYVTEGMRKPAFLSGEQKKAIVDLLFKTNRKVTVKQLKEDYFKKIECFDSVEISGVEDRFNASLGTYHDLLKIIKDKDFLDNEENEDILEDIVL
TLTLFEDREMIEERLKTYAHLFDDKVMKQLKRRRYTGWGRLSRKLINGIRDKQSGKTILDFLKSDGFANRNFMQLIHDDSLTFKEDIQKAQVSGQGDSLHEHIANLAG
SPAIKKGILQTVKVVDELVKVMGRHKPENIVIEMARENQTTQKGQKNSRERMKRIEEGIKELGSQILKEHPVENTQLQNEKLYLYYLQNGRDMYVDQELDINRLSDYD
VDAIVPQSFLKDDSIDNKVLTRSDKNRGKSDNVPSEEVVKKMKNYWRQLLNAKLITQRKFDNLTKAERGGLSELDKAGFIKRQLVETRQITKHVAQILDSRMNTKYDE
NDKLIREVKVITLKSKLVSDFRKDFQFYKVREINNYHHAHDAYLNAVVGTALIKKYPKLESEFVYGDYKVYDVRKMIAKSEGQGKATAKYFFYSNIMNFFKTEITLANG
EIRKRPLIETNGETGEIVWDKGRDFATVRKVLSMPQVNIVKKTEVQTGGFSKESILPKRNSDKLIARKKDWDPKKYGGFDSPTVAYSVLVVAKVEKGKSKKLKSVKEL
LGITIMERSSFEKNPIDFLEAKGYKEVKKDLIIKLPKYSLFELENGRKRMLASAGELQKGNELALPSKYVNFLYLASHYEKLKGSPEDNEQKQLFVEQHKHYLDEIIEQI
SEFSKRVILADANLDKVLSAYNKHRDKPIREQAENIIHLFTLTNLGAPAAFKYFDTTIDRKRYTSTKEVLDATLIHQSITGLYETRIDLSQLGGDPIAGSKASPKKKRKVG
RA
YPYDVPDYAS

FIG. 15C dCasgp380 Core (D1399Y), (Addgene Plasmid 61358) amino acid sequence; Nuclear Localization Sequence, *Streptococcus pyogenes* Cas9 (D10A, H840A), D1399Y, "HA" Epitope (SEQ ID NO: 142)

MAPKKKRKVGRGMDKKYSIGLAIGTNSVGWAVITDEYKVPSKKFKVLGNTDRHSIKKNLIGALLFDSGETAEATRLKRTARRRY
TRRKNRICYLQEIFSNEMAKVDDSFFHRLEESFLVEEDKKHERHPIFGNIVDEVAYHEKYPTIYHLRKKLVDSTDKADLRLIYLALAHMIKFRGHFLIEGDLNPDNSDVD
KLFIQLVQTYNQLFEENPINASGVDAKAILSARLSKSRRLENLIAQLPGEKKNGLFGNLIALSLGLTPNFKSNFDLAEDAKLQLSKDTYDDDLDNLLAQIGDQYADLFL
AAKNLSDAILLSDILRVNTEITKAPLSASMIKRYDEHHQDLTLLKALVRQQLPEKYKEIFFDQSKNGYAGYIDGGASQEEFYKFIKPILEKMDGTEELLVKLNREDLLRK
QRTFDNGSIPHQIHLGELHAILRRQEDFYPFLKDNREKIEKILTFRIPYYVGPLARGNSRFAWMTRKSEETITPWNFEEVVDKGASAQSFIERMTNFDKNLPNEKVLPK
HSLLYEYFTVYNELTKVKYVTEGMRKPAFLSGEQKKAIVDLLFKTNRKVTVKQLKEDYFKKIECFDSVEISGVEDRFNASLGTYHDLLKIIKDKDFLDNEENEDILEDIVL
TLTLFEDREMIEERLKTYAHLFDDKVMKQLKRRRYTGWGRLSRKLINGIRDKQSGKTILDFLKSDGFANRNFMQLIHDDSLTFKEDIQKAQVSGQGDSLHEHIANLAG
SPAIKKGILQTVKVVDELVKVMGRHKPENIVIEMARENQTTQKGQKNSRERMKRIEEGIKELGSQILKEHPVENTQLQNEKLYLYYLQNGRDMYVDQELDINRLSDYD
VDAIVPQSFLKDDSIDNKVLTRSDKNRGKSDNVPSEEVVKKMKNYWRQLLNAKLITQRKFDNLTKAERGGLSELDKAGFIKRQLVETRQITKHVAQILDSRMNTKYD
ENDKLIREVKVITLKSKLVSDFRKDFQFYKVREINNYHHAHDAYLNAVVGTALIKKYPKLESEFVYGDYKVYDVRKMIAKSEQEIGKATAKYFFYSNIMNFFKTEITLAN
GEIRKRPLIETNGETGEIVWDKGRDFATVRKVLSMPQVNIVKKTEVQTGGFSKESILPKRNSDKLIARKKDWDPKKYGGFDSPTVAYSVLVVAKVEKGKSKKLKSVK
ELLGITIMERSSFEKNPIDFLEAKGYKEVKKDLIIKLPKYSLFELENGRKRMLASAGELQKGNELALPSKYVNFLYLASHYEKLKGSPEDNEQKQLFVEQHKHYLDEIIE
QISEFSKRVILADANLDKVLSAYNKHRDKPIREQAENIIHLFTLTNLGAPAAFKYFDTTIDRKRYTSTKEVLDATLIHQSITGLYETRIDLSQLGGDPIAGSKASPKKKRKV
GRA YPYDVPDYAS

FIG. 15D dCasp9p300 Core (1645/1646 RR/EE); (Addgene Plasmid 61359) amino acid sequence; Nuclear Localization Sequence, *Streptococcus pyogenes* Cas9 (D10A, H840A), 1645/1646 RR/EE "HA" Epitope (SEQ ID NO: 143)

MAPKKKRKVGRGMDKKYSIGLAIGTNSVGWAVITDEYKVPSKKFKVLGNTDRHSIKKNLIGALLFDSGETAEATRLKRTARRRY
TRRKNRICYLQEIFSNEMAKVDDSFFHRLEESFLVEEDKKHERHPIFGNIVDEVAYHEKYPTIYHLRKKLVDSTDKADLRLIYLALAHMIKFRGHFLIEGDLNPDNSDVD
KLFIQLVQTYNQLFEENPINASGVDAKAILSARLSKSRRLENLIAQLPGEKKNGLFGNLIALSLGLTPNFKSNFDLAEDAKLQLSKDTYDDDLDNLLAQIGDQYADLFLA
AKNLSDAILLSDILRVNTEITKAPLSASMIKRYDEHHQDLTLLKALVRQQLPEKYKEIFFDQSKNGYAGYIDGGASQEEFYKFIKPILEKMDGTEELLVKLNREDLLRKQ
RTFDNGSIPHQIHLGELHAILRRQEDFYPFLKDNREKIEKILTFRIPYYVGPLARGNSRFAWMTRKSEETITPWNFEEVVDKGASAQSFIERMTNFDKNLPNEKVLPKHS
LLYEYFTVYNELTKVKYVTEGMRKPAFLSGEQKKAIVDLLFKTNRKVTVKQLKEDYFKKIECFDSVEISGVEDRFNASLGTYHDLLKIIKDKDFLDNEENEDILEDIVLTL
TLFEDREMIEERLKTYAHLFDDKVMKQLKRRRYTGWGRLSRKLINGIRDKQSGKTILDFLKSDGFANRNFMQLIHDDSLTFKEDIQKAQVSGQGDSLHEHIANLAGSP
AIKKGILQTVKVVDELVKVMGRHKPENIVIEMARENQTTQKGQKNSRERMKRIEEGIKELGSQILKEHPVENTQLQNEKLYLYYLQNGRDMYVDQELDINRLSDYDVD
AIVPQSFLKDDSIDNKVLTRSDKNRGKSDNVPSEEVVKKMKNYWRQLLNAKLITQRKFDNLTKAERGGLSELDKAGFIKRQLVETRQITKHVAQILDSRMNTKYDEHD
KLIREVKVITLKSKLVSDFRKDFQFYKVREINNYHHAHDAYLNAVVGTALIKKYPKLESEFVYGDYKVYDVRKMIAKSEQEIGKATAKYFFYSNIMNFFKTEITLANGEIR
KRPLIETNGETGEIVWDKGRDFATVRKVLSMPQVNIVKKTEVQTGGFSKESILPKRNSDKLIARKKDWDPKKYGGFDSPTVAYSVLVVAKVEKGKSKKLKSVKELLGI
TIMERSSFEKNPIDFLEAKGYKEVKKDLIIKLPKYSLFELENGRKRMLASAGELQKGNELALPSKYVNFLYLASHYEKLKGSPEDNEQKQLFVEQHKHYLDEIIEQISE
FSKRVILADANLDKVLSAYNKHRDKPIREQAENIIHLFTLTNLGAPAAFKYFDTTIDRKRYTSTKEVLDATLIHQSITGLYETRIDLSQLGGDPIAGSKASPKKKRKVGRA

EE

YPYDVPDYAS

FIG. 15E dCasgp300 Core (C1204R); (Addgene Plasmid 61361) amino acid sequence; ▓▓▓ Nuclear Localization Sequence, *Streptococcus pyogenes* Cas9 (D10A, H840A), C1204R, "HA" Epitope (SEQ ID NO: 144)

MAPKKKRKVGRGMDKKYSIGLAIGTNSVGWAVITDEYKVPSKKFKVLGNTDRHSIKKNLIGALLFDSGETAEATRLKRTARRR
YTRRKNRICYLQEIFSNEMAKVDDSFFHRLEESFLVEEDKKHERHPIFGNIVDEVAYHEKYPTIYHLRKKLVDSTDKADLRLIYLALAHMIKFRGHFLIEGDLNPDNSDV
DKLFIQLVQTYNQLFEENPINASGVDAKAILSARLSKSRRLENLIAQLPGEKKNGLFGNLIALSLGLTPNFKSNFDLAEDAKLQLSKDTYDDDLDNLLAQIGDQYADL
FLAAKNLSDAILLSDILRVNTEITKAPLSASMIKRYDEHHQDLTLLKALVRQQLPEKYKEIFFDQSKNGYAGYIDGGASQEEFYKFIKPILEKMDGTEELLVKLNREDLL
RKQRTFDNGSIPHQIHLGELHAILRRQEDFYPFLKDNREKIEKILTFRIPYYVGPLARGNSRFAWMTRKSEETITPWNFEEVVDKGASAQSFIERMTNFDKNLPNEKVL
PKHSLLYEYFTVYNELTKVKYVTEGMRKPAFLSGEQKKAIVDLLFKTNRKVTVKQLKEDYFKKIECFDSVEISGVEDRFNASLGTYHDLLKIIKDKDFLDNEENEDIE
DIVLTLTLFEDREMIEERLKTYAHLFDDKVMKQLKRRRYTGWGRLSRKLINGIRDKQSGKTILDFLKSDGFANRNFMQLIHDDSLTFKEDIQKAQVSGQGDSLHEHIA
NLAGSPAIKKGILQTVKVVDELVKVMGRHKPENIVIEMARENQTTQKGQKNSRERMKRIEEGIKELGSQILKEHPVENTQLQNEKLYLYYLQNGRDMYVDQELDINR
LSDYDVDAIVPQSFLKDDSIDNKVLTRSDKNRGKSDNVPSEEVVKKMKNYWRQLLNAKLITQRKFDNLTKAERGGLSELDKAGFIKRQLVETRQITKHVAQILDSRM
NTKYDENDKLIREVKVITLKSKLVSDFRKDFQFYKVREINNYHHAHDAYLNAVVGTALIKKYPKLESEFVYGDYKVYDVRKMIAKSEQEIGKATAKYFFYSNIMNFFKT
EITLANGEIRKRPLIETNGETGEIVWDKGRDFATVRKVLSMPQVNIVKKTEVQTGGFSKESILPKRNSDKLIARKKDWDPKKYGGFDSPTVAYSVLVVAKVEKGKSK
KLKSVKELLGITIMERSSFEKNPIDFLEAKGYKEVKKDLIIKLPKYSLFELENGRKRMLASAGELQKGNELALPSKYVNFLYLASHYEKLKGSPEDNEQKQLFVECHK
HYLDEIIEGISEFSKRVILADANLDKVLSAYNKHRDKPIREQAENIIHLFTLTNLGAPAAFKYFDTTIDRKRYTSTKEVLDATLIHQSITGLYETRIDLSQLGGD PIAGSKAS
PKKKRKVGRA                                                                                    YPYDVPDYAS

FIG. 15F dCas9d300 Core (Y1467F); (Addgene Plasmid 61362) amino acid sequence; ▒▒▒▒▒▒▒ Nuclear Localization Sequence, *Streptococcus pyogenes* Cas9 (D10A, H840A), Y1467F, "HA" Epitope (SEQ ID NO: 145)

MDKKYSIGLDIGTNSVGWAVITDEYKVPSKKFKVLGNTDRHSIKKNLIGALLFDSGETAEATRLKRTARR
RYTRRKNRICYLQEIFSNEMAKVDDSFFHRLEESFLVEEDKKHERHPIFGNIVDEVAYHEKYPTIYHLRKKL
VDSTDKADLRLIYLALAHMIKFRGHFLIEGDLNPDNS
DVDKLFIQLVQTYNQLFEENPINASGVDAKAILSARLSKSRRLENLIAQLPGEKKNGLFGNLIALSLGLTPNFK
SNFDLAEDAKLQLSKDTYDDDLDNLLAQIGDQY
ADLFLAAKNLSDAILLSDILRVNTEITKAPLSASMIKRYDEHHQDLTLLKALVRQQLPEKYKEIFFDQSKNG
YAGYIDGGASQEEFYKFIKPILEKMDGTEELLVKLNR
EDLLRKQRTFDNGSIPHQIHLGELHAILRRQEDFYPFLKDNREKIEKILTFRIPYYVGPLARGNSRFAWMTRKSEETITPWNFEEVVDKGASAQSFIERMTNFDKNLP
NEKVLPKHSLLYEYFTVYNELTKVKYVTEGMRKPAFLSGEQKKAIVDLLFKTNRKVTVKQLKEDYFKKIEC
FDSVEISGVEDRFNASLGTYHDLLKIIKDKDFLDNEE
NEDILEDIVLTLTLFEDREMIEERLKTYAHLFDDKVMKQLKRRRYTGWGRLSRKLINGIRDKQSGKTILDFLK
SDGFANRNFMQLIHDDSLTFKEDIQKAQVSGQGD
SLHEHIANLAGSPAIKKGILQTVKVVDELVKVMGRHKPENIVIEMARENQTTQKGQKNSRERMKRIEEGIKELGSQILKEHPVENTQLQNEKLYLYYLQNGRDMYVD
QELDINRLSDYDVDAIVPQSFLKDDSIDNKVLTRSDKNRGKSDNVPSEEVVKKMKNYWRQLLNAKLITQRKFDNLTKAERGGLSELDKAGFIKRQLVETRQITKHV
AQILDSRMNTKYDENDKLIREVKVITLKSKLVSDFRKDFQFYKVREINNYHHAHDAYLNAVVGTALIKKYPK
LESEFVYGDYKVYDVRKMIAKSEQEIGKATAKYFF
YSNIMNFFKTEITLANGEIRKRPLIETNGETGEIVWDKGRDFATVRKVLSMPQVNIVKKTEVQTGGFSNESILPKRNSDKLIARKKDWDPKKYGGFDSPTVAYSVLV
VAKVEKGKSKKLKSVKELLGITIMERSSFEKNPIDFLEAKGYKEVKKDLIIKLPKYSLFELENGRKRMLASAGELQKGNELALPSKYVNFLYLASHYEKLKGSPEDN
EQKQLFVEQHKHYLDEIIEQISEFSKRVILADANLDKVLSAYNKHRDKPIREQAENIHLFTLTNLGAPAAFKYFDTTIDRKRYTSTKEVLDATLIHQSITGLYETRIDLS
QLGGDPIAGSKASPKKKRKVGRA▒▒▒▒▒▒▒▒▒▒▒▒▒▒

YPYDVPDYAS

FIG. 15G dCas9p300 Core(1396/1397 SY/WW): (Addgene Plasmid 61363) amino acid sequence; Nuclear Localization Sequence, *Streptococcus pyogenes* Cas9 (D10A, H840A), 1396/1397 SY/WW, "HA" Epitope (SEQ ID NO: 146)

MAPKKKRKVGRGMDKKYSIGLAIGTNSVGWAVITDEYKVPSKKFKVLGNTDRHSIKKNLIGALLFDSGETAEATRLKRTARR
RYTRRKNRICYLQEIFSNEMAKVDDSFFHRLEESFLVEEDKKHERHPFIGNIVDEVAYHEKYPTIYHLRKKLVDSTDKADLRLIYLALAHMIKFRGHFLIEGDLNPDNS
DVDKLFIQLVQTYNQLFEENPINASGVDAKAILSARLSKSRRLENLIAQLPGEKKNGLFGNLIALSLGLTPNFKSNFDLAEDAKLQLSKDTYDDDLDNLLAQIGDQYA
DLFLAAKNLSDAILLSDILRVNTEITKAPLSASMIKRYDEHHQDLTLLKALVRQQLPEKYKEIFFDQSKNGYAGYIDGGASQEEFYKFIKPILEKMDGTEELLVKLNRE
DLLRKQRTFDNGSIPHQIHLGELHAILRRQEDFYPFLKDNREKIEKILTFRIPYYVGPLARGNSRFAWMTRKSEETITPWNFEEVVDKGASAQSFIEKMTNFDKNLPN
EKVLPKHSLLYEYFTVYNELTKVKYVTEGMRKPAFLSGEQKKAIVDLLFKTNRKVTVKQLKEDYFKKIECFDSVEISGVEDRFNASLGTYHDLLKIIKDKDFLDNEEN
EDILEDIVLTLTLFEDREMIEERLKTYAHLFDDKVMKQLKRRRYTGWGRLSRKLINGIRDKQSGKTILDFLKSDGFANRNFMQLIHDDSLTFKEDIQKAQVSGQGDSL
HEHIANLAGSPAIKKGILQTVKVVDELVKVMGRHKPENIVIEMARENQTTQKGQKNSRERMKRIEEGIKELGSQILKEHPVENTQLQNEKLYLYYLQNGRDMYVDQE
LDINRLSDYDVDAIVPQSFLKDDSIDNKVLTRSDKNRGKSDNVPSEEVVKKMKNYWRQLLNAKLITQRKFDNLTKAERGGLSELDKAGFIKRQLVETRQITKHVAQI
LDSRMNTKYDENDKLIREVKVITLKSKLVSDFRKDFQFYKVREINNYHHAHDAYLNAVVGTALIKKYPKLESEFVYGDYKVYDVRKMIAKSEQEIGKATAKYFFYSNI
MNFFKTEITLANGEIRKRPLIETNGETGEIVWDKGRDFATVRKVLSMPQVNIVKKTEVQTGGFSKESILPKRNSDKLIARKKDWDPKKYGGFDSPTVAYSVLVVAKV
EKGKSKKLKSVKELLGTTIMERSSFEKNPIDFLEAKGYKEVKKDLIIKLPKYSLFELENGRKRMLASAGELQKGNELALPSKYVNFLYLASHYEKLKGSPEDNEQKQ
LFVEQHKHYLDEIIEQISEFSKRVILADANLDKVLSAYNKHRDKPIREQAENIIHLFTLTNLGAPAAFKYFDTTIDRKRYTSTKEVLDATLIHQSITGLYETRIDLSQLGG
DPIAGSKASPKKKRKVGRA
YPYDVPDYAS

FIG. 15H dCasgp300 Core (H415A E1423A Y1424A L1428S Y1430A H1434A): Nuclear Localization Sequence,
Streptococcus pyogenes Cas9 (D10A, H840A), H1415A E1423A Y1424A L1428S Y1430A H1434A, "HA" Epitope (SEQ ID NO: 147)

MAPKKKRKVGRGMDKKYSIGLAIGTNSVGWAVITDEYKVPSKKFKVLGNTDRHSIKKNLIGALLFDSGETAEATRLKRTARR
RYTRRKNRICYLQEIFSNEMAKVDDSFFHRLEESFLVEEDKKHERHPIFGNIVDEVAYHEKYPTIYHLRKKLVDSTDKADLRLIYLALAHMIKFRGHFLIEGDLNPDNS
DVDKLFIQLVQTYNQLFEENPINASGVDAKAILSARLSKSRRLENLIAQLPGEKKNGLFGNLIALSLGLTPNFKSNFDLAEDAKLQLSKDTYDDDLDNLLAQIGDQY
ADLFLAAKNLSDAILLSDILRVNTEITKAPLSASMIKRYDEHHQDLTLLKALVRQQLPEKYKEIFDSGKNGYAGYIDGGASQEEFYKFIKPILEKMDGTEELLVKLNR
EDLLRKQRTFDNGSIPHQHLGELHAILRRQEDFYPFLKDNREKIEKILTFRIPYYVGPLARGNSRFAWMTRKSEETITPWNFEEVVDKGASAQSFIERMTNFDKNLP
NEKVLPKHSLLYEYFTVYNELTKVKYVTEGMRKPAFLSGEQKKAIVDLLFKTNRKVTVKQLKEDYFKKIECFDSVEISGVEDRFNASLGTYHDLLKIIKDKDFLDNEE
NEDILEDIVLTLFEDREMIEERLKTYAHLFDDKVMKQLKRRRYTGWGRLSRKLINGIRDKQSGKTILDFLKSDGFANRNFMQLIHDDSLTFKEDIQKAQVSGQGD
SLHEHIANLAGSPAIKKGILQTVKVVDELVKVMGRHKPENIVIEMARENQTTQKGQKNSRERMKRIEEGIKELGSQILKEHPVENTQLQNEKLYLYLQNGRDMYVD
QELDINRLSDYDVDHIVPQSFLKDDSIDNKVLTRSDKNRGKSDNVPSEEVVKKMKNYWRQLLNAKLITQRKFDNLTKAERGGLSELDKAGFIKRQLVETRQITKHV
AQILDSRMNTKYDENDKLIREVKVITLKSKLVSDFRKDFQFYKVREINNYHHAHDAYLNAVVGTALIKKYPKLESEFVYGDYKVYDVRKMIAKSEQEIGKATAKYFFY
SNIMNFFKTEITLANGEIRKRPLIETNGETGEIVWDKGRDFATVRKVLSMPQVNIVKKTEVQTGGFSKESILPKRNSDKLIARKKDWDPKKYGGFDSPTVAYSVLVVA
KVEKGKSKKLKSVKELLGTIIMERSSFEKNPIDFLEAKGYKEVKKDLIIKLPKYSLFELENGRKRMLASAGELQKGNELALPSKYVNFLYLASHYEKLKGSPEDNEQ
KQLFVEQHKHYLDEIIEQISEFSKRVILADANLDKVLSAYNKHRDKPIREQAEMIBHLFTLTNLGAPAAFKYFDTTIDRKRYTSTKEVLDATLIHQSIFGLYETRIDLSQL
GGDPIAGSKASPKKKRKVGRA

YPYDVPDYAS

FIG. 15I

Nm-dCas9VP64, amino acid sequence (Addgene Plasmid #48676); *Neisseria meningitidis* Cas9 (D16A, D587A, H588A, N611A), Nuclear Localization Sequence, SR (SEQ ID NO: 148)

MAAFKPNPINYILGLAIGIASVGWAMVEIDEDENPICLIDLGVRVFERAEVPKTGDSLAMARRLARSVRRLTRRRAHRLLRARRLLKREGVLQAADFDENGLIKS
LPNTPWQLRAAALDRKLTPLEWSAVLLHLIKHRGYLSQRKNEGETADKELGALLKGVADNAHALQTGDFRTPAELALNKFEKESGHIRNQRGDYSHTFSRKD
LQAEILLLFEKQKEFGNPHVSGGLKEGIETLLMTQRPALSGDAVQKMLGHCTFEPAEPKAAKNTYTAERFIWLTKLNNLRILEQGSERPLTDTERATLMDEPYR
LSKLTYAQARKLLGLEDTAFFKGLRYGKDNAEASTLMEMKAYHAISRALEKEGLKDKKSPLNLSPELQDEIGTAFSLFKTDEDITGRLKDRIQPEILEALLKHISF
DKFVQISLKALRRIVPLMEQGKRYDEACAEIYGDHYGKKNTEEKIYLPPIPADEIRNPVVLRALSQARKVINGVVRRYGSPARIHETAREVGKSFKDRKEIEKRQE
ENRKDREKAAAKFREYFPNFVGEPKSKKDILKLRLYEQQHGKCLYSGKEINLGRLNEKGYVEIAALPFSRTWDDSFNNKVLVLGSEAQNKGNQTPYEYFNGKD
NSREWQEFKARVETSRFPRSKKQRILLQKFDEDGFKERNLNDTRYVNRFLCQFVADRMRLTGKGKRVFASNGQITNLLRGFWGLRKVRAENDRHHALDAVV
VACSTVAMQQKITRFVRYKEMNAFDGKTIDKETGEVLHQKTHFPQPWEFFAQEVMIRVFGKPDGKPEFEEADTPEKLRTLLAEKLSSRPEAVHEYVTPLFVSRA
PNRKMSGQGHMETVKSAKRLDEGVSVLRVPLTQLKLKDLEKMVNREREPKLYEALKARLEAHKDDPAKAFAEPFYKYDKAGNRTQQVKAVRVEQVQKTGV
VVRMHNGIADNATMVRVDVFEKGDKYYLVPIYSWQVAKGILPDRAVVQGKDEEDWQLIDDSFNFKFSLHPNDLVEVITKKARMFGYFASCHRGTGNINIRIHDL
DHKIGKNGILEGIGVKTALSFQKYQIDELGKEIRPCRLKKRPPVRSRADPKKKRKVEAS

Nm-dCas9p300 Core, (Addgene Plasmid 61365) amino acid sequence; *Neisseria meningitidis* Cas9 (D16A, D587A, H588A, N611A), Nuclear Localization Sequence, "HA" Epitope (SEQ ID NO: 149)

MAAFKPNPINYILGLAIGIASVGWAMVEIDEDENPICLIDLGVRVFERAEVPKTGDSLAMARRLARSVRRLTRRRAHRLLRARRLLKREGVLQAADFDENGLIKSL
PNTPWQLRAAALDRKLTPLEWSAVLLHLIKHRGYLSQRKNEGETADKELGALLKGVADNAHALQTGDFRTPAELALNKFEKESGHIRNQRGDYSHTFSRKDLQ
AEILLLFEKQKEFGNPHVSGGLKEGIETLLMTQRPALSGDAVQKMLGHCTFEPAEPKAAKNTYTAERFIWLTKLNNLRILEQGSERPLTDTERATLMDEPYRKSK
LTYAQARKLLGLEDTAFFKGLRYGKDNAEASTLMEMKAYHAISRALEKEGLKDKKSPLNLSPELQDEIGTAFSLFKTDEDITGRLKDRIQPEILEALLKHISFDKFV
QISLKALRRIVPLMEQGKRYDEACAEIYGDHYGKKNTEEKIYLPPIPADEIRNPVVLRALSQARKVINGVVRRYGSPARIHETAREVGKSFKDRKEIEKRQEENRK
DREKAAAKFREYFPNFVGEPKSKKQRILLQKFDEDGFKERNLNDTRYVNRFLCQFVADRMRLTGKGKRVFASNGQITNLLRGFWGLRKVRAENDRHHALDAVVACS
TVAMQQKITRFVRYKEMNAFDGKTIDKETGEVLHQKTHFPQPWEFFAQEVMIRVFGKPDGKPEFEEADTPEKLRTLLAEKLSSRPEAVHEYVTPLFVSRAPNRK
MSGQGHMETVKSAKRLDEGVSVLRVPLTQLKLKDLEKMVNREREPKLYEALKARLEAHKDDPAKAFAEPFYKYDKAGNRTQQVKAVRVEQVQKTGVWVRMH
NGIADNATMVRVDVFEKGDKYYLVPIYSWQVAKGILPDRAVVQGKDEEDWQLIDDSFNFKFSLHPNDLVEVITKKARMFGYFASCHRGTGNINIRIHDLDHKIGKN
GILEGIGVKTALSFQKYQIDELGKEIRPCRLKKRPPVRSRADPKKKRKVEASGRAYPYDVPDYAS

FIG. 15J

*ICAM1* ZF^VP64 amino acid sequence; Nuclear Localization Sequence, Zinc Finger Helix, "HA" Epitope (SEQ ID NO: 150)

MAPKKKRKVGRGMAQAALEPGEKPYACPECGKSFSDCRDLARHQRTHTGEKPYKCPECGKSFSRSDLVRHQRTHTGEK
PYKCPECGKSFSQSSNLVRHQRTHTGEKPYKCPECGKSFSQRAHLERHQRTHTGEKPYKCPECGKSFSQAGHLAS
HQRTHTGKKTSGQAGQASPKKKRKVGRA...INYPYDVPDYAS

*ICAM1* ZF^p300 Core amino acid sequence; Nuclear Localization Sequence, Zinc Finger Helix, "HA" Epitope (SEQ ID NO: 151)

MAPKKKRKVGRGMAQAALEPGEKPYACPECGKSFSDCRDLARHQRTHTGEKPYKCPECGKSFSRSDLVRHQRTHTGEK
PYKCPECGKSFSQSSNLVRHQRTHTGEKPYKCPECGKSFSQRAHLERHQRTHTGEKPYKCPECGKSFSQAGHLAS
HQRTHTGKKTSGQAGQASPKKKRKVGRA...YPYDVPDYAS

FIG. 16

SEQUENCE LISTING

<160> NUMBER OF SEQ ID NOS: 278

<210> SEQ ID NO 1
<211> LENGTH: 1368
<212> TYPE: PRT
<213> ORGANISM: Streptococcus pyogenes

<400> SEQUENCE: 1

```
Met Asp Lys Lys Tyr Ser Ile Gly Leu Ala Ile Gly Thr Asn Ser Val
 1               5                  10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
           100                 105                 110

His Glu Arg His Pro Ile Phe Gly Asn Ile Val Asp Glu Val Ala Tyr
       115                 120                 125

His Glu Lys Tyr Pro Thr Ile Tyr His Leu Arg Lys Lys Leu Val Asp
   130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365
```

```
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
                435                 440                 445
Pro Tyr Tyr Val Gly Pro Leu Ala Arg Gly Asn Ser Arg Phe Ala Trp
        450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
        595                 600                 605
Asn Glu Glu Asn Glu Asp Ile Leu Glu Asp Ile Val Leu Thr Leu Thr
        610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
        675                 680                 685
Ala Asn Arg Asn Phe Met Gln Leu Ile His Asp Asp Ser Leu Thr Phe
    690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
        755                 760                 765
Thr Thr Gln Lys Gly Gln Lys Asn Ser Arg Glu Arg Met Lys Arg Ile
    770                 775                 780
Glu Glu Gly Ile Lys Glu Leu Gly Ser Gln Ile Leu Lys Glu His Pro
```

```
                785                 790                 795                 800
Val Glu Asn Thr Gln Leu Gln Asn Gly Lys Leu Tyr Leu Tyr Tyr Leu
                    805                 810                 815
Gln Asn Gly Arg Asp Met Tyr Val Asp Gln Glu Leu Asp Ile Asn Arg
                820                 825                 830
Leu Ser Asp Tyr Asp Val Asp Ala Ile Val Pro Gln Ser Phe Leu Lys
            835                 840                 845
Asp Asp Ser Ile Asp Asn Lys Val Leu Thr Arg Ser Asp Lys Asn Arg
    850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
    930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
        1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
```

```
Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 2
<211> LENGTH: 2414
<212> TYPE: PRT
<213> ORGANISM: Homo sapiens

<400> SEQUENCE: 2

Met Ala Glu Asn Val Val Glu Pro Gly Pro Pro Ser Ala Lys Arg Pro
1               5                   10                  15

Lys Leu Ser Ser Pro Ala Leu Ser Ala Ser Ala Ser Asp Gly Thr Asp
                20                  25                  30

Phe Gly Ser Leu Phe Asp Leu Glu His Asp Leu Pro Asp Glu Leu Ile
            35                  40                  45

Asn Ser Thr Glu Leu Gly Leu Thr Asn Gly Gly Asp Ile Asn Gln Leu
        50                  55                  60

Gln Thr Ser Leu Gly Met Val Gln Asp Ala Ala Ser Lys His Lys Gln
65                  70                  75                  80

Leu Ser Glu Leu Leu Arg Ser Gly Ser Ser Pro Asn Leu Asn Met Gly
                85                  90                  95

Val Gly Gly Pro Gly Gln Val Met Ala Ser Gln Ala Gln Gln Ser Ser
                100                 105                 110

Pro Gly Leu Gly Leu Ile Asn Ser Met Val Lys Ser Pro Met Thr Gln
            115                 120                 125

Ala Gly Leu Thr Ser Pro Asn Met Gly Met Gly Thr Ser Gly Pro Asn
        130                 135                 140

Gln Gly Pro Thr Gln Ser Thr Gly Met Met Asn Ser Pro Val Asn Gln
145                 150                 155                 160

Pro Ala Met Gly Met Asn Thr Gly Met Asn Ala Gly Met Asn Pro Gly
                165                 170                 175

Met Leu Ala Ala Gly Asn Gly Gln Gly Ile Met Pro Asn Gln Val Met
            180                 185                 190

Asn Gly Ser Ile Gly Ala Gly Arg Gly Arg Gln Asn Met Gln Tyr Pro
```

```
            195                 200                 205
Asn Pro Gly Met Gly Ser Ala Gly Asn Leu Leu Thr Glu Pro Leu Gln
210                 215                 220

Gln Gly Ser Pro Gln Met Gly Gln Thr Gly Leu Arg Gly Pro Gln
225                 230                 235                 240

Pro Leu Lys Met Gly Met Met Asn Asn Pro Asn Pro Tyr Gly Ser Pro
                    245                 250                 255

Tyr Thr Gln Asn Pro Gly Gln Gln Ile Gly Ala Ser Gly Leu Gly Leu
            260                 265                 270

Gln Ile Gln Thr Lys Thr Val Leu Ser Asn Asn Leu Ser Pro Phe Ala
        275                 280                 285

Met Asp Lys Lys Ala Val Pro Gly Gly Gly Met Pro Asn Met Gly Gln
    290                 295                 300

Gln Pro Ala Pro Gln Val Gln Gln Pro Gly Leu Val Thr Pro Val Ala
305                 310                 315                 320

Gln Gly Met Gly Ser Gly Ala His Thr Ala Asp Pro Glu Lys Arg Lys
                    325                 330                 335

Leu Ile Gln Gln Gln Leu Val Leu Leu Leu His Ala His Lys Cys Gln
            340                 345                 350

Arg Arg Glu Gln Ala Asn Gly Glu Val Arg Gln Cys Asn Leu Pro His
        355                 360                 365

Cys Arg Thr Met Lys Asn Val Leu Asn His Met Thr His Cys Gln Ser
    370                 375                 380

Gly Lys Ser Cys Gln Val Ala His Cys Ala Ser Ser Arg Gln Ile Ile
385                 390                 395                 400

Ser His Trp Lys Asn Cys Thr Arg His Asp Cys Pro Val Cys Leu Pro
                    405                 410                 415

Leu Lys Asn Ala Gly Asp Lys Arg Asn Gln Gln Pro Ile Leu Thr Gly
            420                 425                 430

Ala Pro Val Gly Leu Gly Asn Pro Ser Ser Leu Gly Val Gly Gln Gln
        435                 440                 445

Ser Ala Pro Asn Leu Ser Thr Val Ser Gln Ile Asp Pro Ser Ser Ile
    450                 455                 460

Glu Arg Ala Tyr Ala Ala Leu Gly Leu Pro Tyr Gln Val Asn Gln Met
465                 470                 475                 480

Pro Thr Gln Pro Gln Val Gln Ala Lys Asn Gln Gln Asn Gln Gln Pro
                    485                 490                 495

Gly Gln Ser Pro Gln Gly Met Arg Pro Met Ser Asn Met Ser Ala Ser
            500                 505                 510

Pro Met Gly Val Asn Gly Gly Val Gly Val Gln Thr Pro Ser Leu Leu
        515                 520                 525

Ser Asp Ser Met Leu His Ser Ala Ile Asn Ser Asn Pro Met Met
    530                 535                 540

Ser Glu Asn Ala Ser Val Pro Ser Met Gly Pro Met Pro Thr Ala Ala
545                 550                 555                 560

Gln Pro Ser Thr Thr Gly Ile Arg Lys Gln Trp His Glu Asp Ile Thr
                    565                 570                 575

Gln Asp Leu Arg Asn His Leu Val His Lys Leu Val Gln Ala Ile Phe
            580                 585                 590

Pro Thr Pro Asp Pro Ala Ala Leu Lys Asp Arg Arg Met Glu Asn Leu
        595                 600                 605

Val Ala Tyr Ala Arg Lys Val Glu Gly Asp Met Tyr Glu Ser Ala Asn
    610                 615                 620
```

-continued

```
Asn Arg Ala Glu Tyr Tyr His Leu Leu Ala Glu Lys Ile Tyr Lys Ile
625                 630                 635                 640

Gln Lys Glu Leu Glu Glu Lys Arg Arg Thr Arg Leu Gln Lys Gln Asn
            645                 650                 655

Met Leu Pro Asn Ala Ala Gly Met Val Pro Val Ser Met Asn Pro Gly
        660                 665                 670

Pro Asn Met Gly Gln Pro Gln Pro Gly Met Thr Ser Asn Gly Pro Leu
    675                 680                 685

Pro Asp Pro Ser Met Ile Arg Gly Ser Val Pro Asn Gln Met Met Pro
690                 695                 700

Arg Ile Thr Pro Gln Ser Gly Leu Asn Gln Phe Gly Gln Met Ser Met
705                 710                 715                 720

Ala Gln Pro Pro Ile Val Pro Arg Gln Thr Pro Pro Leu Gln His His
            725                 730                 735

Gly Gln Leu Ala Gln Pro Gly Ala Leu Asn Pro Pro Met Gly Tyr Gly
        740                 745                 750

Pro Arg Met Gln Gln Pro Ser Asn Gln Gly Gln Phe Leu Pro Gln Thr
    755                 760                 765

Gln Phe Pro Ser Gln Gly Met Asn Val Thr Asn Ile Pro Leu Ala Pro
770                 775                 780

Ser Ser Gly Gln Ala Pro Val Ser Gln Ala Gln Met Ser Ser Ser Ser
785                 790                 795                 800

Cys Pro Val Asn Ser Pro Ile Met Pro Pro Gly Ser Gln Gly Ser His
            805                 810                 815

Ile His Cys Pro Gln Leu Pro Gln Pro Ala Leu His Gln Asn Ser Pro
        820                 825                 830

Ser Pro Val Pro Ser Arg Thr Pro Thr Pro His His Thr Pro Pro Ser
    835                 840                 845

Ile Gly Ala Gln Gln Pro Pro Ala Thr Thr Ile Pro Ala Pro Val Pro
850                 855                 860

Thr Pro Pro Ala Met Pro Pro Gly Pro Gln Ser Gln Ala Leu His Pro
865                 870                 875                 880

Pro Pro Arg Gln Thr Pro Thr Pro Pro Thr Thr Gln Leu Pro Gln Gln
            885                 890                 895

Val Gln Pro Ser Leu Pro Ala Ala Pro Ser Ala Asp Gln Pro Gln Gln
        900                 905                 910

Gln Pro Arg Ser Gln Gln Ser Thr Ala Ala Ser Val Pro Thr Pro Thr
    915                 920                 925

Ala Pro Leu Leu Pro Pro Gln Pro Ala Thr Pro Leu Ser Gln Pro Ala
930                 935                 940

Val Ser Ile Glu Gly Gln Val Ser Asn Pro Pro Ser Thr Ser Ser Thr
945                 950                 955                 960

Glu Val Asn Ser Gln Ala Ile Ala Glu Lys Gln Pro Ser Gln Glu Val
            965                 970                 975

Lys Met Glu Ala Lys Met Glu Val Asp Gln Pro Glu Pro Ala Asp Thr
        980                 985                 990

Gln Pro Glu Asp Ile Ser Glu Ser Lys Val Glu Asp Cys Lys Met Glu
    995                 1000                1005

Ser Thr Glu Thr Glu Glu Arg Ser Thr Glu Leu Lys Thr Glu Ile
    1010                1015                1020

Lys Glu Glu Glu Asp Gln Pro Ser Thr Ser Ala Thr Gln Ser Ser
    1025                1030                1035
```

-continued

```
Pro Ala Pro Gly Gln Ser Lys Lys Ile Phe Lys Pro Glu Glu
    1040                1045                1050

Leu Arg Gln Ala Leu Met Pro Thr Leu Glu Ala Leu Tyr Arg Gln
    1055                1060                1065

Asp Pro Glu Ser Leu Pro Phe Arg Gln Pro Val Asp Pro Gln Leu
    1070                1075                1080

Leu Gly Ile Pro Asp Tyr Phe Asp Ile Val Lys Ser Pro Met Asp
    1085                1090                1095

Leu Ser Thr Ile Lys Arg Lys Leu Asp Thr Gly Gln Tyr Gln Glu
    1100                1105                1110

Pro Trp Gln Tyr Val Asp Asp Ile Trp Leu Met Phe Asn Asn Ala
    1115                1120                1125

Trp Leu Tyr Asn Arg Lys Thr Ser Arg Val Tyr Lys Tyr Cys Ser
    1130                1135                1140

Lys Leu Ser Glu Val Phe Glu Gln Glu Ile Asp Pro Val Met Gln
    1145                1150                1155

Ser Leu Gly Tyr Cys Cys Gly Arg Lys Leu Glu Phe Ser Pro Gln
    1160                1165                1170

Thr Leu Cys Cys Tyr Gly Lys Gln Leu Cys Thr Ile Pro Arg Asp
    1175                1180                1185

Ala Thr Tyr Tyr Ser Tyr Gln Asn Arg Tyr His Phe Cys Glu Lys
    1190                1195                1200

Cys Phe Asn Glu Ile Gln Gly Glu Ser Val Ser Leu Gly Asp Asp
    1205                1210                1215

Pro Ser Gln Pro Gln Thr Thr Ile Asn Lys Glu Gln Phe Ser Lys
    1220                1225                1230

Arg Lys Asn Asp Thr Leu Asp Pro Glu Leu Phe Val Glu Cys Thr
    1235                1240                1245

Glu Cys Gly Arg Lys Met His Gln Ile Cys Val Leu His His Glu
    1250                1255                1260

Ile Ile Trp Pro Ala Gly Phe Val Cys Asp Gly Cys Leu Lys Lys
    1265                1270                1275

Ser Ala Arg Thr Arg Lys Glu Asn Lys Phe Ser Ala Lys Arg Leu
    1280                1285                1290

Pro Ser Thr Arg Leu Gly Thr Phe Leu Glu Asn Arg Val Asn Asp
    1295                1300                1305

Phe Leu Arg Arg Gln Asn His Pro Glu Ser Gly Glu Val Thr Val
    1310                1315                1320

Arg Val Val His Ala Ser Asp Lys Thr Val Glu Val Lys Pro Gly
    1325                1330                1335

Met Lys Ala Arg Phe Val Asp Ser Gly Glu Met Ala Glu Ser Phe
    1340                1345                1350

Pro Tyr Arg Thr Lys Ala Leu Phe Ala Phe Glu Glu Ile Asp Gly
    1355                1360                1365

Val Asp Leu Cys Phe Phe Gly Met His Val Gln Glu Tyr Gly Ser
    1370                1375                1380

Asp Cys Pro Pro Pro Asn Gln Arg Arg Val Tyr Ile Ser Tyr Leu
    1385                1390                1395

Asp Ser Val His Phe Phe Arg Pro Lys Cys Leu Arg Thr Ala Val
    1400                1405                1410

Tyr His Glu Ile Leu Ile Gly Tyr Leu Glu Tyr Val Lys Lys Leu
    1415                1420                1425

Gly Tyr Thr Thr Gly His Ile Trp Ala Cys Pro Pro Ser Glu Gly
```

```
                1430                1435                1440

Asp Asp Tyr Ile Phe His Cys His Pro Pro Asp Gln Lys Ile Pro
    1445                1450                1455

Lys Pro Lys Arg Leu Gln Glu Trp Tyr Lys Lys Met Leu Asp Lys
    1460                1465                1470

Ala Val Ser Glu Arg Ile Val His Asp Tyr Lys Asp Ile Phe Lys
    1475                1480                1485

Gln Ala Thr Glu Asp Arg Leu Thr Ser Ala Lys Glu Leu Pro Tyr
    1490                1495                1500

Phe Glu Gly Asp Phe Trp Pro Asn Val Leu Glu Glu Ser Ile Lys
    1505                1510                1515

Glu Leu Glu Gln Glu Glu Glu Arg Lys Arg Glu Glu Asn Thr
    1520                1525                1530

Ser Asn Glu Ser Thr Asp Val Thr Lys Gly Asp Ser Lys Asn Ala
    1535                1540                1545

Lys Lys Lys Asn Asn Lys Lys Thr Ser Lys Asn Lys Ser Ser Leu
    1550                1555                1560

Ser Arg Gly Asn Lys Lys Lys Pro Gly Met Pro Asn Val Ser Asn
    1565                1570                1575

Asp Leu Ser Gln Lys Leu Tyr Ala Thr Met Glu Lys His Lys Glu
    1580                1585                1590

Val Phe Phe Val Ile Arg Leu Ile Ala Gly Pro Ala Ala Asn Ser
    1595                1600                1605

Leu Pro Pro Ile Val Asp Pro Asp Pro Leu Ile Pro Cys Asp Leu
    1610                1615                1620

Met Asp Gly Arg Asp Ala Phe Leu Thr Leu Ala Arg Asp Lys His
    1625                1630                1635

Leu Glu Phe Ser Ser Leu Arg Arg Ala Gln Trp Ser Thr Met Cys
    1640                1645                1650

Met Leu Val Glu Leu His Thr Gln Ser Gln Asp Arg Phe Val Tyr
    1655                1660                1665

Thr Cys Asn Glu Cys Lys His His Val Glu Thr Arg Trp His Cys
    1670                1675                1680

Thr Val Cys Glu Asp Tyr Asp Leu Cys Ile Thr Cys Tyr Asn Thr
    1685                1690                1695

Lys Asn His Asp His Lys Met Glu Lys Leu Gly Leu Gly Leu Asp
    1700                1705                1710

Asp Glu Ser Asn Asn Gln Gln Ala Ala Ala Thr Gln Ser Pro Gly
    1715                1720                1725

Asp Ser Arg Arg Leu Ser Ile Gln Arg Cys Ile Gln Ser Leu Val
    1730                1735                1740

His Ala Cys Gln Cys Arg Asn Ala Asn Cys Ser Leu Pro Ser Cys
    1745                1750                1755

Gln Lys Met Lys Arg Val Val Gln His Thr Lys Gly Cys Lys Arg
    1760                1765                1770

Lys Thr Asn Gly Gly Cys Pro Ile Cys Lys Gln Leu Ile Ala Leu
    1775                1780                1785

Cys Cys Tyr His Ala Lys His Cys Gln Glu Asn Lys Cys Pro Val
    1790                1795                1800

Pro Phe Cys Leu Asn Ile Lys Gln Lys Leu Arg Gln Gln Gln Leu
    1805                1810                1815

Gln His Arg Leu Gln Gln Ala Gln Met Leu Arg Arg Arg Met Ala
    1820                1825                1830
```

```
Ser Met Gln Arg Thr Gly Val Val Gly Gln Gln Gln Gly Leu Pro
1835                1840                1845

Ser Pro Thr Pro Ala Thr Pro Thr Thr Pro Thr Gly Gln Gln Pro
1850                1855                1860

Thr Thr Pro Gln Thr Pro Gln Pro Thr Ser Gln Pro Gln Pro Thr
1865                1870                1875

Pro Pro Asn Ser Met Pro Pro Tyr Leu Pro Arg Thr Gln Ala Ala
1880                1885                1890

Gly Pro Val Ser Gln Gly Lys Ala Ala Gly Gln Val Thr Pro Pro
1895                1900                1905

Thr Pro Pro Gln Thr Ala Gln Pro Pro Leu Pro Gly Pro Pro Pro
1910                1915                1920

Ala Ala Val Glu Met Ala Met Gln Ile Gln Arg Ala Ala Glu Thr
1925                1930                1935

Gln Arg Gln Met Ala His Val Gln Ile Phe Gln Arg Pro Ile Gln
1940                1945                1950

His Gln Met Pro Pro Met Thr Pro Met Ala Pro Met Gly Met Asn
1955                1960                1965

Pro Pro Pro Met Thr Arg Gly Pro Ser Gly His Leu Glu Pro Gly
1970                1975                1980

Met Gly Pro Thr Gly Met Gln Gln Pro Pro Trp Ser Gln Gly
1985                1990                1995

Gly Leu Pro Gln Pro Gln Gln Leu Gln Ser Gly Met Pro Arg Pro
2000                2005                2010

Ala Met Met Ser Val Ala Gln His Gly Gln Pro Leu Asn Met Ala
2015                2020                2025

Pro Gln Pro Gly Leu Gly Gln Val Gly Ile Ser Pro Leu Lys Pro
2030                2035                2040

Gly Thr Val Ser Gln Gln Ala Leu Gln Asn Leu Leu Arg Thr Leu
2045                2050                2055

Arg Ser Pro Ser Ser Pro Leu Gln Gln Gln Gln Val Leu Ser Ile
2060                2065                2070

Leu His Ala Asn Pro Gln Leu Leu Ala Ala Phe Ile Lys Gln Arg
2075                2080                2085

Ala Ala Lys Tyr Ala Asn Ser Asn Pro Gln Pro Ile Pro Gly Gln
2090                2095                2100

Pro Gly Met Pro Gln Gly Gln Pro Gly Leu Gln Pro Pro Thr Met
2105                2110                2115

Pro Gly Gln Gln Gly Val His Ser Asn Pro Ala Met Gln Asn Met
2120                2125                2130

Asn Pro Met Gln Ala Gly Val Gln Arg Ala Gly Leu Pro Gln Gln
2135                2140                2145

Gln Pro Gln Gln Gln Leu Gln Pro Pro Met Gly Gly Met Ser Pro
2150                2155                2160

Gln Ala Gln Gln Met Asn Met Asn His Asn Thr Met Pro Ser Gln
2165                2170                2175

Phe Arg Asp Ile Leu Arg Arg Gln Gln Met Met Gln Gln Gln Gln
2180                2185                2190

Gln Gln Gly Ala Gly Pro Gly Ile Gly Pro Gly Met Ala Asn His
2195                2200                2205

Asn Gln Phe Gln Gln Pro Gln Gly Val Gly Tyr Pro Pro Gln Gln
2210                2215                2220
```

-continued

Gln Gln Arg Met Gln His His Met Gln Gln Met Gln Gln Gly Asn
2225                2230                2235

Met Gly Gln Ile Gly Gln Leu Pro Gln Ala Leu Gly Ala Glu Ala
2240                2245                2250

Gly Ala Ser Leu Gln Ala Tyr Gln Gln Arg Leu Leu Gln Gln Gln
2255                2260                2265

Met Gly Ser Pro Val Gln Pro Asn Pro Met Ser Pro Gln Gln His
2270                2275                2280

Met Leu Pro Asn Gln Ala Gln Ser Pro His Leu Gln Gly Gln Gln
2285                2290                2295

Ile Pro Asn Ser Leu Ser Asn Gln Val Arg Ser Pro Gln Pro Val
2300                2305                2310

Pro Ser Pro Arg Pro Gln Ser Gln Pro Pro His Ser Ser Pro Ser
2315                2320                2325

Pro Arg Met Gln Pro Gln Pro Ser Pro His His Val Ser Pro Gln
2330                2335                2340

Thr Ser Ser Pro His Pro Gly Leu Val Ala Ala Gln Ala Asn Pro
2345                2350                2355

Met Glu Gln Gly His Phe Ala Ser Pro Asp Gln Asn Ser Met Leu
2360                2365                2370

Ser Gln Leu Ala Ser Asn Pro Gly Met Ala Asn Leu His Gly Ala
2375                2380                2385

Ser Ala Thr Asp Leu Gly Leu Ser Thr Asp Asn Ser Asp Leu Asn
2390                2395                2400

Ser Asn Leu Ser Gln Ser Thr Leu Asp Ile His
2405                2410

<210> SEQ ID NO 3
<211> LENGTH: 617
<212> TYPE: PRT
<213> ORGANISM: Homo sapiens

<400> SEQUENCE: 3

Ile Phe Lys Pro Glu Glu Leu Arg Gln Ala Leu Met Pro Thr Leu Glu
1               5                   10                  15

Ala Leu Tyr Arg Gln Asp Pro Glu Ser Leu Pro Phe Arg Gln Pro Val
                20                  25                  30

Asp Pro Gln Leu Leu Gly Ile Pro Asp Tyr Phe Asp Ile Val Lys Ser
            35                  40                  45

Pro Met Asp Leu Ser Thr Ile Lys Arg Lys Leu Asp Thr Gly Gln Tyr
        50                  55                  60

Gln Glu Pro Trp Gln Tyr Val Asp Asp Ile Trp Leu Met Phe Asn Asn
65                  70                  75                  80

Ala Trp Leu Tyr Asn Arg Lys Thr Ser Arg Val Tyr Lys Tyr Cys Ser
                85                  90                  95

Lys Leu Ser Glu Val Phe Glu Gln Glu Ile Asp Pro Val Met Gln Ser
                100                 105                 110

Leu Gly Tyr Cys Cys Gly Arg Lys Leu Glu Phe Ser Pro Gln Thr Leu
            115                 120                 125

Cys Cys Tyr Gly Lys Gln Leu Cys Thr Ile Pro Arg Asp Ala Thr Tyr
        130                 135                 140

Tyr Ser Tyr Gln Asn Arg Tyr His Phe Cys Glu Lys Cys Phe Asn Glu
145                 150                 155                 160

Ile Gln Gly Glu Ser Val Ser Leu Gly Asp Asp Pro Ser Gln Pro Gln
                165                 170                 175

```
Thr Thr Ile Asn Lys Glu Gln Phe Ser Lys Arg Lys Asn Asp Thr Leu
            180                 185                 190

Asp Pro Glu Leu Phe Val Glu Cys Thr Glu Cys Gly Arg Lys Met His
        195                 200                 205

Gln Ile Cys Val Leu His His Glu Ile Ile Trp Pro Ala Gly Phe Val
    210                 215                 220

Cys Asp Gly Cys Leu Lys Lys Ser Ala Arg Thr Arg Lys Glu Asn Lys
225                 230                 235                 240

Phe Ser Ala Lys Arg Leu Pro Ser Thr Arg Leu Gly Thr Phe Leu Glu
                245                 250                 255

Asn Arg Val Asn Asp Phe Leu Arg Arg Gln Asn His Pro Glu Ser Gly
            260                 265                 270

Glu Val Thr Val Arg Val His Ala Ser Asp Lys Thr Val Glu Val
        275                 280                 285

Lys Pro Gly Met Lys Ala Arg Phe Val Asp Ser Gly Glu Met Ala Glu
        290                 295                 300

Ser Phe Pro Tyr Arg Thr Lys Ala Leu Phe Ala Phe Glu Glu Ile Asp
305                 310                 315                 320

Gly Val Asp Leu Cys Phe Phe Gly Met His Val Gln Glu Tyr Gly Ser
                325                 330                 335

Asp Cys Pro Pro Asn Gln Arg Arg Val Tyr Ile Ser Tyr Leu Asp
            340                 345                 350

Ser Val His Phe Phe Arg Pro Lys Cys Leu Arg Thr Ala Val Tyr His
            355                 360                 365

Glu Ile Leu Ile Gly Tyr Leu Glu Tyr Val Lys Lys Leu Gly Tyr Thr
    370                 375                 380

Thr Gly His Ile Trp Ala Cys Pro Pro Ser Glu Gly Asp Asp Tyr Ile
385                 390                 395                 400

Phe His Cys His Pro Pro Asp Gln Lys Ile Pro Lys Pro Lys Arg Leu
                405                 410                 415

Gln Glu Trp Tyr Lys Lys Met Leu Asp Lys Ala Val Ser Glu Arg Ile
        420                 425                 430

Val His Asp Tyr Lys Asp Ile Phe Lys Gln Ala Thr Glu Asp Arg Leu
    435                 440                 445

Thr Ser Ala Lys Glu Leu Pro Tyr Phe Glu Gly Asp Phe Trp Pro Asn
450                 455                 460

Val Leu Glu Glu Ser Ile Lys Glu Leu Glu Gln Glu Glu Glu Glu Arg
465                 470                 475                 480

Lys Arg Glu Glu Asn Thr Ser Asn Glu Ser Thr Asp Val Thr Lys Gly
                485                 490                 495

Asp Ser Lys Asn Ala Lys Lys Lys Asn Asn Lys Lys Thr Ser Lys Asn
            500                 505                 510

Lys Ser Ser Leu Ser Arg Gly Asn Lys Lys Pro Gly Met Pro Asn
        515                 520                 525

Val Ser Asn Asp Leu Ser Gln Lys Leu Tyr Ala Thr Met Glu Lys His
    530                 535                 540

Lys Glu Val Phe Phe Val Ile Arg Leu Ile Ala Gly Pro Ala Ala Asn
545                 550                 555                 560

Ser Leu Pro Pro Ile Val Asp Pro Asp Pro Leu Ile Pro Cys Asp Leu
                565                 570                 575

Met Asp Gly Arg Asp Ala Phe Leu Thr Leu Ala Arg Asp Lys His Leu
            580                 585                 590
```

```
Glu Phe Ser Ser Leu Arg Arg Ala Gln Trp Ser Thr Met Cys Met Leu
            595                 600                 605

Val Glu Leu His Thr Gln Ser Gln Asp
    610                 615

<210> SEQ ID NO 4
<211> LENGTH: 617
<212> TYPE: PRT
<213> ORGANISM: Homo sapiens

<400> SEQUENCE: 4

Ile Phe Lys Pro Glu Glu Leu Arg Gln Ala Leu Met Pro Thr Leu Glu
1               5                   10                  15

Ala Leu Tyr Arg Gln Asp Pro Glu Ser Leu Pro Phe Arg Gln Pro Val
            20                  25                  30

Asp Pro Gln Leu Leu Gly Ile Pro Asp Tyr Phe Asp Ile Val Lys Ser
            35                  40                  45

Pro Met Asp Leu Ser Thr Ile Lys Arg Lys Leu Asp Thr Gly Gln Tyr
        50                  55                  60

Gln Glu Pro Trp Gln Tyr Val Asp Asp Ile Trp Leu Met Phe Asn Asn
65              70                  75                  80

Ala Trp Leu Tyr Asn Arg Lys Thr Ser Arg Val Tyr Lys Tyr Cys Ser
                85                  90                  95

Lys Leu Ser Glu Val Phe Glu Gln Glu Ile Asp Pro Val Met Gln Ser
            100                 105                 110

Leu Gly Tyr Cys Cys Gly Arg Lys Leu Glu Phe Ser Pro Gln Thr Leu
        115                 120                 125

Cys Cys Tyr Gly Lys Gln Leu Cys Thr Ile Pro Arg Asp Ala Thr Tyr
    130                 135                 140

Tyr Ser Tyr Gln Asn Arg Tyr His Phe Cys Glu Lys Cys Phe Asn Glu
145             150                 155                 160

Ile Gln Gly Glu Ser Val Ser Leu Gly Asp Asp Pro Ser Gln Pro Gln
                165                 170                 175

Thr Thr Ile Asn Lys Glu Gln Phe Ser Lys Arg Lys Asn Asp Thr Leu
            180                 185                 190

Asp Pro Glu Leu Phe Val Glu Cys Thr Glu Cys Gly Arg Lys Met His
        195                 200                 205

Gln Ile Cys Val Leu His His Glu Ile Ile Trp Pro Ala Gly Phe Val
    210                 215                 220

Cys Asp Gly Cys Leu Lys Lys Ser Ala Arg Thr Arg Lys Glu Asn Lys
225             230                 235                 240

Phe Ser Ala Lys Arg Leu Pro Ser Thr Arg Leu Gly Thr Phe Leu Glu
                245                 250                 255

Asn Arg Val Asn Asp Phe Leu Arg Arg Gln Asn His Pro Glu Ser Gly
            260                 265                 270

Glu Val Thr Val Arg Val Val His Ala Ser Asp Lys Thr Val Glu Val
        275                 280                 285

Lys Pro Gly Met Lys Ala Arg Phe Val Asp Ser Gly Glu Met Ala Glu
    290                 295                 300

Ser Phe Pro Tyr Arg Thr Lys Ala Leu Phe Ala Phe Glu Glu Ile Asp
305             310                 315                 320

Gly Val Asp Leu Cys Phe Phe Gly Met His Val Gln Glu Tyr Gly Ser
                325                 330                 335

Asp Cys Pro Pro Pro Asn Gln Arg Arg Val Tyr Ile Ser Tyr Leu Tyr
            340                 345                 350
```

```
Ser Val His Phe Phe Arg Pro Lys Cys Leu Arg Thr Ala Val Tyr His
        355                 360                 365

Glu Ile Leu Ile Gly Tyr Leu Glu Tyr Val Lys Lys Leu Gly Tyr Thr
370                 375                 380

Thr Gly His Ile Trp Ala Cys Pro Pro Ser Glu Gly Asp Asp Tyr Ile
385                 390                 395                 400

Phe His Cys His Pro Asp Gln Lys Ile Pro Lys Pro Lys Arg Leu
                405                 410                 415

Gln Glu Trp Tyr Lys Lys Met Leu Asp Lys Ala Val Ser Glu Arg Ile
                420                 425                 430

Val His Asp Tyr Lys Asp Ile Phe Lys Gln Ala Thr Glu Asp Arg Leu
        435                 440                 445

Thr Ser Ala Lys Glu Leu Pro Tyr Phe Glu Gly Asp Phe Trp Pro Asn
450                 455                 460

Val Leu Glu Glu Ser Ile Lys Glu Leu Glu Gln Glu Glu Glu Glu Arg
465                 470                 475                 480

Lys Arg Glu Glu Asn Thr Ser Asn Glu Ser Thr Asp Val Thr Lys Gly
                485                 490                 495

Asp Ser Lys Asn Ala Lys Lys Asn Asn Lys Lys Thr Ser Lys Asn
        500                 505                 510

Lys Ser Ser Leu Ser Arg Gly Asn Lys Lys Pro Gly Met Pro Asn
        515                 520                 525

Val Ser Asn Asp Leu Ser Gln Lys Leu Tyr Ala Thr Met Glu Lys His
530                 535                 540

Lys Glu Val Phe Phe Val Ile Arg Leu Ile Ala Gly Pro Ala Ala Asn
545                 550                 555                 560

Ser Leu Pro Pro Ile Val Asp Pro Asp Pro Leu Ile Pro Cys Asp Leu
                565                 570                 575

Met Asp Gly Arg Asp Ala Phe Leu Thr Leu Ala Arg Asp Lys His Leu
                580                 585                 590

Glu Phe Ser Ser Leu Arg Arg Ala Gln Trp Ser Thr Met Cys Met Leu
        595                 600                 605

Val Glu Leu His Thr Gln Ser Gln Asp
        610                 615

<210> SEQ ID NO 5
<211> LENGTH: 617
<212> TYPE: PRT
<213> ORGANISM: Homo sapiens

<400> SEQUENCE: 5

Ile Phe Lys Pro Glu Glu Leu Arg Gln Ala Leu Met Pro Thr Leu Glu
1               5                   10                  15

Ala Leu Tyr Arg Gln Asp Pro Glu Ser Leu Pro Phe Arg Gln Pro Val
                20                  25                  30

Asp Pro Gln Leu Leu Gly Ile Pro Asp Tyr Phe Asp Ile Val Lys Ser
        35                  40                  45

Pro Met Asp Leu Ser Thr Ile Lys Arg Lys Leu Asp Thr Gly Gln Tyr
50                  55                  60

Gln Glu Pro Trp Gln Tyr Val Asp Asp Ile Trp Leu Met Phe Asn Asn
65                  70                  75                  80

Ala Trp Leu Tyr Asn Arg Lys Thr Ser Arg Val Tyr Lys Tyr Cys Ser
                85                  90                  95

Lys Leu Ser Glu Val Phe Glu Gln Glu Ile Asp Pro Val Met Gln Ser
```

```
                100              105               110
Leu Gly Tyr Cys Cys Gly Arg Lys Leu Glu Phe Ser Pro Gln Thr Leu
            115             120             125

Cys Cys Tyr Gly Lys Gln Leu Cys Thr Ile Pro Arg Asp Ala Thr Tyr
            130             135             140

Tyr Ser Tyr Gln Asn Arg Tyr His Phe Cys Glu Lys Cys Phe Asn Glu
145             150             155             160

Ile Gln Gly Glu Ser Val Ser Leu Gly Asp Asp Pro Ser Gln Pro Gln
                165             170             175

Thr Thr Ile Asn Lys Glu Gln Phe Ser Lys Arg Lys Asn Asp Thr Leu
            180             185             190

Asp Pro Glu Leu Phe Val Glu Cys Thr Glu Cys Gly Arg Lys Met His
            195             200             205

Gln Ile Cys Val Leu His His Glu Ile Ile Trp Pro Ala Gly Phe Val
            210             215             220

Cys Asp Gly Cys Leu Lys Lys Ser Ala Arg Thr Arg Lys Glu Asn Lys
225             230             235             240

Phe Ser Ala Lys Arg Leu Pro Ser Thr Arg Leu Gly Thr Phe Leu Glu
                245             250             255

Asn Arg Val Asn Asp Phe Leu Arg Arg Gln Asn His Pro Glu Ser Gly
            260             265             270

Glu Val Thr Val Arg Val Val His Ala Ser Asp Lys Thr Val Glu Val
            275             280             285

Lys Pro Gly Met Lys Ala Arg Phe Val Asp Ser Gly Glu Met Ala Glu
            290             295             300

Ser Phe Pro Tyr Arg Thr Lys Ala Leu Phe Ala Phe Glu Glu Ile Asp
305             310             315             320

Gly Val Asp Leu Cys Phe Phe Gly Met His Val Gln Glu Tyr Gly Ser
                325             330             335

Asp Cys Pro Pro Pro Asn Gln Arg Arg Val Tyr Ile Ser Tyr Leu Asp
            340             345             350

Ser Val His Phe Phe Arg Pro Lys Cys Leu Arg Thr Ala Val Tyr His
            355             360             365

Glu Ile Leu Ile Gly Tyr Leu Glu Tyr Val Lys Lys Leu Gly Tyr Thr
            370             375             380

Thr Gly His Ile Trp Ala Cys Pro Pro Ser Glu Gly Asp Asp Tyr Ile
385             390             395             400

Phe His Cys His Pro Asp Gln Lys Ile Pro Lys Pro Lys Arg Leu
            405             410             415

Gln Glu Trp Tyr Lys Lys Met Leu Asp Lys Ala Val Ser Glu Arg Ile
            420             425             430

Val His Asp Tyr Lys Asp Ile Phe Lys Gln Ala Thr Glu Asp Arg Leu
            435             440             445

Thr Ser Ala Lys Glu Leu Pro Tyr Phe Glu Gly Asp Phe Trp Pro Asn
450             455             460

Val Leu Glu Glu Ser Ile Lys Glu Leu Glu Gln Glu Glu Glu Glu Arg
465             470             475             480

Lys Arg Glu Glu Asn Thr Ser Asn Glu Ser Thr Asp Val Thr Lys Gly
            485             490             495

Asp Ser Lys Asn Ala Lys Lys Asn Asn Lys Lys Thr Ser Lys Asn
            500             505             510

Lys Ser Ser Leu Ser Arg Gly Asn Lys Lys Pro Gly Met Pro Asn
            515             520             525
```

```
Val Ser Asn Asp Leu Ser Gln Lys Leu Tyr Ala Thr Met Glu Lys His
    530                 535                 540

Lys Glu Val Phe Phe Val Ile Arg Leu Ile Ala Gly Pro Ala Ala Asn
545                 550                 555                 560

Ser Leu Pro Pro Ile Val Asp Pro Asp Pro Leu Ile Pro Cys Asp Leu
                565                 570                 575

Met Asp Gly Arg Asp Ala Phe Leu Thr Leu Ala Arg Asp Lys His Leu
            580                 585                 590

Glu Phe Ser Ser Leu Glu Glu Ala Gln Trp Ser Thr Met Cys Met Leu
        595                 600                 605

Val Glu Leu His Thr Gln Ser Gln Asp
    610                 615
```

<210> SEQ ID NO 6
<211> LENGTH: 617
<212> TYPE: PRT
<213> ORGANISM: Homo sapiens

<400> SEQUENCE: 6

```
Ile Phe Lys Pro Glu Glu Leu Arg Gln Ala Leu Met Pro Thr Leu Glu
1               5                   10                  15

Ala Leu Tyr Arg Gln Asp Pro Glu Ser Leu Pro Phe Arg Gln Pro Val
                20                  25                  30

Asp Pro Gln Leu Leu Gly Ile Pro Asp Tyr Phe Asp Ile Val Lys Ser
            35                  40                  45

Pro Met Asp Leu Ser Thr Ile Lys Arg Lys Leu Asp Thr Gly Gln Tyr
        50                  55                  60

Gln Glu Pro Trp Gln Tyr Val Asp Asp Ile Trp Leu Met Phe Asn Asn
65                  70                  75                  80

Ala Trp Leu Tyr Asn Arg Lys Thr Ser Arg Val Tyr Lys Tyr Cys Ser
                85                  90                  95

Lys Leu Ser Glu Val Phe Glu Gln Glu Ile Asp Pro Val Met Gln Ser
                100                 105                 110

Leu Gly Tyr Cys Cys Gly Arg Lys Leu Glu Phe Ser Pro Gln Thr Leu
            115                 120                 125

Cys Cys Tyr Gly Lys Gln Leu Cys Thr Ile Pro Arg Asp Ala Thr Tyr
        130                 135                 140

Tyr Ser Tyr Gln Asn Arg Tyr His Phe Cys Glu Lys Arg Phe Asn Glu
145                 150                 155                 160

Ile Gln Gly Glu Ser Val Ser Leu Gly Asp Asp Pro Ser Gln Pro Gln
                165                 170                 175

Thr Thr Ile Asn Lys Glu Gln Phe Ser Lys Arg Lys Asn Asp Thr Leu
            180                 185                 190

Asp Pro Glu Leu Phe Val Glu Cys Thr Glu Cys Gly Arg Lys Met His
        195                 200                 205

Gln Ile Cys Val Leu His His Glu Ile Ile Trp Pro Ala Gly Phe Val
    210                 215                 220

Cys Asp Gly Cys Leu Lys Lys Ser Ala Arg Thr Arg Lys Glu Asn Lys
225                 230                 235                 240

Phe Ser Ala Lys Arg Leu Pro Ser Thr Arg Leu Gly Thr Phe Leu Glu
                245                 250                 255

Asn Arg Val Asn Asp Phe Leu Arg Arg Gln Asn His Pro Glu Ser Gly
            260                 265                 270

Glu Val Thr Val Arg Val Val His Ala Ser Asp Lys Thr Val Glu Val
```

```
                275                 280                 285
Lys Pro Gly Met Lys Ala Arg Phe Val Asp Ser Gly Glu Met Ala Glu
            290                 295                 300

Ser Phe Pro Tyr Arg Thr Lys Ala Leu Phe Ala Phe Glu Glu Ile Asp
305                 310                 315                 320

Gly Val Asp Leu Cys Phe Phe Gly Met His Val Gln Glu Tyr Gly Ser
                325                 330                 335

Asp Cys Pro Pro Asn Gln Arg Arg Val Tyr Ile Ser Tyr Leu Asp
            340                 345                 350

Ser Val His Phe Phe Arg Pro Lys Cys Leu Arg Thr Ala Val Tyr His
                355                 360                 365

Glu Ile Leu Ile Gly Tyr Leu Glu Tyr Val Lys Lys Leu Gly Tyr Thr
            370                 375                 380

Thr Gly His Ile Trp Ala Cys Pro Pro Ser Glu Gly Asp Asp Tyr Ile
385                 390                 395                 400

Phe His Cys His Pro Pro Asp Gln Lys Ile Pro Lys Pro Lys Arg Leu
                405                 410                 415

Gln Glu Trp Tyr Lys Lys Met Leu Asp Lys Ala Val Ser Glu Arg Ile
            420                 425                 430

Val His Asp Tyr Lys Asp Ile Phe Lys Gln Ala Thr Glu Asp Arg Leu
                435                 440                 445

Thr Ser Ala Lys Glu Leu Pro Tyr Phe Glu Gly Asp Phe Trp Pro Asn
450                 455                 460

Val Leu Glu Glu Ser Ile Lys Glu Leu Glu Gln Glu Glu Glu Glu Arg
465                 470                 475                 480

Lys Arg Glu Glu Asn Thr Ser Asn Glu Ser Thr Asp Val Thr Lys Gly
                485                 490                 495

Asp Ser Lys Asn Ala Lys Lys Asn Lys Lys Thr Ser Lys Asn
            500                 505                 510

Lys Ser Ser Leu Ser Arg Gly Asn Lys Lys Pro Gly Met Pro Asn
515                 520                 525

Val Ser Asn Asp Leu Ser Gln Lys Leu Tyr Ala Thr Met Glu Lys His
            530                 535                 540

Lys Glu Val Phe Phe Val Ile Arg Leu Ile Ala Gly Pro Ala Ala Asn
545                 550                 555                 560

Ser Leu Pro Pro Ile Val Asp Pro Asp Pro Leu Ile Pro Cys Asp Leu
                565                 570                 575

Met Asp Gly Arg Asp Ala Phe Leu Thr Leu Ala Arg Asp Lys His Leu
            580                 585                 590

Glu Phe Ser Ser Leu Arg Arg Ala Gln Trp Ser Thr Met Cys Met Leu
            595                 600                 605

Val Glu Leu His Thr Gln Ser Gln Asp
            610                 615

<210> SEQ ID NO 7
<211> LENGTH: 617
<212> TYPE: PRT
<213> ORGANISM: Homo sapiens

<400> SEQUENCE: 7

Ile Phe Lys Pro Glu Glu Leu Arg Gln Ala Leu Met Pro Thr Leu Glu
1               5                   10                  15

Ala Leu Tyr Arg Gln Asp Pro Glu Ser Leu Pro Phe Arg Gln Pro Val
            20                  25                  30
```

-continued

Asp Pro Gln Leu Leu Gly Ile Pro Asp Tyr Phe Asp Ile Val Lys Ser
            35                  40                  45

Pro Met Asp Leu Ser Thr Ile Lys Arg Lys Leu Asp Thr Gly Gln Tyr
 50                  55                  60

Gln Glu Pro Trp Gln Tyr Val Asp Asp Ile Trp Leu Met Phe Asn Asn
 65                  70                  75                  80

Ala Trp Leu Tyr Asn Arg Lys Thr Ser Arg Val Tyr Lys Tyr Cys Ser
                85                  90                  95

Lys Leu Ser Glu Val Phe Glu Gln Glu Ile Asp Pro Val Met Gln Ser
            100                 105                 110

Leu Gly Tyr Cys Cys Gly Arg Lys Leu Glu Phe Ser Pro Gln Thr Leu
            115                 120                 125

Cys Cys Tyr Gly Lys Gln Leu Cys Thr Ile Pro Arg Asp Ala Thr Tyr
    130                 135                 140

Tyr Ser Tyr Gln Asn Arg Tyr His Phe Cys Glu Lys Cys Phe Asn Glu
145                 150                 155                 160

Ile Gln Gly Glu Ser Val Ser Leu Gly Asp Asp Pro Ser Gln Pro Gln
                165                 170                 175

Thr Thr Ile Asn Lys Glu Gln Phe Ser Lys Arg Lys Asn Asp Thr Leu
            180                 185                 190

Asp Pro Glu Leu Phe Val Glu Cys Thr Glu Cys Gly Arg Lys Met His
            195                 200                 205

Gln Ile Cys Val Leu His Glu Ile Ile Trp Pro Ala Gly Phe Val
    210                 215                 220

Cys Asp Gly Cys Leu Lys Lys Ser Ala Arg Thr Arg Lys Glu Asn Lys
225                 230                 235                 240

Phe Ser Ala Lys Arg Leu Pro Ser Thr Arg Leu Gly Thr Phe Leu Glu
                245                 250                 255

Asn Arg Val Asn Asp Phe Leu Arg Arg Gln Asn His Pro Glu Ser Gly
            260                 265                 270

Glu Val Thr Val Arg Val Val His Ala Ser Asp Lys Thr Val Glu Val
            275                 280                 285

Lys Pro Gly Met Lys Ala Arg Phe Val Asp Ser Gly Glu Met Ala Glu
290                 295                 300

Ser Phe Pro Tyr Arg Thr Lys Ala Leu Phe Ala Phe Glu Glu Ile Asp
305                 310                 315                 320

Gly Val Asp Leu Cys Phe Phe Gly Met His Val Gln Glu Tyr Gly Ser
                325                 330                 335

Asp Cys Pro Pro Pro Asn Gln Arg Arg Val Tyr Ile Ser Tyr Leu Asp
            340                 345                 350

Ser Val His Phe Phe Arg Pro Lys Cys Leu Arg Thr Ala Val Tyr His
            355                 360                 365

Glu Ile Leu Ile Gly Tyr Leu Glu Tyr Val Lys Lys Leu Gly Tyr Thr
370                 375                 380

Thr Gly His Ile Trp Ala Cys Pro Pro Ser Glu Gly Asp Asp Tyr Ile
385                 390                 395                 400

Phe His Cys His Pro Asp Gln Lys Ile Pro Lys Pro Lys Arg Leu
                405                 410                 415

Gln Glu Trp Phe Lys Lys Met Leu Asp Lys Ala Val Ser Glu Arg Ile
            420                 425                 430

Val His Asp Tyr Lys Asp Ile Phe Lys Gln Ala Thr Glu Asp Arg Leu
            435                 440                 445

Thr Ser Ala Lys Glu Leu Pro Tyr Phe Glu Gly Asp Phe Trp Pro Asn

```
                     450                 455                 460
Val Leu Glu Glu Ser Ile Lys Glu Leu Glu Gln Glu Glu Glu Arg
465                 470                 475                 480

Lys Arg Glu Glu Asn Thr Ser Asn Glu Ser Thr Asp Val Thr Lys Gly
                    485                 490                 495

Asp Ser Lys Asn Ala Lys Lys Asn Asn Lys Lys Thr Ser Lys Asn
                500                 505                 510

Lys Ser Ser Leu Ser Arg Gly Asn Lys Lys Pro Gly Met Pro Asn
            515                 520                 525

Val Ser Asn Asp Leu Ser Gln Lys Leu Tyr Ala Thr Met Glu Lys His
            530                 535                 540

Lys Glu Val Phe Phe Val Ile Arg Leu Ile Ala Gly Pro Ala Ala Asn
545                 550                 555                 560

Ser Leu Pro Pro Ile Val Asp Pro Asp Pro Leu Ile Pro Cys Asp Leu
                565                 570                 575

Met Asp Gly Arg Asp Ala Phe Leu Thr Leu Ala Arg Asp Lys His Leu
            580                 585                 590

Glu Phe Ser Ser Leu Arg Arg Ala Gln Trp Ser Thr Met Cys Met Leu
        595                 600                 605

Val Glu Leu His Thr Gln Ser Gln Asp
    610                 615

<210> SEQ ID NO 8
<211> LENGTH: 617
<212> TYPE: PRT
<213> ORGANISM: Homo sapiens

<400> SEQUENCE: 8

Ile Phe Lys Pro Glu Glu Leu Arg Gln Ala Leu Met Pro Thr Leu Glu
1               5                   10                  15

Ala Leu Tyr Arg Gln Asp Pro Glu Ser Leu Pro Phe Arg Gln Pro Val
                20                  25                  30

Asp Pro Gln Leu Leu Gly Ile Pro Asp Tyr Phe Asp Ile Val Lys Ser
            35                  40                  45

Pro Met Asp Leu Ser Thr Ile Lys Arg Lys Leu Asp Thr Gly Gln Tyr
        50                  55                  60

Gln Glu Pro Trp Gln Tyr Val Asp Asp Ile Trp Leu Met Phe Asn Asn
65                  70                  75                  80

Ala Trp Leu Tyr Asn Arg Lys Thr Ser Arg Val Tyr Lys Tyr Cys Ser
                85                  90                  95

Lys Leu Ser Glu Val Phe Glu Gln Glu Ile Asp Pro Val Met Gln Ser
            100                 105                 110

Leu Gly Tyr Cys Cys Gly Arg Lys Leu Glu Phe Ser Pro Gln Thr Leu
        115                 120                 125

Cys Cys Tyr Gly Lys Gln Leu Cys Thr Ile Pro Arg Asp Ala Thr Tyr
    130                 135                 140

Tyr Ser Tyr Gln Asn Arg Tyr His Phe Cys Glu Lys Cys Phe Asn Glu
145                 150                 155                 160

Ile Gln Gly Glu Ser Val Ser Leu Gly Asp Asp Pro Ser Gln Pro Gln
                165                 170                 175

Thr Thr Ile Asn Lys Glu Gln Phe Ser Lys Arg Lys Asn Asp Thr Leu
            180                 185                 190

Asp Pro Glu Leu Phe Val Glu Cys Thr Glu Cys Gly Arg Lys Met His
        195                 200                 205
```

```
Gln Ile Cys Val Leu His His Glu Ile Ile Trp Pro Ala Gly Phe Val
    210                 215                 220
Cys Asp Gly Cys Leu Lys Lys Ser Ala Arg Thr Arg Lys Glu Asn Lys
225                 230                 235                 240
Phe Ser Ala Lys Arg Leu Pro Ser Thr Arg Leu Gly Thr Phe Leu Glu
                245                 250                 255
Asn Arg Val Asn Asp Phe Leu Arg Arg Gln Asn His Pro Glu Ser Gly
            260                 265                 270
Glu Val Thr Val Arg Val Val His Ala Ser Asp Lys Thr Val Glu Val
        275                 280                 285
Lys Pro Gly Met Lys Ala Arg Phe Val Asp Ser Gly Glu Met Ala Glu
290                 295                 300
Ser Phe Pro Tyr Arg Thr Lys Ala Leu Phe Ala Phe Glu Glu Ile Asp
305                 310                 315                 320
Gly Val Asp Leu Cys Phe Phe Gly Met His Val Gln Glu Tyr Gly Ser
                325                 330                 335
Asp Cys Pro Pro Pro Asn Gln Arg Arg Val Tyr Ile Trp Trp Leu Asp
            340                 345                 350
Ser Val His Phe Phe Arg Pro Lys Cys Leu Arg Thr Ala Val Tyr His
        355                 360                 365
Glu Ile Leu Ile Gly Tyr Leu Glu Tyr Val Lys Lys Leu Gly Tyr Thr
370                 375                 380
Thr Gly His Ile Trp Ala Cys Pro Pro Ser Glu Gly Asp Asp Tyr Ile
385                 390                 395                 400
Phe His Cys His Pro Pro Asp Gln Lys Ile Pro Lys Pro Lys Arg Leu
                405                 410                 415
Gln Glu Trp Tyr Lys Lys Met Leu Asp Lys Ala Val Ser Glu Arg Ile
            420                 425                 430
Val His Asp Tyr Lys Asp Ile Phe Lys Gln Ala Thr Glu Asp Arg Leu
        435                 440                 445
Thr Ser Ala Lys Glu Leu Pro Tyr Phe Glu Gly Asp Phe Trp Pro Asn
450                 455                 460
Val Leu Glu Glu Ser Ile Lys Glu Leu Glu Gln Glu Glu Glu Glu Arg
465                 470                 475                 480
Lys Arg Glu Glu Asn Thr Ser Asn Glu Ser Thr Asp Val Thr Lys Gly
                485                 490                 495
Asp Ser Lys Asn Ala Lys Lys Asn Asn Lys Lys Thr Ser Lys Asn
            500                 505                 510
Lys Ser Ser Leu Ser Arg Gly Asn Lys Lys Pro Gly Met Pro Asn
        515                 520                 525
Val Ser Asn Asp Leu Ser Gln Lys Leu Tyr Ala Thr Met Glu Lys His
530                 535                 540
Lys Glu Val Phe Phe Val Ile Arg Leu Ile Ala Gly Pro Ala Ala Asn
545                 550                 555                 560
Ser Leu Pro Pro Ile Val Asp Pro Asp Pro Leu Ile Pro Cys Asp Leu
                565                 570                 575
Met Asp Gly Arg Asp Ala Phe Leu Thr Leu Ala Arg Asp Lys His Leu
            580                 585                 590
Glu Phe Ser Ser Leu Arg Arg Ala Gln Trp Ser Thr Met Cys Met Leu
        595                 600                 605
Val Glu Leu His Thr Gln Ser Gln Asp
    610                 615
```

```
<210> SEQ ID NO 9
<211> LENGTH: 617
<212> TYPE: PRT
<213> ORGANISM: Homo sapiens

<400> SEQUENCE: 9

Ile Phe Lys Pro Glu Glu Leu Arg Gln Ala Leu Met Pro Thr Leu Glu
1               5                   10                  15

Ala Leu Tyr Arg Gln Asp Pro Glu Ser Leu Pro Phe Arg Gln Pro Val
            20                  25                  30

Asp Pro Gln Leu Leu Gly Ile Pro Asp Tyr Phe Asp Ile Val Lys Ser
        35                  40                  45

Pro Met Asp Leu Ser Thr Ile Lys Arg Lys Leu Asp Thr Gly Gln Tyr
50                  55                  60

Gln Glu Pro Trp Gln Tyr Val Asp Asp Ile Trp Leu Met Phe Asn Asn
65                  70                  75                  80

Ala Trp Leu Tyr Asn Arg Lys Thr Ser Arg Val Tyr Lys Tyr Cys Ser
                85                  90                  95

Lys Leu Ser Glu Val Phe Glu Gln Glu Ile Asp Pro Val Met Gln Ser
            100                 105                 110

Leu Gly Tyr Cys Cys Gly Arg Lys Leu Glu Phe Ser Pro Gln Thr Leu
        115                 120                 125

Cys Cys Tyr Gly Lys Gln Leu Cys Thr Ile Pro Arg Asp Ala Thr Tyr
130                 135                 140

Tyr Ser Tyr Gln Asn Arg Tyr His Phe Cys Glu Lys Cys Phe Asn Glu
145                 150                 155                 160

Ile Gln Gly Glu Ser Val Ser Leu Gly Asp Asp Pro Ser Gln Pro Gln
                165                 170                 175

Thr Thr Ile Asn Lys Glu Gln Phe Ser Lys Arg Lys Asn Asp Thr Leu
            180                 185                 190

Asp Pro Glu Leu Phe Val Glu Cys Thr Glu Cys Gly Arg Lys Met His
        195                 200                 205

Gln Ile Cys Val Leu His His Glu Ile Ile Trp Pro Ala Gly Phe Val
210                 215                 220

Cys Asp Gly Cys Leu Lys Lys Ser Ala Arg Thr Arg Lys Glu Asn Lys
225                 230                 235                 240

Phe Ser Ala Lys Arg Leu Pro Ser Thr Arg Leu Gly Thr Phe Leu Glu
                245                 250                 255

Asn Arg Val Asn Asp Phe Leu Arg Arg Gln Asn His Pro Glu Ser Gly
            260                 265                 270

Glu Val Thr Val Arg Val Val His Ala Ser Asp Lys Thr Val Glu Val
        275                 280                 285

Lys Pro Gly Met Lys Ala Arg Phe Val Asp Ser Gly Glu Met Ala Glu
290                 295                 300

Ser Phe Pro Tyr Arg Thr Lys Ala Leu Phe Ala Phe Glu Glu Ile Asp
305                 310                 315                 320

Gly Val Asp Leu Cys Phe Phe Gly Met His Val Gln Glu Tyr Gly Ser
                325                 330                 335

Asp Cys Pro Pro Pro Asn Gln Arg Arg Val Tyr Ile Ser Tyr Leu Asp
            340                 345                 350

Ser Val His Phe Phe Arg Pro Lys Cys Leu Arg Thr Ala Val Tyr Ala
        355                 360                 365

Glu Ile Leu Ile Gly Tyr Leu Ala Ala Val Lys Lys Ser Gly Ala Thr
370                 375                 380
```

Thr Gly Ala Ile Trp Ala Cys Pro Pro Ser Glu Gly Asp Asp Tyr Ile
385                 390                 395                 400

Phe His Cys His Pro Pro Asp Gln Lys Ile Pro Lys Pro Lys Arg Leu
            405                 410                 415

Gln Glu Trp Tyr Lys Lys Met Leu Asp Lys Ala Val Ser Glu Arg Ile
        420                 425                 430

Val His Asp Tyr Lys Asp Ile Phe Lys Gln Ala Thr Glu Asp Arg Leu
    435                 440                 445

Thr Ser Ala Lys Glu Leu Pro Tyr Phe Glu Gly Asp Phe Trp Pro Asn
450                 455                 460

Val Leu Glu Glu Ser Ile Lys Glu Leu Glu Gln Glu Glu Glu Glu Arg
465                 470                 475                 480

Lys Arg Glu Glu Asn Thr Ser Asn Glu Ser Thr Asp Val Thr Lys Gly
                485                 490                 495

Asp Ser Lys Asn Ala Lys Lys Asn Asn Lys Lys Thr Ser Lys Asn
            500                 505                 510

Lys Ser Ser Leu Ser Arg Gly Asn Lys Lys Pro Gly Met Pro Asn
515                 520                 525

Val Ser Asn Asp Leu Ser Gln Lys Leu Tyr Ala Thr Met Glu Lys His
530                 535                 540

Lys Glu Val Phe Phe Val Ile Arg Leu Ile Ala Gly Pro Ala Ala Asn
545                 550                 555                 560

Ser Leu Pro Pro Ile Val Asp Pro Asp Pro Leu Ile Pro Cys Asp Leu
                565                 570                 575

Met Asp Gly Arg Asp Ala Phe Leu Thr Leu Ala Arg Asp Lys His Leu
            580                 585                 590

Glu Phe Ser Ser Leu Arg Arg Ala Gln Trp Ser Thr Met Cys Met Leu
        595                 600                 605

Val Glu Leu His Thr Gln Ser Gln Asp
    610                 615

<210> SEQ ID NO 10
<211> LENGTH: 1082
<212> TYPE: PRT
<213> ORGANISM: Neisseria meningitidis

<400> SEQUENCE: 10

Met Ala Ala Phe Lys Pro Asn Pro Ile Asn Tyr Ile Leu Gly Leu Ala
1               5                   10                  15

Ile Gly Ile Ala Ser Val Gly Trp Ala Met Val Glu Ile Asp Glu Asp
            20                  25                  30

Glu Asn Pro Ile Cys Leu Ile Asp Leu Gly Val Arg Val Phe Glu Arg
        35                  40                  45

Ala Glu Val Pro Lys Thr Gly Asp Ser Leu Ala Met Ala Arg Arg Leu
    50                  55                  60

Ala Arg Ser Val Arg Arg Leu Thr Arg Arg Arg Ala His Arg Leu Leu
65                  70                  75                  80

Arg Ala Arg Arg Leu Leu Lys Arg Glu Gly Val Leu Gln Ala Ala Asp
                85                  90                  95

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
        115                 120                 125

Ala Val Leu Leu His Leu Ile Lys His Arg Gly Tyr Leu Ser Gln Arg
    130                 135                 140

```
Lys Asn Glu Gly Glu Thr Ala Asp Lys Glu Leu Gly Ala Leu Leu Lys
145                 150                 155                 160

Gly Val Ala Asp Asn Ala His Ala Leu Gln Thr Gly Asp Phe Arg Thr
            165                 170                 175

Pro Ala Glu Leu Ala Leu Asn Lys Phe Glu Lys Glu Ser Gly His Ile
            180                 185                 190

Arg Asn Gln Arg Gly Asp Tyr Ser His Thr Phe Ser Arg Lys Asp Leu
            195                 200                 205

Gln Ala Glu Leu Ile Leu Leu Phe Glu Lys Gln Lys Glu Phe Gly Asn
210                 215                 220

Pro His Val Ser Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
            245                 250                 255

His Cys Thr Phe Glu Pro Ala Glu Pro Lys Ala Ala Lys Asn Thr Tyr
            260                 265                 270

Thr Ala Glu Arg Phe Ile Trp Leu Thr Lys Leu Asn Asn Leu Arg Ile
            275                 280                 285

Leu Glu Gln Gly Ser Glu Arg Pro Leu Thr Asp Thr Glu Arg Ala Thr
290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
            325                 330                 335

Tyr Gly Lys Asp Asn Ala Glu Ala Ser Thr Leu Met Glu Met Lys Ala
            340                 345                 350

Tyr His Ala Ile Ser Arg Ala Leu Glu Lys Glu Gly Leu Lys Asp Lys
            355                 360                 365

Lys Ser Pro Leu Asn Leu Ser Pro Glu Leu Gln Asp Glu Ile Gly Thr
            370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
            405                 410                 415

Phe Asp Lys Phe Val Gln Ile Ser Leu Lys Ala Leu Arg Arg Ile Val
            420                 425                 430

Pro Leu Met Glu Gln Gly Lys Arg Tyr Asp Glu Ala Cys Ala Glu Ile
            435                 440                 445

Tyr Gly Asp His Tyr Gly Lys Lys Asn Thr Glu Glu Lys Ile Tyr Leu
            450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
            485                 490                 495

Ser Pro Ala Arg Ile His Ile Glu Thr Ala Arg Glu Val Gly Lys Ser
            500                 505                 510

Phe Lys Asp Arg Lys Glu Ile Glu Lys Arg Gln Glu Glu Asn Arg Lys
            515                 520                 525

Asp Arg Glu Lys Ala Ala Ala Lys Phe Arg Glu Tyr Phe Pro Asn Phe
            530                 535                 540

Val Gly Glu Pro Lys Ser Lys Asp Ile Leu Lys Leu Arg Leu Tyr Glu
545                 550                 555                 560
```

-continued

```
Gln Gln His Gly Lys Cys Leu Tyr Ser Gly Lys Glu Ile Asn Leu Gly
                565                 570                 575
Arg Leu Asn Glu Lys Gly Tyr Val Glu Ile Ala Ala Ala Leu Pro Phe
            580                 585                 590
Ser Arg Thr Trp Asp Ser Phe Asn Asn Lys Val Leu Val Leu Gly
        595                 600                 605
Ser Glu Ala Gln Asn Lys Gly Asn Gln Thr Pro Tyr Glu Tyr Phe Asn
    610                 615                 620
Gly Lys Asp Asn Ser Arg Glu Trp Gln Glu Phe Lys Ala Arg Val Glu
625                 630                 635                 640
Thr Ser Arg Phe Pro Arg Ser Lys Lys Gln Arg Ile Leu Leu Gln Lys
                645                 650                 655
Phe Asp Glu Asp Gly Phe Lys Glu Arg Asn Leu Asn Asp Thr Arg Tyr
            660                 665                 670
Val Asn Arg Phe Leu Cys Gln Phe Val Ala Asp Arg Met Arg Leu Thr
        675                 680                 685
Gly Lys Gly Lys Lys Arg Val Phe Ala Ser Asn Gly Gln Ile Thr Asn
    690                 695                 700
Leu Leu Arg Gly Phe Trp Gly Leu Arg Lys Val Arg Ala Glu Asn Asp
705                 710                 715                 720
Arg His His Ala Leu Asp Ala Val Val Ala Cys Ser Thr Val Ala
                725                 730                 735
Met Gln Gln Lys Ile Thr Arg Phe Val Arg Tyr Lys Glu Met Asn Ala
            740                 745                 750
Phe Asp Gly Lys Thr Ile Asp Lys Glu Thr Gly Glu Val Leu His Gln
        755                 760                 765
Lys Thr His Phe Pro Gln Pro Trp Glu Phe Phe Ala Gln Glu Val Met
    770                 775                 780
Ile Arg Val Phe Gly Lys Pro Asp Gly Lys Pro Glu Phe Glu Glu Ala
785                 790                 795                 800
Asp Thr Pro Glu Lys Leu Arg Thr Leu Leu Ala Glu Lys Leu Ser Ser
                805                 810                 815
Arg Pro Glu Ala Val His Glu Tyr Val Thr Pro Leu Phe Val Ser Arg
            820                 825                 830
Ala Pro Asn Arg Lys Met Ser Gly Gln Gly His Met Glu Thr Val Lys
        835                 840                 845
Ser Ala Lys Arg Leu Asp Glu Gly Val Ser Val Leu Arg Val Pro Leu
    850                 855                 860
Thr Gln Leu Lys Leu Lys Asp Leu Glu Lys Met Val Asn Arg Glu Arg
865                 870                 875                 880
Glu Pro Lys Leu Tyr Glu Ala Leu Lys Ala Arg Leu Glu Ala His Lys
                885                 890                 895
Asp Asp Pro Ala Lys Ala Phe Ala Glu Pro Phe Tyr Lys Tyr Asp Lys
            900                 905                 910
Ala Gly Asn Arg Thr Gln Gln Val Lys Ala Val Arg Val Glu Gln Val
        915                 920                 925
Gln Lys Thr Gly Val Trp Val Arg Asn His Asn Gly Ile Ala Asp Asn
    930                 935                 940
Ala Thr Met Val Arg Val Asp Val Phe Glu Lys Gly Asp Lys Tyr Tyr
945                 950                 955                 960
Leu Val Pro Ile Tyr Ser Trp Gln Val Ala Lys Gly Ile Leu Pro Asp
                965                 970                 975
Arg Ala Val Val Gln Gly Lys Asp Glu Glu Asp Trp Gln Leu Ile Asp
```

```
                      980             985             990
Asp Ser Phe Asn Phe Lys Phe Ser  Leu His Pro Asn Asp  Leu Val Glu
            995              1000                 1005

Val Ile  Thr Lys Lys Ala Arg  Met Phe Gly Tyr Phe  Ala Ser Cys
    1010             1015                 1020

His Arg  Gly Thr Gly Asn Ile  Asn Ile Arg Ile His  Asp Leu Asp
    1025             1030                 1035

His Lys  Ile Gly Lys Asn Gly  Ile Leu Glu Gly Ile  Gly Val Lys
    1040             1045                 1050

Thr Ala  Leu Ser Phe Gln Lys  Tyr Gln Ile Asp Glu  Leu Gly Lys
    1055             1060                 1065

Glu Ile  Arg Pro Cys Arg Leu  Lys Lys Arg Pro  Val Arg
    1070             1075             1080

<210> SEQ ID NO 11
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Tyr Lys Asp His Asp Gly Asp  Tyr Lys Asp His Asp  Ile Asp Tyr
1               5                10                   15

Lys Asp Asp Asp Asp Lys
            20

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Lys Lys Lys Arg Lys Val Gly
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Pro Tyr Asp Val Pro Asp Tyr Ala Ser
1               5                   10

<210> SEQ ID NO 14
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ala Leu Asp Asp Phe Asp Leu Asp Met Leu Gly Ser Asp Ala Leu
1               5                   10                  15
```

-continued

```
Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45

Met Leu
    50

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gggctcctcc ttgtact                                                  17

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
acgcagataa gaaccagt                                                 18

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ggcatcaagt cagccat                                                  17

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agcctgagtc accctcct                                                 18

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gggctcctcc ttgtact                                                  17

<210> SEQ ID NO 20
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 20
acgcagataa gaaccagt                                                 18

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ggcatcaagt cagccat                                                  17

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agcctgagtc accctcct                                                 18

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tgtactctct gaggtgctc                                                19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
acgcagataa gaaccagtt                                                19

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
catcaagtca gccatcagc                                                19

<210> SEQ ID NO 26
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 26
gagtcaccct cctggaaac                                                     19

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cctgggctcc ggggcgttt                                                     19

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28 ggccctgcg gccaccccg                                                      19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ctccctccct gcccggtag                                                     19

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aggtttggaa agggcgtgc                                                     19

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
actccactgc actccagtct                                                    20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 32
tctgtggggg acctgcactg                                              20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ggggcgccag ttgtgtctcc                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
acaccattgc caccaccatt                                              20

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tgttttcagc ttccaaact                                               19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
catgaagaca gcagaagcc                                               19

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ggcccacatt cctttccag                                               19

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 38
ggctggattg ggtttccag                                                    19

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
caactgagtc ctgaggttt                                                    19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ctcacagcac agccagtgt                                                    19

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cagcagctgg tcacaaagc                                                    19

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cttcctataa acttctgag                                                    19

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
agtgataaga cacccgcttt                                                   20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 44
cagacatcta ataccacggt                                               20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
agggagaacg gggcctaccg                                               20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
acttcaggtt caaagaagcc                                               20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ttttccccac ccagggccta                                               20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ccctgggtgg ggaaaaccag                                               20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ggaggaacat gcttcggaac                                               20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
```
gtgccgtgat ggttctgtcc                                             20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ggtctgccgg aaggtctaca                                             20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52 tcggcttta actgcccaaa                                              20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gcatgacaaa ggtgccgtga                                             20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
cctgcctttt gggcagttaa                                             20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
aatatgtcac attctgtctc                                             20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ggactatggg aggtcactaa                                        20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gaaggttaca cagaaccaga                                        20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gccctgtaag catcctgctg                                        20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ccactgctaa ctgaaagaga                                        20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
agccacagtt tcagcgcagt                                        20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ctgtttcatc ttagaaaaat                                        20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gaatgttctt tggcaggtac                                        20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
cgcacatctt atgtcttaga                                              20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cttaagagag ctagaactgg                                              20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tcccaaagta cagtaccttg                                              20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tccctagaga ggacagacag                                              20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
tcatagagaa atgaaaagag                                              20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ataatatacc ctgactccta                                              20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
aggccacctg caagataaat					20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
tgttgttatc aattgccata					20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
atcccttcca gcatcctcat					20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gtgcttcaaa accatttgct					20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gatacatgtt ttattcttat					20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
caatgacccc ttcattgacc					20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ttgattttgg agggatctcg                                              20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ggaatccatg gagggaagat                                              20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tgttctcgct caggtcagtg                                              20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tccctctttc acggtctcac                                              20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
aacacccgac tgctgtatcc                                              20

<210> SEQ ID NO 80
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cgaaagagaa agcgaaccag tatcgagaac                                   30

<210> SEQ ID NO 81

```
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
cgttgtgcat agtcgctgct tgatcgc                                         27

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gcacgtggat cctgagaact                                                 20

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
attggacagc aagaaagcga g                                               21

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gcacgtggat cctgagaact                                                 20

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
caggaaacag tccaggatct ca                                              22

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gctgagtgaa ctgcactgtg a                                               21

<210> SEQ ID NO 87
<211> LENGTH: 20
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gaattctttg ccgaaatgga                                          20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
tcactagcaa gctctcaggc                                          20

<210> SEQ ID NO 89
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
aacaacgagg agtctgccc                                           19

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gcagacagtg accatctaca gctt                                     24

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
caatccctct cgtccagtcg                                          20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
tgcttggact atgggaggtc                                          20

<210> SEQ ID NO 93
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 93
gcaggtgctt caaaaccatt                                                     20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
tcaggtggtc agcttctcct                                                     20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
aagcaaacct tctggctcaa                                                     20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ccacacaggt gaacccttTt                                                     20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
ggacacatgc tcacatacgg                                                     20

<210> SEQ ID NO 98
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
attcgatcca tgtgcctga                                                      19

<210> SEQ ID NO 99
<211> LENGTH: 20
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 99
caatgctgga atttgtggaa                                            20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ggggtgattc cctagagagg                                            20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
aagcaggaca gacaggcaag                                            20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gagggtcagc agtgatggat                                            20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
tggaaaagga gaatgggaga                                            20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
tggtcaagtt tgccttgtca                                            20

<210> SEQ ID NO 105
<211> LENGTH: 21
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 105
ggaatgactg aatcggaaca a                                           21

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
cctccagcat cttccacatt                                             20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gaagcaccct tcagcagttc                                             20

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
ccacagtttc agcgcagtaa ta                                          22

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
atcagccagc acacacactt                                             20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
ccctgtcagg agggacagat                                             20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 111
ggctcaccgg aagcatgaat                                                20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
aagctacaag caggttcgct                                                20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
aataacaggg tccatcccgc                                                20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
tgttccctcc acctggaata                                                20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
gggaaaatcc aaagcaggat                                                20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
tcctaggtcc ctcaaaagca                                                20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gtccccaacg ctctaacaaa                                              20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gttagagcgt tggggacctt                                              20

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
cacatgcaga gaactgagct g                                            21

<210> SEQ ID NO 120
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
gttggggtaa gcacgaagg                                               19

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
tttccaggag ggtgactcag                                              20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
ttctctgcat gtgacctccc                                              20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
acacactcac agagggttgg                                            20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
tgagtcaccc tcctggaaac                                            20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
ctccttccag agcacctcag                                            20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
gctgggctcc tccttgtact                                            20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gctgctgccc ataaagtagc                                            20

<210> SEQ ID NO 128
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
ggactgtggc ccaggtact                                             19

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
ggcctcatag gacaggaggt                                              20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
ttatgggcag cagctcagtt                                              20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
gacattttcc tggacgcttg                                              20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
ccctccccat ggctttaggt                                              20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
agctccatgc gcttgacatt                                              20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
agcgtccagg aaaatgtcaa                                              20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135

```
atgaccctca cactccaagg                                               20
```

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136

```
gttgggtgct ccagctttta                                               20
```

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137

```
cctcaaaact cctggactcg                                               20
```

<210> SEQ ID NO 138
<211> LENGTH: 1434
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Arg Gly Met Asp Lys Lys Tyr Ser Ile Gly Leu Ala Ile Gly Thr
            35                  40                  45

Asn Ser Val Gly Trp Ala Val Ile Thr Asp Glu Tyr Lys Val Pro Ser
        50                  55                  60

Lys Lys Phe Lys Val Leu Gly Asn Thr Asp Arg His Ser Ile Lys Lys
65                  70                  75                  80

Asn Leu Ile Gly Ala Leu Leu Phe Asp Ser Gly Glu Thr Ala Glu Ala
                85                  90                  95

Thr Arg Leu Lys Arg Thr Ala Arg Arg Arg Tyr Thr Arg Arg Lys Asn
            100                 105                 110

Arg Ile Cys Tyr Leu Gln Glu Ile Phe Ser Asn Glu Met Ala Lys Val
        115                 120                 125

Asp Asp Ser Phe Phe His Arg Leu Glu Glu Ser Phe Leu Val Glu Glu
    130                 135                 140

Asp Lys Lys His Glu Arg His Pro Ile Phe Gly Asn Ile Val Asp Glu
145                 150                 155                 160

Val Ala Tyr His Glu Lys Tyr Pro Thr Ile Tyr His Leu Arg Lys Lys
                165                 170                 175

Leu Val Asp Ser Thr Asp Lys Ala Asp Leu Arg Leu Ile Tyr Leu Ala
            180                 185                 190

Leu Ala His Met Ile Lys Phe Arg Gly His Phe Leu Ile Glu Gly Asp
        195                 200                 205

Leu Asn Pro Asp Asn Ser Asp Val Asp Lys Leu Phe Ile Gln Leu Val
```

```
            210                 215                 220
Gln Thr Tyr Asn Gln Leu Phe Glu Glu Asn Pro Ile Asn Ala Ser Gly
225                 230                 235                 240

Val Asp Ala Lys Ala Ile Leu Ser Ala Arg Leu Ser Lys Ser Arg Arg
                245                 250                 255

Leu Glu Asn Leu Ile Ala Gln Leu Pro Gly Glu Lys Lys Asn Gly Leu
            260                 265                 270

Phe Gly Asn Leu Ile Ala Leu Ser Leu Gly Leu Thr Pro Asn Phe Lys
                275                 280                 285

Ser Asn Phe Asp Leu Ala Glu Asp Ala Lys Leu Gln Leu Ser Lys Asp
            290                 295                 300

Thr Tyr Asp Asp Asp Leu Asp Asn Leu Leu Ala Gln Ile Gly Asp Gln
305                 310                 315                 320

Tyr Ala Asp Leu Phe Leu Ala Ala Lys Asn Leu Ser Asp Ala Ile Leu
                325                 330                 335

Leu Ser Asp Ile Leu Arg Val Asn Thr Glu Ile Thr Lys Ala Pro Leu
            340                 345                 350

Ser Ala Ser Met Ile Lys Arg Tyr Asp Glu His His Gln Asp Leu Thr
                355                 360                 365

Leu Leu Lys Ala Leu Val Arg Gln Gln Leu Pro Glu Lys Tyr Lys Glu
            370                 375                 380

Ile Phe Phe Asp Gln Ser Lys Asn Gly Tyr Ala Gly Tyr Ile Asp Gly
385                 390                 395                 400

Gly Ala Ser Gln Glu Glu Phe Tyr Lys Phe Ile Lys Pro Ile Leu Glu
                405                 410                 415

Lys Met Asp Gly Thr Glu Glu Leu Leu Val Lys Leu Asn Arg Glu Asp
            420                 425                 430

Leu Leu Arg Lys Gln Arg Thr Phe Asp Asn Gly Ser Ile Pro His Gln
            435                 440                 445

Ile His Leu Gly Glu Leu His Ala Ile Leu Arg Arg Gln Glu Asp Phe
            450                 455                 460

Tyr Pro Phe Leu Lys Asp Asn Arg Glu Lys Ile Glu Lys Ile Leu Thr
465                 470                 475                 480

Phe Arg Ile Pro Tyr Tyr Val Gly Pro Leu Ala Arg Gly Asn Ser Arg
                485                 490                 495

Phe Ala Trp Met Thr Arg Lys Ser Glu Glu Thr Ile Thr Pro Trp Asn
            500                 505                 510

Phe Glu Glu Val Val Asp Lys Gly Ala Ser Ala Gln Ser Phe Ile Glu
            515                 520                 525

Arg Met Thr Asn Phe Asp Lys Asn Leu Pro Asn Glu Lys Val Leu Pro
530                 535                 540

Lys His Ser Leu Leu Tyr Glu Tyr Phe Thr Val Tyr Asn Glu Leu Thr
545                 550                 555                 560

Lys Val Lys Tyr Val Thr Glu Gly Met Arg Lys Pro Ala Phe Leu Ser
                565                 570                 575

Gly Glu Gln Lys Lys Ala Ile Val Asp Leu Leu Phe Lys Thr Asn Arg
            580                 585                 590

Lys Val Thr Val Lys Gln Leu Lys Glu Asp Tyr Phe Lys Lys Ile Glu
            595                 600                 605

Cys Phe Asp Ser Val Glu Ile Ser Gly Val Glu Asp Arg Phe Asn Ala
            610                 615                 620

Ser Leu Gly Thr Tyr His Asp Leu Leu Lys Ile Ile Lys Asp Lys Asp
625                 630                 635                 640
```

```
Phe Leu Asp Asn Glu Glu Asn Glu Asp Ile Leu Glu Asp Ile Val Leu
                645                 650                 655

Thr Leu Thr Leu Phe Glu Asp Arg Glu Met Ile Glu Glu Arg Leu Lys
            660                 665                 670

Thr Tyr Ala His Leu Phe Asp Asp Lys Val Met Lys Gln Leu Lys Arg
        675                 680                 685

Arg Arg Tyr Thr Gly Trp Gly Arg Leu Ser Arg Lys Leu Ile Asn Gly
    690                 695                 700

Ile Arg Asp Lys Gln Ser Gly Lys Thr Ile Leu Asp Phe Leu Lys Ser
705                 710                 715                 720

Asp Gly Phe Ala Asn Arg Asn Phe Met Gln Leu Ile His Asp Asp Ser
                725                 730                 735

Leu Thr Phe Lys Glu Asp Ile Gln Lys Ala Gln Val Ser Gly Gln Gly
            740                 745                 750

Asp Ser Leu His Glu His Ile Ala Asn Leu Ala Gly Ser Pro Ala Ile
        755                 760                 765

Lys Lys Gly Ile Leu Gln Thr Val Lys Val Val Asp Glu Leu Val Lys
770                 775                 780

Val Met Gly Arg His Lys Pro Glu Asn Ile Val Ile Glu Met Ala Arg
785                 790                 795                 800

Glu Asn Gln Thr Thr Gln Lys Gly Gln Lys Asn Ser Arg Glu Arg Met
                805                 810                 815

Lys Arg Ile Glu Glu Gly Ile Lys Glu Leu Gly Ser Gln Ile Leu Lys
            820                 825                 830

Glu His Pro Val Glu Asn Thr Gln Leu Gln Asn Glu Lys Leu Tyr Leu
        835                 840                 845

Tyr Tyr Leu Gln Asn Gly Arg Asp Met Tyr Val Asp Gln Glu Leu Asp
    850                 855                 860

Ile Asn Arg Leu Ser Asp Tyr Asp Val Asp Ala Ile Val Pro Gln Ser
865                 870                 875                 880

Phe Leu Lys Asp Asp Ser Ile Asp Asn Lys Val Leu Thr Arg Ser Asp
                885                 890                 895

Lys Asn Arg Gly Lys Ser Asp Asn Val Pro Ser Glu Glu Val Val Lys
            900                 905                 910

Lys Met Lys Asn Tyr Trp Arg Gln Leu Leu Asn Ala Lys Leu Ile Thr
        915                 920                 925

Gln Arg Lys Phe Asp Asn Leu Thr Lys Ala Glu Arg Gly Gly Leu Ser
    930                 935                 940

Glu Leu Asp Lys Ala Gly Phe Ile Lys Arg Gln Leu Val Glu Thr Arg
945                 950                 955                 960

Gln Ile Thr Lys His Val Ala Gln Ile Leu Asp Ser Arg Met Asn Thr
                965                 970                 975

Lys Tyr Asp Glu Asn Asp Lys Leu Ile Arg Glu Val Lys Val Ile Thr
            980                 985                 990

Leu Lys Ser Lys Leu Val Ser Asp Phe Arg Lys Asp Phe Gln Phe Tyr
        995                1000                1005

Lys Val Arg Glu Ile Asn Asn Tyr His His Ala His Asp Ala Tyr
   1010                1015                1020

Leu Asn Ala Val Val Gly Thr Ala Leu Ile Lys Lys Tyr Pro Lys
   1025                1030                1035

Leu Glu Ser Glu Phe Val Tyr Gly Asp Tyr Lys Val Tyr Asp Val
   1040                1045                1050
```

```
Arg Lys Met Ile Ala Lys Ser Glu Gln Glu Ile Gly Lys Ala Thr
1055                1060                1065
Ala Lys Tyr Phe Phe Tyr Ser Asn Ile Met Asn Phe Phe Lys Thr
1070                1075                1080
Glu Ile Thr Leu Ala Asn Gly Glu Ile Arg Lys Arg Pro Leu Ile
1085                1090                1095
Glu Thr Asn Gly Glu Thr Gly Glu Ile Val Trp Asp Lys Gly Arg
1100                1105                1110
Asp Phe Ala Thr Val Arg Lys Val Leu Ser Met Pro Gln Val Asn
1115                1120                1125
Ile Val Lys Lys Thr Glu Val Gln Thr Gly Gly Phe Ser Lys Glu
1130                1135                1140
Ser Ile Leu Pro Lys Arg Asn Ser Asp Lys Leu Ile Ala Arg Lys
1145                1150                1155
Lys Asp Trp Asp Pro Lys Lys Tyr Gly Gly Phe Asp Ser Pro Thr
1160                1165                1170
Val Ala Tyr Ser Val Leu Val Val Ala Lys Val Glu Lys Gly Lys
1175                1180                1185
Ser Lys Lys Leu Lys Ser Val Lys Glu Leu Leu Gly Ile Thr Ile
1190                1195                1200
Met Glu Arg Ser Ser Phe Glu Lys Asn Pro Ile Asp Phe Leu Glu
1205                1210                1215
Ala Lys Gly Tyr Lys Glu Val Lys Lys Asp Leu Ile Ile Lys Leu
1220                1225                1230
Pro Lys Tyr Ser Leu Phe Glu Leu Glu Asn Gly Arg Lys Arg Met
1235                1240                1245
Leu Ala Ser Ala Gly Glu Leu Gln Lys Gly Asn Glu Leu Ala Leu
1250                1255                1260
Pro Ser Lys Tyr Val Asn Phe Leu Tyr Leu Ala Ser His Tyr Glu
1265                1270                1275
Lys Leu Lys Gly Ser Pro Glu Asp Asn Glu Gln Lys Gln Leu Phe
1280                1285                1290
Val Glu Gln His Lys His Tyr Leu Asp Glu Ile Ile Glu Gln Ile
1295                1300                1305
Ser Glu Phe Ser Lys Arg Val Ile Leu Ala Asp Ala Asn Leu Asp
1310                1315                1320
Lys Val Leu Ser Ala Tyr Asn Lys His Arg Asp Lys Pro Ile Arg
1325                1330                1335
Glu Gln Ala Glu Asn Ile Ile His Leu Phe Thr Leu Thr Asn Leu
1340                1345                1350
Gly Ala Pro Ala Ala Phe Lys Tyr Phe Asp Thr Thr Ile Asp Arg
1355                1360                1365
Lys Arg Tyr Thr Ser Thr Lys Glu Val Leu Asp Ala Thr Leu Ile
1370                1375                1380
His Gln Ser Ile Thr Gly Leu Tyr Glu Thr Arg Ile Asp Leu Ser
1385                1390                1395
Gln Leu Gly Gly Asp Pro Ile Ala Gly Ser Lys Ala Ser Pro Lys
1400                1405                1410
Lys Lys Arg Lys Val Gly Arg Ala Leu Ile Asn Tyr Pro Tyr Asp
1415                1420                1425
Val Pro Asp Tyr Ala Ser
1430
```

```
<210> SEQ ID NO 139
<211> LENGTH: 1483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Lys Arg Lys Val
            20                  25                  30

Gly Arg Gly Met Asp Lys Lys Tyr Ser Ile Gly Leu Ala Ile Gly Thr
        35                  40                  45

Asn Ser Val Gly Trp Ala Val Ile Thr Asp Glu Tyr Lys Val Pro Ser
    50                  55                  60

Lys Lys Phe Lys Val Leu Gly Asn Thr Asp Arg His Ser Ile Lys Lys
65                  70                  75                  80

Asn Leu Ile Gly Ala Leu Leu Phe Asp Ser Gly Glu Thr Ala Glu Ala
                85                  90                  95

Thr Arg Leu Lys Arg Thr Ala Arg Arg Arg Tyr Thr Arg Arg Lys Asn
            100                 105                 110

Arg Ile Cys Tyr Leu Gln Glu Ile Phe Ser Asn Glu Met Ala Lys Val
        115                 120                 125

Asp Asp Ser Phe Phe His Arg Leu Glu Glu Ser Phe Leu Val Glu Glu
130                 135                 140

Asp Lys Lys His Glu Arg His Pro Ile Phe Gly Asn Ile Val Asp Glu
145                 150                 155                 160

Val Ala Tyr His Glu Lys Tyr Pro Thr Ile Tyr His Leu Arg Lys Lys
                165                 170                 175

Leu Val Asp Ser Thr Asp Lys Ala Asp Leu Arg Leu Ile Tyr Leu Ala
            180                 185                 190

Leu Ala His Met Ile Lys Phe Arg Gly His Phe Leu Ile Glu Gly Asp
        195                 200                 205

Leu Asn Pro Asp Asn Ser Asp Val Asp Lys Leu Phe Ile Gln Leu Val
    210                 215                 220

Gln Thr Tyr Asn Gln Leu Phe Glu Glu Asn Pro Ile Asn Ala Ser Gly
225                 230                 235                 240

Val Asp Ala Lys Ala Ile Leu Ser Ala Arg Leu Ser Lys Ser Arg Arg
                245                 250                 255

Leu Glu Asn Leu Ile Ala Gln Leu Pro Gly Glu Lys Lys Asn Gly Leu
            260                 265                 270

Phe Gly Asn Leu Ile Ala Leu Ser Leu Gly Leu Thr Pro Asn Phe Lys
        275                 280                 285

Ser Asn Phe Asp Leu Ala Glu Asp Ala Lys Leu Gln Leu Ser Lys Asp
    290                 295                 300

Thr Tyr Asp Asp Asp Leu Asp Asn Leu Leu Ala Gln Ile Gly Asp Gln
305                 310                 315                 320

Tyr Ala Asp Leu Phe Leu Ala Ala Lys Asn Leu Ser Asp Ala Ile Leu
                325                 330                 335

Leu Ser Asp Ile Leu Arg Val Asn Thr Glu Ile Thr Lys Ala Pro Leu
            340                 345                 350

Ser Ala Ser Met Ile Lys Arg Tyr Asp Glu His His Gln Asp Leu Thr
        355                 360                 365
```

```
Leu Leu Lys Ala Leu Val Arg Gln Gln Leu Pro Glu Lys Tyr Lys Glu
370                 375                 380

Ile Phe Phe Asp Gln Ser Lys Asn Gly Tyr Ala Gly Tyr Ile Asp Gly
385                 390                 395                 400

Gly Ala Ser Gln Glu Glu Phe Tyr Lys Phe Ile Lys Pro Ile Leu Glu
                405                 410                 415

Lys Met Asp Gly Thr Glu Glu Leu Leu Val Lys Leu Asn Arg Glu Asp
                420                 425                 430

Leu Leu Arg Lys Gln Arg Thr Phe Asp Asn Gly Ser Ile Pro His Gln
            435                 440                 445

Ile His Leu Gly Glu Leu His Ala Ile Leu Arg Arg Gln Glu Asp Phe
450                 455                 460

Tyr Pro Phe Leu Lys Asp Asn Arg Glu Lys Ile Glu Lys Ile Leu Thr
465                 470                 475                 480

Phe Arg Ile Pro Tyr Tyr Val Gly Pro Leu Ala Arg Gly Asn Ser Arg
                485                 490                 495

Phe Ala Trp Met Thr Arg Lys Ser Glu Glu Thr Ile Thr Pro Trp Asn
                500                 505                 510

Phe Glu Glu Val Val Asp Lys Gly Ala Ser Ala Gln Ser Phe Ile Glu
                515                 520                 525

Arg Met Thr Asn Phe Asp Lys Asn Leu Pro Asn Glu Lys Val Leu Pro
                530                 535                 540

Lys His Ser Leu Leu Tyr Glu Tyr Phe Thr Val Tyr Asn Glu Leu Thr
545                 550                 555                 560

Lys Val Lys Tyr Val Thr Glu Gly Met Arg Lys Pro Ala Phe Leu Ser
                565                 570                 575

Gly Glu Gln Lys Lys Ala Ile Val Asp Leu Leu Phe Lys Thr Asn Arg
                580                 585                 590

Lys Val Thr Val Lys Gln Leu Lys Glu Asp Tyr Phe Lys Lys Ile Glu
                595                 600                 605

Cys Phe Asp Ser Val Glu Ile Ser Gly Val Glu Asp Arg Phe Asn Ala
610                 615                 620

Ser Leu Gly Thr Tyr His Asp Leu Leu Lys Ile Ile Lys Asp Lys Asp
625                 630                 635                 640

Phe Leu Asp Asn Glu Glu Asn Glu Asp Ile Leu Glu Asp Ile Val Leu
                645                 650                 655

Thr Leu Thr Leu Phe Glu Asp Arg Glu Met Ile Glu Glu Arg Leu Lys
                660                 665                 670

Thr Tyr Ala His Leu Phe Asp Asp Lys Val Met Lys Gln Leu Lys Arg
                675                 680                 685

Arg Arg Tyr Thr Gly Trp Gly Arg Leu Ser Arg Lys Leu Ile Asn Gly
            690                 695                 700

Ile Arg Asp Lys Gln Ser Gly Lys Thr Ile Leu Asp Phe Leu Lys Ser
705                 710                 715                 720

Asp Gly Phe Ala Asn Arg Asn Phe Met Gln Leu Ile His Asp Asp Ser
                725                 730                 735

Leu Thr Phe Lys Glu Asp Ile Gln Lys Ala Gln Val Ser Gly Gln Gly
                740                 745                 750

Asp Ser Leu His Glu His Ile Ala Asn Leu Ala Gly Ser Pro Ala Ile
            755                 760                 765

Lys Lys Gly Ile Leu Gln Thr Val Lys Val Val Asp Glu Leu Val Lys
770                 775                 780

Val Met Gly Arg His Lys Pro Glu Asn Ile Val Ile Glu Met Ala Arg
```

```
              785              790              795              800
        Glu Asn Gln Thr Thr Gln Lys Gly Gln Lys Asn Ser Arg Glu Arg Met
                        805              810              815
        Lys Arg Ile Glu Glu Gly Ile Lys Glu Leu Gly Ser Gln Ile Leu Lys
                        820              825              830
        Glu His Pro Val Glu Asn Thr Gln Leu Gln Asn Glu Lys Leu Tyr Leu
                        835              840              845
        Tyr Tyr Leu Gln Asn Gly Arg Asp Met Tyr Val Asp Gln Glu Leu Asp
                        850              855              860
        Ile Asn Arg Leu Ser Asp Tyr Asp Val Asp Ala Ile Val Pro Gln Ser
        865              870              875              880
        Phe Leu Lys Asp Asp Ser Ile Asp Asn Lys Val Leu Thr Arg Ser Asp
                        885              890              895
        Lys Asn Arg Gly Lys Ser Asp Asn Val Pro Ser Glu Glu Val Val Lys
                        900              905              910
        Lys Met Lys Asn Tyr Trp Arg Gln Leu Leu Asn Ala Lys Leu Ile Thr
                        915              920              925
        Gln Arg Lys Phe Asp Asn Leu Thr Lys Ala Glu Arg Gly Gly Leu Ser
                        930              935              940
        Glu Leu Asp Lys Ala Gly Phe Ile Lys Arg Gln Leu Val Glu Thr Arg
        945              950              955              960
        Gln Ile Thr Lys His Val Ala Gln Ile Leu Asp Ser Arg Met Asn Thr
                        965              970              975
        Lys Tyr Asp Glu Asn Asp Lys Leu Ile Arg Glu Val Lys Val Ile Thr
                        980              985              990
        Leu Lys Ser Lys Leu Val Ser Asp Phe Arg Lys Asp Phe Gln Phe Tyr
                        995             1000             1005
        Lys Val Arg Glu Ile Asn Asn Tyr His His Ala His Asp Ala Tyr
                       1010             1015             1020
        Leu Asn Ala Val Val Gly Thr Ala Leu Ile Lys Lys Tyr Pro Lys
                       1025             1030             1035
        Leu Glu Ser Glu Phe Val Tyr Gly Asp Tyr Lys Val Tyr Asp Val
                       1040             1045             1050
        Arg Lys Met Ile Ala Lys Ser Glu Gln Glu Ile Gly Lys Ala Thr
                       1055             1060             1065
        Ala Lys Tyr Phe Phe Tyr Ser Asn Ile Met Asn Phe Phe Lys Thr
                       1070             1075             1080
        Glu Ile Thr Leu Ala Asn Gly Glu Ile Arg Lys Arg Pro Leu Ile
                       1085             1090             1095
        Glu Thr Asn Gly Glu Thr Gly Glu Ile Val Trp Asp Lys Gly Arg
                       1100             1105             1110
        Asp Phe Ala Thr Val Arg Lys Val Leu Ser Met Pro Gln Val Asn
                       1115             1120             1125
        Ile Val Lys Lys Thr Glu Val Gln Thr Gly Gly Phe Ser Lys Glu
                       1130             1135             1140
        Ser Ile Leu Pro Lys Arg Asn Ser Asp Lys Leu Ile Ala Arg Lys
                       1145             1150             1155
        Lys Asp Trp Asp Pro Lys Lys Tyr Gly Gly Phe Asp Ser Pro Thr
                       1160             1165             1170
        Val Ala Tyr Ser Val Leu Val Ala Lys Val Glu Lys Gly Lys
                       1175             1180             1185
        Ser Lys Lys Leu Lys Ser Val Lys Glu Leu Leu Gly Ile Thr Ile
                       1190             1195             1200
```

-continued

```
Met Glu Arg Ser Ser Phe Glu Lys Asn Pro Ile Asp Phe Leu Glu
    1205                1210                1215

Ala Lys Gly Tyr Lys Glu Val Lys Lys Asp Leu Ile Ile Lys Leu
    1220                1225                1230

Pro Lys Tyr Ser Leu Phe Glu Leu Glu Asn Gly Arg Lys Arg Met
    1235                1240                1245

Leu Ala Ser Ala Gly Glu Leu Gln Lys Gly Asn Glu Leu Ala Leu
    1250                1255                1260

Pro Ser Lys Tyr Val Asn Phe Leu Tyr Leu Ala Ser His Tyr Glu
    1265                1270                1275

Lys Leu Lys Gly Ser Pro Glu Asp Asn Glu Gln Lys Gln Leu Phe
    1280                1285                1290

Val Glu Gln His Lys His Tyr Leu Asp Glu Ile Ile Glu Gln Ile
    1295                1300                1305

Ser Glu Phe Ser Lys Arg Val Ile Leu Ala Asp Ala Asn Leu Asp
    1310                1315                1320

Lys Val Leu Ser Ala Tyr Asn Lys His Arg Asp Lys Pro Ile Arg
    1325                1330                1335

Glu Gln Ala Glu Asn Ile Ile His Leu Phe Thr Leu Thr Asn Leu
    1340                1345                1350

Gly Ala Pro Ala Ala Phe Lys Tyr Phe Asp Thr Thr Ile Asp Arg
    1355                1360                1365

Lys Arg Tyr Thr Ser Thr Lys Glu Val Leu Asp Ala Thr Leu Ile
    1370                1375                1380

His Gln Ser Ile Thr Gly Leu Tyr Glu Thr Arg Ile Asp Leu Ser
    1385                1390                1395

Gln Leu Gly Gly Asp Pro Ile Ala Gly Ser Lys Ala Ser Pro Lys
    1400                1405                1410

Lys Lys Arg Lys Val Gly Arg Ala Asp Ala Leu Asp Asp Phe Asp
    1415                1420                1425

Leu Asp Met Leu Gly Ser Asp Ala Leu Asp Asp Phe Asp Leu Asp
    1430                1435                1440

Met Leu Gly Ser Asp Ala Leu Asp Asp Phe Asp Leu Asp Met Leu
    1445                1450                1455

Gly Ser Asp Ala Leu Asp Asp Phe Asp Leu Asp Met Leu Ile Asn
    1460                1465                1470

Tyr Pro Tyr Asp Val Pro Asp Tyr Ala Ser
    1475                1480
```

<210> SEQ ID NO 140
<211> LENGTH: 3844
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 140

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
                20                  25                  30

Gly Arg Gly Met Asp Lys Lys Tyr Ser Ile Gly Leu Ala Ile Gly Thr
            35                  40                  45

Asn Ser Val Gly Trp Ala Val Ile Thr Asp Glu Tyr Lys Val Pro Ser
```

```
                50                  55                  60
Lys Lys Phe Lys Val Leu Gly Asn Thr Asp Arg His Ser Ile Lys Lys
65                  70                  75                  80

Asn Leu Ile Gly Ala Leu Leu Phe Asp Ser Gly Glu Thr Ala Glu Ala
                85                  90                  95

Thr Arg Leu Lys Arg Thr Ala Arg Arg Tyr Thr Arg Arg Lys Asn
                100                 105                 110

Arg Ile Cys Tyr Leu Gln Glu Ile Phe Ser Asn Glu Met Ala Lys Val
                115                 120                 125

Asp Asp Ser Phe Phe His Arg Leu Glu Glu Ser Phe Leu Val Glu Glu
            130                 135                 140

Asp Lys Lys His Glu Arg His Pro Ile Phe Gly Asn Ile Val Asp Glu
145                 150                 155                 160

Val Ala Tyr His Glu Lys Tyr Pro Thr Ile Tyr His Leu Arg Lys Lys
                165                 170                 175

Leu Val Asp Ser Thr Asp Lys Ala Asp Leu Arg Leu Ile Tyr Leu Ala
                180                 185                 190

Leu Ala His Met Ile Lys Phe Arg Gly His Phe Leu Ile Glu Gly Asp
                195                 200                 205

Leu Asn Pro Asp Asn Ser Asp Val Asp Lys Leu Phe Ile Gln Leu Val
            210                 215                 220

Gln Thr Tyr Asn Gln Leu Phe Glu Glu Asn Pro Ile Asn Ala Ser Gly
225                 230                 235                 240

Val Asp Ala Lys Ala Ile Leu Ser Ala Arg Leu Ser Lys Ser Arg Arg
                245                 250                 255

Leu Glu Asn Leu Ile Ala Gln Leu Pro Gly Glu Lys Lys Asn Gly Leu
                260                 265                 270

Phe Gly Asn Leu Ile Ala Leu Ser Leu Gly Leu Thr Pro Asn Phe Lys
                275                 280                 285

Ser Asn Phe Asp Leu Ala Glu Asp Ala Lys Leu Gln Leu Ser Lys Asp
            290                 295                 300

Thr Tyr Asp Asp Asp Leu Asp Asn Leu Leu Ala Gln Ile Gly Asp Gln
305                 310                 315                 320

Tyr Ala Asp Leu Phe Leu Ala Ala Lys Asn Leu Ser Asp Ala Ile Leu
                325                 330                 335

Leu Ser Asp Ile Leu Arg Val Asn Thr Glu Ile Thr Lys Ala Pro Leu
                340                 345                 350

Ser Ala Ser Met Ile Lys Arg Tyr Asp Glu His His Gln Asp Leu Thr
                355                 360                 365

Leu Leu Lys Ala Leu Val Arg Gln Gln Leu Pro Glu Lys Tyr Lys Glu
            370                 375                 380

Ile Phe Phe Asp Gln Ser Lys Asn Gly Tyr Ala Gly Tyr Ile Asp Gly
385                 390                 395                 400

Gly Ala Ser Gln Glu Glu Phe Tyr Lys Phe Ile Lys Pro Ile Leu Glu
                405                 410                 415

Lys Met Asp Gly Thr Glu Glu Leu Leu Val Lys Leu Asn Arg Glu Asp
                420                 425                 430

Leu Leu Arg Lys Gln Arg Thr Phe Asp Asn Gly Ser Ile Pro His Gln
            435                 440                 445

Ile His Leu Gly Glu Leu His Ala Ile Leu Arg Arg Gln Glu Asp Phe
                450                 455                 460

Tyr Pro Phe Leu Lys Asp Asn Arg Glu Lys Ile Glu Lys Ile Leu Thr
465                 470                 475                 480
```

-continued

```
Phe Arg Ile Pro Tyr Tyr Val Gly Pro Leu Ala Arg Gly Asn Ser Arg
                485             490                 495

Phe Ala Trp Met Thr Arg Lys Ser Glu Glu Thr Ile Thr Pro Trp Asn
            500                 505                 510

Phe Glu Glu Val Val Asp Lys Gly Ala Ser Ala Gln Ser Phe Ile Glu
            515                 520                 525

Arg Met Thr Asn Phe Asp Lys Asn Leu Pro Asn Glu Lys Val Leu Pro
        530                 535                 540

Lys His Ser Leu Leu Tyr Glu Tyr Phe Thr Val Tyr Asn Glu Leu Thr
545                 550                 555                 560

Lys Val Lys Tyr Val Thr Glu Gly Met Arg Lys Pro Ala Phe Leu Ser
                565                 570                 575

Gly Glu Gln Lys Lys Ala Ile Val Asp Leu Leu Phe Lys Thr Asn Arg
                580                 585                 590

Lys Val Thr Val Lys Gln Leu Lys Glu Asp Tyr Phe Lys Lys Ile Glu
                595                 600                 605

Cys Phe Asp Ser Val Glu Ile Ser Gly Val Glu Asp Arg Phe Asn Ala
            610                 615                 620

Ser Leu Gly Thr Tyr His Asp Leu Leu Lys Ile Ile Lys Asp Lys Asp
625                 630                 635                 640

Phe Leu Asp Asn Glu Glu Asn Glu Asp Ile Leu Glu Asp Ile Val Leu
                645                 650                 655

Thr Leu Thr Leu Phe Glu Asp Arg Glu Met Ile Glu Glu Arg Leu Lys
                660                 665                 670

Thr Tyr Ala His Leu Phe Asp Asp Lys Val Met Lys Gln Leu Lys Arg
            675                 680                 685

Arg Arg Tyr Thr Gly Trp Gly Arg Leu Ser Arg Lys Leu Ile Asn Gly
        690                 695                 700

Ile Arg Asp Lys Gln Ser Gly Lys Thr Ile Leu Asp Phe Leu Lys Ser
705                 710                 715                 720

Asp Gly Phe Ala Asn Arg Asn Phe Met Gln Leu Ile His Asp Asp Ser
                725                 730                 735

Leu Thr Phe Lys Glu Asp Ile Gln Lys Ala Gln Val Ser Gly Gln Gly
                740                 745                 750

Asp Ser Leu His Glu His Ile Ala Asn Leu Ala Gly Ser Pro Ala Ile
            755                 760                 765

Lys Lys Gly Ile Leu Gln Thr Val Lys Val Val Asp Glu Leu Val Lys
770                 775                 780

Val Met Gly Arg His Lys Pro Glu Asn Ile Val Ile Glu Met Ala Arg
785                 790                 795                 800

Glu Asn Gln Thr Thr Gln Lys Gly Gln Lys Asn Ser Arg Glu Arg Met
                805                 810                 815

Lys Arg Ile Glu Glu Gly Ile Lys Glu Leu Gly Ser Gln Ile Leu Lys
            820                 825                 830

Glu His Pro Val Glu Asn Thr Gln Leu Gln Asn Glu Lys Leu Tyr Leu
            835                 840                 845

Tyr Tyr Leu Gln Asn Gly Arg Asp Met Tyr Val Asp Gln Glu Leu Asp
        850                 855                 860

Ile Asn Arg Leu Ser Asp Tyr Asp Val Asp Ala Ile Val Pro Gln Ser
865                 870                 875                 880

Phe Leu Lys Asp Asp Ser Ile Asp Asn Lys Val Leu Thr Arg Ser Asp
                885                 890                 895
```

-continued

Lys Asn Arg Gly Lys Ser Asp Asn Val Pro Ser Glu Glu Val Lys
                900                 905                 910

Lys Met Lys Asn Tyr Trp Arg Gln Leu Leu Asn Ala Lys Leu Ile Thr
            915                 920                 925

Gln Arg Lys Phe Asp Asn Leu Thr Lys Ala Glu Arg Gly Gly Leu Ser
        930                 935                 940

Glu Leu Asp Lys Ala Gly Phe Ile Lys Arg Gln Leu Val Glu Thr Arg
945                 950                 955                 960

Gln Ile Thr Lys His Val Ala Gln Ile Leu Asp Ser Arg Met Asn Thr
                965                 970                 975

Lys Tyr Asp Glu Asn Asp Lys Leu Ile Arg Glu Val Lys Val Ile Thr
            980                 985                 990

Leu Lys Ser Lys Leu Val Ser Asp Phe Arg Lys Asp Phe Gln Phe Tyr
        995                 1000                1005

Lys Val Arg Glu Ile Asn Asn Tyr His His Ala His Asp Ala Tyr
        1010                1015                1020

Leu Asn Ala Val Val Gly Thr Ala Leu Ile Lys Lys Tyr Pro Lys
        1025                1030                1035

Leu Glu Ser Glu Phe Val Tyr Gly Asp Tyr Lys Val Tyr Asp Val
        1040                1045                1050

Arg Lys Met Ile Ala Lys Ser Glu Gln Glu Ile Gly Lys Ala Thr
        1055                1060                1065

Ala Lys Tyr Phe Phe Tyr Ser Asn Ile Met Asn Phe Phe Lys Thr
        1070                1075                1080

Glu Ile Thr Leu Ala Asn Gly Glu Ile Arg Lys Arg Pro Leu Ile
        1085                1090                1095

Glu Thr Asn Gly Glu Thr Gly Glu Ile Val Trp Asp Lys Gly Arg
        1100                1105                1110

Asp Phe Ala Thr Val Arg Lys Val Leu Ser Met Pro Gln Val Asn
        1115                1120                1125

Ile Val Lys Lys Thr Glu Val Gln Thr Gly Gly Phe Ser Lys Glu
        1130                1135                1140

Ser Ile Leu Pro Lys Arg Asn Ser Asp Lys Leu Ile Ala Arg Lys
        1145                1150                1155

Lys Asp Trp Asp Pro Lys Lys Tyr Gly Gly Phe Asp Ser Pro Thr
        1160                1165                1170

Val Ala Tyr Ser Val Leu Val Val Ala Lys Val Glu Lys Gly Lys
        1175                1180                1185

Ser Lys Lys Leu Lys Ser Val Lys Glu Leu Leu Gly Ile Thr Ile
        1190                1195                1200

Met Glu Arg Ser Ser Phe Glu Lys Asn Pro Ile Asp Phe Leu Glu
        1205                1210                1215

Ala Lys Gly Tyr Lys Glu Val Lys Lys Asp Leu Ile Ile Lys Leu
        1220                1225                1230

Pro Lys Tyr Ser Leu Phe Glu Leu Glu Asn Gly Arg Lys Arg Met
        1235                1240                1245

Leu Ala Ser Ala Gly Glu Leu Gln Lys Gly Asn Glu Leu Ala Leu
        1250                1255                1260

Pro Ser Lys Tyr Val Asn Phe Leu Tyr Leu Ala Ser His Tyr Glu
        1265                1270                1275

Lys Leu Lys Gly Ser Pro Glu Asp Asn Glu Gln Lys Gln Leu Phe
        1280                1285                1290

Val Glu Gln His Lys His Tyr Leu Asp Glu Ile Ile Glu Gln Ile

```
          1295                1300                1305
Ser Glu Phe Ser Lys Arg Val Ile Leu Ala Asp Ala Asn Leu Asp
          1310                1315                1320
Lys Val Leu Ser Ala Tyr Asn Lys His Arg Asp Lys Pro Ile Arg
          1325                1330                1335
Glu Gln Ala Glu Asn Ile Ile His Leu Phe Thr Leu Thr Asn Leu
          1340                1345                1350
Gly Ala Pro Ala Ala Phe Lys Tyr Phe Asp Thr Thr Ile Asp Arg
          1355                1360                1365
Lys Arg Tyr Thr Ser Thr Lys Glu Val Leu Asp Ala Thr Leu Ile
          1370                1375                1380
His Gln Ser Ile Thr Gly Leu Tyr Glu Thr Arg Ile Asp Leu Ser
          1385                1390                1395
Gln Leu Gly Gly Asp Pro Ile Ala Gly Ser Lys Ala Ser Pro Lys
          1400                1405                1410
Lys Lys Arg Lys Val Gly Arg Ala Ala Glu Asn Val Val Glu Pro
          1415                1420                1425
Gly Pro Pro Ser Ala Lys Arg Pro Lys Leu Ser Ser Pro Ala Leu
          1430                1435                1440
Ser Ala Ser Ala Ser Asp Gly Thr Asp Phe Gly Ser Leu Phe Asp
          1445                1450                1455
Leu Glu His Asp Leu Pro Asp Glu Leu Ile Asn Ser Thr Glu Leu
          1460                1465                1470
Gly Leu Thr Asn Gly Gly Asp Ile Asn Gln Leu Gln Thr Ser Leu
          1475                1480                1485
Gly Met Val Gln Asp Ala Ala Ser Lys His Lys Gln Leu Ser Glu
          1490                1495                1500
Leu Leu Arg Ser Gly Ser Ser Pro Asn Leu Asn Met Gly Val Gly
          1505                1510                1515
Gly Pro Gly Gln Val Met Ala Ser Gln Ala Gln Ser Ser Pro
          1520                1525                1530
Gly Leu Gly Leu Ile Asn Ser Met Val Lys Ser Pro Met Thr Gln
          1535                1540                1545
Ala Gly Leu Thr Ser Pro Asn Met Gly Met Gly Thr Ser Gly Pro
          1550                1555                1560
Asn Gln Gly Pro Thr Gln Ser Thr Gly Met Met Asn Ser Pro Val
          1565                1570                1575
Asn Gln Pro Ala Met Gly Met Asn Thr Gly Met Asn Ala Gly Met
          1580                1585                1590
Asn Pro Gly Met Leu Ala Ala Gly Asn Gly Gln Gly Ile Met Pro
          1595                1600                1605
Asn Gln Val Met Asn Gly Ser Ile Gly Ala Gly Arg Gly Arg Gln
          1610                1615                1620
Asn Met Gln Tyr Pro Asn Pro Gly Met Gly Ser Ala Gly Asn Leu
          1625                1630                1635
Leu Thr Glu Pro Leu Gln Gln Gly Ser Pro Gln Met Gly Gly Gln
          1640                1645                1650
Thr Gly Leu Arg Gly Pro Gln Pro Leu Lys Met Gly Met Met Asn
          1655                1660                1665
Asn Pro Asn Pro Tyr Gly Ser Pro Tyr Thr Gln Asn Pro Gly Gln
          1670                1675                1680
Gln Ile Gly Ala Ser Gly Leu Gly Leu Gln Ile Gln Thr Lys Thr
          1685                1690                1695
```

```
Val Leu Ser Asn Asn Leu Ser Pro Phe Ala Met Asp Lys Lys Ala
    1700                1705                1710

Val Pro Gly Gly Gly Met Pro Asn Met Gly Gln Gln Pro Ala Pro
    1715                1720                1725

Gln Val Gln Gln Pro Gly Leu Val Thr Pro Val Ala Gln Gly Met
    1730                1735                1740

Gly Ser Gly Ala His Thr Ala Asp Pro Glu Lys Arg Lys Leu Ile
    1745                1750                1755

Gln Gln Gln Leu Val Leu Leu His Ala His Lys Cys Gln Arg
    1760                1765                1770

Arg Glu Gln Ala Asn Gly Glu Val Arg Gln Cys Asn Leu Pro His
    1775                1780                1785

Cys Arg Thr Met Lys Asn Val Leu Asn His Met Thr His Cys Gln
    1790                1795                1800

Ser Gly Lys Ser Cys Gln Val Ala His Cys Ala Ser Ser Arg Gln
    1805                1810                1815

Ile Ile Ser His Trp Lys Asn Cys Thr Arg His Asp Cys Pro Val
    1820                1825                1830

Cys Leu Pro Leu Lys Asn Ala Gly Asp Lys Arg Asn Gln Gln Pro
    1835                1840                1845

Ile Leu Thr Gly Ala Pro Val Gly Leu Gly Asn Pro Ser Ser Leu
    1850                1855                1860

Gly Val Gly Gln Gln Ser Ala Pro Asn Leu Ser Thr Val Ser Gln
    1865                1870                1875

Ile Asp Pro Ser Ser Ile Glu Arg Ala Tyr Ala Ala Leu Gly Leu
    1880                1885                1890

Pro Tyr Gln Val Asn Gln Met Pro Thr Gln Pro Gln Val Gln Ala
    1895                1900                1905

Lys Asn Gln Gln Asn Gln Gln Pro Gly Gln Ser Pro Gln Gly Met
    1910                1915                1920

Arg Pro Met Ser Asn Met Ser Ala Ser Pro Met Gly Val Asn Gly
    1925                1930                1935

Gly Val Gly Val Gln Thr Pro Ser Leu Leu Ser Asp Ser Met Leu
    1940                1945                1950

His Ser Ala Ile Asn Ser Gln Asn Pro Met Met Ser Glu Asn Ala
    1955                1960                1965

Ser Val Pro Ser Met Gly Pro Met Pro Thr Ala Ala Gln Pro Ser
    1970                1975                1980

Thr Thr Gly Ile Arg Lys Gln Trp His Glu Asp Ile Thr Gln Asp
    1985                1990                1995

Leu Arg Asn His Leu Val His Lys Leu Val Gln Ala Ile Phe Pro
    2000                2005                2010

Thr Pro Asp Pro Ala Ala Leu Lys Asp Arg Arg Met Glu Asn Leu
    2015                2020                2025

Val Ala Tyr Ala Arg Lys Val Glu Gly Asp Met Tyr Glu Ser Ala
    2030                2035                2040

Asn Asn Arg Ala Glu Tyr Tyr His Leu Leu Ala Glu Lys Ile Tyr
    2045                2050                2055

Lys Ile Gln Lys Glu Leu Glu Glu Lys Arg Arg Thr Arg Leu Gln
    2060                2065                2070

Lys Gln Asn Met Leu Pro Asn Ala Ala Gly Met Val Pro Val Ser
    2075                2080                2085
```

-continued

Met Asn Pro Gly Pro Asn Met Gly Gln Pro Gln Pro Gly Met Thr
2090                    2095                    2100

Ser Asn Gly Pro Leu Pro Asp Pro Ser Met Ile Arg Gly Ser Val
2105                    2110                    2115

Pro Asn Gln Met Met Pro Arg Ile Thr Pro Gln Ser Gly Leu Asn
2120                    2125                    2130

Gln Phe Gly Gln Met Ser Met Ala Gln Pro Pro Ile Val Pro Arg
2135                    2140                    2145

Gln Thr Pro Pro Leu Gln His His Gly Gln Leu Ala Gln Pro Gly
2150                    2155                    2160

Ala Leu Asn Pro Pro Met Gly Tyr Gly Pro Arg Met Gln Gln Pro
2165                    2170                    2175

Ser Asn Gln Gly Gln Phe Leu Pro Gln Thr Gln Phe Pro Ser Gln
2180                    2185                    2190

Gly Met Asn Val Thr Asn Ile Pro Leu Ala Pro Ser Ser Gly Gln
2195                    2200                    2205

Ala Pro Val Ser Gln Ala Gln Met Ser Ser Ser Cys Pro Val
2210                    2215                    2220

Asn Ser Pro Ile Met Pro Pro Gly Ser Gln Gly Ser His Ile His
2225                    2230                    2235

Cys Pro Gln Leu Pro Gln Pro Ala Leu His Gln Asn Ser Pro Ser
2240                    2245                    2250

Pro Val Pro Ser Arg Thr Pro Thr Pro His His Thr Pro Pro Ser
2255                    2260                    2265

Ile Gly Ala Gln Gln Pro Pro Ala Thr Thr Ile Pro Ala Pro Val
2270                    2275                    2280

Pro Thr Pro Pro Ala Met Pro Pro Gly Pro Gln Ser Gln Ala Leu
2285                    2290                    2295

His Pro Pro Pro Arg Gln Thr Pro Thr Pro Pro Thr Thr Gln Leu
2300                    2305                    2310

Pro Gln Gln Val Gln Pro Ser Leu Pro Ala Ala Pro Ser Ala Asp
2315                    2320                    2325

Gln Pro Gln Gln Gln Pro Arg Ser Gln Gln Ser Thr Ala Ala Ser
2330                    2335                    2340

Val Pro Thr Pro Thr Ala Pro Leu Leu Pro Pro Gln Pro Ala Thr
2345                    2350                    2355

Pro Leu Ser Gln Pro Ala Val Ser Ile Glu Gly Gln Val Ser Asn
2360                    2365                    2370

Pro Pro Ser Thr Ser Ser Thr Glu Val Asn Ser Gln Ala Ile Ala
2375                    2380                    2385

Glu Lys Gln Pro Ser Gln Glu Val Lys Met Glu Ala Lys Met Glu
2390                    2395                    2400

Val Asp Gln Pro Glu Pro Ala Asp Thr Gln Pro Glu Asp Ile Ser
2405                    2410                    2415

Glu Ser Lys Val Glu Asp Cys Lys Met Glu Ser Thr Glu Thr Glu
2420                    2425                    2430

Glu Arg Ser Thr Glu Leu Lys Thr Glu Ile Lys Glu Glu Glu Asp
2435                    2440                    2445

Gln Pro Ser Thr Ser Ala Thr Gln Ser Ser Pro Ala Pro Gly Gln
2450                    2455                    2460

Ser Lys Lys Lys Ile Phe Lys Pro Glu Glu Leu Arg Gln Ala Leu
2465                    2470                    2475

Met Pro Thr Leu Glu Ala Leu Tyr Arg Gln Asp Pro Glu Ser Leu

```
            2480              2485              2490
Pro Phe Arg Gln Pro Val Asp Pro Gln Leu Leu Gly Ile Pro Asp
    2495              2500              2505
Tyr Phe Asp Ile Val Lys Ser Pro Met Asp Leu Ser Thr Ile Lys
    2510              2515              2520
Arg Lys Leu Asp Thr Gly Gln Tyr Gln Glu Pro Trp Gln Tyr Val
    2525              2530              2535
Asp Asp Ile Trp Leu Met Phe Asn Asn Ala Trp Leu Tyr Asn Arg
    2540              2545              2550
Lys Thr Ser Arg Val Tyr Lys Tyr Cys Ser Lys Leu Ser Glu Val
    2555              2560              2565
Phe Glu Gln Glu Ile Asp Pro Val Met Gln Ser Leu Gly Tyr Cys
    2570              2575              2580
Cys Gly Arg Lys Leu Glu Phe Ser Pro Gln Thr Leu Cys Cys Tyr
    2585              2590              2595
Gly Lys Gln Leu Cys Thr Ile Pro Arg Asp Ala Thr Tyr Tyr Ser
    2600              2605              2610
Tyr Gln Asn Arg Tyr His Phe Cys Glu Lys Cys Phe Asn Glu Ile
    2615              2620              2625
Gln Gly Glu Ser Val Ser Leu Gly Asp Asp Pro Ser Gln Pro Gln
    2630              2635              2640
Thr Thr Ile Asn Lys Glu Gln Phe Ser Lys Arg Lys Asn Asp Thr
    2645              2650              2655
Leu Asp Pro Glu Leu Phe Val Glu Cys Thr Glu Cys Gly Arg Lys
    2660              2665              2670
Met His Gln Ile Cys Val Leu His His Glu Ile Ile Trp Pro Ala
    2675              2680              2685
Gly Phe Val Cys Asp Gly Cys Leu Lys Lys Ser Ala Arg Thr Arg
    2690              2695              2700
Lys Glu Asn Lys Phe Ser Ala Lys Arg Leu Pro Ser Thr Arg Leu
    2705              2710              2715
Gly Thr Phe Leu Glu Asn Arg Val Asn Asp Phe Leu Arg Arg Gln
    2720              2725              2730
Asn His Pro Glu Ser Gly Glu Val Thr Val Arg Val Val His Ala
    2735              2740              2745
Ser Asp Lys Thr Val Glu Val Lys Pro Gly Met Lys Ala Arg Phe
    2750              2755              2760
Val Asp Ser Gly Glu Met Ala Glu Ser Phe Pro Tyr Arg Thr Lys
    2765              2770              2775
Ala Leu Phe Ala Phe Glu Glu Ile Asp Gly Val Asp Leu Cys Phe
    2780              2785              2790
Phe Gly Met His Val Gln Glu Tyr Gly Ser Asp Cys Pro Pro Pro
    2795              2800              2805
Asn Gln Arg Arg Val Tyr Ile Ser Tyr Leu Asp Ser Val His Phe
    2810              2815              2820
Phe Arg Pro Lys Cys Leu Arg Thr Ala Val Tyr His Glu Ile Leu
    2825              2830              2835
Ile Gly Tyr Leu Glu Tyr Val Lys Lys Leu Gly Tyr Thr Thr Gly
    2840              2845              2850
His Ile Trp Ala Cys Pro Pro Ser Glu Gly Asp Asp Tyr Ile Phe
    2855              2860              2865
His Cys His Pro Pro Asp Gln Lys Ile Pro Lys Pro Lys Arg Leu
    2870              2875              2880
```

-continued

```
Gln Glu Trp Tyr Lys Lys Met Leu Asp Lys Ala Val Ser Glu Arg
    2885            2890            2895

Ile Val His Asp Tyr Lys Asp Ile Phe Lys Gln Ala Thr Glu Asp
    2900            2905            2910

Arg Leu Thr Ser Ala Lys Glu Leu Pro Tyr Phe Glu Gly Asp Phe
    2915            2920            2925

Trp Pro Asn Val Leu Glu Glu Ser Ile Lys Glu Leu Glu Gln Glu
    2930            2935            2940

Glu Glu Glu Arg Lys Arg Glu Glu Asn Thr Ser Asn Glu Ser Thr
    2945            2950            2955

Asp Val Thr Lys Gly Asp Ser Lys Asn Ala Lys Lys Lys Asn Asn
    2960            2965            2970

Lys Lys Thr Ser Lys Asn Lys Ser Ser Leu Ser Arg Gly Asn Lys
    2975            2980            2985

Lys Lys Pro Gly Met Pro Asn Val Ser Asn Asp Leu Ser Gln Lys
    2990            2995            3000

Leu Tyr Ala Thr Met Glu Lys His Lys Glu Val Phe Phe Val Ile
    3005            3010            3015

Arg Leu Ile Ala Gly Pro Ala Ala Asn Ser Leu Pro Pro Ile Val
    3020            3025            3030

Asp Pro Asp Pro Leu Ile Pro Cys Asp Leu Met Asp Gly Arg Asp
    3035            3040            3045

Ala Phe Leu Thr Leu Ala Arg Asp Lys His Leu Glu Phe Ser Ser
    3050            3055            3060

Leu Arg Arg Ala Gln Trp Ser Thr Met Cys Met Leu Val Glu Leu
    3065            3070            3075

His Thr Gln Ser Gln Asp Arg Phe Val Tyr Thr Cys Asn Glu Cys
    3080            3085            3090

Lys His His Val Glu Thr Arg Trp His Cys Thr Val Cys Glu Asp
    3095            3100            3105

Tyr Asp Leu Cys Ile Thr Cys Tyr Asn Thr Lys Asn His Asp His
    3110            3115            3120

Lys Met Glu Lys Leu Gly Leu Gly Leu Asp Asp Glu Ser Asn Asn
    3125            3130            3135

Gln Gln Ala Ala Ala Thr Gln Ser Pro Gly Asp Ser Arg Arg Leu
    3140            3145            3150

Ser Ile Gln Arg Cys Ile Gln Ser Leu Val His Ala Cys Gln Cys
    3155            3160            3165

Arg Asn Ala Asn Cys Ser Leu Pro Ser Cys Gln Lys Met Lys Arg
    3170            3175            3180

Val Val Gln His Thr Lys Gly Cys Lys Arg Lys Thr Asn Gly Gly
    3185            3190            3195

Cys Pro Ile Cys Lys Gln Leu Ile Ala Leu Cys Cys Tyr His Ala
    3200            3205            3210

Lys His Cys Gln Glu Asn Lys Cys Pro Val Pro Phe Cys Leu Asn
    3215            3220            3225

Ile Lys Gln Lys Leu Arg Gln Gln Leu Gln His Arg Leu Gln
    3230            3235            3240

Gln Ala Gln Met Leu Arg Arg Arg Met Ala Ser Met Gln Arg Thr
    3245            3250            3255

Gly Val Val Gly Gln Gln Gln Gly Leu Pro Ser Pro Thr Pro Ala
    3260            3265            3270
```

```
Thr Pro Thr Thr Pro Thr Gly Gln Gln Pro Thr Thr Pro Gln Thr
    3275            3280                3285

Pro Gln Pro Thr Ser Gln Pro Gln Pro Thr Pro Pro Asn Ser Met
    3290            3295                3300

Pro Pro Tyr Leu Pro Arg Thr Gln Ala Ala Gly Pro Val Ser Gln
    3305            3310                3315

Gly Lys Ala Ala Gly Gln Val Thr Pro Pro Thr Pro Pro Gln Thr
    3320            3325                3330

Ala Gln Pro Pro Leu Pro Gly Pro Pro Pro Ala Ala Val Glu Met
    3335            3340                3345

Ala Met Gln Ile Gln Arg Ala Ala Glu Thr Gln Arg Gln Met Ala
    3350            3355                3360

His Val Gln Ile Phe Gln Arg Pro Ile Gln His Gln Met Pro Pro
    3365            3370                3375

Met Thr Pro Met Ala Pro Met Gly Met Asn Pro Pro Pro Met Thr
    3380            3385                3390

Arg Gly Pro Ser Gly His Leu Glu Pro Gly Met Gly Pro Thr Gly
    3395            3400                3405

Met Gln Gln Gln Pro Pro Trp Ser Gln Gly Gly Leu Pro Gln Pro
    3410            3415                3420

Gln Gln Leu Gln Ser Gly Met Pro Arg Pro Ala Met Met Ser Val
    3425            3430                3435

Ala Gln His Gly Gln Pro Leu Asn Met Ala Pro Gln Pro Gly Leu
    3440            3445                3450

Gly Gln Val Gly Ile Ser Pro Leu Lys Pro Gly Thr Val Ser Gln
    3455            3460                3465

Gln Ala Leu Gln Asn Leu Leu Arg Thr Leu Arg Ser Pro Ser Ser
    3470            3475                3480

Pro Leu Gln Gln Gln Gln Val Leu Ser Ile Leu His Ala Asn Pro
    3485            3490                3495

Gln Leu Leu Ala Ala Phe Ile Lys Gln Arg Ala Ala Lys Tyr Ala
    3500            3505                3510

Asn Ser Asn Pro Gln Pro Ile Pro Gly Gln Pro Gly Met Pro Gln
    3515            3520                3525

Gly Gln Pro Gly Leu Gln Pro Pro Thr Met Pro Gly Gln Gln Gly
    3530            3535                3540

Val His Ser Asn Pro Ala Met Gln Asn Met Asn Pro Met Gln Ala
    3545            3550                3555

Gly Val Gln Arg Ala Gly Leu Pro Gln Gln Gln Pro Gln Gln Gln
    3560            3565                3570

Leu Gln Pro Pro Met Gly Gly Met Ser Pro Gln Ala Gln Gln Met
    3575            3580                3585

Asn Met Asn His Asn Thr Met Pro Ser Gln Phe Arg Asp Ile Leu
    3590            3595                3600

Arg Arg Gln Gln Met Met Gln Gln Gln Gln Gln Gly Ala Gly
    3605            3610                3615

Pro Gly Ile Gly Pro Gly Met Ala Asn His Asn Gln Phe Gln Gln
    3620            3625                3630

Pro Gln Gly Val Gly Tyr Pro Pro Gln Gln Gln Arg Met Gln
    3635            3640                3645

His His Met Gln Gln Met Gln Gln Gly Asn Met Gly Gln Ile Gly
    3650            3655                3660

Gln Leu Pro Gln Ala Leu Gly Ala Glu Ala Gly Ala Ser Leu Gln
```

```
                3665                3670                3675

Ala Tyr Gln Gln Arg Leu Leu Gln Gln Gln Met Gly Ser Pro Val
    3680                3685                3690

Gln Pro Asn Pro Met Ser Pro Gln Gln His Met Leu Pro Asn Gln
    3695                3700                3705

Ala Gln Ser Pro His Leu Gln Gly Gln Gln Ile Pro Asn Ser Leu
    3710                3715                3720

Ser Asn Gln Val Arg Ser Pro Gln Pro Val Pro Ser Pro Arg Pro
    3725                3730                3735

Gln Ser Gln Pro Pro His Ser Ser Pro Ser Pro Arg Met Gln Pro
    3740                3745                3750

Gln Pro Ser Pro His His Val Ser Pro Gln Thr Ser Ser Pro His
    3755                3760                3765

Pro Gly Leu Val Ala Ala Gln Ala Asn Pro Met Glu Gln Gly His
    3770                3775                3780

Phe Ala Ser Pro Asp Gln Asn Ser Met Leu Ser Gln Leu Ala Ser
    3785                3790                3795

Asn Pro Gly Met Ala Asn Leu His Gly Ala Ser Ala Thr Asp Leu
    3800                3805                3810

Gly Leu Ser Thr Asp Asn Ser Asp Leu Asn Ser Asn Leu Ser Gln
    3815                3820                3825

Ser Thr Leu Asp Ile His Tyr Pro Tyr Asp Val Pro Asp Tyr Ala
    3830                3835                3840

Ser

<210> SEQ ID NO 141
<211> LENGTH: 2048
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Gly Met Asp Lys Lys Tyr Ser Ile Gly Leu Ala Ile Gly Thr
            35                  40                  45

Asn Ser Val Gly Trp Ala Val Ile Thr Asp Glu Tyr Lys Val Pro Ser
50                  55                  60

Lys Lys Phe Lys Val Leu Gly Asn Thr Asp Arg His Ser Ile Lys Lys
65                  70                  75                  80

Asn Leu Ile Gly Ala Leu Leu Phe Asp Ser Gly Glu Thr Ala Glu Ala
                85                  90                  95

Thr Arg Leu Lys Arg Thr Ala Arg Arg Tyr Thr Arg Arg Lys Asn
            100                 105                 110

Arg Ile Cys Tyr Leu Gln Glu Ile Phe Ser Asn Glu Met Ala Lys Val
            115                 120                 125

Asp Asp Ser Phe Phe His Arg Leu Glu Glu Ser Phe Leu Val Glu Glu
            130                 135                 140

Asp Lys Lys His Glu Arg His Pro Ile Phe Gly Asn Ile Val Asp Glu
145                 150                 155                 160

Val Ala Tyr His Glu Lys Tyr Pro Thr Ile Tyr His Leu Arg Lys Lys
```

-continued

```
                165                 170                 175
Leu Val Asp Ser Thr Asp Lys Ala Asp Leu Arg Leu Ile Tyr Leu Ala
            180                 185                 190
Leu Ala His Met Ile Lys Phe Arg Gly His Phe Leu Ile Glu Gly Asp
            195                 200                 205
Leu Asn Pro Asp Asn Ser Asp Val Asp Lys Leu Phe Ile Gln Leu Val
            210                 215                 220
Gln Thr Tyr Asn Gln Leu Phe Glu Glu Asn Pro Ile Asn Ala Ser Gly
225                 230                 235                 240
Val Asp Ala Lys Ala Ile Leu Ser Ala Arg Leu Ser Lys Ser Arg Arg
                245                 250                 255
Leu Glu Asn Leu Ile Ala Gln Leu Pro Gly Glu Lys Lys Asn Gly Leu
            260                 265                 270
Phe Gly Asn Leu Ile Ala Leu Ser Leu Gly Leu Thr Pro Asn Phe Lys
            275                 280                 285
Ser Asn Phe Asp Leu Ala Glu Asp Ala Lys Leu Gln Leu Ser Lys Asp
            290                 295                 300
Thr Tyr Asp Asp Asp Leu Asp Asn Leu Leu Ala Gln Ile Gly Asp Gln
305                 310                 315                 320
Tyr Ala Asp Leu Phe Leu Ala Ala Lys Asn Leu Ser Asp Ala Ile Leu
                325                 330                 335
Leu Ser Asp Ile Leu Arg Val Asn Thr Glu Ile Thr Lys Ala Pro Leu
            340                 345                 350
Ser Ala Ser Met Ile Lys Arg Tyr Asp Glu His His Gln Asp Leu Thr
            355                 360                 365
Leu Leu Lys Ala Leu Val Arg Gln Gln Leu Pro Glu Lys Tyr Lys Glu
            370                 375                 380
Ile Phe Phe Asp Gln Ser Lys Asn Gly Tyr Ala Gly Tyr Ile Asp Gly
385                 390                 395                 400
Gly Ala Ser Gln Glu Glu Phe Tyr Lys Phe Ile Lys Pro Ile Leu Glu
                405                 410                 415
Lys Met Asp Gly Thr Glu Glu Leu Leu Val Lys Leu Asn Arg Glu Asp
            420                 425                 430
Leu Leu Arg Lys Gln Arg Thr Phe Asp Asn Gly Ser Ile Pro His Gln
            435                 440                 445
Ile His Leu Gly Glu Leu His Ala Ile Leu Arg Arg Gln Glu Asp Phe
            450                 455                 460
Tyr Pro Phe Leu Lys Asp Asn Arg Glu Lys Ile Glu Lys Ile Leu Thr
465                 470                 475                 480
Phe Arg Ile Pro Tyr Tyr Val Gly Pro Leu Ala Arg Gly Asn Ser Arg
                485                 490                 495
Phe Ala Trp Met Thr Arg Lys Ser Glu Glu Thr Ile Thr Pro Trp Asn
            500                 505                 510
Phe Glu Glu Val Val Asp Lys Gly Ala Ser Ala Gln Ser Phe Ile Glu
            515                 520                 525
Arg Met Thr Asn Phe Asp Lys Asn Leu Pro Asn Glu Lys Val Leu Pro
            530                 535                 540
Lys His Ser Leu Leu Tyr Glu Tyr Phe Thr Val Tyr Asn Glu Leu Thr
545                 550                 555                 560
Lys Val Lys Tyr Val Thr Glu Gly Met Arg Lys Pro Ala Phe Leu Ser
                565                 570                 575
Gly Glu Gln Lys Lys Ala Ile Val Asp Leu Leu Phe Lys Thr Asn Arg
            580                 585                 590
```

-continued

```
Lys Val Thr Val Lys Gln Leu Lys Glu Asp Tyr Phe Lys Ile Glu
            595                 600                 605

Cys Phe Asp Ser Val Glu Ile Ser Gly Val Glu Asp Arg Phe Asn Ala
610                 615                 620

Ser Leu Gly Thr Tyr His Asp Leu Leu Lys Ile Ile Lys Asp Lys Asp
625                 630                 635                 640

Phe Leu Asp Asn Glu Glu Asn Glu Asp Ile Leu Glu Asp Ile Val Leu
                645                 650                 655

Thr Leu Thr Leu Phe Glu Asp Arg Glu Met Ile Glu Glu Arg Leu Lys
                660                 665                 670

Thr Tyr Ala His Leu Phe Asp Asp Lys Val Met Lys Gln Leu Lys Arg
            675                 680                 685

Arg Arg Tyr Thr Gly Trp Gly Arg Leu Ser Arg Lys Leu Ile Asn Gly
        690                 695                 700

Ile Arg Asp Lys Gln Ser Gly Lys Thr Ile Leu Asp Phe Leu Lys Ser
705                 710                 715                 720

Asp Gly Phe Ala Asn Arg Asn Phe Met Gln Leu Ile His Asp Asp Ser
                725                 730                 735

Leu Thr Phe Lys Glu Asp Ile Gln Lys Ala Gln Val Ser Gly Gln Gly
            740                 745                 750

Asp Ser Leu His Glu His Ile Ala Asn Leu Ala Gly Ser Pro Ala Ile
        755                 760                 765

Lys Lys Gly Ile Leu Gln Thr Val Lys Val Val Asp Glu Leu Val Lys
    770                 775                 780

Val Met Gly Arg His Lys Pro Glu Asn Ile Val Ile Glu Met Ala Arg
785                 790                 795                 800

Glu Asn Gln Thr Thr Gln Lys Gly Gln Lys Asn Ser Arg Glu Arg Met
                805                 810                 815

Lys Arg Ile Glu Glu Gly Ile Lys Glu Leu Gly Ser Gln Ile Leu Lys
            820                 825                 830

Glu His Pro Val Glu Asn Thr Gln Leu Gln Asn Glu Lys Leu Tyr Leu
        835                 840                 845

Tyr Tyr Leu Gln Asn Gly Arg Asp Met Tyr Val Asp Gln Glu Leu Asp
    850                 855                 860

Ile Asn Arg Leu Ser Asp Tyr Asp Val Asp Ala Ile Val Pro Gln Ser
865                 870                 875                 880

Phe Leu Lys Asp Asp Ser Ile Asp Asn Lys Val Leu Thr Arg Ser Asp
                885                 890                 895

Lys Asn Arg Gly Lys Ser Asp Asn Val Pro Ser Glu Glu Val Val Lys
            900                 905                 910

Lys Met Lys Asn Tyr Trp Arg Gln Leu Leu Asn Ala Lys Leu Ile Thr
        915                 920                 925

Gln Arg Lys Phe Asp Asn Leu Thr Lys Ala Glu Arg Gly Gly Leu Ser
    930                 935                 940

Glu Leu Asp Lys Ala Gly Phe Ile Lys Arg Gln Leu Val Glu Thr Arg
945                 950                 955                 960

Gln Ile Thr Lys His Val Ala Gln Ile Leu Asp Ser Arg Met Asn Thr
                965                 970                 975

Lys Tyr Asp Glu Asn Asp Lys Leu Ile Arg Glu Val Lys Val Ile Thr
            980                 985                 990

Leu Lys Ser Lys Leu Val Ser Asp Phe Arg Lys Asp Phe Gln Phe Tyr
        995                 1000                1005
```

```
Lys Val Arg Glu Ile Asn Asn Tyr His His Ala His Asp Ala Tyr
1010                1015                1020

Leu Asn Ala Val Val Gly Thr Ala Leu Ile Lys Lys Tyr Pro Lys
1025                1030                1035

Leu Glu Ser Glu Phe Val Tyr Gly Asp Tyr Lys Val Tyr Asp Val
1040                1045                1050

Arg Lys Met Ile Ala Lys Ser Glu Gln Glu Ile Gly Lys Ala Thr
1055                1060                1065

Ala Lys Tyr Phe Phe Tyr Ser Asn Ile Met Asn Phe Phe Lys Thr
1070                1075                1080

Glu Ile Thr Leu Ala Asn Gly Glu Ile Arg Lys Arg Pro Leu Ile
1085                1090                1095

Glu Thr Asn Gly Glu Thr Gly Glu Ile Val Trp Asp Lys Gly Arg
1100                1105                1110

Asp Phe Ala Thr Val Arg Lys Val Leu Ser Met Pro Gln Val Asn
1115                1120                1125

Ile Val Lys Lys Thr Glu Val Gln Thr Gly Gly Phe Ser Lys Glu
1130                1135                1140

Ser Ile Leu Pro Lys Arg Asn Ser Asp Lys Leu Ile Ala Arg Lys
1145                1150                1155

Lys Asp Trp Asp Pro Lys Lys Tyr Gly Gly Phe Asp Ser Pro Thr
1160                1165                1170

Val Ala Tyr Ser Val Leu Val Val Ala Lys Val Glu Lys Gly Lys
1175                1180                1185

Ser Lys Lys Leu Lys Ser Val Lys Glu Leu Leu Gly Ile Thr Ile
1190                1195                1200

Met Glu Arg Ser Ser Phe Glu Lys Asn Pro Ile Asp Phe Leu Glu
1205                1210                1215

Ala Lys Gly Tyr Lys Glu Val Lys Lys Asp Leu Ile Ile Lys Leu
1220                1225                1230

Pro Lys Tyr Ser Leu Phe Glu Leu Glu Asn Gly Arg Lys Arg Met
1235                1240                1245

Leu Ala Ser Ala Gly Glu Leu Gln Lys Gly Asn Glu Leu Ala Leu
1250                1255                1260

Pro Ser Lys Tyr Val Asn Phe Leu Tyr Leu Ala Ser His Tyr Glu
1265                1270                1275

Lys Leu Lys Gly Ser Pro Glu Asp Asn Glu Gln Lys Gln Leu Phe
1280                1285                1290

Val Glu Gln His Lys His Tyr Leu Asp Glu Ile Ile Glu Gln Ile
1295                1300                1305

Ser Glu Phe Ser Lys Arg Val Ile Leu Ala Asp Ala Asn Leu Asp
1310                1315                1320

Lys Val Leu Ser Ala Tyr Asn Lys His Arg Asp Lys Pro Ile Arg
1325                1330                1335

Glu Gln Ala Glu Asn Ile Ile His Leu Phe Thr Leu Thr Asn Leu
1340                1345                1350

Gly Ala Pro Ala Ala Phe Lys Tyr Phe Asp Thr Thr Ile Asp Arg
1355                1360                1365

Lys Arg Tyr Thr Ser Thr Lys Glu Val Leu Asp Ala Thr Leu Ile
1370                1375                1380

His Gln Ser Ile Thr Gly Leu Tyr Glu Thr Arg Ile Asp Leu Ser
1385                1390                1395

Gln Leu Gly Gly Asp Pro Ile Ala Gly Ser Lys Ala Ser Pro Lys
```

-continued

```
              1400                1405               1410
Lys Lys Arg Lys Val Gly Arg Ala Ile Phe Lys Pro Glu Glu Leu
    1415                1420                1425
Arg Gln Ala Leu Met Pro Thr Leu Glu Ala Leu Tyr Arg Gln Asp
    1430                1435                1440
Pro Glu Ser Leu Pro Phe Arg Gln Pro Val Asp Pro Gln Leu Leu
    1445                1450                1455
Gly Ile Pro Asp Tyr Phe Asp Ile Val Lys Ser Pro Met Asp Leu
    1460                1465                1470
Ser Thr Ile Lys Arg Lys Leu Asp Thr Gly Gln Tyr Gln Glu Pro
    1475                1480                1485
Trp Gln Tyr Val Asp Asp Ile Trp Leu Met Phe Asn Asn Ala Trp
    1490                1495                1500
Leu Tyr Asn Arg Lys Thr Ser Arg Val Tyr Lys Tyr Cys Ser Lys
    1505                1510                1515
Leu Ser Glu Val Phe Glu Gln Glu Ile Asp Pro Val Met Gln Ser
    1520                1525                1530
Leu Gly Tyr Cys Cys Gly Arg Lys Leu Glu Phe Ser Pro Gln Thr
    1535                1540                1545
Leu Cys Cys Tyr Gly Lys Gln Leu Cys Thr Ile Pro Arg Asp Ala
    1550                1555                1560
Thr Tyr Tyr Ser Tyr Gln Asn Arg Tyr His Phe Cys Glu Lys Cys
    1565                1570                1575
Phe Asn Glu Ile Gln Gly Glu Ser Val Ser Leu Gly Asp Asp Pro
    1580                1585                1590
Ser Gln Pro Gln Thr Thr Ile Asn Lys Glu Gln Phe Ser Lys Arg
    1595                1600                1605
Lys Asn Asp Thr Leu Asp Pro Glu Leu Phe Val Glu Cys Thr Glu
    1610                1615                1620
Cys Gly Arg Lys Met His Gln Ile Cys Val Leu His His Glu Ile
    1625                1630                1635
Ile Trp Pro Ala Gly Phe Val Cys Asp Gly Cys Leu Lys Lys Ser
    1640                1645                1650
Ala Arg Thr Arg Lys Glu Asn Lys Phe Ser Ala Lys Arg Leu Pro
    1655                1660                1665
Ser Thr Arg Leu Gly Thr Phe Leu Glu Asn Arg Val Asn Asp Phe
    1670                1675                1680
Leu Arg Arg Gln Asn His Pro Glu Ser Gly Glu Val Thr Val Arg
    1685                1690                1695
Val Val His Ala Ser Asp Lys Thr Val Glu Val Lys Pro Gly Met
    1700                1705                1710
Lys Ala Arg Phe Val Asp Ser Gly Glu Met Ala Glu Ser Phe Pro
    1715                1720                1725
Tyr Arg Thr Lys Ala Leu Phe Ala Phe Glu Glu Ile Asp Gly Val
    1730                1735                1740
Asp Leu Cys Phe Phe Gly Met His Val Gln Glu Tyr Gly Ser Asp
    1745                1750                1755
Cys Pro Pro Pro Asn Gln Arg Arg Val Tyr Ile Ser Tyr Leu Asp
    1760                1765                1770
Ser Val His Phe Phe Arg Pro Lys Cys Leu Arg Thr Ala Val Tyr
    1775                1780                1785
His Glu Ile Leu Ile Gly Tyr Leu Glu Tyr Val Lys Lys Leu Gly
    1790                1795                1800
```

-continued

```
Tyr Thr Thr Gly His Ile Trp Ala Cys Pro Pro Ser Glu Gly Asp
    1805                1810                1815

Asp Tyr Ile Phe His Cys His Pro Pro Asp Gln Lys Ile Pro Lys
    1820                1825                1830

Pro Lys Arg Leu Gln Glu Trp Tyr Lys Lys Met Leu Asp Lys Ala
    1835                1840                1845

Val Ser Glu Arg Ile Val His Asp Tyr Lys Asp Ile Phe Lys Gln
    1850                1855                1860

Ala Thr Glu Asp Arg Leu Thr Ser Ala Lys Glu Leu Pro Tyr Phe
    1865                1870                1875

Glu Gly Asp Phe Trp Pro Asn Val Leu Glu Glu Ser Ile Lys Glu
    1880                1885                1890

Leu Glu Gln Glu Glu Glu Glu Arg Lys Arg Glu Glu Asn Thr Ser
    1895                1900                1905

Asn Glu Ser Thr Asp Val Thr Lys Gly Asp Ser Lys Asn Ala Lys
    1910                1915                1920

Lys Lys Asn Asn Lys Lys Thr Ser Lys Asn Lys Ser Ser Leu Ser
    1925                1930                1935

Arg Gly Asn Lys Lys Lys Pro Gly Met Pro Asn Val Ser Asn Asp
    1940                1945                1950

Leu Ser Gln Lys Leu Tyr Ala Thr Met Glu Lys His Lys Glu Val
    1955                1960                1965

Phe Phe Val Ile Arg Leu Ile Ala Gly Pro Ala Ala Asn Ser Leu
    1970                1975                1980

Pro Pro Ile Val Asp Pro Asp Pro Leu Ile Pro Cys Asp Leu Met
    1985                1990                1995

Asp Gly Arg Asp Ala Phe Leu Thr Leu Ala Arg Asp Lys His Leu
    2000                2005                2010

Glu Phe Ser Ser Leu Arg Arg Ala Gln Trp Ser Thr Met Cys Met
    2015                2020                2025

Leu Val Glu Leu His Thr Gln Ser Gln Asp Tyr Pro Tyr Asp Val
    2030                2035                2040

Pro Asp Tyr Ala Ser
    2045
```

<210> SEQ ID NO 142
<211> LENGTH: 2048
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 142

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
                20                  25                  30

Gly Arg Gly Met Asp Lys Lys Tyr Ser Ile Gly Leu Ala Ile Gly Thr
            35                  40                  45

Asn Ser Val Gly Trp Ala Val Ile Thr Asp Glu Tyr Lys Val Pro Ser
        50                  55                  60

Lys Lys Phe Lys Val Leu Gly Asn Thr Asp Arg His Ser Ile Lys Lys
65                  70                  75                  80

Asn Leu Ile Gly Ala Leu Leu Phe Asp Ser Gly Glu Thr Ala Glu Ala
```

```
                       85                  90                  95
Thr Arg Leu Lys Arg Thr Ala Arg Arg Tyr Thr Arg Arg Lys Asn
                100                 105                 110
Arg Ile Cys Tyr Leu Gln Glu Ile Phe Ser Asn Glu Met Ala Lys Val
                115                 120                 125
Asp Asp Ser Phe Phe His Arg Leu Glu Glu Ser Phe Leu Val Glu Glu
            130                 135                 140
Asp Lys Lys His Glu Arg His Pro Ile Phe Gly Asn Ile Val Asp Glu
145                 150                 155                 160
Val Ala Tyr His Glu Lys Tyr Pro Thr Ile Tyr His Leu Arg Lys Lys
                165                 170                 175
Leu Val Asp Ser Thr Asp Lys Ala Asp Leu Arg Leu Ile Tyr Leu Ala
                180                 185                 190
Leu Ala His Met Ile Lys Phe Arg Gly His Phe Leu Ile Glu Gly Asp
                195                 200                 205
Leu Asn Pro Asp Asn Ser Asp Val Asp Lys Leu Phe Ile Gln Leu Val
                210                 215                 220
Gln Thr Tyr Asn Gln Leu Phe Glu Glu Asn Pro Ile Asn Ala Ser Gly
225                 230                 235                 240
Val Asp Ala Lys Ala Ile Leu Ser Ala Arg Leu Ser Lys Ser Arg Arg
                245                 250                 255
Leu Glu Asn Leu Ile Ala Gln Leu Pro Gly Glu Lys Lys Asn Gly Leu
                260                 265                 270
Phe Gly Asn Leu Ile Ala Leu Ser Leu Gly Leu Thr Pro Asn Phe Lys
                275                 280                 285
Ser Asn Phe Asp Leu Ala Glu Asp Ala Lys Leu Gln Leu Ser Lys Asp
                290                 295                 300
Thr Tyr Asp Asp Asp Leu Asp Asn Leu Leu Ala Gln Ile Gly Asp Gln
305                 310                 315                 320
Tyr Ala Asp Leu Phe Leu Ala Ala Lys Asn Leu Ser Asp Ala Ile Leu
                325                 330                 335
Leu Ser Asp Ile Leu Arg Val Asn Thr Glu Ile Thr Lys Ala Pro Leu
                340                 345                 350
Ser Ala Ser Met Ile Lys Arg Tyr Asp Glu His His Gln Asp Leu Thr
                355                 360                 365
Leu Leu Lys Ala Leu Val Arg Gln Gln Leu Pro Glu Lys Tyr Lys Glu
                370                 375                 380
Ile Phe Phe Asp Gln Ser Lys Asn Gly Tyr Ala Gly Tyr Ile Asp Gly
385                 390                 395                 400
Gly Ala Ser Gln Glu Glu Phe Tyr Lys Phe Ile Lys Pro Ile Leu Glu
                405                 410                 415
Lys Met Asp Gly Thr Glu Glu Leu Leu Val Lys Leu Asn Arg Glu Asp
                420                 425                 430
Leu Leu Arg Lys Gln Arg Thr Phe Asp Asn Gly Ser Ile Pro His Gln
                435                 440                 445
Ile His Leu Gly Glu Leu His Ala Ile Leu Arg Arg Gln Glu Asp Phe
                450                 455                 460
Tyr Pro Phe Leu Lys Asp Asn Arg Glu Lys Ile Glu Lys Ile Leu Thr
465                 470                 475                 480
Phe Arg Ile Pro Tyr Tyr Val Gly Pro Leu Ala Arg Gly Asn Ser Arg
                485                 490                 495
Phe Ala Trp Met Thr Arg Lys Ser Glu Glu Thr Ile Thr Pro Trp Asn
                500                 505                 510
```

```
Phe Glu Glu Val Val Asp Lys Gly Ala Ser Ala Gln Ser Phe Ile Glu
            515                 520                 525

Arg Met Thr Asn Phe Asp Lys Asn Leu Pro Asn Glu Lys Val Leu Pro
    530                 535                 540

Lys His Ser Leu Leu Tyr Glu Tyr Phe Thr Val Tyr Asn Glu Leu Thr
545                 550                 555                 560

Lys Val Lys Tyr Val Thr Glu Gly Met Arg Lys Pro Ala Phe Leu Ser
                565                 570                 575

Gly Glu Gln Lys Lys Ala Ile Val Asp Leu Leu Phe Lys Thr Asn Arg
                580                 585                 590

Lys Val Thr Val Lys Gln Leu Lys Glu Asp Tyr Phe Lys Lys Ile Glu
                595                 600                 605

Cys Phe Asp Ser Val Glu Ile Ser Gly Val Glu Asp Arg Phe Asn Ala
            610                 615                 620

Ser Leu Gly Thr Tyr His Asp Leu Leu Lys Ile Ile Lys Asp Lys Asp
625                 630                 635                 640

Phe Leu Asp Asn Glu Glu Asn Glu Asp Ile Leu Glu Asp Ile Val Leu
                645                 650                 655

Thr Leu Thr Leu Phe Glu Asp Arg Glu Met Ile Glu Glu Arg Leu Lys
            660                 665                 670

Thr Tyr Ala His Leu Phe Asp Asp Lys Val Met Lys Gln Leu Lys Arg
            675                 680                 685

Arg Arg Tyr Thr Gly Trp Gly Arg Leu Ser Arg Lys Leu Ile Asn Gly
    690                 695                 700

Ile Arg Asp Lys Gln Ser Gly Lys Thr Ile Leu Asp Phe Leu Lys Ser
705                 710                 715                 720

Asp Gly Phe Ala Asn Arg Asn Phe Met Gln Leu Ile His Asp Asp Ser
                725                 730                 735

Leu Thr Phe Lys Glu Asp Ile Gln Lys Ala Gln Val Ser Gly Gln Gly
            740                 745                 750

Asp Ser Leu His Glu His Ile Ala Asn Leu Ala Gly Ser Pro Ala Ile
            755                 760                 765

Lys Lys Gly Ile Leu Gln Thr Val Lys Val Val Asp Glu Leu Val Lys
    770                 775                 780

Val Met Gly Arg His Lys Pro Glu Asn Ile Val Ile Glu Met Ala Arg
785                 790                 795                 800

Glu Asn Gln Thr Thr Gln Lys Gly Gln Lys Asn Ser Arg Glu Arg Met
                805                 810                 815

Lys Arg Ile Glu Glu Gly Ile Lys Glu Leu Gly Ser Gln Ile Leu Lys
            820                 825                 830

Glu His Pro Val Glu Asn Thr Gln Leu Gln Asn Glu Lys Leu Tyr Leu
            835                 840                 845

Tyr Tyr Leu Gln Asn Gly Arg Asp Met Tyr Val Asp Gln Glu Leu Asp
850                 855                 860

Ile Asn Arg Leu Ser Asp Tyr Asp Val Asp Ala Ile Val Pro Gln Ser
865                 870                 875                 880

Phe Leu Lys Asp Asp Ser Ile Asp Asn Lys Val Leu Thr Arg Ser Asp
                885                 890                 895

Lys Asn Arg Gly Lys Ser Asp Asn Val Pro Ser Glu Glu Val Val Lys
                900                 905                 910

Lys Met Lys Asn Tyr Trp Arg Gln Leu Leu Asn Ala Lys Leu Ile Thr
            915                 920                 925
```

```
Gln Arg Lys Phe Asp Asn Leu Thr Lys Ala Glu Arg Gly Gly Leu Ser
            930                 935                 940

Glu Leu Asp Lys Ala Gly Phe Ile Lys Arg Gln Leu Val Glu Thr Arg
945                 950                 955                 960

Gln Ile Thr Lys His Val Ala Gln Ile Leu Asp Ser Arg Met Asn Thr
                965                 970                 975

Lys Tyr Asp Glu Asn Asp Lys Leu Ile Arg Glu Val Lys Val Ile Thr
            980                 985                 990

Leu Lys Ser Lys Leu Val Ser Asp Phe Arg Lys Asp Phe Gln Phe Tyr
            995                 1000                1005

Lys Val Arg Glu Ile Asn Asn Tyr His His Ala His Asp Ala Tyr
    1010                1015                1020

Leu Asn Ala Val Val Gly Thr Ala Leu Ile Lys Lys Tyr Pro Lys
    1025                1030                1035

Leu Glu Ser Glu Phe Val Tyr Gly Asp Tyr Lys Val Tyr Asp Val
    1040                1045                1050

Arg Lys Met Ile Ala Lys Ser Glu Gln Glu Ile Gly Lys Ala Thr
    1055                1060                1065

Ala Lys Tyr Phe Phe Tyr Ser Asn Ile Met Asn Phe Phe Lys Thr
    1070                1075                1080

Glu Ile Thr Leu Ala Asn Gly Glu Ile Arg Lys Arg Pro Leu Ile
    1085                1090                1095

Glu Thr Asn Gly Glu Thr Gly Glu Ile Val Trp Asp Lys Gly Arg
    1100                1105                1110

Asp Phe Ala Thr Val Arg Lys Val Leu Ser Met Pro Gln Val Asn
    1115                1120                1125

Ile Val Lys Lys Thr Glu Val Gln Thr Gly Gly Phe Ser Lys Glu
    1130                1135                1140

Ser Ile Leu Pro Lys Arg Asn Ser Asp Lys Leu Ile Ala Arg Lys
    1145                1150                1155

Lys Asp Trp Asp Pro Lys Lys Tyr Gly Gly Phe Asp Ser Pro Thr
    1160                1165                1170

Val Ala Tyr Ser Val Leu Val Val Ala Lys Val Glu Lys Gly Lys
    1175                1180                1185

Ser Lys Lys Leu Lys Ser Val Lys Glu Leu Leu Gly Ile Thr Ile
    1190                1195                1200

Met Glu Arg Ser Ser Phe Glu Lys Asn Pro Ile Asp Phe Leu Glu
    1205                1210                1215

Ala Lys Gly Tyr Lys Glu Val Lys Lys Asp Leu Ile Ile Lys Leu
    1220                1225                1230

Pro Lys Tyr Ser Leu Phe Glu Leu Glu Asn Gly Arg Lys Arg Met
    1235                1240                1245

Leu Ala Ser Ala Gly Glu Leu Gln Lys Gly Asn Glu Leu Ala Leu
    1250                1255                1260

Pro Ser Lys Tyr Val Asn Phe Leu Tyr Leu Ala Ser His Tyr Glu
    1265                1270                1275

Lys Leu Lys Gly Ser Pro Glu Asp Asn Glu Gln Lys Gln Leu Phe
    1280                1285                1290

Val Glu Gln His Lys His Tyr Leu Asp Glu Ile Ile Glu Gln Ile
    1295                1300                1305

Ser Glu Phe Ser Lys Arg Val Ile Leu Ala Asp Ala Asn Leu Asp
    1310                1315                1320

Lys Val Leu Ser Ala Tyr Asn Lys His Arg Asp Lys Pro Ile Arg
```

```
              1325                1330                1335

Glu Gln Ala Glu Asn Ile Ile His Leu Phe Thr Leu Thr Asn Leu
    1340                1345                1350

Gly Ala Pro Ala Ala Phe Lys Tyr Phe Asp Thr Thr Ile Asp Arg
    1355                1360                1365

Lys Arg Tyr Thr Ser Thr Lys Glu Val Leu Asp Ala Thr Leu Ile
    1370                1375                1380

His Gln Ser Ile Thr Gly Leu Tyr Glu Thr Arg Ile Asp Leu Ser
    1385                1390                1395

Gln Leu Gly Gly Asp Pro Ile Ala Gly Ser Lys Ala Ser Pro Lys
    1400                1405                1410

Lys Lys Arg Lys Val Gly Arg Ala Ile Phe Lys Pro Glu Glu Leu
    1415                1420                1425

Arg Gln Ala Leu Met Pro Thr Leu Glu Ala Leu Tyr Arg Gln Asp
    1430                1435                1440

Pro Glu Ser Leu Pro Phe Arg Gln Pro Val Asp Pro Gln Leu Leu
    1445                1450                1455

Gly Ile Pro Asp Tyr Phe Asp Ile Val Lys Ser Pro Met Asp Leu
    1460                1465                1470

Ser Thr Ile Lys Arg Lys Leu Asp Thr Gly Gln Tyr Gln Glu Pro
    1475                1480                1485

Trp Gln Tyr Val Asp Asp Ile Trp Leu Met Phe Asn Asn Ala Trp
    1490                1495                1500

Leu Tyr Asn Arg Lys Thr Ser Arg Val Tyr Lys Tyr Cys Ser Lys
    1505                1510                1515

Leu Ser Glu Val Phe Glu Gln Glu Ile Asp Pro Val Met Gln Ser
    1520                1525                1530

Leu Gly Tyr Cys Cys Gly Arg Lys Leu Glu Phe Ser Pro Gln Thr
    1535                1540                1545

Leu Cys Cys Tyr Gly Lys Gln Leu Cys Thr Ile Pro Arg Asp Ala
    1550                1555                1560

Thr Tyr Tyr Ser Tyr Gln Asn Arg Tyr His Phe Cys Glu Lys Cys
    1565                1570                1575

Phe Asn Glu Ile Gln Gly Glu Ser Val Ser Leu Gly Asp Asp Pro
    1580                1585                1590

Ser Gln Pro Gln Thr Thr Ile Asn Lys Glu Gln Phe Ser Lys Arg
    1595                1600                1605

Lys Asn Asp Thr Leu Asp Pro Glu Leu Phe Val Glu Cys Thr Glu
    1610                1615                1620

Cys Gly Arg Lys Met His Gln Ile Cys Val Leu His His Glu Ile
    1625                1630                1635

Ile Trp Pro Ala Gly Phe Val Cys Asp Gly Cys Leu Lys Lys Ser
    1640                1645                1650

Ala Arg Thr Arg Lys Glu Asn Lys Phe Ser Ala Lys Arg Leu Pro
    1655                1660                1665

Ser Thr Arg Leu Gly Thr Phe Leu Glu Asn Arg Val Asn Asp Phe
    1670                1675                1680

Leu Arg Arg Gln Asn His Pro Glu Ser Gly Glu Val Thr Val Arg
    1685                1690                1695

Val Val His Ala Ser Asp Lys Thr Val Glu Val Lys Pro Gly Met
    1700                1705                1710

Lys Ala Arg Phe Val Asp Ser Gly Glu Met Ala Glu Ser Phe Pro
    1715                1720                1725
```

Tyr Arg Thr Lys Ala Leu Phe Ala Phe Glu Glu Ile Asp Gly Val
        1730                1735                1740

Asp Leu Cys Phe Phe Gly Met His Val Gln Glu Tyr Gly Ser Asp
        1745                1750                1755

Cys Pro Pro Pro Asn Gln Arg Arg Val Tyr Ile Ser Tyr Leu Tyr
        1760                1765                1770

Ser Val His Phe Phe Arg Pro Lys Cys Leu Arg Thr Ala Val Tyr
        1775                1780                1785

His Glu Ile Leu Ile Gly Tyr Leu Glu Tyr Val Lys Lys Leu Gly
        1790                1795                1800

Tyr Thr Thr Gly His Ile Trp Ala Cys Pro Pro Ser Glu Gly Asp
        1805                1810                1815

Asp Tyr Ile Phe His Cys His Pro Pro Asp Gln Lys Ile Pro Lys
        1820                1825                1830

Pro Lys Arg Leu Gln Glu Trp Tyr Lys Lys Met Leu Asp Lys Ala
        1835                1840                1845

Val Ser Glu Arg Ile Val His Asp Tyr Lys Asp Ile Phe Lys Gln
        1850                1855                1860

Ala Thr Glu Asp Arg Leu Thr Ser Ala Lys Glu Leu Pro Tyr Phe
        1865                1870                1875

Glu Gly Asp Phe Trp Pro Asn Val Leu Glu Glu Ser Ile Lys Glu
        1880                1885                1890

Leu Glu Gln Glu Glu Glu Glu Arg Lys Arg Glu Glu Asn Thr Ser
        1895                1900                1905

Asn Glu Ser Thr Asp Val Thr Lys Gly Asp Ser Lys Asn Ala Lys
        1910                1915                1920

Lys Lys Asn Asn Lys Lys Thr Ser Lys Asn Lys Ser Ser Leu Ser
        1925                1930                1935

Arg Gly Asn Lys Lys Pro Gly Met Pro Asn Val Ser Asn Asp
        1940                1945                1950

Leu Ser Gln Lys Leu Tyr Ala Thr Met Glu Lys His Lys Glu Val
        1955                1960                1965

Phe Phe Val Ile Arg Leu Ile Ala Gly Pro Ala Ala Asn Ser Leu
        1970                1975                1980

Pro Pro Ile Val Asp Pro Asp Pro Leu Ile Pro Cys Asp Leu Met
        1985                1990                1995

Asp Gly Arg Asp Ala Phe Leu Thr Leu Ala Arg Asp Lys His Leu
        2000                2005                2010

Glu Phe Ser Ser Leu Arg Arg Ala Gln Trp Ser Thr Met Cys Met
        2015                2020                2025

Leu Val Glu Leu His Thr Gln Ser Gln Asp Tyr Pro Tyr Asp Val
        2030                2035                2040

Pro Asp Tyr Ala Ser
        2045

<210> SEQ ID NO 143
<211> LENGTH: 2048
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Met Asp Tyr Lys Asp His Asp Gly Asp Tyr Lys Asp His Asp Ile Asp

```
1               5                   10                  15
Tyr Lys Asp Asp Asp Lys Met Ala Pro Lys Lys Arg Lys Val
            20                  25                  30
Gly Arg Gly Met Asp Lys Lys Tyr Ser Ile Gly Leu Ala Ile Gly Thr
            35                  40                  45
Asn Ser Val Gly Trp Ala Val Ile Thr Asp Glu Tyr Lys Val Pro Ser
            50                  55                  60
Lys Lys Phe Lys Val Leu Gly Asn Thr Asp Arg His Ser Ile Lys Lys
65                  70                  75                  80
Asn Leu Ile Gly Ala Leu Leu Phe Asp Ser Gly Glu Thr Ala Glu Ala
                    85                  90                  95
Thr Arg Leu Lys Arg Thr Ala Arg Arg Arg Tyr Thr Arg Arg Lys Asn
                    100                 105                 110
Arg Ile Cys Tyr Leu Gln Glu Ile Phe Ser Asn Glu Met Ala Lys Val
                    115                 120                 125
Asp Asp Ser Phe Phe His Arg Leu Glu Glu Ser Phe Leu Val Glu Glu
            130                 135                 140
Asp Lys Lys His Glu Arg His Pro Ile Phe Gly Asn Ile Val Asp Glu
145                 150                 155                 160
Val Ala Tyr His Glu Lys Tyr Pro Thr Ile Tyr His Leu Arg Lys Lys
                    165                 170                 175
Leu Val Asp Ser Thr Asp Lys Ala Asp Leu Arg Leu Ile Tyr Leu Ala
                    180                 185                 190
Leu Ala His Met Ile Lys Phe Arg Gly His Phe Leu Ile Glu Gly Asp
                    195                 200                 205
Leu Asn Pro Asp Asn Ser Asp Val Asp Lys Leu Phe Ile Gln Leu Val
            210                 215                 220
Gln Thr Tyr Asn Gln Leu Phe Glu Glu Asn Pro Ile Asn Ala Ser Gly
225                 230                 235                 240
Val Asp Ala Lys Ala Ile Leu Ser Ala Arg Leu Ser Lys Ser Arg Arg
                    245                 250                 255
Leu Glu Asn Leu Ile Ala Gln Leu Pro Gly Glu Lys Lys Asn Gly Leu
                    260                 265                 270
Phe Gly Asn Leu Ile Ala Leu Ser Leu Gly Leu Thr Pro Asn Phe Lys
                    275                 280                 285
Ser Asn Phe Asp Leu Ala Glu Asp Ala Lys Leu Gln Leu Ser Lys Asp
            290                 295                 300
Thr Tyr Asp Asp Asp Leu Asp Asn Leu Leu Ala Gln Ile Gly Asp Gln
305                 310                 315                 320
Tyr Ala Asp Leu Phe Leu Ala Ala Lys Asn Leu Ser Asp Ala Ile Leu
                    325                 330                 335
Leu Ser Asp Ile Leu Arg Val Asn Thr Glu Ile Thr Lys Ala Pro Leu
                    340                 345                 350
Ser Ala Ser Met Ile Lys Arg Tyr Asp Glu His His Gln Asp Leu Thr
                    355                 360                 365
Leu Leu Lys Ala Leu Val Arg Gln Gln Leu Pro Glu Lys Tyr Lys Glu
            370                 375                 380
Ile Phe Phe Asp Gln Ser Lys Asn Gly Tyr Ala Gly Tyr Ile Asp Gly
385                 390                 395                 400
Gly Ala Ser Gln Glu Glu Phe Tyr Lys Phe Ile Lys Pro Ile Leu Glu
                    405                 410                 415
Lys Met Asp Gly Thr Glu Glu Leu Leu Val Lys Leu Asn Arg Glu Asp
            420                 425                 430
```

```
Leu Leu Arg Lys Gln Arg Thr Phe Asp Asn Gly Ser Ile Pro His Gln
        435                 440                 445

Ile His Leu Gly Glu Leu His Ala Ile Leu Arg Arg Gln Glu Asp Phe
450                 455                 460

Tyr Pro Phe Leu Lys Asp Asn Arg Glu Lys Ile Glu Lys Ile Leu Thr
465                 470                 475                 480

Phe Arg Ile Pro Tyr Tyr Val Gly Pro Leu Ala Arg Gly Asn Ser Arg
                    485                 490                 495

Phe Ala Trp Met Thr Arg Lys Ser Glu Glu Thr Ile Thr Pro Trp Asn
                500                 505                 510

Phe Glu Glu Val Val Asp Lys Gly Ala Ser Ala Gln Ser Phe Ile Glu
            515                 520                 525

Arg Met Thr Asn Phe Asp Lys Asn Leu Pro Asn Glu Lys Val Leu Pro
        530                 535                 540

Lys His Ser Leu Leu Tyr Glu Tyr Phe Thr Val Tyr Asn Glu Leu Thr
545                 550                 555                 560

Lys Val Lys Tyr Val Thr Glu Gly Met Arg Lys Pro Ala Phe Leu Ser
                    565                 570                 575

Gly Glu Gln Lys Lys Ala Ile Val Asp Leu Leu Phe Lys Thr Asn Arg
                580                 585                 590

Lys Val Thr Val Lys Gln Leu Lys Glu Asp Tyr Phe Lys Lys Ile Glu
            595                 600                 605

Cys Phe Asp Ser Val Glu Ile Ser Gly Val Glu Asp Arg Phe Asn Ala
        610                 615                 620

Ser Leu Gly Thr Tyr His Asp Leu Leu Lys Ile Ile Lys Asp Lys Asp
625                 630                 635                 640

Phe Leu Asp Asn Glu Glu Asn Glu Asp Ile Leu Glu Asp Ile Val Leu
                    645                 650                 655

Thr Leu Thr Leu Phe Glu Asp Arg Glu Met Ile Glu Glu Arg Leu Lys
                660                 665                 670

Thr Tyr Ala His Leu Phe Asp Asp Lys Val Met Lys Gln Leu Lys Arg
            675                 680                 685

Arg Arg Tyr Thr Gly Trp Gly Arg Leu Ser Arg Lys Leu Ile Asn Gly
        690                 695                 700

Ile Arg Asp Lys Gln Ser Gly Lys Thr Ile Leu Asp Phe Leu Lys Ser
705                 710                 715                 720

Asp Gly Phe Ala Asn Arg Asn Phe Met Gln Leu Ile His Asp Asp Ser
                    725                 730                 735

Leu Thr Phe Lys Glu Asp Ile Gln Lys Ala Gln Val Ser Gly Gln Gly
                740                 745                 750

Asp Ser Leu His Glu His Ile Ala Asn Leu Ala Gly Ser Pro Ala Ile
            755                 760                 765

Lys Lys Gly Ile Leu Gln Thr Val Lys Val Val Asp Glu Leu Val Lys
        770                 775                 780

Val Met Gly Arg His Lys Pro Glu Asn Ile Val Ile Glu Met Ala Arg
785                 790                 795                 800

Glu Asn Gln Thr Thr Gln Lys Gly Gln Lys Asn Ser Arg Glu Arg Met
                    805                 810                 815

Lys Arg Ile Glu Glu Gly Ile Lys Glu Leu Gly Ser Gln Ile Leu Lys
                820                 825                 830

Glu His Pro Val Glu Asn Thr Gln Leu Gln Asn Glu Lys Leu Tyr Leu
            835                 840                 845
```

```
Tyr Tyr Leu Gln Asn Gly Arg Asp Met Tyr Val Asp Gln Glu Leu Asp
850                 855                 860

Ile Asn Arg Leu Ser Asp Tyr Asp Val Asp Ala Ile Val Pro Gln Ser
865                 870                 875                 880

Phe Leu Lys Asp Asp Ser Ile Asp Asn Lys Val Leu Thr Arg Ser Asp
                885                 890                 895

Lys Asn Arg Gly Lys Ser Asp Asn Val Pro Ser Glu Glu Val Val Lys
            900                 905                 910

Lys Met Lys Asn Tyr Trp Arg Gln Leu Leu Asn Ala Lys Leu Ile Thr
            915                 920                 925

Gln Arg Lys Phe Asp Asn Leu Thr Lys Ala Glu Arg Gly Gly Leu Ser
930                 935                 940

Glu Leu Asp Lys Ala Gly Phe Ile Lys Arg Gln Leu Val Glu Thr Arg
945                 950                 955                 960

Gln Ile Thr Lys His Val Ala Gln Ile Leu Asp Ser Arg Met Asn Thr
                965                 970                 975

Lys Tyr Asp Glu Asn Asp Lys Leu Ile Arg Glu Val Lys Val Ile Thr
            980                 985                 990

Leu Lys Ser Lys Leu Val Ser Asp Phe Arg Lys Asp Phe Gln Phe Tyr
            995                 1000                1005

Lys Val Arg Glu Ile Asn Asn Tyr His His Ala His Asp Ala Tyr
    1010                1015                1020

Leu Asn Ala Val Val Gly Thr Ala Leu Ile Lys Lys Tyr Pro Lys
    1025                1030                1035

Leu Glu Ser Glu Phe Val Tyr Gly Asp Tyr Lys Val Tyr Asp Val
    1040                1045                1050

Arg Lys Met Ile Ala Lys Ser Glu Gln Glu Ile Gly Lys Ala Thr
    1055                1060                1065

Ala Lys Tyr Phe Phe Tyr Ser Asn Ile Met Asn Phe Phe Lys Thr
    1070                1075                1080

Glu Ile Thr Leu Ala Asn Gly Glu Ile Arg Lys Arg Pro Leu Ile
    1085                1090                1095

Glu Thr Asn Gly Glu Thr Gly Glu Ile Val Trp Asp Lys Gly Arg
    1100                1105                1110

Asp Phe Ala Thr Val Arg Lys Val Leu Ser Met Pro Gln Val Asn
    1115                1120                1125

Ile Val Lys Lys Thr Glu Val Gln Thr Gly Gly Phe Ser Lys Glu
    1130                1135                1140

Ser Ile Leu Pro Lys Arg Asn Ser Asp Lys Leu Ile Ala Arg Lys
    1145                1150                1155

Lys Asp Trp Asp Pro Lys Lys Tyr Gly Gly Phe Asp Ser Pro Thr
    1160                1165                1170

Val Ala Tyr Ser Val Leu Val Val Ala Lys Val Glu Lys Gly Lys
    1175                1180                1185

Ser Lys Lys Leu Lys Ser Val Lys Glu Leu Leu Gly Ile Thr Ile
    1190                1195                1200

Met Glu Arg Ser Ser Phe Glu Lys Asn Pro Ile Asp Phe Leu Glu
    1205                1210                1215

Ala Lys Gly Tyr Lys Glu Val Lys Lys Asp Leu Ile Ile Lys Leu
    1220                1225                1230

Pro Lys Tyr Ser Leu Phe Glu Leu Glu Asn Gly Arg Lys Arg Met
    1235                1240                1245

Leu Ala Ser Ala Gly Glu Leu Gln Lys Gly Asn Glu Leu Ala Leu
```

```
            1250                1255                1260

Pro Ser Lys Tyr Val Asn Phe Leu Tyr Leu Ala Ser His Tyr Glu
        1265                1270                1275

Lys Leu Lys Gly Ser Pro Glu Asp Asn Glu Gln Lys Gln Leu Phe
        1280                1285                1290

Val Glu Gln His Lys His Tyr Leu Asp Glu Ile Ile Glu Gln Ile
        1295                1300                1305

Ser Glu Phe Ser Lys Arg Val Ile Leu Ala Asp Ala Asn Leu Asp
        1310                1315                1320

Lys Val Leu Ser Ala Tyr Asn Lys His Arg Asp Lys Pro Ile Arg
        1325                1330                1335

Glu Gln Ala Glu Asn Ile Ile His Leu Phe Thr Leu Thr Asn Leu
        1340                1345                1350

Gly Ala Pro Ala Ala Phe Lys Tyr Phe Asp Thr Thr Ile Asp Arg
        1355                1360                1365

Lys Arg Tyr Thr Ser Thr Lys Glu Val Leu Asp Ala Thr Leu Ile
        1370                1375                1380

His Gln Ser Ile Thr Gly Leu Tyr Glu Thr Arg Ile Asp Leu Ser
        1385                1390                1395

Gln Leu Gly Gly Asp Pro Ile Ala Gly Ser Lys Ala Ser Pro Lys
        1400                1405                1410

Lys Lys Arg Lys Val Gly Arg Ala Ile Phe Lys Pro Glu Glu Leu
        1415                1420                1425

Arg Gln Ala Leu Met Pro Thr Leu Glu Ala Leu Tyr Arg Gln Asp
        1430                1435                1440

Pro Glu Ser Leu Pro Phe Arg Gln Pro Val Asp Pro Gln Leu Leu
        1445                1450                1455

Gly Ile Pro Asp Tyr Phe Asp Ile Val Lys Ser Pro Met Asp Leu
        1460                1465                1470

Ser Thr Ile Lys Arg Lys Leu Asp Thr Gly Gln Tyr Gln Glu Pro
        1475                1480                1485

Trp Gln Tyr Val Asp Asp Ile Trp Leu Met Phe Asn Asn Ala Trp
        1490                1495                1500

Leu Tyr Asn Arg Lys Thr Ser Arg Val Tyr Lys Tyr Cys Ser Lys
        1505                1510                1515

Leu Ser Glu Val Phe Glu Gln Glu Ile Asp Pro Val Met Gln Ser
        1520                1525                1530

Leu Gly Tyr Cys Cys Gly Arg Lys Leu Glu Phe Ser Pro Gln Thr
        1535                1540                1545

Leu Cys Cys Tyr Gly Lys Gln Leu Cys Thr Ile Pro Arg Asp Ala
        1550                1555                1560

Thr Tyr Tyr Ser Tyr Gln Asn Arg Tyr His Phe Cys Glu Lys Cys
        1565                1570                1575

Phe Asn Glu Ile Gln Gly Glu Ser Val Ser Leu Gly Asp Asp Pro
        1580                1585                1590

Ser Gln Pro Gln Thr Thr Ile Asn Lys Glu Gln Phe Ser Lys Arg
        1595                1600                1605

Lys Asn Asp Thr Leu Asp Pro Glu Leu Phe Val Glu Cys Thr Glu
        1610                1615                1620

Cys Gly Arg Lys Met His Gln Ile Cys Val Leu His His Glu Ile
        1625                1630                1635

Ile Trp Pro Ala Gly Phe Val Cys Asp Gly Cys Leu Lys Lys Ser
        1640                1645                1650
```

Ala Arg Thr Arg Lys Glu Asn Lys Phe Ser Ala Lys Arg Leu Pro
1655                1660               1665

Ser Thr Arg Leu Gly Thr Phe Leu Glu Asn Arg Val Asn Asp Phe
1670                1675               1680

Leu Arg Arg Gln Asn His Pro Glu Ser Gly Glu Val Thr Val Arg
1685                1690               1695

Val Val His Ala Ser Asp Lys Thr Val Glu Val Lys Pro Gly Met
1700                1705               1710

Lys Ala Arg Phe Val Asp Ser Gly Glu Met Ala Glu Ser Phe Pro
1715                1720               1725

Tyr Arg Thr Lys Ala Leu Phe Ala Phe Glu Glu Ile Asp Gly Val
1730                1735               1740

Asp Leu Cys Phe Phe Gly Met His Val Gln Glu Tyr Gly Ser Asp
1745                1750               1755

Cys Pro Pro Pro Asn Gln Arg Arg Val Tyr Ile Ser Tyr Leu Asp
1760                1765               1770

Ser Val His Phe Phe Arg Pro Lys Cys Leu Arg Thr Ala Val Tyr
1775                1780               1785

His Glu Ile Leu Ile Gly Tyr Leu Glu Tyr Val Lys Lys Leu Gly
1790                1795               1800

Tyr Thr Thr Gly His Ile Trp Ala Cys Pro Pro Ser Glu Gly Asp
1805                1810               1815

Asp Tyr Ile Phe His Cys His Pro Pro Asp Gln Lys Ile Pro Lys
1820                1825               1830

Pro Lys Arg Leu Gln Glu Trp Tyr Lys Lys Met Leu Asp Lys Ala
1835                1840               1845

Val Ser Glu Arg Ile Val His Asp Tyr Lys Asp Ile Phe Lys Gln
1850                1855               1860

Ala Thr Glu Asp Arg Leu Thr Ser Ala Lys Glu Leu Pro Tyr Phe
1865                1870               1875

Glu Gly Asp Phe Trp Pro Asn Val Leu Glu Glu Ser Ile Lys Glu
1880                1885               1890

Leu Glu Gln Glu Glu Glu Glu Arg Lys Arg Glu Glu Asn Thr Ser
1895                1900               1905

Asn Glu Ser Thr Asp Val Thr Lys Gly Asp Ser Lys Asn Ala Lys
1910                1915               1920

Lys Lys Asn Asn Lys Lys Thr Ser Lys Asn Lys Ser Ser Leu Ser
1925                1930               1935

Arg Gly Asn Lys Lys Lys Pro Gly Met Pro Asn Val Ser Asn Asp
1940                1945               1950

Leu Ser Gln Lys Leu Tyr Ala Thr Met Glu Lys His Lys Glu Val
1955                1960               1965

Phe Phe Val Ile Arg Leu Ile Ala Gly Pro Ala Ala Asn Ser Leu
1970                1975               1980

Pro Pro Ile Val Asp Pro Asp Pro Leu Ile Pro Cys Asp Leu Met
1985                1990               1995

Asp Gly Arg Asp Ala Phe Leu Thr Leu Ala Arg Asp Lys His Leu
2000                2005               2010

Glu Phe Ser Ser Leu Glu Glu Ala Gln Trp Ser Thr Met Cys Met
2015                2020               2025

Leu Val Glu Leu His Thr Gln Ser Gln Asp Tyr Pro Tyr Asp Val
2030                2035               2040

Pro Asp Tyr Ala Ser
    2045

<210> SEQ ID NO 144
<211> LENGTH: 2048
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
                20                  25                  30

Gly Arg Gly Met Asp Lys Lys Tyr Ser Ile Gly Leu Ala Ile Gly Thr
            35                  40                  45

Asn Ser Val Gly Trp Ala Val Ile Thr Asp Glu Tyr Lys Val Pro Ser
    50                  55                  60

Lys Lys Phe Lys Val Leu Gly Asn Thr Asp Arg His Ser Ile Lys Lys
65                  70                  75                  80

Asn Leu Ile Gly Ala Leu Leu Phe Asp Ser Gly Glu Thr Ala Glu Ala
                85                  90                  95

Thr Arg Leu Lys Arg Thr Ala Arg Arg Arg Tyr Thr Arg Arg Lys Asn
            100                 105                 110

Arg Ile Cys Tyr Leu Gln Glu Ile Phe Ser Asn Glu Met Ala Lys Val
        115                 120                 125

Asp Asp Ser Phe Phe His Arg Leu Glu Glu Ser Phe Leu Val Glu Glu
    130                 135                 140

Asp Lys Lys His Glu Arg His Pro Ile Phe Gly Asn Ile Val Asp Glu
145                 150                 155                 160

Val Ala Tyr His Glu Lys Tyr Pro Thr Ile Tyr His Leu Arg Lys Lys
                165                 170                 175

Leu Val Asp Ser Thr Asp Lys Ala Asp Leu Arg Leu Ile Tyr Leu Ala
            180                 185                 190

Leu Ala His Met Ile Lys Phe Arg Gly His Phe Leu Ile Glu Gly Asp
        195                 200                 205

Leu Asn Pro Asp Asn Ser Asp Val Asp Lys Leu Phe Ile Gln Leu Val
    210                 215                 220

Gln Thr Tyr Asn Gln Leu Phe Glu Glu Asn Pro Ile Asn Ala Ser Gly
225                 230                 235                 240

Val Asp Ala Lys Ala Ile Leu Ser Ala Arg Leu Ser Lys Ser Arg Arg
                245                 250                 255

Leu Glu Asn Leu Ile Ala Gln Leu Pro Gly Glu Lys Lys Asn Gly Leu
            260                 265                 270

Phe Gly Asn Leu Ile Ala Leu Ser Leu Gly Leu Thr Pro Asn Phe Lys
        275                 280                 285

Ser Asn Phe Asp Leu Ala Glu Asp Ala Lys Leu Gln Leu Ser Lys Asp
    290                 295                 300

Thr Tyr Asp Asp Asp Leu Asp Asn Leu Leu Ala Gln Ile Gly Asp Gln
305                 310                 315                 320

Tyr Ala Asp Leu Phe Leu Ala Ala Lys Asn Leu Ser Asp Ala Ile Leu
                325                 330                 335

Leu Ser Asp Ile Leu Arg Val Asn Thr Glu Ile Thr Lys Ala Pro Leu
            340                 345                 350

-continued

Ser Ala Ser Met Ile Lys Arg Tyr Asp Glu His His Gln Asp Leu Thr
        355                 360                 365

Leu Leu Lys Ala Leu Val Arg Gln Gln Leu Pro Glu Lys Tyr Lys Glu
    370                 375                 380

Ile Phe Phe Asp Gln Ser Lys Asn Gly Tyr Ala Gly Tyr Ile Asp Gly
385                 390                 395                 400

Gly Ala Ser Gln Glu Glu Phe Tyr Lys Phe Ile Lys Pro Ile Leu Glu
                405                 410                 415

Lys Met Asp Gly Thr Glu Glu Leu Leu Val Lys Leu Asn Arg Glu Asp
            420                 425                 430

Leu Leu Arg Lys Gln Arg Thr Phe Asp Asn Gly Ser Ile Pro His Gln
        435                 440                 445

Ile His Leu Gly Glu Leu His Ala Ile Leu Arg Arg Gln Glu Asp Phe
    450                 455                 460

Tyr Pro Phe Leu Lys Asp Asn Arg Glu Lys Ile Glu Lys Ile Leu Thr
465                 470                 475                 480

Phe Arg Ile Pro Tyr Tyr Val Gly Pro Leu Ala Arg Gly Asn Ser Arg
                485                 490                 495

Phe Ala Trp Met Thr Arg Lys Ser Glu Glu Thr Ile Thr Pro Trp Asn
            500                 505                 510

Phe Glu Glu Val Val Asp Lys Gly Ala Ser Ala Gln Ser Phe Ile Glu
        515                 520                 525

Arg Met Thr Asn Phe Asp Lys Asn Leu Pro Asn Glu Lys Val Leu Pro
    530                 535                 540

Lys His Ser Leu Leu Tyr Glu Tyr Phe Thr Val Tyr Asn Glu Leu Thr
545                 550                 555                 560

Lys Val Lys Tyr Val Thr Glu Gly Met Arg Lys Pro Ala Phe Leu Ser
                565                 570                 575

Gly Glu Gln Lys Lys Ala Ile Val Asp Leu Leu Phe Lys Thr Asn Arg
            580                 585                 590

Lys Val Thr Val Lys Gln Leu Lys Glu Asp Tyr Phe Lys Lys Ile Glu
        595                 600                 605

Cys Phe Asp Ser Val Glu Ile Ser Gly Val Glu Asp Arg Phe Asn Ala
    610                 615                 620

Ser Leu Gly Thr Tyr His Asp Leu Leu Lys Ile Ile Lys Asp Lys Asp
625                 630                 635                 640

Phe Leu Asp Asn Glu Glu Asn Glu Asp Ile Leu Glu Asp Ile Val Leu
                645                 650                 655

Thr Leu Thr Leu Phe Glu Asp Arg Glu Met Ile Glu Glu Arg Leu Lys
            660                 665                 670

Thr Tyr Ala His Leu Phe Asp Asp Lys Val Met Lys Gln Leu Lys Arg
        675                 680                 685

Arg Arg Tyr Thr Gly Trp Gly Arg Leu Ser Arg Lys Leu Ile Asn Gly
    690                 695                 700

Ile Arg Asp Lys Gln Ser Gly Lys Thr Ile Leu Asp Phe Leu Lys Ser
705                 710                 715                 720

Asp Gly Phe Ala Asn Arg Asn Phe Met Gln Leu Ile His Asp Asp Ser
                725                 730                 735

Leu Thr Phe Lys Glu Asp Ile Gln Lys Ala Gln Val Ser Gly Gln Gly
            740                 745                 750

Asp Ser Leu His Glu His Ile Ala Asn Leu Ala Gly Ser Pro Ala Ile
        755                 760                 765

```
Lys Lys Gly Ile Leu Gln Thr Val Lys Val Val Asp Glu Leu Val Lys
770                 775                 780

Val Met Gly Arg His Lys Pro Glu Asn Ile Val Ile Glu Met Ala Arg
785                 790                 795                 800

Glu Asn Gln Thr Thr Gln Lys Gly Gln Lys Asn Ser Arg Glu Arg Met
                805                 810                 815

Lys Arg Ile Glu Glu Gly Ile Lys Glu Leu Gly Ser Gln Ile Leu Lys
                820                 825                 830

Glu His Pro Val Glu Asn Thr Gln Leu Gln Asn Glu Lys Leu Tyr Leu
                835                 840                 845

Tyr Tyr Leu Gln Asn Gly Arg Asp Met Tyr Val Asp Gln Glu Leu Asp
850                 855                 860

Ile Asn Arg Leu Ser Asp Tyr Asp Val Asp Ala Ile Val Pro Gln Ser
865                 870                 875                 880

Phe Leu Lys Asp Asp Ser Ile Asp Asn Lys Val Leu Thr Arg Ser Asp
                885                 890                 895

Lys Asn Arg Gly Lys Ser Asp Asn Val Pro Ser Glu Glu Val Val Lys
                900                 905                 910

Lys Met Lys Asn Tyr Trp Arg Gln Leu Leu Asn Ala Lys Leu Ile Thr
                915                 920                 925

Gln Arg Lys Phe Asp Asn Leu Thr Lys Ala Glu Arg Gly Gly Leu Ser
930                 935                 940

Glu Leu Asp Lys Ala Gly Phe Ile Lys Arg Gln Leu Val Glu Thr Arg
945                 950                 955                 960

Gln Ile Thr Lys His Val Ala Gln Ile Leu Asp Ser Arg Met Asn Thr
                965                 970                 975

Lys Tyr Asp Glu Asn Asp Lys Leu Ile Arg Glu Val Lys Val Ile Thr
                980                 985                 990

Leu Lys Ser Lys Leu Val Ser Asp Phe Arg Lys Asp Phe Gln Phe Tyr
                995                 1000                1005

Lys Val Arg Glu Ile Asn Asn Tyr His His Ala His Asp Ala Tyr
        1010                1015                1020

Leu Asn Ala Val Val Gly Thr Ala Leu Ile Lys Lys Tyr Pro Lys
        1025                1030                1035

Leu Glu Ser Glu Phe Val Tyr Gly Asp Tyr Lys Val Tyr Asp Val
        1040                1045                1050

Arg Lys Met Ile Ala Lys Ser Glu Gln Glu Ile Gly Lys Ala Thr
        1055                1060                1065

Ala Lys Tyr Phe Phe Tyr Ser Asn Ile Met Asn Phe Phe Lys Thr
        1070                1075                1080

Glu Ile Thr Leu Ala Asn Gly Glu Ile Arg Lys Arg Pro Leu Ile
        1085                1090                1095

Glu Thr Asn Gly Glu Thr Gly Glu Ile Val Trp Asp Lys Gly Arg
        1100                1105                1110

Asp Phe Ala Thr Val Arg Lys Val Leu Ser Met Pro Gln Val Asn
        1115                1120                1125

Ile Val Lys Lys Thr Glu Val Gln Thr Gly Gly Phe Ser Lys Glu
        1130                1135                1140

Ser Ile Leu Pro Lys Arg Asn Ser Asp Lys Leu Ile Ala Arg Lys
        1145                1150                1155

Lys Asp Trp Asp Pro Lys Lys Tyr Gly Gly Phe Asp Ser Pro Thr
        1160                1165                1170

Val Ala Tyr Ser Val Leu Val Val Ala Lys Val Glu Lys Gly Lys
```

```
           1175                1180                1185
Ser  Lys  Lys  Leu  Lys  Ser  Val  Lys  Glu  Leu  Leu  Gly  Ile  Thr  Ile
           1190                1195                1200
Met  Glu  Arg  Ser  Ser  Phe  Glu  Lys  Asn  Pro  Ile  Asp  Phe  Leu  Glu
           1205                1210                1215
Ala  Lys  Gly  Tyr  Lys  Glu  Val  Lys  Lys  Asp  Leu  Ile  Ile  Lys  Leu
           1220                1225                1230
Pro  Lys  Tyr  Ser  Leu  Phe  Glu  Leu  Glu  Asn  Gly  Arg  Lys  Arg  Met
           1235                1240                1245
Leu  Ala  Ser  Ala  Gly  Glu  Leu  Gln  Lys  Gly  Asn  Glu  Leu  Ala  Leu
           1250                1255                1260
Pro  Ser  Lys  Tyr  Val  Asn  Phe  Leu  Tyr  Leu  Ala  Ser  His  Tyr  Glu
           1265                1270                1275
Lys  Leu  Lys  Gly  Ser  Pro  Glu  Asp  Asn  Glu  Gln  Lys  Gln  Leu  Phe
           1280                1285                1290
Val  Glu  Gln  His  Lys  His  Tyr  Leu  Asp  Glu  Ile  Ile  Glu  Gln  Ile
           1295                1300                1305
Ser  Glu  Phe  Ser  Lys  Arg  Val  Ile  Leu  Ala  Asp  Ala  Asn  Leu  Asp
           1310                1315                1320
Lys  Val  Leu  Ser  Ala  Tyr  Asn  Lys  His  Arg  Asp  Lys  Pro  Ile  Arg
           1325                1330                1335
Glu  Gln  Ala  Glu  Asn  Ile  Ile  His  Leu  Phe  Thr  Leu  Thr  Asn  Leu
           1340                1345                1350
Gly  Ala  Pro  Ala  Ala  Phe  Lys  Tyr  Phe  Asp  Thr  Thr  Ile  Asp  Arg
           1355                1360                1365
Lys  Arg  Tyr  Thr  Ser  Thr  Lys  Glu  Val  Leu  Asp  Ala  Thr  Leu  Ile
           1370                1375                1380
His  Gln  Ser  Ile  Thr  Gly  Leu  Tyr  Glu  Thr  Arg  Ile  Asp  Leu  Ser
           1385                1390                1395
Gln  Leu  Gly  Gly  Asp  Pro  Ile  Ala  Gly  Ser  Lys  Ala  Ser  Pro  Lys
           1400                1405                1410
Lys  Lys  Arg  Lys  Val  Gly  Arg  Ala  Ile  Phe  Lys  Pro  Glu  Glu  Leu
           1415                1420                1425
Arg  Gln  Ala  Leu  Met  Pro  Thr  Leu  Glu  Ala  Leu  Tyr  Arg  Gln  Asp
           1430                1435                1440
Pro  Glu  Ser  Leu  Pro  Phe  Arg  Gln  Pro  Val  Asp  Pro  Gln  Leu  Leu
           1445                1450                1455
Gly  Ile  Pro  Asp  Tyr  Phe  Asp  Ile  Val  Lys  Ser  Pro  Met  Asp  Leu
           1460                1465                1470
Ser  Thr  Ile  Lys  Arg  Lys  Leu  Asp  Thr  Gly  Gln  Tyr  Gln  Glu  Pro
           1475                1480                1485
Trp  Gln  Tyr  Val  Asp  Asp  Ile  Trp  Leu  Met  Phe  Asn  Asn  Ala  Trp
           1490                1495                1500
Leu  Tyr  Asn  Arg  Lys  Thr  Ser  Arg  Val  Tyr  Lys  Tyr  Cys  Ser  Lys
           1505                1510                1515
Leu  Ser  Glu  Val  Phe  Glu  Gln  Glu  Ile  Asp  Pro  Val  Met  Gln  Ser
           1520                1525                1530
Leu  Gly  Tyr  Cys  Cys  Gly  Arg  Lys  Leu  Glu  Phe  Ser  Pro  Gln  Thr
           1535                1540                1545
Leu  Cys  Cys  Tyr  Gly  Lys  Gln  Leu  Cys  Thr  Ile  Pro  Arg  Asp  Ala
           1550                1555                1560
Thr  Tyr  Tyr  Ser  Tyr  Gln  Asn  Arg  Tyr  His  Phe  Cys  Glu  Lys  Arg
           1565                1570                1575
```

```
Phe Asn Glu Ile Gln Gly Glu Ser Val Ser Leu Gly Asp Asp Pro
    1580            1585            1590

Ser Gln Pro Gln Thr Thr Ile Asn Lys Glu Gln Phe Ser Lys Arg
    1595            1600            1605

Lys Asn Asp Thr Leu Asp Pro Glu Leu Phe Val Glu Cys Thr Glu
    1610            1615            1620

Cys Gly Arg Lys Met His Gln Ile Cys Val Leu His His Glu Ile
    1625            1630            1635

Ile Trp Pro Ala Gly Phe Val Cys Asp Gly Cys Leu Lys Lys Ser
    1640            1645            1650

Ala Arg Thr Arg Lys Glu Asn Lys Phe Ser Ala Lys Arg Leu Pro
    1655            1660            1665

Ser Thr Arg Leu Gly Thr Phe Leu Glu Asn Arg Val Asn Asp Phe
    1670            1675            1680

Leu Arg Arg Gln Asn His Pro Glu Ser Gly Glu Val Thr Val Arg
    1685            1690            1695

Val Val His Ala Ser Asp Lys Thr Val Glu Val Lys Pro Gly Met
    1700            1705            1710

Lys Ala Arg Phe Val Asp Ser Gly Glu Met Ala Glu Ser Phe Pro
    1715            1720            1725

Tyr Arg Thr Lys Ala Leu Phe Ala Phe Glu Glu Ile Asp Gly Val
    1730            1735            1740

Asp Leu Cys Phe Phe Gly Met His Val Gln Glu Tyr Gly Ser Asp
    1745            1750            1755

Cys Pro Pro Pro Asn Gln Arg Arg Val Tyr Ile Ser Tyr Leu Asp
    1760            1765            1770

Ser Val His Phe Phe Arg Pro Lys Cys Leu Arg Thr Ala Val Tyr
    1775            1780            1785

His Glu Ile Leu Ile Gly Tyr Leu Glu Tyr Val Lys Lys Leu Gly
    1790            1795            1800

Tyr Thr Thr Gly His Ile Trp Ala Cys Pro Pro Ser Glu Gly Asp
    1805            1810            1815

Asp Tyr Ile Phe His Cys His Pro Pro Asp Gln Lys Ile Pro Lys
    1820            1825            1830

Pro Lys Arg Leu Gln Glu Trp Tyr Lys Lys Met Leu Asp Lys Ala
    1835            1840            1845

Val Ser Glu Arg Ile Val His Asp Tyr Lys Asp Ile Phe Lys Gln
    1850            1855            1860

Ala Thr Glu Asp Arg Leu Thr Ser Ala Lys Glu Leu Pro Tyr Phe
    1865            1870            1875

Glu Gly Asp Phe Trp Pro Asn Val Leu Glu Glu Ser Ile Lys Glu
    1880            1885            1890

Leu Glu Gln Glu Glu Glu Glu Arg Lys Arg Glu Glu Asn Thr Ser
    1895            1900            1905

Asn Glu Ser Thr Asp Val Thr Lys Gly Asp Ser Lys Asn Ala Lys
    1910            1915            1920

Lys Lys Asn Asn Lys Lys Thr Ser Lys Asn Lys Ser Ser Leu Ser
    1925            1930            1935

Arg Gly Asn Lys Lys Lys Pro Gly Met Pro Asn Val Ser Asn Asp
    1940            1945            1950

Leu Ser Gln Lys Leu Tyr Ala Thr Met Glu Lys His Lys Glu Val
    1955            1960            1965
```

```
Phe Phe Val Ile Arg Leu Ile Ala Gly Pro Ala Ala Asn Ser Leu
    1970                1975                1980

Pro Pro Ile Val Asp Pro Asp Pro Leu Ile Pro Cys Asp Leu Met
    1985                1990                1995

Asp Gly Arg Asp Ala Phe Leu Thr Leu Ala Arg Asp Lys His Leu
    2000                2005                2010

Glu Phe Ser Ser Leu Arg Arg Ala Gln Trp Ser Thr Met Cys Met
    2015                2020                2025

Leu Val Glu Leu His Thr Gln Ser Gln Asp Tyr Pro Tyr Asp Val
    2030                2035                2040

Pro Asp Tyr Ala Ser
    2045

<210> SEQ ID NO 145
<211> LENGTH: 2048
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Gly Met Asp Lys Lys Tyr Ser Ile Gly Leu Ala Ile Gly Thr
                35                  40                  45

Asn Ser Val Gly Trp Ala Val Ile Thr Asp Glu Tyr Lys Val Pro Ser
50                  55                  60

Lys Lys Phe Lys Val Leu Gly Asn Thr Asp Arg His Ser Ile Lys Lys
65                  70                  75                  80

Asn Leu Ile Gly Ala Leu Leu Phe Asp Ser Gly Glu Thr Ala Glu Ala
                85                  90                  95

Thr Arg Leu Lys Arg Thr Ala Arg Arg Arg Tyr Thr Arg Arg Lys Asn
            100                 105                 110

Arg Ile Cys Tyr Leu Gln Glu Ile Phe Ser Asn Glu Met Ala Lys Val
        115                 120                 125

Asp Asp Ser Phe Phe His Arg Leu Glu Glu Ser Phe Leu Val Glu Glu
    130                 135                 140

Asp Lys Lys His Glu Arg His Pro Ile Phe Gly Asn Ile Val Asp Glu
145                 150                 155                 160

Val Ala Tyr His Glu Lys Tyr Pro Thr Ile Tyr His Leu Arg Lys Lys
                165                 170                 175

Leu Val Asp Ser Thr Asp Lys Ala Asp Leu Arg Leu Ile Tyr Leu Ala
            180                 185                 190

Leu Ala His Met Ile Lys Phe Arg Gly His Phe Leu Ile Glu Gly Asp
        195                 200                 205

Leu Asn Pro Asp Asn Ser Asp Val Asp Lys Leu Phe Ile Gln Leu Val
    210                 215                 220

Gln Thr Tyr Asn Gln Leu Phe Glu Glu Asn Pro Ile Asn Ala Ser Gly
225                 230                 235                 240

Val Asp Ala Lys Ala Ile Leu Ser Ala Arg Leu Ser Lys Ser Arg Arg
                245                 250                 255

Leu Glu Asn Leu Ile Ala Gln Leu Pro Gly Glu Lys Lys Asn Gly Leu
            260                 265                 270
```

```
Phe Gly Asn Leu Ile Ala Leu Ser Leu Gly Leu Thr Pro Asn Phe Lys
        275                 280                 285

Ser Asn Phe Asp Leu Ala Glu Asp Ala Lys Leu Gln Leu Ser Lys Asp
    290                 295                 300

Thr Tyr Asp Asp Leu Asp Asn Leu Leu Ala Gln Ile Gly Asp Gln
305                 310                 315                 320

Tyr Ala Asp Leu Phe Leu Ala Ala Lys Asn Leu Ser Asp Ala Ile Leu
                325                 330                 335

Leu Ser Asp Ile Leu Arg Val Asn Thr Glu Ile Thr Lys Ala Pro Leu
                340                 345                 350

Ser Ala Ser Met Ile Lys Arg Tyr Asp Glu His His Gln Asp Leu Thr
            355                 360                 365

Leu Leu Lys Ala Leu Val Arg Gln Gln Leu Pro Glu Lys Tyr Lys Glu
    370                 375                 380

Ile Phe Phe Asp Gln Ser Lys Asn Gly Tyr Ala Gly Tyr Ile Asp Gly
385                 390                 395                 400

Gly Ala Ser Gln Glu Glu Phe Tyr Lys Phe Ile Lys Pro Ile Leu Glu
                405                 410                 415

Lys Met Asp Gly Thr Glu Glu Leu Leu Val Lys Leu Asn Arg Glu Asp
            420                 425                 430

Leu Leu Arg Lys Gln Arg Thr Phe Asp Asn Gly Ser Ile Pro His Gln
    435                 440                 445

Ile His Leu Gly Glu Leu His Ala Ile Leu Arg Arg Gln Glu Asp Phe
450                 455                 460

Tyr Pro Phe Leu Lys Asp Asn Arg Glu Lys Ile Glu Lys Ile Leu Thr
465                 470                 475                 480

Phe Arg Ile Pro Tyr Tyr Val Gly Pro Leu Ala Arg Gly Asn Ser Arg
                485                 490                 495

Phe Ala Trp Met Thr Arg Lys Ser Glu Glu Thr Ile Thr Pro Trp Asn
            500                 505                 510

Phe Glu Glu Val Val Asp Lys Gly Ala Ser Ala Gln Ser Phe Ile Glu
    515                 520                 525

Arg Met Thr Asn Phe Asp Lys Asn Leu Pro Asn Glu Lys Val Leu Pro
530                 535                 540

Lys His Ser Leu Leu Tyr Glu Tyr Phe Thr Val Tyr Asn Glu Leu Thr
545                 550                 555                 560

Lys Val Lys Tyr Val Thr Glu Gly Met Arg Lys Pro Ala Phe Leu Ser
                565                 570                 575

Gly Glu Gln Lys Lys Ala Ile Val Asp Leu Leu Phe Lys Thr Asn Arg
            580                 585                 590

Lys Val Thr Val Lys Gln Leu Lys Glu Asp Tyr Phe Lys Lys Ile Glu
    595                 600                 605

Cys Phe Asp Ser Val Glu Ile Ser Gly Val Glu Asp Arg Phe Asn Ala
610                 615                 620

Ser Leu Gly Thr Tyr His Asp Leu Leu Lys Ile Ile Lys Asp Lys Asp
625                 630                 635                 640

Phe Leu Asp Asn Glu Glu Asn Glu Asp Ile Leu Glu Asp Ile Val Leu
                645                 650                 655

Thr Leu Thr Leu Phe Glu Asp Arg Glu Met Ile Glu Glu Arg Leu Lys
            660                 665                 670

Thr Tyr Ala His Leu Phe Asp Asp Lys Val Met Lys Gln Leu Lys Arg
    675                 680                 685
```

```
Arg Arg Tyr Thr Gly Trp Gly Arg Leu Ser Arg Lys Leu Ile Asn Gly
    690             695                 700

Ile Arg Asp Lys Gln Ser Gly Lys Thr Ile Leu Asp Phe Leu Lys Ser
705             710                 715                 720

Asp Gly Phe Ala Asn Arg Asn Phe Met Gln Leu Ile His Asp Asp Ser
                725                 730                 735

Leu Thr Phe Lys Glu Asp Ile Gln Lys Ala Gln Val Ser Gly Gln Gly
                740                 745                 750

Asp Ser Leu His Glu His Ile Ala Asn Leu Ala Gly Ser Pro Ala Ile
            755                 760                 765

Lys Lys Gly Ile Leu Gln Thr Val Lys Val Val Asp Glu Leu Val Lys
770             775                 780

Val Met Gly Arg His Lys Pro Glu Asn Ile Val Ile Glu Met Ala Arg
785             790                 795                 800

Glu Asn Gln Thr Thr Gln Lys Gly Gln Lys Asn Ser Arg Glu Arg Met
                805                 810                 815

Lys Arg Ile Glu Glu Gly Ile Lys Glu Leu Gly Ser Gln Ile Leu Lys
                820                 825                 830

Glu His Pro Val Glu Asn Thr Gln Leu Gln Asn Glu Lys Leu Tyr Leu
            835                 840                 845

Tyr Tyr Leu Gln Asn Gly Arg Asp Met Tyr Val Asp Gln Glu Leu Asp
850                 855                 860

Ile Asn Arg Leu Ser Asp Tyr Asp Val Asp Ala Ile Val Pro Gln Ser
865             870                 875                 880

Phe Leu Lys Asp Asp Ser Ile Asp Asn Lys Val Leu Thr Arg Ser Asp
                885                 890                 895

Lys Asn Arg Gly Lys Ser Asp Asn Val Pro Ser Glu Glu Val Val Lys
                900                 905                 910

Lys Met Lys Asn Tyr Trp Arg Gln Leu Leu Asn Ala Lys Leu Ile Thr
            915                 920                 925

Gln Arg Lys Phe Asp Asn Leu Thr Lys Ala Glu Arg Gly Gly Leu Ser
    930                 935                 940

Glu Leu Asp Lys Ala Gly Phe Ile Lys Arg Gln Leu Val Glu Thr Arg
945                 950                 955                 960

Gln Ile Thr Lys His Val Ala Gln Ile Leu Asp Ser Arg Met Asn Thr
                965                 970                 975

Lys Tyr Asp Glu Asn Asp Lys Leu Ile Arg Glu Val Lys Val Ile Thr
                980                 985                 990

Leu Lys Ser Lys Leu Val Ser Asp Phe Arg Lys Asp Phe Gln Phe Tyr
    995                 1000                1005

Lys Val Arg Glu Ile Asn Asn Tyr His His Ala His Asp Ala Tyr
    1010                1015                1020

Leu Asn Ala Val Val Gly Thr Ala Leu Ile Lys Lys Tyr Pro Lys
    1025                1030                1035

Leu Glu Ser Glu Phe Val Tyr Gly Asp Tyr Lys Val Tyr Asp Val
    1040                1045                1050

Arg Lys Met Ile Ala Lys Ser Glu Gln Glu Ile Gly Lys Ala Thr
    1055                1060                1065

Ala Lys Tyr Phe Phe Tyr Ser Asn Ile Met Asn Phe Phe Lys Thr
    1070                1075                1080

Glu Ile Thr Leu Ala Asn Gly Glu Ile Arg Lys Arg Pro Leu Ile
    1085                1090                1095

Glu Thr Asn Gly Glu Thr Gly Glu Ile Val Trp Asp Lys Gly Arg
```

```
            1100                1105                1110

Asp Phe Ala Thr Val Arg Lys Val Leu Ser Met Pro Gln Val Asn
    1115                1120                1125

Ile Val Lys Lys Thr Glu Val Gln Thr Gly Gly Phe Ser Lys Glu
    1130                1135                1140

Ser Ile Leu Pro Lys Arg Asn Ser Asp Lys Leu Ile Ala Arg Lys
    1145                1150                1155

Lys Asp Trp Asp Pro Lys Lys Tyr Gly Gly Phe Asp Ser Pro Thr
    1160                1165                1170

Val Ala Tyr Ser Val Leu Val Ala Lys Val Glu Lys Gly Lys
    1175                1180                1185

Ser Lys Lys Leu Lys Ser Val Lys Glu Leu Leu Gly Ile Thr Ile
    1190                1195                1200

Met Glu Arg Ser Ser Phe Glu Lys Asn Pro Ile Asp Phe Leu Glu
    1205                1210                1215

Ala Lys Gly Tyr Lys Glu Val Lys Lys Asp Leu Ile Ile Lys Leu
    1220                1225                1230

Pro Lys Tyr Ser Leu Phe Glu Leu Glu Asn Gly Arg Lys Arg Met
    1235                1240                1245

Leu Ala Ser Ala Gly Glu Leu Gln Lys Gly Asn Glu Leu Ala Leu
    1250                1255                1260

Pro Ser Lys Tyr Val Asn Phe Leu Tyr Leu Ala Ser His Tyr Glu
    1265                1270                1275

Lys Leu Lys Gly Ser Pro Glu Asp Asn Glu Gln Lys Gln Leu Phe
    1280                1285                1290

Val Glu Gln His Lys His Tyr Leu Asp Glu Ile Ile Glu Gln Ile
    1295                1300                1305

Ser Glu Phe Ser Lys Arg Val Ile Leu Ala Asp Ala Asn Leu Asp
    1310                1315                1320

Lys Val Leu Ser Ala Tyr Asn Lys His Arg Asp Lys Pro Ile Arg
    1325                1330                1335

Glu Gln Ala Glu Asn Ile Ile His Leu Phe Thr Leu Thr Asn Leu
    1340                1345                1350

Gly Ala Pro Ala Ala Phe Lys Tyr Phe Asp Thr Thr Ile Asp Arg
    1355                1360                1365

Lys Arg Tyr Thr Ser Thr Lys Glu Val Leu Asp Ala Thr Leu Ile
    1370                1375                1380

His Gln Ser Ile Thr Gly Leu Tyr Glu Thr Arg Ile Asp Leu Ser
    1385                1390                1395

Gln Leu Gly Gly Asp Pro Ile Ala Gly Ser Lys Ala Ser Pro Lys
    1400                1405                1410

Lys Lys Arg Lys Val Gly Arg Ala Ile Phe Lys Pro Glu Glu Leu
    1415                1420                1425

Arg Gln Ala Leu Met Pro Thr Leu Glu Ala Leu Tyr Arg Gln Asp
    1430                1435                1440

Pro Glu Ser Leu Pro Phe Arg Gln Pro Val Asp Pro Gln Leu Leu
    1445                1450                1455

Gly Ile Pro Asp Tyr Phe Asp Ile Val Lys Ser Pro Met Asp Leu
    1460                1465                1470

Ser Thr Ile Lys Arg Lys Leu Asp Thr Gly Gln Tyr Gln Glu Pro
    1475                1480                1485

Trp Gln Tyr Val Asp Asp Ile Trp Leu Met Phe Asn Asn Ala Trp
    1490                1495                1500
```

-continued

```
Leu Tyr Asn Arg Lys Thr Ser Arg Val Tyr Lys Tyr Cys Ser Lys
    1505                1510                1515

Leu Ser Glu Val Phe Glu Gln Glu Ile Asp Pro Val Met Gln Ser
    1520                1525                1530

Leu Gly Tyr Cys Cys Gly Arg Lys Leu Glu Phe Ser Pro Gln Thr
    1535                1540                1545

Leu Cys Cys Tyr Gly Lys Gln Leu Cys Thr Ile Pro Arg Asp Ala
    1550                1555                1560

Thr Tyr Tyr Ser Tyr Gln Asn Arg Tyr His Phe Cys Glu Lys Cys
    1565                1570                1575

Phe Asn Glu Ile Gln Gly Glu Ser Val Ser Leu Gly Asp Asp Pro
    1580                1585                1590

Ser Gln Pro Gln Thr Thr Ile Asn Lys Glu Gln Phe Ser Lys Arg
    1595                1600                1605

Lys Asn Asp Thr Leu Asp Pro Glu Leu Phe Val Glu Cys Thr Glu
    1610                1615                1620

Cys Gly Arg Lys Met His Gln Ile Cys Val Leu His His Glu Ile
    1625                1630                1635

Ile Trp Pro Ala Gly Phe Val Cys Asp Gly Cys Leu Lys Lys Ser
    1640                1645                1650

Ala Arg Thr Arg Lys Glu Asn Lys Phe Ser Ala Lys Arg Leu Pro
    1655                1660                1665

Ser Thr Arg Leu Gly Thr Phe Leu Glu Asn Arg Val Asn Asp Phe
    1670                1675                1680

Leu Arg Arg Gln Asn His Pro Glu Ser Gly Glu Val Thr Val Arg
    1685                1690                1695

Val Val His Ala Ser Asp Lys Thr Val Glu Val Lys Pro Gly Met
    1700                1705                1710

Lys Ala Arg Phe Val Asp Ser Gly Glu Met Ala Glu Ser Phe Pro
    1715                1720                1725

Tyr Arg Thr Lys Ala Leu Phe Ala Phe Glu Glu Ile Asp Gly Val
    1730                1735                1740

Asp Leu Cys Phe Phe Gly Met His Val Gln Glu Tyr Gly Ser Asp
    1745                1750                1755

Cys Pro Pro Pro Asn Gln Arg Arg Val Tyr Ile Ser Tyr Leu Asp
    1760                1765                1770

Ser Val His Phe Phe Arg Pro Lys Cys Leu Arg Thr Ala Val Tyr
    1775                1780                1785

His Glu Ile Leu Ile Gly Tyr Leu Glu Tyr Val Lys Lys Leu Gly
    1790                1795                1800

Tyr Thr Thr Gly His Ile Trp Ala Cys Pro Pro Ser Glu Gly Asp
    1805                1810                1815

Asp Tyr Ile Phe His Cys His Pro Pro Asp Gln Lys Ile Pro Lys
    1820                1825                1830

Pro Lys Arg Leu Gln Glu Trp Phe Lys Lys Met Leu Asp Lys Ala
    1835                1840                1845

Val Ser Glu Arg Ile Val His Asp Tyr Lys Asp Ile Phe Lys Gln
    1850                1855                1860

Ala Thr Glu Asp Arg Leu Thr Ser Ala Lys Glu Leu Pro Tyr Phe
    1865                1870                1875

Glu Gly Asp Phe Trp Pro Asn Val Leu Glu Glu Ser Ile Lys Glu
    1880                1885                1890
```

Leu Glu Gln Glu Glu Glu Arg Lys Arg Glu Glu Asn Thr Ser
    1895                1900               1905

Asn Glu Ser Thr Asp Val Thr Lys Gly Asp Ser Lys Asn Ala Lys
    1910            1915                1920

Lys Lys Asn Asn Lys Lys Thr Ser Lys Asn Lys Ser Ser Leu Ser
    1925            1930                1935

Arg Gly Asn Lys Lys Pro Gly Met Pro Asn Val Ser Asn Asp
    1940            1945                1950

Leu Ser Gln Lys Leu Tyr Ala Thr Met Glu Lys His Lys Glu Val
    1955            1960                1965

Phe Phe Val Ile Arg Leu Ile Ala Gly Pro Ala Ala Asn Ser Leu
    1970            1975                1980

Pro Pro Ile Val Asp Pro Pro Leu Ile Pro Cys Asp Leu Met
    1985            1990                1995

Asp Gly Arg Asp Ala Phe Leu Thr Leu Ala Arg Asp Lys His Leu
    2000            2005                2010

Glu Phe Ser Ser Leu Arg Arg Ala Gln Trp Ser Thr Met Cys Met
    2015            2020                2025

Leu Val Glu Leu His Thr Gln Ser Gln Asp Tyr Pro Tyr Asp Val
    2030            2035                2040

Pro Asp Tyr Ala Ser
    2045

<210> SEQ ID NO 146
<211> LENGTH: 2048
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Arg Gly Met Asp Lys Lys Tyr Ser Ile Gly Leu Ala Ile Gly Thr
            35                  40                  45

Asn Ser Val Gly Trp Ala Val Ile Thr Asp Glu Tyr Lys Val Pro Ser
        50                  55                  60

Lys Lys Phe Lys Val Leu Gly Asn Thr Asp Arg His Ser Ile Lys Lys
65                  70                  75                  80

Asn Leu Ile Gly Ala Leu Leu Phe Asp Ser Gly Glu Thr Ala Glu Ala
                85                  90                  95

Thr Arg Leu Lys Arg Thr Ala Arg Arg Tyr Thr Arg Arg Lys Asn
            100                 105                 110

Arg Ile Cys Tyr Leu Gln Glu Ile Phe Ser Asn Glu Met Ala Lys Val
        115                 120                 125

Asp Asp Ser Phe Phe His Arg Leu Glu Glu Ser Phe Leu Val Glu Glu
    130                 135                 140

Asp Lys Lys His Glu Arg His Pro Ile Phe Gly Asn Ile Val Asp Glu
145                 150                 155                 160

Val Ala Tyr His Glu Lys Tyr Pro Thr Ile Tyr His Leu Arg Lys Lys
                165                 170                 175

Leu Val Asp Ser Thr Asp Lys Ala Asp Leu Arg Leu Ile Tyr Leu Ala
            180                 185                 190

```
Leu Ala His Met Ile Lys Phe Arg Gly His Phe Leu Ile Glu Gly Asp
            195                 200                 205

Leu Asn Pro Asp Asn Ser Asp Val Asp Lys Leu Phe Ile Gln Leu Val
            210                 215                 220

Gln Thr Tyr Asn Gln Leu Phe Glu Glu Asn Pro Ile Asn Ala Ser Gly
225                 230                 235                 240

Val Asp Ala Lys Ala Ile Leu Ser Ala Arg Leu Ser Lys Ser Arg Arg
                245                 250                 255

Leu Glu Asn Leu Ile Ala Gln Leu Pro Gly Glu Lys Lys Asn Gly Leu
            260                 265                 270

Phe Gly Asn Leu Ile Ala Leu Ser Leu Gly Leu Thr Pro Asn Phe Lys
            275                 280                 285

Ser Asn Phe Asp Leu Ala Glu Asp Ala Lys Leu Gln Leu Ser Lys Asp
            290                 295                 300

Thr Tyr Asp Asp Asp Leu Asp Asn Leu Leu Ala Gln Ile Gly Asp Gln
305                 310                 315                 320

Tyr Ala Asp Leu Phe Leu Ala Ala Lys Asn Leu Ser Asp Ala Ile Leu
                325                 330                 335

Leu Ser Asp Ile Leu Arg Val Asn Thr Glu Ile Thr Lys Ala Pro Leu
            340                 345                 350

Ser Ala Ser Met Ile Lys Arg Tyr Asp Glu His His Gln Asp Leu Thr
            355                 360                 365

Leu Leu Lys Ala Leu Val Arg Gln Gln Leu Pro Glu Lys Tyr Lys Glu
            370                 375                 380

Ile Phe Phe Asp Gln Ser Lys Asn Gly Tyr Ala Gly Tyr Ile Asp Gly
385                 390                 395                 400

Gly Ala Ser Gln Glu Glu Phe Tyr Lys Phe Ile Lys Pro Ile Leu Glu
                405                 410                 415

Lys Met Asp Gly Thr Glu Glu Leu Leu Val Lys Leu Asn Arg Glu Asp
            420                 425                 430

Leu Leu Arg Lys Gln Arg Thr Phe Asp Asn Gly Ser Ile Pro His Gln
            435                 440                 445

Ile His Leu Gly Glu Leu His Ala Ile Leu Arg Arg Gln Glu Asp Phe
            450                 455                 460

Tyr Pro Phe Leu Lys Asp Asn Arg Glu Lys Ile Glu Lys Ile Leu Thr
465                 470                 475                 480

Phe Arg Ile Pro Tyr Tyr Val Gly Pro Leu Ala Arg Gly Asn Ser Arg
                485                 490                 495

Phe Ala Trp Met Thr Arg Lys Ser Glu Glu Thr Ile Thr Pro Trp Asn
            500                 505                 510

Phe Glu Glu Val Val Asp Lys Gly Ala Ser Ala Gln Ser Phe Ile Glu
            515                 520                 525

Arg Met Thr Asn Phe Asp Lys Asn Leu Pro Asn Glu Lys Val Leu Pro
530                 535                 540

Lys His Ser Leu Leu Tyr Glu Tyr Phe Thr Val Tyr Asn Glu Leu Thr
545                 550                 555                 560

Lys Val Lys Tyr Val Thr Glu Gly Met Arg Lys Pro Ala Phe Leu Ser
                565                 570                 575

Gly Glu Gln Lys Lys Ala Ile Val Asp Leu Leu Phe Lys Thr Asn Arg
            580                 585                 590

Lys Val Thr Val Lys Gln Leu Lys Glu Asp Tyr Phe Lys Lys Ile Glu
            595                 600                 605
```

```
Cys Phe Asp Ser Val Glu Ile Ser Gly Val Glu Asp Arg Phe Asn Ala
610                 615                 620

Ser Leu Gly Thr Tyr His Asp Leu Leu Lys Ile Ile Lys Asp Lys Asp
625                 630                 635                 640

Phe Leu Asp Asn Glu Glu Asn Glu Asp Ile Leu Glu Asp Ile Val Leu
                645                 650                 655

Thr Leu Thr Leu Phe Glu Asp Arg Glu Met Ile Glu Glu Arg Leu Lys
            660                 665                 670

Thr Tyr Ala His Leu Phe Asp Asp Lys Val Met Lys Gln Leu Lys Arg
        675                 680                 685

Arg Arg Tyr Thr Gly Trp Gly Arg Leu Ser Arg Lys Leu Ile Asn Gly
690                 695                 700

Ile Arg Asp Lys Gln Ser Gly Lys Thr Ile Leu Asp Phe Leu Lys Ser
705                 710                 715                 720

Asp Gly Phe Ala Asn Arg Asn Phe Met Gln Leu Ile His Asp Asp Ser
                725                 730                 735

Leu Thr Phe Lys Glu Asp Ile Gln Lys Ala Gln Val Ser Gly Gln Gly
            740                 745                 750

Asp Ser Leu His Glu His Ile Ala Asn Leu Ala Gly Ser Pro Ala Ile
        755                 760                 765

Lys Lys Gly Ile Leu Gln Thr Val Lys Val Val Asp Glu Leu Val Lys
770                 775                 780

Val Met Gly Arg His Lys Pro Glu Asn Ile Val Ile Glu Met Ala Arg
785                 790                 795                 800

Glu Asn Gln Thr Thr Gln Lys Gly Gln Lys Asn Ser Arg Glu Arg Met
                805                 810                 815

Lys Arg Ile Glu Glu Gly Ile Lys Glu Leu Gly Ser Gln Ile Leu Lys
            820                 825                 830

Glu His Pro Val Glu Asn Thr Gln Leu Gln Asn Glu Lys Leu Tyr Leu
        835                 840                 845

Tyr Tyr Leu Gln Asn Gly Arg Asp Met Tyr Val Asp Gln Glu Leu Asp
850                 855                 860

Ile Asn Arg Leu Ser Asp Tyr Asp Val Asp Ala Ile Val Pro Gln Ser
865                 870                 875                 880

Phe Leu Lys Asp Asp Ser Ile Asp Asn Lys Val Leu Thr Arg Ser Asp
                885                 890                 895

Lys Asn Arg Gly Lys Ser Asp Asn Val Pro Ser Glu Glu Val Val Lys
            900                 905                 910

Lys Met Lys Asn Tyr Trp Arg Gln Leu Leu Asn Ala Lys Leu Ile Thr
        915                 920                 925

Gln Arg Lys Phe Asp Asn Leu Thr Lys Ala Glu Arg Gly Gly Leu Ser
930                 935                 940

Glu Leu Asp Lys Ala Gly Phe Ile Lys Arg Gln Leu Val Glu Thr Arg
945                 950                 955                 960

Gln Ile Thr Lys His Val Ala Gln Ile Leu Asp Ser Arg Met Asn Thr
                965                 970                 975

Lys Tyr Asp Glu Asn Asp Lys Leu Ile Arg Glu Val Lys Val Ile Thr
            980                 985                 990

Leu Lys Ser Lys Leu Val Ser Asp Phe Arg Lys Asp Phe Gln Phe Tyr
        995                 1000                1005

Lys Val Arg Glu Ile Asn Asn Tyr His His Ala His Asp Ala Tyr
    1010                1015                1020

Leu Asn Ala Val Val Gly Thr Ala Leu Ile Lys Lys Tyr Pro Lys
```

```
             1025                1030                1035

Leu Glu Ser Glu Phe Val Tyr Gly Asp Tyr Lys Val Tyr Asp Val
            1040                1045                1050

Arg Lys Met Ile Ala Lys Ser Glu Gln Glu Ile Gly Lys Ala Thr
            1055                1060                1065

Ala Lys Tyr Phe Phe Tyr Ser Asn Ile Met Asn Phe Phe Lys Thr
            1070                1075                1080

Glu Ile Thr Leu Ala Asn Gly Glu Ile Arg Lys Arg Pro Leu Ile
            1085                1090                1095

Glu Thr Asn Gly Glu Thr Gly Glu Ile Val Trp Asp Lys Gly Arg
            1100                1105                1110

Asp Phe Ala Thr Val Arg Lys Val Leu Ser Met Pro Gln Val Asn
            1115                1120                1125

Ile Val Lys Lys Thr Glu Val Gln Thr Gly Gly Phe Ser Lys Glu
            1130                1135                1140

Ser Ile Leu Pro Lys Arg Asn Ser Asp Lys Leu Ile Ala Arg Lys
            1145                1150                1155

Lys Asp Trp Asp Pro Lys Lys Tyr Gly Gly Phe Asp Ser Pro Thr
            1160                1165                1170

Val Ala Tyr Ser Val Leu Val Val Ala Lys Val Glu Lys Gly Lys
            1175                1180                1185

Ser Lys Lys Leu Lys Ser Val Lys Glu Leu Leu Gly Ile Thr Ile
            1190                1195                1200

Met Glu Arg Ser Ser Phe Glu Lys Asn Pro Ile Asp Phe Leu Glu
            1205                1210                1215

Ala Lys Gly Tyr Lys Glu Val Lys Lys Asp Leu Ile Ile Lys Leu
            1220                1225                1230

Pro Lys Tyr Ser Leu Phe Glu Leu Glu Asn Gly Arg Lys Arg Met
            1235                1240                1245

Leu Ala Ser Ala Gly Glu Leu Gln Lys Gly Asn Glu Leu Ala Leu
            1250                1255                1260

Pro Ser Lys Tyr Val Asn Phe Leu Tyr Leu Ala Ser His Tyr Glu
            1265                1270                1275

Lys Leu Lys Gly Ser Pro Glu Asp Asn Glu Gln Lys Gln Leu Phe
            1280                1285                1290

Val Glu Gln His Lys His Tyr Leu Asp Glu Ile Ile Glu Gln Ile
            1295                1300                1305

Ser Glu Phe Ser Lys Arg Val Ile Leu Ala Asp Ala Asn Leu Asp
            1310                1315                1320

Lys Val Leu Ser Ala Tyr Asn Lys His Arg Asp Lys Pro Ile Arg
            1325                1330                1335

Glu Gln Ala Glu Asn Ile Ile His Leu Phe Thr Leu Thr Asn Leu
            1340                1345                1350

Gly Ala Pro Ala Ala Phe Lys Tyr Phe Asp Thr Thr Ile Asp Arg
            1355                1360                1365

Lys Arg Tyr Thr Ser Thr Lys Glu Val Leu Asp Ala Thr Leu Ile
            1370                1375                1380

His Gln Ser Ile Thr Gly Leu Tyr Glu Thr Arg Ile Asp Leu Ser
            1385                1390                1395

Gln Leu Gly Gly Asp Pro Ile Ala Gly Ser Lys Ala Ser Pro Lys
            1400                1405                1410

Lys Lys Arg Lys Val Gly Arg Ala Ile Phe Lys Pro Glu Glu Leu
            1415                1420                1425
```

-continued

```
Arg Gln Ala Leu Met Pro Thr Leu Glu Ala Leu Tyr Arg Gln Asp
1430                1435                1440

Pro Glu Ser Leu Pro Phe Arg Gln Pro Val Asp Pro Gln Leu Leu
1445                1450                1455

Gly Ile Pro Asp Tyr Phe Asp Ile Val Lys Ser Pro Met Asp Leu
1460                1465                1470

Ser Thr Ile Lys Arg Lys Leu Asp Thr Gly Gln Tyr Gln Glu Pro
1475                1480                1485

Trp Gln Tyr Val Asp Asp Ile Trp Leu Met Phe Asn Asn Ala Trp
1490                1495                1500

Leu Tyr Asn Arg Lys Thr Ser Arg Val Tyr Lys Tyr Cys Ser Lys
1505                1510                1515

Leu Ser Glu Val Phe Glu Gln Glu Ile Asp Pro Val Met Gln Ser
1520                1525                1530

Leu Gly Tyr Cys Cys Gly Arg Lys Leu Glu Phe Ser Pro Gln Thr
1535                1540                1545

Leu Cys Cys Tyr Gly Lys Gln Leu Cys Thr Ile Pro Arg Asp Ala
1550                1555                1560

Thr Tyr Tyr Ser Tyr Gln Asn Arg Tyr His Phe Cys Glu Lys Cys
1565                1570                1575

Phe Asn Glu Ile Gln Gly Glu Ser Val Ser Leu Gly Asp Asp Pro
1580                1585                1590

Ser Gln Pro Gln Thr Thr Ile Asn Lys Glu Gln Phe Ser Lys Arg
1595                1600                1605

Lys Asn Asp Thr Leu Asp Pro Glu Leu Phe Val Glu Cys Thr Glu
1610                1615                1620

Cys Gly Arg Lys Met His Gln Ile Cys Val Leu His His Glu Ile
1625                1630                1635

Ile Trp Pro Ala Gly Phe Val Cys Asp Gly Cys Leu Lys Lys Ser
1640                1645                1650

Ala Arg Thr Arg Lys Glu Asn Lys Phe Ser Ala Lys Arg Leu Pro
1655                1660                1665

Ser Thr Arg Leu Gly Thr Phe Leu Glu Asn Arg Val Asn Asp Phe
1670                1675                1680

Leu Arg Arg Gln Asn His Pro Glu Ser Gly Glu Val Thr Val Arg
1685                1690                1695

Val Val His Ala Ser Asp Lys Thr Val Glu Val Lys Pro Gly Met
1700                1705                1710

Lys Ala Arg Phe Val Asp Ser Gly Glu Met Ala Glu Ser Phe Pro
1715                1720                1725

Tyr Arg Thr Lys Ala Leu Phe Ala Phe Glu Glu Ile Asp Gly Val
1730                1735                1740

Asp Leu Cys Phe Phe Gly Met His Val Gln Glu Tyr Gly Ser Asp
1745                1750                1755

Cys Pro Pro Pro Asn Gln Arg Arg Val Tyr Ile Trp Trp Leu Asp
1760                1765                1770

Ser Val His Phe Phe Arg Pro Lys Cys Leu Arg Thr Ala Val Tyr
1775                1780                1785

His Glu Ile Leu Ile Gly Tyr Leu Glu Tyr Val Lys Lys Leu Gly
1790                1795                1800

Tyr Thr Thr Gly His Ile Trp Ala Cys Pro Pro Ser Glu Gly Asp
1805                1810                1815
```

-continued

```
Asp Tyr Ile Phe His Cys His Pro Pro Asp Gln Lys Ile Pro Lys
    1820                1825                1830

Pro Lys Arg Leu Gln Glu Trp Tyr Lys Lys Met Leu Asp Lys Ala
    1835                1840                1845

Val Ser Glu Arg Ile Val His Asp Tyr Lys Asp Ile Phe Lys Gln
    1850                1855                1860

Ala Thr Glu Asp Arg Leu Thr Ser Ala Lys Glu Leu Pro Tyr Phe
    1865                1870                1875

Glu Gly Asp Phe Trp Pro Asn Val Leu Glu Glu Ser Ile Lys Glu
    1880                1885                1890

Leu Glu Gln Glu Glu Glu Arg Lys Arg Glu Glu Asn Thr Ser
    1895                1900                1905

Asn Glu Ser Thr Asp Val Thr Lys Gly Asp Ser Lys Asn Ala Lys
    1910                1915                1920

Lys Lys Asn Asn Lys Lys Thr Ser Lys Asn Lys Ser Ser Leu Ser
    1925                1930                1935

Arg Gly Asn Lys Lys Lys Pro Gly Met Pro Asn Val Ser Asn Asp
    1940                1945                1950

Leu Ser Gln Lys Leu Tyr Ala Thr Met Glu Lys His Lys Glu Val
    1955                1960                1965

Phe Phe Val Ile Arg Leu Ile Ala Gly Pro Ala Ala Asn Ser Leu
    1970                1975                1980

Pro Pro Ile Val Asp Pro Asp Pro Leu Ile Pro Cys Asp Leu Met
    1985                1990                1995

Asp Gly Arg Asp Ala Phe Leu Thr Leu Ala Arg Asp Lys His Leu
    2000                2005                2010

Glu Phe Ser Ser Leu Arg Arg Ala Gln Trp Ser Thr Met Cys Met
    2015                2020                2025

Leu Val Glu Leu His Thr Gln Ser Gln Asp Tyr Pro Tyr Asp Val
    2030                2035                2040

Pro Asp Tyr Ala Ser
    2045

<210> SEQ ID NO 147
<211> LENGTH: 2048
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Lys Arg Lys Val
                20                  25                  30

Gly Arg Gly Met Asp Lys Lys Tyr Ser Ile Gly Leu Ala Ile Gly Thr
            35                  40                  45

Asn Ser Val Gly Trp Ala Val Ile Thr Asp Glu Tyr Lys Val Pro Ser
        50                  55                  60

Lys Lys Phe Lys Val Leu Gly Asn Thr Asp Arg His Ser Ile Lys Lys
65                  70                  75                  80

Asn Leu Ile Gly Ala Leu Leu Phe Asp Ser Gly Glu Thr Ala Glu Ala
                85                  90                  95

Thr Arg Leu Lys Arg Thr Ala Arg Arg Arg Tyr Thr Arg Arg Lys Asn
                100                 105                 110
```

```
Arg Ile Cys Tyr Leu Gln Glu Ile Phe Ser Asn Glu Met Ala Lys Val
        115                 120                 125

Asp Asp Ser Phe Phe His Arg Leu Glu Glu Ser Phe Leu Val Glu Glu
130                 135                 140

Asp Lys His Glu Arg His Pro Ile Phe Gly Asn Ile Val Asp Glu
145                 150                 155                 160

Val Ala Tyr His Glu Lys Tyr Pro Thr Ile Tyr His Leu Arg Lys Lys
                165                 170                 175

Leu Val Asp Ser Thr Asp Lys Ala Asp Leu Arg Leu Ile Tyr Leu Ala
                180                 185                 190

Leu Ala His Met Ile Lys Phe Arg Gly His Phe Leu Ile Glu Gly Asp
                195                 200                 205

Leu Asn Pro Asp Asn Ser Asp Val Asp Lys Leu Phe Ile Gln Leu Val
210                 215                 220

Gln Thr Tyr Asn Gln Leu Phe Glu Glu Asn Pro Ile Asn Ala Ser Gly
225                 230                 235                 240

Val Asp Ala Lys Ala Ile Leu Ser Ala Arg Leu Ser Lys Ser Arg Arg
                245                 250                 255

Leu Glu Asn Leu Ile Ala Gln Leu Pro Gly Glu Lys Lys Asn Gly Leu
            260                 265                 270

Phe Gly Asn Leu Ile Ala Leu Ser Leu Gly Leu Thr Pro Asn Phe Lys
            275                 280                 285

Ser Asn Phe Asp Leu Ala Glu Asp Ala Lys Leu Gln Leu Ser Lys Asp
            290                 295                 300

Thr Tyr Asp Asp Asp Leu Asp Asn Leu Leu Ala Gln Ile Gly Asp Gln
305                 310                 315                 320

Tyr Ala Asp Leu Phe Leu Ala Ala Lys Asn Leu Ser Asp Ala Ile Leu
                325                 330                 335

Leu Ser Asp Ile Leu Arg Val Asn Thr Glu Ile Thr Lys Ala Pro Leu
                340                 345                 350

Ser Ala Ser Met Ile Lys Arg Tyr Asp Glu His His Gln Asp Leu Thr
            355                 360                 365

Leu Leu Lys Ala Leu Val Arg Gln Gln Leu Pro Glu Lys Tyr Lys Glu
            370                 375                 380

Ile Phe Phe Asp Gln Ser Lys Asn Gly Tyr Ala Gly Tyr Ile Asp Gly
385                 390                 395                 400

Gly Ala Ser Gln Glu Glu Phe Tyr Lys Phe Ile Lys Pro Ile Leu Glu
                405                 410                 415

Lys Met Asp Gly Thr Glu Glu Leu Leu Val Lys Leu Asn Arg Glu Asp
            420                 425                 430

Leu Leu Arg Lys Gln Arg Thr Phe Asp Asn Gly Ser Ile Pro His Gln
            435                 440                 445

Ile His Leu Gly Glu Leu His Ala Ile Leu Arg Arg Gln Glu Asp Phe
450                 455                 460

Tyr Pro Phe Leu Lys Asp Asn Arg Glu Lys Ile Glu Lys Ile Leu Thr
465                 470                 475                 480

Phe Arg Ile Pro Tyr Tyr Val Gly Pro Leu Ala Arg Gly Asn Ser Arg
                485                 490                 495

Phe Ala Trp Met Thr Arg Lys Ser Glu Glu Thr Ile Thr Pro Trp Asn
            500                 505                 510

Phe Glu Glu Val Val Asp Lys Gly Ala Ser Ala Gln Ser Phe Ile Glu
            515                 520                 525
```

```
Arg Met Thr Asn Phe Asp Lys Asn Leu Pro Asn Glu Lys Val Leu Pro
    530                 535                 540

Lys His Ser Leu Leu Tyr Glu Tyr Phe Thr Val Tyr Asn Glu Leu Thr
545                 550                 555                 560

Lys Val Lys Tyr Val Thr Glu Gly Met Arg Lys Pro Ala Phe Leu Ser
                565                 570                 575

Gly Glu Gln Lys Lys Ala Ile Val Asp Leu Leu Phe Lys Thr Asn Arg
                580                 585                 590

Lys Val Thr Val Lys Gln Leu Lys Glu Asp Tyr Phe Lys Lys Ile Glu
                595                 600                 605

Cys Phe Asp Ser Val Glu Ile Ser Gly Val Glu Asp Arg Phe Asn Ala
610                 615                 620

Ser Leu Gly Thr Tyr His Asp Leu Leu Lys Ile Ile Lys Asp Lys Asp
625                 630                 635                 640

Phe Leu Asp Asn Glu Glu Asn Glu Asp Ile Leu Glu Asp Ile Val Leu
                645                 650                 655

Thr Leu Thr Leu Phe Glu Asp Arg Glu Met Ile Glu Glu Arg Leu Lys
                660                 665                 670

Thr Tyr Ala His Leu Phe Asp Asp Lys Val Met Lys Gln Leu Lys Arg
                675                 680                 685

Arg Arg Tyr Thr Gly Trp Gly Arg Leu Ser Arg Lys Leu Ile Asn Gly
690                 695                 700

Ile Arg Asp Lys Gln Ser Gly Lys Thr Ile Leu Asp Phe Leu Lys Ser
705                 710                 715                 720

Asp Gly Phe Ala Asn Arg Asn Phe Met Gln Leu Ile His Asp Asp Ser
                725                 730                 735

Leu Thr Phe Lys Glu Asp Ile Gln Lys Ala Gln Val Ser Gly Gln Gly
                740                 745                 750

Asp Ser Leu His Glu His Ile Ala Asn Leu Ala Gly Ser Pro Ala Ile
            755                 760                 765

Lys Lys Gly Ile Leu Gln Thr Val Lys Val Val Asp Glu Leu Val Lys
770                 775                 780

Val Met Gly Arg His Lys Pro Glu Asn Ile Val Ile Glu Met Ala Arg
785                 790                 795                 800

Glu Asn Gln Thr Thr Gln Lys Gly Gln Lys Asn Ser Arg Glu Arg Met
                805                 810                 815

Lys Arg Ile Glu Glu Gly Ile Lys Glu Leu Gly Ser Gln Ile Leu Lys
                820                 825                 830

Glu His Pro Val Glu Asn Thr Gln Leu Gln Asn Glu Lys Leu Tyr Leu
                835                 840                 845

Tyr Tyr Leu Gln Asn Gly Arg Asp Met Tyr Val Asp Gln Glu Leu Asp
850                 855                 860

Ile Asn Arg Leu Ser Asp Tyr Asp Val Asp Ala Ile Val Pro Gln Ser
865                 870                 875                 880

Phe Leu Lys Asp Asp Ser Ile Asp Asn Lys Val Leu Thr Arg Ser Asp
                885                 890                 895

Lys Asn Arg Gly Lys Ser Asp Asn Val Pro Ser Glu Glu Val Val Lys
                900                 905                 910

Lys Met Lys Asn Tyr Trp Arg Gln Leu Leu Asn Ala Lys Leu Ile Thr
                915                 920                 925

Gln Arg Lys Phe Asp Asn Leu Thr Lys Ala Glu Arg Gly Gly Leu Ser
930                 935                 940

Glu Leu Asp Lys Ala Gly Phe Ile Lys Arg Gln Leu Val Glu Thr Arg
```

```
            945              950                955               960
        Gln Ile Thr Lys His Val Ala Gln Ile Leu Asp Ser Arg Met Asn Thr
                        965                 970               975
        Lys Tyr Asp Glu Asn Asp Lys Leu Ile Arg Glu Val Lys Val Ile Thr
                        980                 985               990
        Leu Lys Ser Lys Leu Val Ser Asp Phe Arg Lys Asp Phe Gln Phe Tyr
                        995                 1000              1005
        Lys Val Arg Glu Ile Asn Asn Tyr His His Ala His Asp Ala Tyr
                1010                1015                1020
        Leu Asn Ala Val Val Gly Thr Ala Leu Ile Lys Lys Tyr Pro Lys
                1025                1030                1035
        Leu Glu Ser Glu Phe Val Tyr Gly Asp Tyr Lys Val Tyr Asp Val
                1040                1045                1050
        Arg Lys Met Ile Ala Lys Ser Glu Gln Glu Ile Gly Lys Ala Thr
                1055                1060                1065
        Ala Lys Tyr Phe Phe Tyr Ser Asn Ile Met Asn Phe Phe Lys Thr
                1070                1075                1080
        Glu Ile Thr Leu Ala Asn Gly Glu Ile Arg Lys Arg Pro Leu Ile
                1085                1090                1095
        Glu Thr Asn Gly Glu Thr Gly Glu Ile Val Trp Asp Lys Gly Arg
                1100                1105                1110
        Asp Phe Ala Thr Val Arg Lys Val Leu Ser Met Pro Gln Val Asn
                1115                1120                1125
        Ile Val Lys Lys Thr Glu Val Gln Thr Gly Gly Phe Ser Lys Glu
                1130                1135                1140
        Ser Ile Leu Pro Lys Arg Asn Ser Asp Lys Leu Ile Ala Arg Lys
                1145                1150                1155
        Lys Asp Trp Asp Pro Lys Lys Tyr Gly Gly Phe Asp Ser Pro Thr
                1160                1165                1170
        Val Ala Tyr Ser Val Leu Val Val Ala Lys Val Glu Lys Gly Lys
                1175                1180                1185
        Ser Lys Lys Leu Lys Ser Val Lys Glu Leu Leu Gly Ile Thr Ile
                1190                1195                1200
        Met Glu Arg Ser Ser Phe Glu Lys Asn Pro Ile Asp Phe Leu Glu
                1205                1210                1215
        Ala Lys Gly Tyr Lys Glu Val Lys Lys Asp Leu Ile Ile Lys Leu
                1220                1225                1230
        Pro Lys Tyr Ser Leu Phe Glu Leu Glu Asn Gly Arg Lys Arg Met
                1235                1240                1245
        Leu Ala Ser Ala Gly Glu Leu Gln Lys Gly Asn Glu Leu Ala Leu
                1250                1255                1260
        Pro Ser Lys Tyr Val Asn Phe Leu Tyr Leu Ala Ser His Tyr Glu
                1265                1270                1275
        Lys Leu Lys Gly Ser Pro Glu Asp Asn Glu Gln Lys Gln Leu Phe
                1280                1285                1290
        Val Glu Gln His Lys His Tyr Leu Asp Glu Ile Ile Glu Gln Ile
                1295                1300                1305
        Ser Glu Phe Ser Lys Arg Val Ile Leu Ala Asp Ala Asn Leu Asp
                1310                1315                1320
        Lys Val Leu Ser Ala Tyr Asn Lys His Arg Asp Lys Pro Ile Arg
                1325                1330                1335
        Glu Gln Ala Glu Asn Ile Ile His Leu Phe Thr Leu Thr Asn Leu
                1340                1345                1350
```

```
Gly Ala Pro Ala Ala Phe Lys Tyr Phe Asp Thr Thr Ile Asp Arg
            1355                1360                1365

Lys Arg Tyr Thr Ser Thr Lys Glu Val Leu Asp Ala Thr Leu Ile
    1370                1375                1380

His Gln Ser Ile Thr Gly Leu Tyr Glu Thr Arg Ile Asp Leu Ser
        1385                1390                1395

Gln Leu Gly Gly Asp Pro Ile Ala Gly Ser Lys Ala Ser Pro Lys
    1400                1405                1410

Lys Lys Arg Lys Val Gly Arg Ala Ile Phe Lys Pro Glu Glu Leu
    1415                1420                1425

Arg Gln Ala Leu Met Pro Thr Leu Glu Ala Leu Tyr Arg Gln Asp
    1430                1435                1440

Pro Glu Ser Leu Pro Phe Arg Gln Pro Val Asp Pro Gln Leu Leu
    1445                1450                1455

Gly Ile Pro Asp Tyr Phe Asp Ile Val Lys Ser Pro Met Asp Leu
    1460                1465                1470

Ser Thr Ile Lys Arg Lys Leu Asp Thr Gly Gln Tyr Gln Glu Pro
    1475                1480                1485

Trp Gln Tyr Val Asp Asp Ile Trp Leu Met Phe Asn Asn Ala Trp
    1490                1495                1500

Leu Tyr Asn Arg Lys Thr Ser Arg Val Tyr Lys Tyr Cys Ser Lys
    1505                1510                1515

Leu Ser Glu Val Phe Glu Gln Glu Ile Asp Pro Val Met Gln Ser
    1520                1525                1530

Leu Gly Tyr Cys Cys Gly Arg Lys Leu Glu Phe Ser Pro Gln Thr
    1535                1540                1545

Leu Cys Cys Tyr Gly Lys Gln Leu Cys Thr Ile Pro Arg Asp Ala
    1550                1555                1560

Thr Tyr Tyr Ser Tyr Gln Asn Arg Tyr His Phe Cys Glu Lys Cys
    1565                1570                1575

Phe Asn Glu Ile Gln Gly Glu Ser Val Ser Leu Gly Asp Asp Pro
    1580                1585                1590

Ser Gln Pro Gln Thr Thr Ile Asn Lys Glu Gln Phe Ser Lys Arg
    1595                1600                1605

Lys Asn Asp Thr Leu Asp Pro Glu Leu Phe Val Glu Cys Thr Glu
    1610                1615                1620

Cys Gly Arg Lys Met His Gln Ile Cys Val Leu His His Glu Ile
    1625                1630                1635

Ile Trp Pro Ala Gly Phe Val Cys Asp Gly Cys Leu Lys Lys Ser
    1640                1645                1650

Ala Arg Thr Arg Lys Glu Asn Lys Phe Ser Ala Lys Arg Leu Pro
    1655                1660                1665

Ser Thr Arg Leu Gly Thr Phe Leu Glu Asn Arg Val Asn Asp Phe
    1670                1675                1680

Leu Arg Arg Gln Asn His Pro Glu Ser Gly Glu Val Thr Val Arg
    1685                1690                1695

Val Val His Ala Ser Asp Lys Thr Val Glu Val Lys Pro Gly Met
    1700                1705                1710

Lys Ala Arg Phe Val Asp Ser Gly Glu Met Ala Glu Ser Phe Pro
    1715                1720                1725

Tyr Arg Thr Lys Ala Leu Phe Ala Phe Glu Glu Ile Asp Gly Val
    1730                1735                1740
```

```
Asp Leu Cys Phe Phe Gly Met His Val Gln Glu Tyr Gly Ser Asp
    1745                1750                1755

Cys Pro Pro Pro Asn Gln Arg Arg Val Tyr Ile Ser Tyr Leu Asp
    1760                1765                1770

Ser Val His Phe Phe Arg Pro Lys Cys Leu Arg Thr Ala Val Tyr
    1775                1780                1785

Ala Glu Ile Leu Ile Gly Tyr Leu Ala Ala Val Lys Lys Ser Gly
    1790                1795                1800

Ala Thr Thr Gly Ala Ile Trp Ala Cys Pro Pro Ser Glu Gly Asp
    1805                1810                1815

Asp Tyr Ile Phe His Cys His Pro Pro Asp Gln Lys Ile Pro Lys
    1820                1825                1830

Pro Lys Arg Leu Gln Glu Trp Tyr Lys Lys Met Leu Asp Lys Ala
    1835                1840                1845

Val Ser Glu Arg Ile Val His Asp Tyr Lys Asp Ile Phe Lys Gln
    1850                1855                1860

Ala Thr Glu Asp Arg Leu Thr Ser Ala Lys Glu Leu Pro Tyr Phe
    1865                1870                1875

Glu Gly Asp Phe Trp Pro Asn Val Leu Glu Glu Ser Ile Lys Glu
    1880                1885                1890

Leu Glu Gln Glu Glu Glu Glu Arg Lys Arg Glu Glu Asn Thr Ser
    1895                1900                1905

Asn Glu Ser Thr Asp Val Thr Lys Gly Asp Ser Lys Asn Ala Lys
    1910                1915                1920

Lys Lys Asn Asn Lys Lys Thr Ser Lys Asn Lys Ser Ser Leu Ser
    1925                1930                1935

Arg Gly Asn Lys Lys Pro Gly Met Pro Asn Val Ser Asn Asp
    1940                1945                1950

Leu Ser Gln Lys Leu Tyr Ala Thr Met Glu Lys His Lys Glu Val
    1955                1960                1965

Phe Phe Val Ile Arg Leu Ile Ala Gly Pro Ala Ala Asn Ser Leu
    1970                1975                1980

Pro Pro Ile Val Asp Pro Asp Pro Leu Ile Pro Cys Asp Leu Met
    1985                1990                1995

Asp Gly Arg Asp Ala Phe Leu Thr Leu Ala Arg Asp Lys His Leu
    2000                2005                2010

Glu Phe Ser Ser Leu Arg Arg Ala Gln Trp Ser Thr Met Cys Met
    2015                2020                2025

Leu Val Glu Leu His Thr Gln Ser Gln Asp Tyr Pro Tyr Asp Val
    2030                2035                2040

Pro Asp Tyr Ala Ser
    2045

<210> SEQ ID NO 148
<211> LENGTH: 1155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Met Ala Ala Phe Lys Pro Asn Pro Ile Asn Tyr Ile Leu Gly Leu Ala
1               5                   10                  15

Ile Gly Ile Ala Ser Val Gly Trp Ala Met Val Glu Ile Asp Glu Asp
                20                  25                  30
```

-continued

```
Glu Asn Pro Ile Cys Leu Ile Asp Leu Gly Val Arg Val Phe Glu Arg
         35                  40                  45
Ala Glu Val Pro Lys Thr Gly Asp Ser Leu Ala Met Ala Arg Arg Leu
 50                  55                  60
Ala Arg Ser Val Arg Arg Leu Thr Arg Arg Ala His Arg Leu Leu
 65                  70                  75                  80
Arg Ala Arg Arg Leu Leu Lys Arg Glu Gly Val Leu Gln Ala Ala Asp
                 85                  90                  95
Phe Asp Glu Asn Gly Leu Ile Lys Ser Leu Pro Asn Thr Pro Trp Gln
                100                 105                 110
Leu Arg Ala Ala Ala Leu Asp Arg Lys Leu Thr Pro Leu Glu Trp Ser
            115                 120                 125
Ala Val Leu Leu His Leu Ile Lys His Arg Gly Tyr Leu Ser Gln Arg
        130                 135                 140
Lys Asn Glu Gly Glu Thr Ala Asp Lys Glu Leu Gly Ala Leu Leu Lys
145                 150                 155                 160
Gly Val Ala Asp Asn Ala His Ala Leu Gln Thr Gly Asp Phe Arg Thr
                165                 170                 175
Pro Ala Glu Leu Ala Leu Asn Lys Phe Glu Lys Glu Ser Gly His Ile
            180                 185                 190
Arg Asn Gln Arg Gly Asp Tyr Ser His Thr Phe Ser Arg Lys Asp Leu
        195                 200                 205
Gln Ala Glu Leu Ile Leu Leu Phe Glu Lys Gln Lys Glu Phe Gly Asn
    210                 215                 220
Pro His Val Ser Gly Leu Lys Glu Gly Ile Glu Thr Leu Leu Met
225                 230                 235                 240
Thr Gln Arg Pro Ala Leu Ser Gly Asp Ala Val Gln Lys Met Leu Gly
                245                 250                 255
His Cys Thr Phe Glu Pro Ala Glu Pro Lys Ala Ala Lys Asn Thr Tyr
            260                 265                 270
Thr Ala Glu Arg Phe Ile Trp Leu Thr Lys Leu Asn Asn Leu Arg Ile
        275                 280                 285
Leu Glu Gln Gly Ser Glu Arg Pro Leu Thr Asp Thr Glu Arg Ala Thr
    290                 295                 300
Leu Met Asp Glu Pro Tyr Arg Lys Ser Lys Leu Thr Tyr Ala Gln Ala
305                 310                 315                 320
Arg Lys Leu Leu Gly Leu Glu Asp Thr Ala Phe Phe Lys Gly Leu Arg
                325                 330                 335
Tyr Gly Lys Asp Asn Ala Glu Ala Ser Thr Leu Met Glu Met Lys Ala
            340                 345                 350
Tyr His Ala Ile Ser Arg Ala Leu Glu Lys Glu Gly Leu Lys Asp Lys
        355                 360                 365
Lys Ser Pro Leu Asn Leu Ser Pro Glu Leu Gln Asp Glu Ile Gly Thr
    370                 375                 380
Ala Phe Ser Leu Phe Lys Thr Asp Glu Asp Ile Thr Gly Arg Leu Lys
385                 390                 395                 400
Asp Arg Ile Gln Pro Glu Ile Leu Glu Ala Leu Leu Lys His Ile Ser
                405                 410                 415
Phe Asp Lys Phe Val Gln Ile Ser Leu Lys Ala Leu Arg Arg Ile Val
            420                 425                 430
Pro Leu Met Glu Gln Gly Lys Arg Tyr Asp Glu Ala Cys Ala Glu Ile
        435                 440                 445
```

-continued

Tyr Gly Asp His Tyr Gly Lys Lys Asn Thr Glu Glu Lys Ile Tyr Leu
450                     455                 460

Pro Pro Ile Pro Ala Asp Glu Ile Arg Asn Pro Val Val Leu Arg Ala
465                 470                  475                  480

Leu Ser Gln Ala Arg Lys Val Ile Asn Gly Val Val Arg Arg Tyr Gly
            485                 490                  495

Ser Pro Ala Arg Ile His Ile Glu Thr Ala Arg Glu Val Gly Lys Ser
            500                 505                  510

Phe Lys Asp Arg Lys Glu Ile Glu Lys Arg Gln Glu Glu Asn Arg Lys
            515                 520                  525

Asp Arg Glu Lys Ala Ala Ala Lys Phe Arg Glu Tyr Phe Pro Asn Phe
530                 535                  540

Val Gly Glu Pro Lys Ser Lys Asp Ile Leu Lys Leu Arg Leu Tyr Glu
545                 550                  555                  560

Gln Gln His Gly Lys Cys Leu Tyr Ser Gly Lys Glu Ile Asn Leu Gly
            565                 570                  575

Arg Leu Asn Glu Lys Gly Tyr Val Glu Ile Ala Ala Ala Leu Pro Phe
            580                 585                  590

Ser Arg Thr Trp Asp Asp Ser Phe Asn Asn Lys Val Leu Val Leu Gly
            595                 600                  605

Ser Glu Ala Gln Asn Lys Gly Asn Gln Thr Pro Tyr Glu Tyr Phe Asn
            610                 615                  620

Gly Lys Asp Asn Ser Arg Glu Trp Gln Glu Phe Lys Ala Arg Val Glu
625                 630                  635                  640

Thr Ser Arg Phe Pro Arg Ser Lys Lys Gln Arg Ile Leu Leu Gln Lys
                    645                 650                  655

Phe Asp Glu Asp Gly Phe Lys Glu Arg Asn Leu Asn Asp Thr Arg Tyr
                660                 665                  670

Val Asn Arg Phe Leu Cys Gln Phe Val Ala Asp Arg Met Arg Leu Thr
                675                 680                  685

Gly Lys Gly Lys Lys Arg Val Phe Ala Ser Asn Gly Gln Ile Thr Asn
690                 695                  700

Leu Leu Arg Gly Phe Trp Gly Leu Arg Lys Val Arg Ala Glu Asn Asp
705                 710                  715                  720

Arg His His Ala Leu Asp Ala Val Val Val Ala Cys Ser Thr Val Ala
                725                 730                  735

Met Gln Gln Lys Ile Thr Arg Phe Val Arg Tyr Lys Glu Met Asn Ala
                740                 745                  750

Phe Asp Gly Lys Thr Ile Asp Lys Glu Thr Gly Glu Val Leu His Gln
                755                 760                  765

Lys Thr His Phe Pro Gln Pro Trp Glu Phe Phe Ala Gln Glu Val Met
770                 775                  780

Ile Arg Val Phe Gly Lys Pro Asp Gly Lys Pro Glu Phe Glu Glu Ala
785                 790                  795                  800

Asp Thr Pro Glu Lys Leu Arg Thr Leu Leu Ala Glu Lys Leu Ser Ser
                805                 810                  815

Arg Pro Glu Ala Val His Glu Tyr Val Thr Pro Leu Phe Val Ser Arg
                820                 825                  830

Ala Pro Asn Arg Lys Met Ser Gly Gln Gly His Met Glu Thr Val Lys
                835                 840                  845

Ser Ala Lys Arg Leu Asp Glu Gly Val Ser Val Leu Arg Val Pro Leu
850                 855                  860

Thr Gln Leu Lys Leu Lys Asp Leu Glu Lys Met Val Asn Arg Glu Arg

-continued

```
                865                 870                 875                 880
Glu Pro Lys Leu Tyr Glu Ala Leu Lys Ala Arg Leu Glu Ala His Lys
                    885                 890                 895

Asp Asp Pro Ala Lys Ala Phe Ala Glu Pro Phe Tyr Lys Tyr Asp Lys
                900                 905                 910

Ala Gly Asn Arg Thr Gln Gln Val Lys Ala Val Arg Val Glu Gln Val
                915                 920                 925

Gln Lys Thr Gly Val Trp Val Arg Asn His Asn Gly Ile Ala Asp Asn
            930                 935                 940

Ala Thr Met Val Arg Val Asp Val Phe Glu Lys Gly Asp Lys Tyr Tyr
945                 950                 955                 960

Leu Val Pro Ile Tyr Ser Trp Gln Val Ala Lys Gly Ile Leu Pro Asp
                965                 970                 975

Arg Ala Val Val Gln Gly Lys Asp Glu Glu Asp Trp Gln Leu Ile Asp
                980                 985                 990

Asp Ser Phe Asn Phe Lys Phe Ser Leu His Pro Asn Asp Leu Val Glu
                995                 1000                1005

Val Ile Thr Lys Lys Ala Arg Met Phe Gly Tyr Phe Ala Ser Cys
    1010                1015                1020

His Arg Gly Thr Gly Asn Ile Asn Ile Arg Ile His Asp Leu Asp
    1025                1030                1035

His Lys Ile Gly Lys Asn Gly Ile Leu Glu Gly Ile Gly Val Lys
    1040                1045                1050

Thr Ala Leu Ser Phe Gln Lys Tyr Gln Ile Asp Glu Leu Gly Lys
    1055                1060                1065

Glu Ile Arg Pro Cys Arg Leu Lys Lys Arg Pro Pro Val Arg Ser
    1070                1075                1080

Arg Ala Asp Pro Lys Lys Lys Arg Lys Val Glu Ala Ser Gly Ser
    1085                1090                1095

Gly Arg Ala Asp Ala Leu Asp Asp Phe Asp Leu Asp Met Leu Gly
    1100                1105                1110

Ser Asp Ala Leu Asp Asp Phe Asp Leu Asp Met Leu Gly Ser Asp
    1115                1120                1125

Ala Leu Asp Asp Phe Asp Leu Asp Met Leu Gly Ser Asp Ala Leu
    1130                1135                1140

Asp Asp Phe Asp Leu Asp Met Leu Ile Asn Ser Arg
    1145                1150                1155
```

<210> SEQ ID NO 149
<211> LENGTH: 1726
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

```
Met Ala Ala Phe Lys Pro Asn Pro Ile Asn Tyr Ile Leu Gly Leu Ala
1               5                   10                  15

Ile Gly Ile Ala Ser Val Gly Trp Ala Met Val Glu Ile Asp Glu Asp
                20                  25                  30

Glu Asn Pro Ile Cys Leu Ile Asp Leu Gly Val Arg Val Phe Glu Arg
            35                  40                  45

Ala Glu Val Pro Lys Thr Gly Asp Ser Leu Ala Met Ala Arg Arg Leu
        50                  55                  60
```

-continued

```
Ala Arg Ser Val Arg Arg Leu Thr Arg Arg Arg Ala His Arg Leu Leu
 65                  70                  75                  80

Arg Ala Arg Arg Leu Leu Lys Arg Glu Gly Val Leu Gln Ala Ala Asp
                 85                  90                  95

Phe Asp Glu Asn Gly Leu Ile Lys Ser Leu Pro Asn Thr Pro Trp Gln
                100                 105                 110

Leu Arg Ala Ala Ala Leu Asp Arg Lys Leu Thr Pro Leu Glu Trp Ser
                115                 120                 125

Ala Val Leu Leu His Leu Ile Lys His Arg Gly Tyr Leu Ser Gln Arg
            130                 135                 140

Lys Asn Glu Gly Glu Thr Ala Asp Lys Glu Leu Gly Ala Leu Leu Lys
145                 150                 155                 160

Gly Val Ala Asp Asn Ala His Ala Leu Gln Thr Gly Asp Phe Arg Thr
                165                 170                 175

Pro Ala Glu Leu Ala Leu Asn Lys Phe Glu Lys Glu Ser Gly His Ile
                180                 185                 190

Arg Asn Gln Arg Gly Asp Tyr Ser His Thr Phe Ser Arg Lys Asp Leu
            195                 200                 205

Gln Ala Glu Leu Ile Leu Leu Phe Glu Lys Gln Lys Glu Phe Gly Asn
210                 215                 220

Pro His Val Ser Gly Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Ala Glu Pro Lys Ala Ala Lys Asn Thr Tyr
                260                 265                 270

Thr Ala Glu Arg Phe Ile Trp Leu Thr Lys Leu Asn Asn Leu Arg Ile
            275                 280                 285

Leu Glu Gln Gly Ser Glu Arg Pro Leu Thr Asp Thr Glu Arg Ala Thr
290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
            340                 345                 350

Tyr His Ala Ile Ser Arg Ala Leu Glu Lys Glu Gly Leu Lys Asp Lys
            355                 360                 365

Lys Ser Pro Leu Asn Leu Ser Pro Glu Leu Gln Asp Glu Ile Gly Thr
370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
                420                 425                 430

Pro Leu Met Glu Gln Gly Lys Arg Tyr Asp Glu Ala Cys Ala Glu Ile
            435                 440                 445

Tyr Gly Asp His Tyr Gly Lys Lys Asn Thr Glu Glu Lys Ile Tyr Leu
            450                 455                 460

Pro Pro Ile Pro Ala Asp Glu Ile Arg Asn Pro Val Val Leu Arg Ala
465                 470                 475                 480

Leu Ser Gln Ala Arg Lys Val Ile Asn Gly Val Val Arg Arg Tyr Gly
```

```
            485                 490                 495
Ser Pro Ala Arg Ile His Ile Glu Thr Ala Arg Glu Val Gly Lys Ser
            500                 505                 510
Phe Lys Asp Arg Lys Glu Ile Glu Lys Arg Gln Glu Glu Asn Arg Lys
            515                 520                 525
Asp Arg Glu Lys Ala Ala Ala Lys Phe Arg Glu Tyr Phe Pro Asn Phe
            530                 535                 540
Val Gly Glu Pro Lys Ser Lys Asp Ile Leu Lys Leu Arg Leu Tyr Glu
545                 550                 555                 560
Gln Gln His Gly Lys Cys Leu Tyr Ser Gly Lys Glu Ile Asn Leu Gly
                    565                 570                 575
Arg Leu Asn Glu Lys Gly Tyr Val Glu Ile Ala Ala Ala Leu Pro Phe
                    580                 585                 590
Ser Arg Thr Trp Asp Asp Ser Phe Asn Asn Lys Val Leu Val Leu Gly
                    595                 600                 605
Ser Glu Ala Gln Asn Lys Gly Asn Gln Thr Pro Tyr Glu Tyr Phe Asn
                    610                 615                 620
Gly Lys Asp Asn Ser Arg Glu Trp Gln Glu Phe Lys Ala Arg Val Glu
625                 630                 635                 640
Thr Ser Arg Phe Pro Arg Ser Lys Lys Gln Arg Ile Leu Leu Gln Lys
                    645                 650                 655
Phe Asp Glu Asp Gly Phe Lys Glu Arg Asn Leu Asn Asp Thr Arg Tyr
                    660                 665                 670
Val Asn Arg Phe Leu Cys Gln Phe Val Ala Asp Arg Met Arg Leu Thr
                    675                 680                 685
Gly Lys Gly Lys Lys Arg Val Phe Ala Ser Asn Gly Gln Ile Thr Asn
                    690                 695                 700
Leu Leu Arg Gly Phe Trp Gly Leu Arg Lys Val Arg Ala Glu Asn Asp
705                 710                 715                 720
Arg His His Ala Leu Asp Ala Val Val Val Ala Cys Ser Thr Val Ala
                    725                 730                 735
Met Gln Gln Lys Ile Thr Arg Phe Val Arg Tyr Lys Glu Met Asn Ala
                    740                 745                 750
Phe Asp Gly Lys Thr Ile Asp Lys Glu Thr Gly Glu Val Leu His Gln
                    755                 760                 765
Lys Thr His Phe Pro Gln Pro Trp Glu Phe Phe Ala Gln Glu Val Met
                    770                 775                 780
Ile Arg Val Phe Gly Lys Pro Asp Gly Lys Pro Glu Phe Glu Glu Ala
785                 790                 795                 800
Asp Thr Pro Glu Lys Leu Arg Thr Leu Leu Ala Glu Lys Leu Ser Ser
                    805                 810                 815
Arg Pro Glu Ala Val His Glu Tyr Val Thr Pro Leu Phe Val Ser Arg
                    820                 825                 830
Ala Pro Asn Arg Lys Met Ser Gly Gln Gly His Met Glu Thr Val Lys
                    835                 840                 845
Ser Ala Lys Arg Leu Asp Glu Gly Val Ser Val Leu Arg Val Pro Leu
850                 855                 860
Thr Gln Leu Lys Leu Lys Asp Leu Glu Lys Met Val Asn Arg Glu Arg
865                 870                 875                 880
Glu Pro Lys Leu Tyr Glu Ala Leu Lys Ala Arg Leu Glu Ala His Lys
                    885                 890                 895
Asp Asp Pro Ala Lys Ala Phe Ala Glu Pro Phe Tyr Lys Tyr Asp Lys
                    900                 905                 910
```

-continued

```
Ala Gly Asn Arg Thr Gln Gln Val Lys Ala Val Arg Val Glu Gln Val
        915                 920                 925

Gln Lys Thr Gly Val Trp Val Arg Asn His Asn Gly Ile Ala Asp Asn
    930                 935                 940

Ala Thr Met Val Arg Val Asp Val Phe Glu Lys Gly Asp Lys Tyr Tyr
945                 950                 955                 960

Leu Val Pro Ile Tyr Ser Trp Gln Val Ala Lys Gly Ile Leu Pro Asp
                965                 970                 975

Arg Ala Val Val Gln Gly Lys Asp Glu Glu Asp Trp Gln Leu Ile Asp
            980                 985                 990

Asp Ser Phe Asn Phe Lys Phe Ser Leu His Pro Asn Asp Leu Val Glu
        995                 1000                1005

Val Ile Thr Lys Lys Ala Arg Met Phe Gly Tyr Phe Ala Ser Cys
    1010                1015                1020

His Arg Gly Thr Gly Asn Ile Asn Ile Arg Ile His Asp Leu Asp
    1025                1030                1035

His Lys Ile Gly Lys Asn Gly Ile Leu Glu Gly Ile Gly Val Lys
    1040                1045                1050

Thr Ala Leu Ser Phe Gln Lys Tyr Gln Ile Asp Glu Leu Gly Lys
    1055                1060                1065

Glu Ile Arg Pro Cys Arg Leu Lys Lys Arg Pro Val Arg Ser
    1070                1075                1080

Arg Ala Asp Pro Lys Lys Lys Arg Lys Val Glu Ala Ser Gly Arg
    1085                1090                1095

Ala Ile Phe Lys Pro Glu Glu Leu Arg Gln Ala Leu Met Pro Thr
    1100                1105                1110

Leu Glu Ala Leu Tyr Arg Gln Asp Pro Glu Ser Leu Pro Phe Arg
    1115                1120                1125

Gln Pro Val Asp Pro Gln Leu Leu Gly Ile Pro Asp Tyr Phe Asp
    1130                1135                1140

Ile Val Lys Ser Pro Met Asp Leu Ser Thr Ile Lys Arg Lys Leu
    1145                1150                1155

Asp Thr Gly Gln Tyr Gln Glu Pro Trp Gln Tyr Val Asp Asp Ile
    1160                1165                1170

Trp Leu Met Phe Asn Asn Ala Trp Leu Tyr Asn Arg Lys Thr Ser
    1175                1180                1185

Arg Val Tyr Lys Tyr Cys Ser Lys Leu Ser Glu Val Phe Glu Gln
    1190                1195                1200

Glu Ile Asp Pro Val Met Gln Ser Leu Gly Tyr Cys Cys Gly Arg
    1205                1210                1215

Lys Leu Glu Phe Ser Pro Gln Thr Leu Cys Cys Tyr Gly Lys Gln
    1220                1225                1230

Leu Cys Thr Ile Pro Arg Asp Ala Thr Tyr Tyr Ser Tyr Gln Asn
    1235                1240                1245

Arg Tyr His Phe Cys Glu Lys Cys Phe Asn Glu Ile Gln Gly Glu
    1250                1255                1260

Ser Val Ser Leu Gly Asp Asp Pro Ser Gln Pro Gln Thr Thr Ile
    1265                1270                1275

Asn Lys Glu Gln Phe Ser Lys Arg Lys Asn Asp Thr Leu Asp Pro
    1280                1285                1290

Glu Leu Phe Val Glu Cys Thr Glu Cys Gly Arg Lys Met His Gln
    1295                1300                1305
```

```
Ile Cys Val Leu His His Glu Ile Ile Trp Pro Ala Gly Phe Val
1310                1315                1320

Cys Asp Gly Cys Leu Lys Lys Ser Ala Arg Thr Arg Lys Glu Asn
1325                1330                1335

Lys Phe Ser Ala Lys Arg Leu Pro Ser Thr Arg Leu Gly Thr Phe
1340                1345                1350

Leu Glu Asn Arg Val Asn Asp Phe Leu Arg Arg Gln Asn His Pro
1355                1360                1365

Glu Ser Gly Glu Val Thr Val Arg Val Val His Ala Ser Asp Lys
1370                1375                1380

Thr Val Glu Val Lys Pro Gly Met Lys Ala Arg Phe Val Asp Ser
1385                1390                1395

Gly Glu Met Ala Glu Ser Phe Pro Tyr Arg Thr Lys Ala Leu Phe
1400                1405                1410

Ala Phe Glu Glu Ile Asp Gly Val Asp Leu Cys Phe Phe Gly Met
1415                1420                1425

His Val Gln Glu Tyr Gly Ser Asp Cys Pro Pro Asn Gln Arg
1430                1435                1440

Arg Val Tyr Ile Ser Tyr Leu Asp Ser Val His Phe Phe Arg Pro
1445                1450                1455

Lys Cys Leu Arg Thr Ala Val Tyr His Glu Ile Leu Ile Gly Tyr
1460                1465                1470

Leu Glu Tyr Val Lys Lys Leu Gly Tyr Thr Thr Gly His Ile Trp
1475                1480                1485

Ala Cys Pro Pro Ser Glu Gly Asp Asp Tyr Ile Phe His Cys His
1490                1495                1500

Pro Pro Asp Gln Lys Ile Pro Lys Pro Lys Arg Leu Gln Glu Trp
1505                1510                1515

Tyr Lys Lys Met Leu Asp Lys Ala Val Ser Glu Arg Ile Val His
1520                1525                1530

Asp Tyr Lys Asp Ile Phe Lys Gln Ala Thr Glu Asp Arg Leu Thr
1535                1540                1545

Ser Ala Lys Glu Leu Pro Tyr Phe Glu Gly Asp Phe Trp Pro Asn
1550                1555                1560

Val Leu Glu Glu Ser Ile Lys Glu Leu Glu Gln Glu Glu Glu Glu
1565                1570                1575

Arg Lys Arg Glu Glu Asn Thr Ser Asn Glu Ser Thr Asp Val Thr
1580                1585                1590

Lys Gly Asp Ser Lys Asn Ala Lys Lys Lys Asn Lys Lys Thr
1595                1600                1605

Ser Lys Asn Lys Ser Ser Leu Ser Arg Gly Asn Lys Lys Lys Pro
1610                1615                1620

Gly Met Pro Asn Val Ser Asn Asp Leu Ser Gln Lys Leu Tyr Ala
1625                1630                1635

Thr Met Glu Lys His Lys Glu Val Phe Phe Val Ile Arg Leu Ile
1640                1645                1650

Ala Gly Pro Ala Ala Asn Ser Leu Pro Pro Ile Val Asp Pro Asp
1655                1660                1665

Pro Leu Ile Pro Cys Asp Leu Met Asp Gly Arg Asp Ala Phe Leu
1670                1675                1680

Thr Leu Ala Arg Asp Lys His Leu Glu Phe Ser Ser Leu Arg Arg
1685                1690                1695

Ala Gln Trp Ser Thr Met Cys Met Leu Val Glu Leu His Thr Gln
```

```
                 1700                1705                1710
Ser Gln Asp Tyr Pro Tyr Asp  Val Pro Asp Tyr Ala  Ser
         1715                1720                1725

<210> SEQ ID NO 150
<211> LENGTH: 295
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Gly Met Ala Gln Ala Ala Leu Glu Pro Gly Glu Lys Pro Tyr
        35                  40                  45

Ala Cys Pro Glu Cys Gly Lys Ser Phe Ser Asp Cys Arg Asp Leu Ala
    50                  55                  60

Arg His Gln Arg Thr His Thr Gly Glu Lys Pro Tyr Lys Cys Pro Glu
65                  70                  75                  80

Cys Gly Lys Ser Phe Ser Arg Ser Asp Leu Val Arg His Gln Arg
                85                  90                  95

Thr His Thr Gly Glu Lys Pro Tyr Lys Cys Pro Glu Cys Gly Lys Ser
            100                 105                 110

Phe Ser Gln Ser Ser Asn Leu Val Arg His Gln Arg Thr His Thr Gly
        115                 120                 125

Glu Lys Pro Tyr Ala Cys Pro Glu Cys Gly Lys Ser Phe Ser Thr Ser
    130                 135                 140

Gly Glu Leu Val Arg His Gln Arg Thr His Thr Gly Glu Lys Pro Tyr
145                 150                 155                 160

Lys Cys Pro Glu Cys Gly Lys Ser Phe Ser Gln Arg Ala His Leu Glu
                165                 170                 175

Arg His Gln Arg Thr His Thr Gly Glu Lys Pro Tyr Lys Cys Pro Glu
            180                 185                 190

Cys Gly Lys Ser Phe Ser Gln Ala Gly His Leu Ala Ser His Gln Arg
        195                 200                 205

Thr His Thr Gly Lys Lys Thr Ser Gly Gln Ala Gly Gln Ala Ser Pro
    210                 215                 220

Lys Lys Lys Arg Lys Val Gly Arg Ala Asp Ala Leu Asp Asp Phe Asp
225                 230                 235                 240

Leu Asp Met Leu Gly Ser Asp Ala Leu Asp Asp Phe Asp Leu Asp Met
                245                 250                 255

Leu Gly Ser Asp Ala Leu Asp Asp Phe Asp Leu Asp Met Leu Gly Ser
            260                 265                 270

Asp Ala Leu Asp Asp Phe Asp Leu Asp Met Leu Ile Asn Tyr Pro Tyr
        275                 280                 285

Asp Val Pro Asp Tyr Ala Ser
    290                 295

<210> SEQ ID NO 151
<211> LENGTH: 860
<212> TYPE: PRT
<213> ORGANISM: Artificial Sequence
<220> FEATURE:
```

<223> OTHER INFORMATION: Description of Artificial Sequence: Synthetic
       polypeptide

<400> SEQUENCE: 151

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Lys Arg Lys Val
            20                  25                  30

Gly Arg Gly Met Ala Gln Ala Ala Leu Glu Pro Gly Glu Lys Pro Tyr
            35                  40                  45

Ala Cys Pro Glu Cys Gly Lys Ser Phe Ser Asp Cys Arg Asp Leu Ala
        50                  55                  60

Arg His Gln Arg Thr His Thr Gly Glu Lys Pro Tyr Lys Cys Pro Glu
65              70                  75                  80

Cys Gly Lys Ser Phe Ser Arg Ser Asp Asp Leu Val Arg His Gln Arg
            85                  90                  95

Thr His Thr Gly Glu Lys Pro Tyr Lys Cys Pro Glu Cys Gly Lys Ser
            100                 105                 110

Phe Ser Gln Ser Ser Asn Leu Val Arg His Gln Arg Thr His Thr Gly
        115                 120                 125

Glu Lys Pro Tyr Ala Cys Pro Glu Cys Gly Lys Ser Phe Ser Thr Ser
    130                 135                 140

Gly Glu Leu Val Arg His Gln Arg Thr His Thr Gly Glu Lys Pro Tyr
145             150                 155                 160

Lys Cys Pro Glu Cys Gly Lys Ser Phe Ser Gln Arg Ala His Leu Glu
            165                 170                 175

Arg His Gln Arg Thr His Thr Gly Glu Lys Pro Tyr Lys Cys Pro Glu
            180                 185                 190

Cys Gly Lys Ser Phe Ser Gln Ala Gly His Leu Ala Ser His Gln Arg
        195                 200                 205

Thr His Thr Gly Lys Lys Thr Ser Gly Gln Ala Gly Gln Ala Ser Pro
    210                 215                 220

Lys Lys Lys Arg Lys Val Gly Arg Ala Ile Phe Lys Pro Glu Glu Leu
225             230                 235                 240

Arg Gln Ala Leu Met Pro Thr Leu Glu Ala Leu Tyr Arg Gln Asp Pro
            245                 250                 255

Glu Ser Leu Pro Phe Arg Gln Pro Val Asp Pro Gln Leu Leu Gly Ile
            260                 265                 270

Pro Asp Tyr Phe Asp Ile Val Lys Ser Pro Met Asp Leu Ser Thr Ile
            275                 280                 285

Lys Arg Lys Leu Asp Thr Gly Gln Tyr Gln Glu Pro Trp Gln Tyr Val
290                 295                 300

Asp Asp Ile Trp Leu Met Phe Asn Asn Ala Trp Leu Tyr Asn Arg Lys
305             310                 315                 320

Thr Ser Arg Val Tyr Lys Tyr Cys Ser Lys Leu Ser Glu Val Phe Glu
            325                 330                 335

Gln Glu Ile Asp Pro Val Met Gln Ser Leu Gly Tyr Cys Cys Gly Arg
            340                 345                 350

Lys Leu Glu Phe Ser Pro Gln Thr Leu Cys Cys Tyr Gly Lys Gln Leu
        355                 360                 365

Cys Thr Ile Pro Arg Asp Ala Thr Tyr Tyr Ser Tyr Gln Asn Arg Tyr
    370                 375                 380

His Phe Cys Glu Lys Cys Phe Asn Glu Ile Gln Gly Glu Ser Val Ser
385             390                 395                 400
```

```
Leu Gly Asp Asp Pro Ser Gln Pro Gln Thr Thr Ile Asn Lys Glu Gln
            405                 410                 415

Phe Ser Lys Arg Lys Asn Asp Thr Leu Asp Pro Glu Leu Phe Val Glu
            420                 425                 430

Cys Thr Glu Cys Gly Arg Lys Met His Gln Ile Cys Val Leu His His
            435                 440                 445

Glu Ile Ile Trp Pro Ala Gly Phe Val Cys Asp Gly Cys Leu Lys Lys
            450                 455                 460

Ser Ala Arg Thr Arg Lys Glu Asn Lys Phe Ser Ala Lys Arg Leu Pro
465                 470                 475                 480

Ser Thr Arg Leu Gly Thr Phe Leu Glu Asn Arg Val Asn Asp Phe Leu
            485                 490                 495

Arg Arg Gln Asn His Pro Glu Ser Gly Glu Val Thr Val Arg Val Val
            500                 505                 510

His Ala Ser Asp Lys Thr Val Glu Val Lys Pro Gly Met Lys Ala Arg
            515                 520                 525

Phe Val Asp Ser Gly Glu Met Ala Glu Ser Phe Pro Tyr Arg Thr Lys
            530                 535                 540

Ala Leu Phe Ala Phe Glu Glu Ile Asp Gly Val Asp Leu Cys Phe Phe
545                 550                 555                 560

Gly Met His Val Gln Glu Tyr Gly Ser Asp Cys Pro Pro Asn Gln
            565                 570                 575

Arg Arg Val Tyr Ile Ser Tyr Leu Asp Ser Val His Phe Phe Arg Pro
            580                 585                 590

Lys Cys Leu Arg Thr Ala Val Tyr His Glu Ile Leu Ile Gly Tyr Leu
            595                 600                 605

Glu Tyr Val Lys Lys Leu Gly Tyr Thr Thr Gly His Ile Trp Ala Cys
            610                 615                 620

Pro Pro Ser Glu Gly Asp Asp Tyr Ile Phe His Cys His Pro Pro Asp
625                 630                 635                 640

Gln Lys Ile Pro Lys Pro Lys Arg Leu Gln Glu Trp Tyr Lys Lys Met
            645                 650                 655

Leu Asp Lys Ala Val Ser Glu Arg Ile Val His Asp Tyr Lys Asp Ile
            660                 665                 670

Phe Lys Gln Ala Thr Glu Asp Arg Leu Thr Ser Ala Lys Glu Leu Pro
            675                 680                 685

Tyr Phe Glu Gly Asp Phe Trp Pro Asn Val Leu Glu Glu Ser Ile Lys
            690                 695                 700

Glu Leu Glu Gln Glu Glu Glu Arg Lys Arg Glu Glu Asn Thr Ser
705                 710                 715                 720

Asn Glu Ser Thr Asp Val Thr Lys Gly Asp Ser Lys Asn Ala Lys Lys
            725                 730                 735

Lys Asn Asn Lys Lys Thr Ser Lys Asn Lys Ser Ser Leu Ser Arg Gly
            740                 745                 750

Asn Lys Lys Lys Pro Gly Met Pro Asn Val Ser Asn Asp Leu Ser Gln
            755                 760                 765

Lys Leu Tyr Ala Thr Met Glu Lys His Lys Glu Val Phe Phe Val Ile
            770                 775                 780

Arg Leu Ile Ala Gly Pro Ala Ala Asn Ser Leu Pro Pro Ile Val Asp
785                 790                 795                 800

Pro Asp Pro Leu Ile Pro Cys Asp Leu Met Asp Gly Arg Asp Ala Phe
            805                 810                 815
```

```
Leu Thr Leu Ala Arg Asp Lys His Leu Glu Phe Ser Ser Leu Arg Arg
            820                 825                 830

Ala Gln Trp Ser Thr Met Cys Met Leu Val Glu Leu His Thr Gln Ser
        835                 840                 845

Gln Asp Tyr Pro Tyr Asp Val Pro Asp Tyr Ala Ser
    850                 855                 860

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
cctggtcttc aatgagaaga                                              20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
gattaggaca tgaacatggg                                              20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
cctcttctac attaacctta                                              20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
tttttgaagc cagcaatcgt                                              20

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
cgttagtttc tggaggctct                                              20

<210> SEQ ID NO 157
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 157
acaaattacc acgaatgtag                                                 20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
tggcctgggc gcctgtctat                                                 20

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
attttgtaaa taaggtcttc                                                 20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
agcaacaggg gatggggcag                                                 20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
aggactcgta gtatgcaggc                                                 20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
ctgagccacc aactatttaa                                                 20

<210> SEQ ID NO 163
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 163
ctgagccacc aactatttaa                                                   20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
actctgggtc ggttacggaa                                                   20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
gggctgggct tagcttggga                                                   20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
atagggaggg gctctggagc                                                   20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
atgggaaaag atacctgagt                                                   20

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
tgggagcgtt gtgtcgcagc                                                   20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 169
tggaaaggct ttcattttct                                               20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
gtatctcgca gctccaatac                                               20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
acgcattccc ctcggtttga                                               20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
tcggaagctt ttcttctcag                                               20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
cgaaagggcg tgcgcgcccg                                               20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
ccggcgaaag ggaagcggcc                                               20

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 175
ggctgcgcac gcccatcccc                                               20

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
ggggcttgca ggtggttcgc                                               20

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
cgagctaaag agcggatgcc                                               20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
agagggcggg agcagggcca                                               20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
aaccggctct taactctttg                                               20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
caggagcggc gagcggggtc                                               20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 181
gggtatcaga tggcaaagtt                                                 20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
tcataggctg ccggcgattg                                                 20

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
gaggttggcc aggagcagcg                                                 20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
aattagcccc gcacggcgag                                                 20

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
tcccctgggt aggagtacag                                                 20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
ggttgttagc tgcggtcagc                                                 20

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
ggtggagaac aggggggcgcc                                                          20

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 188
cctggtcttc aatgagaaga ngg                                                       23

<210> SEQ ID NO 189
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 189
gattaggaca tgaacatggg ngg                                                       23

<210> SEQ ID NO 190
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 190
cctcttctac attaacctta ngg                                                       23

<210> SEQ ID NO 191
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 191
tttttgaagc cagcaatcgt ngg                                                       23

<210> SEQ ID NO 192
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (21)..(21)
<223> OTHER INFORMATION: a, c, t, g, unknown or other

<400> SEQUENCE: 192
cgttagtttc tggaggctct ngg                                          23

<210> SEQ ID NO 193
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 193
acaaattacc acgaatgtag ngg                                          23

<210> SEQ ID NO 194
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 194
tggcctgggc gcctgtctat ngg                                          23

<210> SEQ ID NO 195
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 195
attttgtaaa taaggtcttc ngg                                          23

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 196
agcaacaggg gatggggcag ngg                                          23

<210> SEQ ID NO 197
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 197
aggactcgta gtatgcaggc ngg                                           23

<210> SEQ ID NO 198
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 198
ctgagccacc aactatttaa ngg                                           23

<210> SEQ ID NO 199
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 199
ctgagccacc aactatttaa ngg                                           23

<210> SEQ ID NO 200
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 200
actctgggtc ggttacggaa ngg                                           23

<210> SEQ ID NO 201
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other
```

```
<400> SEQUENCE: 201
gggctgggct tagcttggga ngg                                           23

<210> SEQ ID NO 202
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 202
atagggaggg gctctggagc ngg                                           23

<210> SEQ ID NO 203
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 203
atgggaaaag atacctgagt ngg                                           23

<210> SEQ ID NO 204
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 204
tgggagcgtt gtgtcgcagc ngg                                           23

<210> SEQ ID NO 205
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 205
tggaaaggct ttcattttct ngg                                           23

<210> SEQ ID NO 206
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 206
gtatctcgca gctccaatac ngg                                              23

<210> SEQ ID NO 207
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 207
acgcattccc ctcggtttga ngg                                              23

<210> SEQ ID NO 208
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 208
tcggaagctt ttcttctcag ngg                                              23

<210> SEQ ID NO 209
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 209
cgaaagggcg tgcgcgcccg ngg                                              23

<210> SEQ ID NO 210
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 210
ccggcgaaag ggaagcggcc ngg                                              23

```
<210> SEQ ID NO 211
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 211
ggctgcgcac gcccatcccc ngg                                              23

<210> SEQ ID NO 212
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 212
ggggcttgca ggtggttcgc ngg                                              23

<210> SEQ ID NO 213
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 213
cgagctaaag agcggatgcc ngg                                              23

<210> SEQ ID NO 214
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 214
agagggcggg agcagggcca ngg                                              23

<210> SEQ ID NO 215
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other
```

<400> SEQUENCE: 215
aaccggctct taactctttg ngg                                               23

<210> SEQ ID NO 216
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 216
caggagcggc gagcggggtc ngg                                               23

<210> SEQ ID NO 217
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 217
gggtatcaga tggcaaagtt ngg                                               23

<210> SEQ ID NO 218
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 218
tcataggctg ccggcgattg ngg                                               23

<210> SEQ ID NO 219
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 219
gaggttggcc aggagcagcg ngg                                               23

<210> SEQ ID NO 220
<211> LENGTH: 23
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 220
aattagcccc gcacggcgag ngg                                          23

<210> SEQ ID NO 221
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 221
tcccctgggt aggagtacag ngg                                          23

<210> SEQ ID NO 222
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 222
ggttgttagc tgcggtcagc ngg                                          23

<210> SEQ ID NO 223
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 223
ggtggagaac aggggggcgcc ngg                                         23

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
gggggcgcga gtgatcagct                                              20

<210> SEQ ID NO 225
<211> LENGTH: 20
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 225
cccgggtctc ctaggggacg                                              20

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
tggtccggag aaagaaggcg                                              20

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
gtctccgggc tcggaaactt                                              20

<210> SEQ ID NO 228
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
agcgccagag cgcgagagcg                                              20

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
cgattccggc cgcgttcccc                                              20

<210> SEQ ID NO 230
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
gttgtgcggg ctgatgcgcc                                              20

<210> SEQ ID NO 231
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 231
cctcgtgtgt tcctgggcct gctgc                                              25

<210> SEQ ID NO 232
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
tcccataaac aggattctgc tcaga                                              25

<210> SEQ ID NO 233
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
caccggccag atgacagaac agaaa                                              25

<210> SEQ ID NO 234
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
ttgtttgaaa atgccatttg tagggct                                            27

<210> SEQ ID NO 235
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
aaacgcagca ggcccaggaa cacac                                              25

<210> SEQ ID NO 236
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
aaactctgag cagaatcctg tttat                                              25

<210> SEQ ID NO 237
<211> LENGTH: 25
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 237
aaactttctg ttctgtcatc tggcc                                           25

<210> SEQ ID NO 238
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
aaacagccct acaaatggca ttttcaa                                         27

<210> SEQ ID NO 239
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
cctcgtctgc ttctgccgaa cctca                                           25

<210> SEQ ID NO 240
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
tcccacctaa agagcttgta ggccg                                           25

<210> SEQ ID NO 241
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
caccgagagc tggctacccg tccct                                           25

<210> SEQ ID NO 242
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
ttgtttgcgg tccttgttta tcagtag                                         27

<210> SEQ ID NO 243
<211> LENGTH: 25
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 243
aaactgaggt tcggcagaag cagac                                          25

<210> SEQ ID NO 244
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
aaaccggcct acaagctctt taggt                                          25

<210> SEQ ID NO 245
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
aaacagggac gggtagccag ctctc                                          25

<210> SEQ ID NO 246
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
aaacctactg ataaacaagg accgcaa                                        27

<210> SEQ ID NO 247
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
cctcggagct ggctacccgt cccta                                          25

<210> SEQ ID NO 248
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
tcccactttg gctgggttta aacca                                          25

<210> SEQ ID NO 249
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
caccggtcag ctcagggttt tggta                                      25

<210> SEQ ID NO 250
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
ttgtttggag ttagctcccc gacccag                                    27

<210> SEQ ID NO 251
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
aaactaggga cgggtagcca gctcc                                      25

<210> SEQ ID NO 252
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
aaactggttt aaacccagcc aaagt                                      25

<210> SEQ ID NO 253
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
aaactaccaa aaccctgagc tgacc                                      25

<210> SEQ ID NO 254
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
aaacctgggt cggggagcta actccaa                                    27

<210> SEQ ID NO 255
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 255
tgtgttcctg ggcctgctgc                                               20

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
taaacaggat tctgctcaga                                               20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
gccagatgac agaacagaaa                                               20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
aaaatgccat ttgtagggct                                               20

<210> SEQ ID NO 259
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
gcagcaggcc caggaacaca                                               20

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
tctgagcaga atcctgttta                                               20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
```
tttctgttct gtcatctggc                                          20

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
agccctacaa atggcatttt                                          20

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
tctgcttctg ccgaacctca                                          20

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
cctaaagagc ttgtaggccg                                          20

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
agagctggct acccgtccct                                          20

<210> SEQ ID NO 266
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
cggtccttgt ttatcagtag                                          20

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
tgaggttcgg cagaagcaga                                            20

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
cggcctacaa gctctttagg                                            20

<210> SEQ ID NO 269
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
agggacgggt agccagctct                                            20

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
ctactgataa acaaggaccg                                            20

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
gagctggcta cccgtcccta                                            20

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
ctttggctgg gtttaaacca                                            20

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
gtcagctcag ggttttggta                                            20

```
<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
gagttagctc cccgacccag                                                    20

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
tagggacggg tagccagctc                                                    20

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
tggtttaaac ccagccaaag                                                    20

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
taccaaaacc ctgagctgac                                                    20

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
ctgggtcggg gagctaactc                                                    20
```

COMPOSITIONS AND METHODS FOR EPIGENOME EDITING

CROSS REFERENCE TO RELATED APPLICATIONS

This patent application is a divisional of Ser. No. 16/865,151, filed May 1, 2020, which is a divisional of U.S. patent application Ser. No. 15/549,842, filed Aug. 9, 2017, which is the U.S. national stage entry, under 35 U.S.C. § 371, of International Application Number PCT/US2016/017221, filed Feb. 9, 2016, which claims priority to U.S. Provisional Application No. 62/113,569, filed Feb. 9, 2015, the entire contents of each of which are incorporated herein by reference.

STATEMENT OF GOVERNMENT INTEREST

This invention was made with Government support under Federal Grant No. 1R01DA036865 awarded by the National Institutes of Health. The Government has certain rights to this invention.

SEQUENCE LISTING

The instant application includes a Sequence Listing which has been submitted electronically in ASCII format is hereby incorporated by reference in its entirety. Said ASCII copy, created on Apr. 16, 2016, is named 028193-9190-WO00_SL_.txt and is 363,858 bytes in size.

TECHNICAL FIELD

The present disclosure is directed to CRISPR/Cas9-based gene activation systems and methods of using said systems.

BACKGROUND

The Human Genome Project was funded and pursued based on the premise that the sequencing of the human genome would reveal the genetic basis for complex diseases that have a strong inheritable component, including cardiovascular disease, neurodegenerative conditions, and metabolic diseases such as diabetes. It was believed that this information would lead to new drug targets for these widespread diseases. However, thousands of genome-wide association studies (GWAS) have shown that the genetic variation associated with these complex diseases does not occur within genes, but rather in intergenic regulatory regions that control the levels of particular genes. Similarly, approximately 20% of Mendelian disorders do not have a detectable coding mutation, suggesting that the causal mutation is in a gene regulatory element. Importantly, it is very difficult to assign functional roles to these regulatory elements as they often are located in distant locations from their target genes. Moreover, many genes and regulatory elements fall into each positive hit of each GWAS study. In fact, follow-up projects to the Human Genome Project, such as the NIH-funded Encyclopedia of DNA Elements (ENCODE) and the Roadmap Epigenomics Project, have identified millions of putative regulatory elements across the human genome for many human cell types and tissues.

A primary challenge of functional genomics is to develop technologies that directly and precisely manipulate genome function at individual loci. Projects such as ENCODE and the Roadmap Epigenomics Project have identified millions of epigenetic marks across the human genome for many human cell types and tissues. Studying the function of those marks, however, has been largely limited to statistical associations with gene expression. Technologies for targeted direct manipulation of these epigenetic properties are necessary to transform such association-based findings into mechanistic principles of gene regulation. Such advances have the potential to benefit human health, as they could lead to gene therapies that modify the epigenetic code at targeted regions of the genome, strategies for regenerative medicine and disease modeling based on the epigenetic reprogramming of cell lineage specification, and the engineering of epigenome-specific drug screening platforms.

Manipulation of the epigenome is possible by treating cells with small molecule drugs, such as inhibitors of histone deacetylases or DNA methyltransferases, or differentiating cells into specific lineages. However, small molecule-based methods globally alter the epigenome and transcriptome, and are not suitable for targeting individual loci. Epigenome editing technologies, including the fusion of epigenome-modifying enzymes to programmable DNA-binding proteins such as zinc finger proteins and transcription activator-like effectors (TALEs), have been effective at achieving targeted DNA methylation, DNA hydroxymethylation, and histone demethylation, methylation, and deacetylation.

Fused to activation domains, such as oligomers of the herpes simplex viral protein 16 (VP16), dCas9 can function as a synthetic transcriptional regulator. However, limitations in the use of dCas9 activators remain, including the need for multiple activation domains or combinations of gRNAs to achieve high levels of gene induction by synergistic effects between activation domains. The conventional activator domains used in these engineered transcriptional factors, such as the VP16 tetramer VP64, function as a scaffold for recruiting multiple components of the preinitiation complex and do not have direct enzymatic function to specifically modulate the chromatin state. This indirect method of epigenetic remodeling does not allow for testing the role of specific epigenetic marks and may not be as potent as the direct programming of epigenetic states. There remains a need for the ability to target direct manipulation of epigenetic properties.

SUMMARY

The present invention is directed to a fusion protein comprising two heterologous polypeptide domains, wherein the first polypeptide domain comprises a Clustered Regularly Interspaced Short Palindromic Repeats associated (Cas) protein and the second polypeptide domain The present invention is directed to a DNA targeting system comprising the fusion protein, described above, and at least one guide RNA (gRNA).

The present invention is directed to a method of activating gene expression of a target gene in a cell, the method comprising contacting the cell with a polynucleotide encoding a DNA targeting system, wherein the DNA targeting system comprises the fusion protein, described above, and at least one guide RNA (gRNA).

BRIEF DESCRIPTION OF THE DRAWINGS

FIGS. 1A-1C show that dCas9$^{p300\ Core}$ fusion protein activates transcription of endogenous genes from proximal promoter regions. FIG. 1A shows a schematic of dCas9 fusion proteins dCas9$^{VP64}$, dCas9$^{FL\ p300}$ and dCas9$^{p300\ Core}$ *Streptococcus pyogenes* dCas9 contains nuclease inactivating mutations D10A and H840A. The D1399 catalytic residue in the p300 HAT domain is indicated. FIG. 1B shows Western blot showing expression levels of dCas9 fusion proteins and GAPDH in co-transfected cells (full blot shown in FIG. 7C). FIG. 1C shows relative mRNA expression of IL1RN, MYOD, and OCT4, determined by qRT-PCR, by the indicated dCas9 fusion protein co-transfected with four gRNAs targeted to each promoter region (Tukey-test, *P-value<0.05, n=3 independent experiments each, error bars: s.e.m.). Numbers above bars indicate mean expression. FLAG, epitope tag; NLS, nuclear localization signal; HA, hemagglutinin epitope tag; CH, cysteine-histidine-rich region; Bd, bromodomain; HAT, histone acetyltransferase domain.

FIG. 2A shows relative MYOD mRNA production in cells co-transfected with a pool of gRNAs targeted to either the proximal or distal regulatory regions and dCas9$^{VP64}$ or dCas9$^{p300\ Core}$; promoter data from FIG. 1C (Tukey-test, *P-value<0.05 compared to mock-transfected cells, Tukey test †P-value<0.05 between dCas9$^{p300\ Core}$ and dCas9$^{VP64}$, n=3 independent experiments, error bars: s.e.m.). The human MYOD locus is schematically depicted with corresponding gRNA locations in red. CE, MyoD core enhancer; DRR, MyoD distal regulatory region. FIG. 2B shows relative OCT4 mRNA production in cells co-transfected with a pool of gRNAs targeted to the proximal and distal regulatory regions and dCas9$^{VP64}$ or dCas9$^{p300\ Core}$; promoter data from FIG. 1C (Tukey-test, *P-value<0.05 compared to mock-transfected cells, Tukey test †P-value<0.05 between dCas9$^{p300\ Core}$ and dCas9$^{VP64}$, n=3 independent experiments, error bars: s.e.m.). The human OCT4 locus is schematically depicted with corresponding gRNA locations in red. DE, Oct4 distal enhancer; PE, Oct4 proximal enhancer. FIG. 2C shows the human β-globin locus is schematically depicted with approximate locations of the hypersensitive site 2 (HS2) enhancer region and downstream genes (HBE, HBG, HBD, and HBB). Corresponding HS2 gRNA locations are shown in red. Relative mRNA production from distal genes in cells co-transfected with four gRNAs targeted to the HS2 enhancer and the indicated dCas9 proteins. Note logarithmic y-axis and dashed red line indicating background expression (Tukey test among conditions for each β-globin gene, †P-value<0.05, n=3 independent experiments, error bars: s.e.m.). n.s., not significant.

FIGS. 3A-3C show MA plots generated from DEseq2 analysis of genome-wide RNA-seq data from HEK293T cells transiently co-transfected with dCas9$^{VP64}$ (FIG. 3A) dCas9$^{p300\ Core}$ (FIG. 3B) or dCas9$^{p300\ Core\ (D1399Y)}$ (FIG. 3C) and four IL1RN promoter-targeting gRNAs compared to HEK293T cells transiently co-transfected with dCas9 and four IL1RN promoter-targeting gRNAs. mRNAs corresponding to IL1RN isoforms are shown in blue and circled in each of FIGS. 3A-3C. Red labeled points in FIGS. 3B and 3C correspond to off-target transcripts significantly enriched after multiple hypothesis testing (KDR, (FDR=1.4×10$^{-3}$); FAM49A, (FDR=0.04); p300, (FDR=1.7×10$^{-4}$) in FIG. 3B; and p300, (FDR=4.4×10$^{-10}$) in FIG. 3C.

FIG. 4A shows the region encompassing the human β-globin locus on chromosome 11 (5,304,000-5,268,000; GRCh37/hg19 assembly) is shown. HS2 gRNA target locations are indicated in red and ChIP-qPCR amplicon regions are depicted in black with corresponding green numbers. ENCODE/Broad Institute H3K27ac enrichment signal in K562 cells is shown for comparison. Magnified insets for the HS2 enhancer, HBE, and HBG1/2 promoter regions are displayed below. FIGS. 4B-4D show H3K27ac ChIP-qPCR enrichment (relative to dCas9; red dotted line) at the HS2 enhancer, HBE promoter, and HBG1/2 promoters in cells co-transfected with four gRNAs targeted to the HS2 enhancer and the indicated dCas9 fusion protein. HBG ChIP amplicons 1 and 2 amplify redundant sequences at the HBG1 and HBG2 promoters (denoted by ‡). Tukey test among conditions for each ChIP-qPCR region, *P-value<0.05 (n=3 independent experiments, error bars: s.e.m.).

FIGS. 5A-5G show that dCas9$^{p300\ Core}$ fusion protein activates transcription of endogenous genes from regulatory regions with a single gRNA. Relative IL1RN (FIG. 5A), MYOD (FIG. 5B) or OCT4 (FIG. 5C) mRNA produced from cells co-transfected with dCas9$^{p300\ Core}$ or dCas9$^{VP64}$ and gRNAs targeting respective promoters (n=3 independent experiments, error bars: s.e.m.). Relative MYOD (FIG. 5D) or OCT4 (FIG. 5E) mRNA produced from cells co-transfected with dCas9$^{p300\ Core}$ and indicated gRNAs targeting the indicated MYOD or OCT4 enhancers (n=3 independent experiments, error bars: s.e.m.). DRR, MYOD distal regulatory region; CE, MYOD core enhancer; PE, OCT4 proximal enhancer; DE, OCT4 distal enhancer. (Tukey test between dCas9$^{p300\ Core}$ and single OCT4 DE gRNAs compared to mock-transfected cells, *P-value<0.05, Tukey test among dCas9$^{p300\ Core}$ and OCT4 DE gRNAs compared to All, †P-value<0.05). Relative HBE (FIG. 5F) or HBG (FIG. 5G) mRNA production in cells co-transfected with dCas9$^{p300\ Core}$ and the indicated gRNAs targeted to the HS2 enhancer (Tukey test between dCas9$^{p300\ Core}$ and single HS2 gRNAs compared to mock-transfected cells, *P-value<0.05, Tukey test among dCas9$^{p300\ Core}$ and HS2 single gRNAs compared to All, †P<0.05, n=3 independent experiments, error bars: s.e.m.). HS2, β-globin locus control region hypersensitive site 2; n.s., not significant using Tukey test.

FIGS. 6A-6H show that the p300 Core can be targeted to genomic loci by diverse programmable DNA-binding proteins. FIG. 6A shows schematic of the *Neisseria meningitidis* (Nm) dCas9 fusion proteins Nm-dCas9$^{VP64}$ and Nm-dCas9$^{p300\ Core}$ *Neisseria meningitidis* dCas9 contains nuclease-inactivating mutations D16A, D587A, H588A, and N611A. FIG. 6B shows relative HBE mRNA in cells co-transfected with five individual or pooled (A-E) Nm gRNAs targeted to the HBE promoter and Nm-dCas9$^{VP64}$ or Nm-dCas9$^{p300\ Core}$ FIGS. 6C-6D Relative HBE (FIG. 6C) or HBG (FIG. 6D) mRNA in cells co-transfected with five individual or pooled (A-E) Nm gRNAs targeted to the HS2 enhancer and Nm-dCas9$^{VP64}$ or Nm-dCas9$^{p300\ Core}$ FIG. 6E shows schematic of TALEs with domains containing IL1RN-targeted repeat variable diresidues (Repeat Domain). FIG. 6F shows relative IL1RN mRNA in cells transfected with individual or pooled (A-D) IL1RN TALE$^{VP64}$ or IL1RN TALE$^{p300\ Core}$ encoding plasmids. FIG. 6G shows schematic of ZF fusion proteins with zinc finger helices 1-6 (F1-F6) targeting the ICAM1 promoter. FIG. 6H shows relative ICAM1 mRNA in cells transfected with ICAM1 ZF$^{VP64}$ or ICAM1 ZF$^{p300\ Core}$ Tukey-test, *P-value<0.05 compared to mock-transfected control, n=3 independent experiments each, error bars: s.e.m. NLS, nuclear localization signal; HA, hemagglutinin tag; Bd, bromodomain; CH, cysteine-histidine-rich region; HAT, histone acetyltransferase domain.

FIGS. 7A-7C show dCas9$^{p300\ Core}$ mutant fusion protein activities. FIG. 7A shows schematic depiction of the WT dCas9$^{p300\ Core}$ fusion protein and p300 Core mutant derivatives. Relative locations of mutated amino acids are displayed as yellow bars within the p300 Core effector domain. FIG. 7B shows dCas9$^{p300\ Core}$ variants were transiently co-transfected with four IL1RN promoter gRNAs and were screened for hyperactivity[1] (amino acid 1645/1646 RR/EE and C1204R mutations) or hypoactivity (denoted by ‡) via mRNA production from the IL1RN locus (top panel, n=2 independent experiments, error bars: s.e.m.). Experiments were performed in duplicate with one well used for RNA isolation and the other for western blotting to validate expression (bottom panels). The nitrocellulose membrane was cut and incubated with α-FLAG primary antibody (top, Sigma-Aldrich cat. #F7425) or α-GAPDH (bottom, Cell Signaling Technology cat. #14C10) then α-Rabbit HRP secondary antibody (Sigma-Aldrich cat. #A6154). FIG. 7C shows full membranes from western blot shown in main text (FIG. 1). The nitrocellulose membrane was cut and incubated with α-FLAG primary antibody (top, Sigma-Aldrich cat. #F7425) or α-GAPDH (bottom, Cell Signaling Technology cat. #14C10) then α-Rabbit HRP secondary antibody (Sigma-Aldrich cat. #A6154). Membrane was imaged for the indicated durations after careful re-alignment of trimmed pieces.

FIG. 9A shows schematic display of the human β-globin locus including *Streptococcus pyogenes* dCas9 (Sp. dCas9) and *Neisseria meningitidis* dCas9 (Nm. dCas9) gRNA locations at the HS2 enhancer. Layered transcription profiles scaled to a vertical viewing range of 8 from nine ENCODE cell lines (GM12878, H1-hESC, HeLa-S3, HepG2, HSMM, HUVEC, K562, NHEK, and NHLF) is shown in addition to ENCODE p300 binding peaks in K562, A549 (EtOH 0.02), HeLa-S3, and SKN_SH_RA cell lines. An ENCODE HEK293T DNase hypersensitive site (HEK293T DHS) is shown in the HS2 Enhancer inset. FIGS. 9B-9E shows relative transcriptional induction of HBE, HBG, HBD, and HBB transcripts from single and pooled Sp. dCas9 gRNAs (A-D) or single and pooled Nm. dCas9 gRNAs (A-E) in response to co-transfection with Sp. dCas9$^{p300\ Core}$ or Nm. dCas9$^{p300\ Core}$ respectively. gRNAs are tiled for each dCas9 ortholog corresponding to their location in GRCh37/hg19. Gray dashed line indicates background expression level in transiently co-transfected HEK293T cells. Note shared logarithmic scale among FIGS. 9B-9E. Numbers above bars in FIGS. 9B-9E indicate mean expression (n=at least 3 independent experiments, error bars. s.e.m.).

FIG. 11A shows the GRCh37/hg19 region encompassing the IL1RN transcription start site is shown schematically along with IL1RN TALE binding sites and dCas9 IL1RN gRNA target sites. FIG. 11B shows direct comparison of IL1RN activation in HEK293T cells when transfected with individual or pooled (A-D) IL1RN TALE$^{VP64}$ fusion proteins or when co-transfected with dCas9$^{VP64}$ and individual or pooled (A-D) IL1RN-targeting gRNAs. FIG. 11C shows direct comparison of IL1RN activation in HEK293T cells when transfected with individual or pooled (A-D) IL1RN TALE$^{p300\ Core}$ fusion proteins or when co-transfected with dCas9$^{p300\ Core}$ and individual or pooled (A-D) IL1RN-targeting gRNAs. Note shared logarithmic scale between FIG. 11B and FIG. 11C. Numbers above bars in FIGS. 11B and 11C indicate mean values. Tukey test, *P-value<0.05, n=at least 3 independent experiments, error bars: s.e.m.

FIG. 12A shows Western blotting was carried out on cells transiently transfected with individual or pooled IL1RN TALE proteins. Nitrocellulose membranes were cut and probed with α-HA primary antibody (1:1000 dilution in TBST+5% Milk, top, Covance cat. #MMS-101P) or α-GAPDH (bottom, Cell Signaling Technology cat. #14C10) then α-Mouse HRP (Santa Cruz, sc-2005) or α-Rabbit HRP (Sigma-Aldrich cat. #A6154) secondary antibody, respectively. FIG. 12B shows Western blotting was carried out on cells transiently transfected with ICAM1 ZF-effector proteins and nitrocellulose membranes were cut and probed with α-FLAG primary antibody (top, Sigma-Aldrich cat. #F7425) or α-GAPDH (bottom, Cell Signaling Technology cat. #14C10) then α-Rabbit HRP secondary antibody (Sigma-Aldrich cat. #A6154). Red asterisk indicates non-specific band.

FIG. 13A shows dCas9$^{p300\ Core}$ was co-transfected at a 1:1 mass ratio to PL-SIN-EF1α-EGFP[3] (GFP), dCas9, or dCas9$^{VP64}$ with four IL1RN promoter gRNAs as indicated (n=2 independent experiments, error bars: s.e.m.). FIG. 13B shows dCas9$^{p300\ Core}$ was co-transfected at a 1:1 mass ratio to GFP, dCas9, or dCas9$^{VP64}$ with four MYOD promoter gRNAs as indicated (n=2 independent experiments, error bars: s.e.m.). No significant differences were observed using Tukey's test (n.s.).

FIGS. 14A-14D show the underlying chromatin context of dCas9$^{p300\ Core}$ target loci. FIGS. 14A-14D show indicated loci along with associated *Streptococcus pyogenes* gRNAs used in this study at corresponding genomic locations in GRCh37/hg19. ENCODE HEK293T DNase hypersensitivity enrichment is shown (note changes in scale) along with regions of significant DNase hypersensitivity in HEK293T cells ("DHS"). In addition ENCODE master DNase clusters across 125 cell types are shown. Layered ENCODE H3K27ac and H3K4me3 enrichment across seven cell lines (GM12878, H1-hESC, HSMM, HUVEC, K562, NHEK, and NHLF) is also displayed and scaled to a vertical viewing range of 50 and 150 respectively. Endogenous p300 binding profiles are also indicated for each locus and respective cell line.

FIG. 14E shows an overview of the information provided in FIGS. 14A-14D.

Figure 15B:
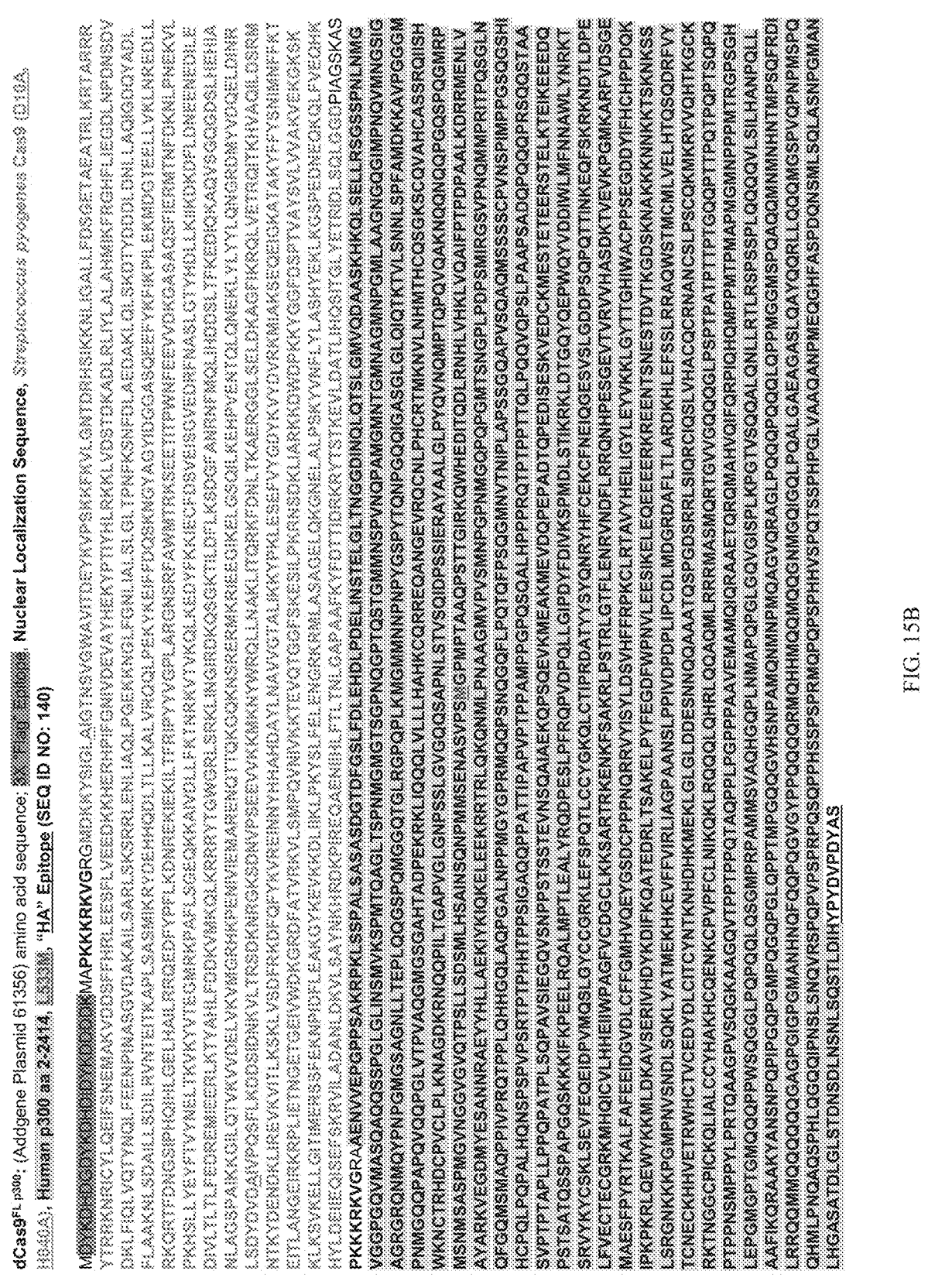

FIGS. 15A-15J show the amino acid sequences of dCas9 constructs.

FIG. 16 shows the amino acid sequences of ICAM1 Zinc Finger[10] effectors.

DETAILED DESCRIPTION

Figures 2A, 2B, 2C:
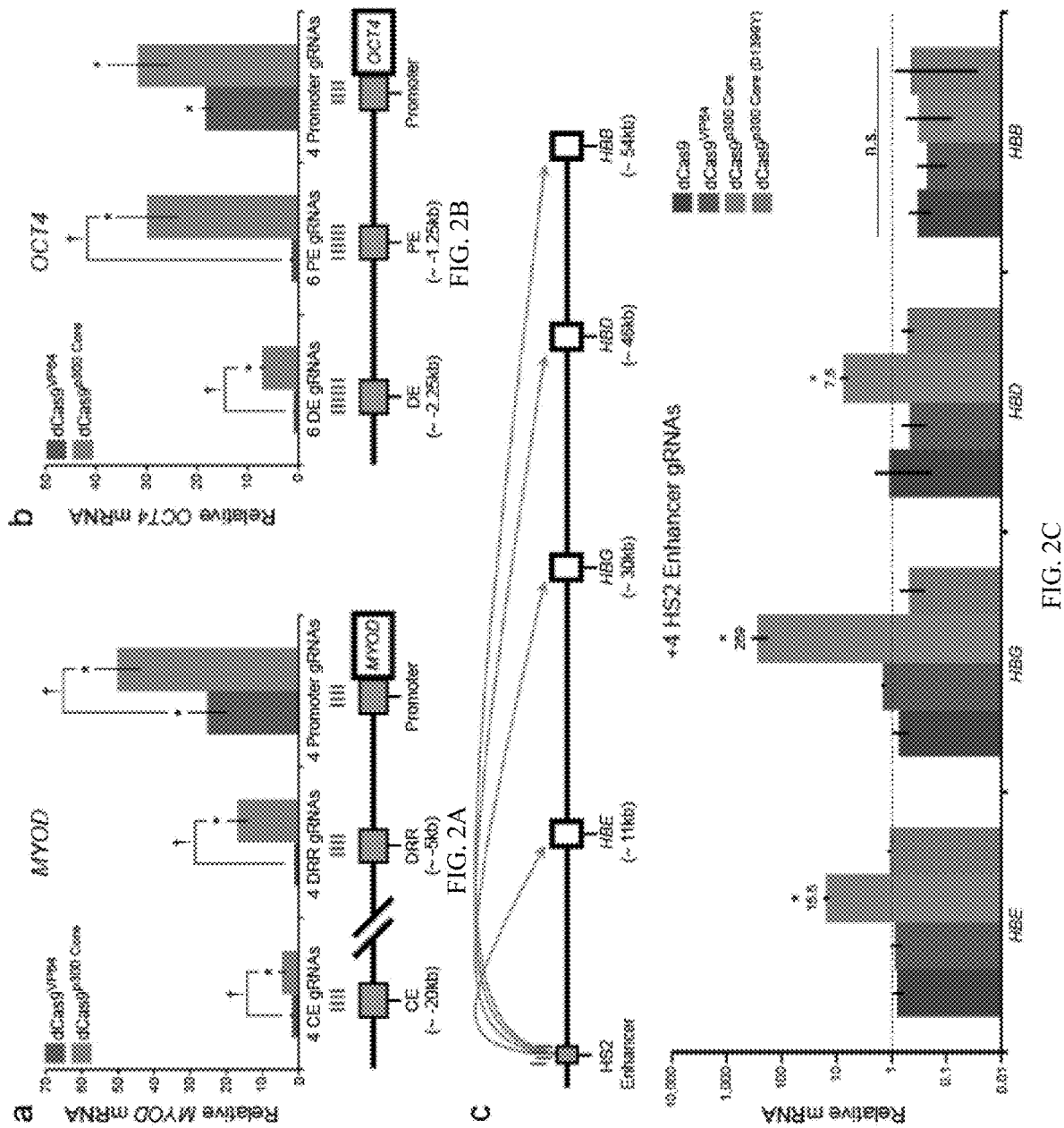
FIGS. 2A-2C show that dCas9$^{p300\ Core}$ fusion protein activates transcription of endogenous genes from distal enhancer regions.

Disclosed herein are CRISPR/Cas9-based gene activation systems and methods of using said systems. The systems provide an easily programmable approach to facilitate robust control of the epigenome and downstream gene expression. The CRISPR/Cas9-based gene activation system includes a CRISPR/Cas9-based acetyltransferase, which is a fusion protein of a Cas9 protein and a protein having histone acetyltransferase activity, such as the catalytic histone acetyltransferase (HAT) core domain of the human E1A-associated protein p300. The Cas9 protein may not have nuclease activity. An example of a Cas9 protein where the nuclease activity has been abolished is dCas9. Recruitment of the acetyltransferase function by dCas9 and a gRNA to the genomic target site allow direct modulation of epigenetic structure, and thus provide an effective means of gene activation.

The disclosed CRISPR/Cas9-based acetyltransferase catalyzes acetylation of histone H3 lysine 27 at its target sites, leading to robust transcriptional activation of target genes from promoters and both proximal and distal enhancers. As disclosed herein, gene activation by these targeted acetyltransferases is highly specific across the genome. The CRISPR/Cas9-based acetyltransferase, which can be targeted to any site in the genome, is uniquely capable of activating distal regulatory elements. In contrast to conventional dCas9-based activators, the CRISPR/Cas9-based acetyltransferase effectively activates genes from enhancer regions and with individual or single guide RNAs.

1. DEFINITIONS

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

"Adeno-associated virus" or "AAV" as used interchangeably herein refers to a small virus belonging to the genus Dependovirus of the Parvoviridae family that infects humans and some other primate species. AAV is not currently known to cause disease and consequently the virus causes a very mild immune response.

"Chromatin" as used herein refers to an organized complex of chromosomal DNA associated with histones.

"Cis-regulatory elements" or "CREs" as used interchangeably herein refers to regions of non-coding DNA which regulate the transcription of nearby genes. CREs are found in the vicinity of the gene, or genes, they regulate. CREs typically regulate gene transcription by functioning as binding sites for transcription factors. Examples of CREs include promoters and enhancers.

"Clustered Regularly Interspaced Short Palindromic Repeats" and "CRISPRs", as used interchangeably herein refers to loci containing multiple short direct repeats that are found in the genomes of approximately 40% of sequenced bacteria and 90% of sequenced archaea.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimize.

"Complement" or "complementary" as used herein means a nucleic acid can mean Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

"Endogenous gene" as used herein refers to a gene that originates from within an organism, tissue, or cell. An endogenous gene is native to a cell, which is in its normal genomic and chromatin context, and which is not heterologous to the cell. Such cellular genes include, e.g., animal genes, plant genes, bacterial genes, protozoal genes, fungal genes, mitochondrial genes, and chloroplastic genes.

"Enhancer" as used herein refers to non-coding DNA sequences containing multiple activator and repressor binding sites. Enhancers range from 200 bp to 1 kb in length and may be either proximal, 5' upstream to the promoter or within the first intron of the regulated gene, or distal, in introns of neighboring genes or intergenic regions far away from the locus. Through DNA looping, active enhancers contact the promoter dependently of the core DNA binding motif promoter specificity. 4 to 5 enhancers may interact with a promoter. Similarly, enhancers may regulate more than one gene without linkage restriction and may "skip" neighboring genes to regulate more distant ones. Transcriptional regulation may involve elements located in a chromosome different to one where the promoter resides. Proximal enhancers or promoters of neighboring genes may serve as platforms to recruit more distal elements.

"Fusion protein" as used herein refers to a chimeric protein created through the joining of two or more genes that originally coded for separate proteins. The translation of the fusion gene results in a single polypeptide with functional properties derived from each of the original proteins.

"Genetic construct" as used herein refers to the DNA or RNA molecules that comprise a nucleotide sequence that encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Histone acetyltransferases" or "HATs" are used interchangeably herein refers to enzymes that acetylate conserved lysine amino acids on histone proteins by transferring an acetyl group from acetyl CoA to form ε-N-acetyllysine. DNA is wrapped around histones, and, by transferring an acetyl group to the histones, genes can be turned on and off. In general, histone acetylation increases gene expression as it is linked to transcriptional activation and associated with euchromatin. Histone acetyltransferases can also acetylate non-histone proteins, such as nuclear receptors and other transcription factors to facilitate gene expression.

"Identical" or "identity" as used herein in the context of two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

"p300 protein," "EP300," or "E1A binding protein p300" as used interchangeably herein refers to the adenovirus E1A-associated cellular p300 transcriptional co-activator protein encoded by the EP300 gene. p300 is a highly conserved acetyltransferase involved in a wide range of cellular processes. p300 functions as a histone acetyltransferase that regulates transcription via chromatin remodeling and is involved with the processes of cell proliferation and differentiation.

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Target enhancer" as used herein refers to enhancer that is targeted by a gRNA and CRISPR/Cas9-based gene activation system. The target enhancer may be within the target region.

"Target gene" as used herein refers to any nucleotide sequence encoding a known or putative gene product. The target gene includes the regulatory regions, such as the promoter and enhancer regions, the transcribed regions, which include the coding regions, and other function sequence regions.

"Target region" as used herein refers to a cis-regulatory region or a trans-regulatory region of a target gene to which the guide RNA is designed to recruit the CRISPR/Cas9-based gene activation system to modulate the epigenetic structure and allow the activation of gene expression of the target gene.

"Target regulatory element" as used herein refers to a regulatory element that is targeted by a gRNA and CRISPR/Cas9-based gene activation system. The target regulatory element may be within the target region.

"Transcribed region" as used herein refers to the region of DNA that is transcribed into single-stranded RNA molecule, known as messenger RNA, resulting in the transfer of genetic information from the DNA molecule to the messenger RNA. During transcription, RNA polymerase reads the template strand in the 3' to 5' direction and synthesizes the RNA from 5' to 3'. The mRNA sequence is complementary to the DNA strand.

"Transcriptional Start Site" or "TSS" as used interchangeably herein refers to the first nucleotide of a transcribed DNA sequence where RNA polymerase begins synthesizing the RNA transcript.

"Transgene" as used herein refers to a gene or genetic material containing a gene sequence that has been isolated from one organism and is introduced into a different organism. This non-native segment of DNA may retain the ability to produce RNA or protein in the transgenic organism, or it may alter the normal function of the transgenic organism's genetic code. The introduction of a transgene has the potential to change the phenotype of an organism.

"Trans-regulatory elements" as used herein refers to regions of non-coding DNA which regulate the transcription of genes distant from the gene from which they were transcribed. Trans-regulatory elements may be on the same or different chromosome from the target gene.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes may be substituted and still retain protein function. In one aspect, amino acids having hydropathic indexes of 2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" as used herein means a nucleic acid sequence containing an origin of replication. A vector may be a viral vector, bacteriophage, bacterial artificial chromosome or yeast artificial chromosome. A vector may be a DNA or RNA vector. A vector may be a self-replicating extrachromosomal vector, and preferably, is a DNA plasmid. For example, the vector may encode a CRISPR/Cas9-based acetyltransferase having an amino acid sequence of SEQ ID NO: 140, 141, or 149 and/or at least one gRNA nucleotide sequence of any one of SEQ ID NOs: 23-73, 188-223, or 224-254.

2. CRISPR/CAS9-BASED GENE ACTIVATION SYSTEM

Provided herein are CRISPR/Cas9-based gene activation systems for use in activating gene expression of a target gene. The CRISPR/Cas9-based gene activation system includes a fusion protein of a Cas9 protein that does not have nuclease activity, such as dCas9, and a histone acetyltransferase or histone acetyltransferase effector domain. Histone acetylation, carried out by histone acetyltransferases (HATs), plays a fundamental role in regulating chromatin dynamics and transcriptional regulation. The histone acetyltransferase protein releases DNA from its heterochromatin state and allows for continued and robust gene expression by the endogenous cellular machinery. The recruitment of an acetyltransferase by dCas9 to a genomic target site may directly modulate epigenetic structure.

The CRISPR/Cas9-based gene activation system may catalyze acetylation of histone H3 lysine 27 at its target sites, leading to robust transcriptional activation of target genes from promoters and proximal and distal enhancers. The CRISPR/Cas9-based gene activation system is highly specific and may be guided to the target gene using as few as one guide RNA. The CRISPR/Cas9-based gene activation system may activate the expression of one gene or a family of genes by targeting enhancers at distant locations in the genome.

a) CRISPR System

The CRISPR system is a microbial nuclease system involved in defense against invading phages and plasmids that provides a form of acquired immunity. The CRISPR loci in microbial hosts contain a combination of CRISPR-associated (Cas) genes as well as non-coding RNA elements capable of programming the specificity of the CRISPR-mediated nucleic acid cleavage. Short segments of foreign DNA, called spacers, are incorporated into the genome between CRISPR repeats, and serve as a 'memory' of past exposures. Cas9 forms a complex with the 3' end of the single guide RNA ("sgRNA"), and the protein-RNA pair recognizes its genomic target by complementary base pairing between the 5' end of the sgRNA sequence and a predefined 20 bp DNA sequence, known as the protospacer. This complex is directed to homologous loci of pathogen DNA via regions encoded within the CRISPR RNA ("crRNA"), i.e., the protospacers, and protospacer-adjacent motifs (PAMs) within the pathogen genome. The non-coding CRISPR array is transcribed and cleaved within direct repeats into short crRNAs containing individual spacer sequences, which direct Cas nucleases to the target site (protospacer). By simply exchanging the 20 bp recognition sequence of the expressed chimeric sgRNA, the Cas9 nuclease can be directed to new genomic targets. CRISPR spacers are used to recognize and silence exogenous genetic elements in a manner analogous to RNAi in eukaryotic organisms.

Three classes of CRISPR systems (Types I, II and III effector systems) are known. The Type II effector system carries out targeted DNA double-strand break in four sequential steps, using a single effector enzyme, Cas9, to cleave dsDNA. Compared to the Type I and Type III effector systems, which require multiple distinct effectors acting as a complex, the Type II effector system may function in alternative contexts such as eukaryotic cells. The Type II effector system consists of a long pre-crRNA, which is transcribed from the spacer-containing CRISPR locus, the Cas9 protein, and a tracrRNA, which is involved in pre-crRNA processing. The tracrRNAs hybridize to the repeat regions separating the spacers of the pre-crRNA, thus initiating dsRNA cleavage by endogenous RNase III. This cleavage is followed by a second cleavage event within each spacer by Cas9, producing mature crRNAs that remain associated with the tracrRNA and Cas9, forming a Cas9: crRNA-tracrRNA complex.

An engineered form of the Type II effector system of Streptococcus pyogenes was shown to function in human cells for genome engineering. In this system, the Cas9 protein was directed to genomic target sites by a synthetically reconstituted "guide RNA" ("gRNA", also used interchangeably herein as a chimeric sgRNA, which is a crRNA-tracrRNA fusion that obviates the need for RNase III and crRNA processing in general.

The Cas9:crRNA-tracrRNA complex unwinds the DNA duplex and searches for sequences matching the crRNA to cleave. Target recognition occurs upon detection of complementarity between a "protospacer" sequence in the target DNA and the remaining spacer sequence in the crRNA. Cas9 mediates cleavage of target DNA if a correct protospacer-adjacent motif (PAM) is also present at the 3' end of the protospacer. For protospacer targeting, the sequence must be immediately followed by the protospacer-adjacent motif (PAM), a short sequence recognized by the Cas9 nuclease that is required for DNA cleavage. Different Type II systems have differing PAM requirements. The S. pyogenes CRISPR system may have the PAM sequence for this Cas9 (SpCas9) as 5'-NRG-3', where R is either A or G, and characterized the specificity of this system in human cells. A unique capability of the CRISPR/Cas9 system is the straightforward ability to simultaneously target multiple distinct genomic loci by co-expressing a single Cas9 protein with two or more sgRNAs. For example, the Streptococcus pyogenes Type II system naturally prefers to use an "NGG" sequence, where "N" can be any nucleotide, but also accepts other PAM sequences, such as "NAG" in engineered systems (Hsu et al., Nature Biotechnology (2013) doi:10.1038/nbt.2647). Similarly, the Cas9 derived from Neisseria meningitidis (NmCas9) normally has a native PAM of NNNNGATT, but has activity across a variety of PAMs, including a highly degenerate NNNNGNNN PAM (Esvelt et al. Nature Methods (2013) doi:10.1038/nmeth.2681).

b) Cas9

The CRISPR/Cas9-based gene activation system may include a Cas9 protein or a Cas9 fusion protein. Cas9 protein is an endonuclease that cleaves nucleic acid and is encoded by the CRISPR loci and is involved in the Type II CRISPR system. The Cas9 protein may be from any bacterial or archaea species, such as Streptococcus pyogenes, Streptococcus thermophiles, or Neisseria meningitides. The Cas9 protein may be mutated so that the nuclease activity is inactivated. In some embodiments, an inactivated Cas9 protein from Streptococcus pyogenes (iCas9, also referred to as "dCas9"; SEQ ID NO: 1) may be used. As used herein, "iCas9" and "dCas9" both refer to a Cas9 protein that has the amino acid substitutions D10A and H840A and has its nuclease activity inactivated. In some embodiments, an inactivated Cas9 protein from Neisseria meningitides, such as NmCas9 having an amino acid sequence of SEQ ID NO: 10, may be used.

c) Histone Acetyltransferase (HAT) Protein

The CRISPR/Cas9-based gene activation system may include a histone acetyltransferase protein, such as a p300 protein, CREB binding protein (CBP; an analog of p300), GCN5, or PCAF, or fragment thereof. The p300 protein regulates the activity of many genes in tissues throughout the body. The p300 protein plays a role in regulating cell growth and division, prompting cells to mature and assume specialized functions (differentiate) and preventing the growth of cancerous tumors. The p300 protein may activate transcription by connecting transcription factors with a complex of proteins that carry out transcription in the cell's nucleus. The p300 protein also functions as a histone acetyltransferase that regulates transcription via chromatin remodeling.

The histone acetyltransferase protein may include a human p300 protein or a fragment thereof. The histone acetyltransferase protein may include a wild-type human p300 protein or a mutant human p300 protein, or fragments thereof. The histone acetyltransferase protein may include the core lysine-acetyltransferase domain of the human p300 protein, i.e., the p300 HAT Core (also known as "p300 Core"). In some embodiments, the histone acetyltransferase protein includes an amino acid sequence of SEQ ID NO: 2 or 3.

i) dCas9$^{p300\ Core}$

The CRISPR/Cas9-based gene activation system may include a histone acetylation effector domain. The histone acetylation effector domain may be the catalytic histone acetyltransferase (HAT) core domain of the human E1A-associated protein p300 (also referred to herein as "p300 Core"). In some embodiments, the p300 Core includes amino acids 1048-1664 of SEQ ID NO: 2 (i.e., SEQ ID NO: 3). In some embodiments, the CRISPR/Cas9-based gene activation system includes a dCas9$^{p300\ Core}$ fusion protein of SEQ ID NO: 141 or an Nm-dCas9$^{p300\ Core}$ fusion protein of SEQ ID NO: 149. The p300 Core acetylates lysine 27 on histone H3 (H3K27ac) and may provide H3K27ac enrichment.

The dCas9$^{p300\ Core}$ fusion protein is a potent and easily programmable tool to synthetically manipulate acetylation at targeted endogenous loci, leading to regulation of proximal and distal enhancer-regulated genes. The fusion of the catalytic core domain of p300 to dCas9 may result in substantially higher transactivation of downstream genes than the direct fusion of full-length p300 protein despite robust protein expression. The dCas9$^{p300\ Core}$ fusion protein may also exhibit an increased transactivation capacity relative to dCas9$^{VP64}$, including in the context of the Nm-dCas9 scaffold, especially at distal enhancer regions, at which dCas9$^{VP64}$ displayed little, if any, measurable downstream transcriptional activity. Additionally, the dCas9$^{p300\ Core}$ displays precise and robust genome-wide transcriptional specificity. dCas9$^{p300\ Core}$ may be capable of potent transcriptional activation and co-enrichment of acetylation at promoters targeted by the epigenetically modified enhancer.

The dCas9$^{p300\ Core}$ may activate gene expression through a single gRNA that target and bind a promoters and/or a characterized enhancer. This technology also affords the ability to synthetically transactivate distal genes from putative and known regulatory regions and simplifies transactivation via the application of a single programmable effector and single target site. These capabilities allow multiplexing to target several promoters and/or enhancers simultaneously. The mammalian origin of p300 may provide advantages over virally-derived effector domains for in vivo applications by minimizing potential immunogenicity.

d) gRNA

The CRISPR/Cas9-based gene activation system may include at least one gRNA that targets a nucleic acid sequence. The gRNA provides the targeting of the CRISPR/Cas9-based gene activation system. The gRNA is a fusion of two noncoding RNAs: a crRNA and a tracrRNA. The sgRNA may target any desired DNA sequence by exchanging the sequence encoding a 20 bp protospacer which confers targeting specificity through complementary base pairing with the desired DNA target. gRNA mimics the naturally occurring crRNA:tracrRNA duplex involved in the Type II Effector system. This duplex, which may include, for example, a 42-nucleotide crRNA and a 75-nucleotide tracrRNA, acts as a guide for the Cas9.

The gRNA may target and bind a target region of a target gene. The target region may be a cis-regulatory region or trans-regulatory region of a target gene. In some embodiments, the target region is a distal or proximal cis-regulatory region of the target gene. The gRNA may target and bind a cis-regulatory region or trans-regulatory region of a target gene. In some embodiments, the gRNA may target and bind an enhancer region, a promoter region, or a transcribed region of a target gene. For example, the gRNA may target and bind the target region is at least one of HS2 enhancer of the human β-globin locus, distal regulatory region (DRR) of the MYOD gene, core enhancer (CE) of the MYOD gene, proximal (PE) enhancer region of the OCT4 gene, or distal (DE) enhancer region of the OCT4 gene. In some embodiments, the target region may be a viral promoter, such as an HIV promoter.

The target region may include a target enhancer or a target regulatory element. In some embodiments, the target enhancer or target regulatory element controls the gene expression of several target genes. In some embodiments, the target enhancer or target regulatory element controls a cell phenotype that involves the gene expression of one or more target genes. In some embodiments, the identity of one or more of the target genes is known. In some embodiments, the identity of one or more of the target genes is unknown. The CRISPR/Cas9-based gene activation system allows the determination of the identity of these unknown genes that are involved in a cell phenotype. Examples of cell phenotypes include, but not limited to, T-cell phenotype, cell differentiation, such as hematopoietic cell differentiation, oncogenesis, immunomodulation, cell response to stimuli, cell death, cell growth, drug resistance, or drug sensitivity.

In some embodiments, at least one gRNA may target and bind a target enhancer or target regulatory element, whereby the expression of one or more genes is activated. For example, between 1 gene and 20 genes, between 1 gene and 15 genes, between 1 gene and 10 genes, between 1 gene and 5 genes, between 2 genes and 20 genes, between 2 genes and 15 genes, between 2 genes and 10 genes, between 2 genes and 5 genes, between 5 genes and 20 genes, between 5 genes and 15 genes, or between 5 genes and 10 genes are activated by at least one gRNA. In some embodiments, at least 1 gene, at least 2 genes, at least 3 genes, at least 4 genes, at least 5 gene, at least 6 genes, at least 7 genes, at least 8 genes, at least 9 gene, at least 10 genes, at least 11 genes, at least 12 genes, at least 13 gene, at least 14 genes, at least 15 genes, or at least 20 genes are activated by at least one gRNA.

The CRISPR/Cas9-based gene activation system may activate genes at both proximal and distal locations relative the transcriptional start site (TSS). The CRISPR/Cas9-based gene activation system may target a region that is at least about 1 base pair to about 100,000 base pairs, at least about 100 base pairs to about 100,000 base pairs, at least about 250 base pairs to about 100,000 base pairs, at least about 500 base pairs to about 100,000 base pairs, at least about 1,000 base pairs to about 100,000 base pairs, at least about 2,000 base pairs to about 100,000 base pairs, at least about 5,000 base pairs to about 100,000 base pairs, at least about 10,000 base pairs to about 100,000 base pairs, at least about 20,000 base pairs to about 100,000 base pairs, at least about 50,000 base pairs to about 100,000 base pairs, at least about 75,000 base pairs to about 100,000 base pairs, at least about 1 base pair to about 75,000 base pairs, at least about 100 base pairs to about 75,000 base pairs, at least about 250 base pairs to about 75,000 base pairs, at least about 500 base pairs to about 75,000 base pairs, at least about 1,000 base pairs to about 75,000 base pairs, at least about 2,000 base pairs to about 75,000 base pairs, at least about 5,000 base pairs to about 75,000 base pairs, at least about 10,000 base pairs to about 75,000 base pairs, at least about 20,000 base pairs to about 75,000 base pairs, at least about 50,000 base pairs to about 75,000 base pairs, at least about 1 base pair to about 50,000 base pairs, at least about 100 base pairs to about 50,000 base pairs, at least about 250 base pairs to about 50,000 base pairs, at least about 500 base pairs to about 50,000 base pairs, at least about 1,000 base pairs to about 50,000 base pairs, at least about 2,000 base pairs to about 50,000 base pairs, at least about 5,000 base pairs to about 50,000 base pairs, at least about 10,000 base pairs to about 50,000 base pairs, at least about 20,000 base pairs to about 50,000 base pairs, at least about 1 base pair to about 25,000 base pairs, at least about 100 base pairs to about 25,000 base pairs, at least about 250 base pairs to about 25,000 base pairs, at least about 500 base pairs to about 25,000 base pairs, at least about 1,000 base pairs to about 25,000 base pairs, at least about 2,000 base pairs to about 25,000 base pairs, at least about 5,000 base pairs to about 25,000 base pairs, at least about 10,000 base pairs to about 25,000 base pairs, at least about 20,000 base pairs to about 25,000 base pairs, at least about 1 base pair to about 10,000 base pairs, at least about 100 base pairs to about 10,000 base pairs, at least about 250 base pairs to about 10,000 base pairs, at least about 500 base pairs to about 10,000 base pairs, at least about 1,000 base pairs to about 10,000 base pairs, at least about 2,000 base pairs to about 10,000 base pairs, at least about 5,000 base pairs to about 10,000 base pairs, at least about 1 base pair to about 5,000 base pairs, at least about 100 base pairs to about 5,000 base pairs, at least about 250 base pairs to about 5,000 base pairs, at least about 500 base pairs to about 5,000 base pairs, at least about 1,000 base pairs to about 5,000 base pairs, or at least about 2,000 base pairs to about 5,000 base pairs upstream from the TSS. The CRISPR/Cas9-based gene activation system may target a region that is at least about 1 base pair, at least about 100 base pairs, at least about 500 base pairs, at least about 1,000 base pairs, at least about 1,250 base pairs, at least about 2,000 base pairs, at least about 2,250 base pairs, at least about 2,500 base pairs, at least about 5,000 base pairs, at least about 10,000 base pairs, at least about 11,000 base pairs, at least about 20,000 base pairs, at least about 30,000 base pairs, at least about 46,000 base pairs, at least about 50,000 base pairs, at least about 54,000 base pairs, at least about 75,000 base pairs, or at least about 100,000 base pairs upstream from the TSS.

The CRISPR/Cas9-based gene activation system may target a region that is at least about 1 base pair to at least about 500 base pairs, at least about 1 base pair to at least about 250 base pairs, at least about 1 base pair to at least about 200 base pairs, at least about 1 base pair to at least about 100 base pairs, at least about 50 base pairs to at least about 500 base pairs, at least about 50 base pairs to at least about 250 base pairs at least about 50 base pairs to at least about 200 base pairs, at least about 50 base pairs to at least about 100 base pairs, at least about 100 base pairs to at least about 500 base pairs, at least about 100 base pairs to at least about 250 base pairs, or at least about 100 base pairs to at least about 200 base pairs downstream from the TSS. The CRISPR/Cas9-based gene activation system may target a region that is at least about 1 base pair, at least about 2 base pairs, at least about 3 base pairs, at least about 4 base pairs, at least about 5 base pairs, at least about 10 base pairs, at least about 15 base pairs, at least about 20 base pairs, at least about 25 base pairs, at least about 30 base pairs, at least about 40 base pairs, at least about 50 base pairs, at least about 60 base pairs, at least about 70 base pairs, at least about 80 base pairs, at least about 90 base pairs, at least about 100 base pairs, at least about 110 base pairs, at least about 120, at least about 130, at least about 140 base pairs, at least about 150 base pairs, at least about 160 base pairs, at least about 170 base pairs, at least about 180 base pairs, at least about 190 base pairs, at least about 200 base pairs, at least about 210 base pairs, at least about 220, at least about 230, at least about 240 base pairs, or at least about 250 base pairs downstream from the TSS.

In some embodiments, the CRISPR/Cas9-based gene activation system may target and bind a target region that is on the same chromosome as the target gene but more than 100,000 base pairs upstream or more than 250 base pairs downstream from the TSS. In some embodiments, the CRISPR/Cas9-based gene activation system may target and bind a target region that is on a different chromosome from the target gene.

The CRISPR/Cas9-based gene activation system may use gRNA of varying sequences and lengths. The gRNA may comprise a complementary polynucleotide sequence of the target DNA sequence followed by NGG. The gRNA may comprise a "G" at the 5' end of the complementary polynucleotide sequence. The gRNA may comprise at least a 10 base pair, at least a 11 base pair, at least a 12 base pair, at least a 13 base pair, at least a 14 base pair, at least a 15 base pair, at least a 16 base pair, at least a 17 base pair, at least a 18 base pair, at least a 19 base pair, at least a 20 base pair, at least a 21 base pair, at least a 22 base pair, at least a 23 base pair, at least a 24 base pair, at least a 25 base pair, at least a 30 base pair, or at least a 35 base pair complementary polynucleotide sequence of the target DNA sequence followed by NGG. The gRNA may target at least one of the promoter region, the enhancer region or the transcribed region of the target gene. The gRNA may include a nucleic acid sequence of at least one of SEQ ID NOs: 23-73, 188-223, or 224-254.

The CRISPR/Cas9-based gene activation system may include at least 1 gRNA, at least 2 different gRNAs, at least 3 different gRNAs at least 4 different gRNAs, at least 5 different gRNAs, at least 6 different gRNAs, at least 7 different gRNAs, at least 8 different gRNAs, at least 9 different gRNAs, or at least 10 different gRNAs. The CRISPR/Cas9-based gene activation system may include between at least 1 gRNA to at least 10 different gRNAs, at least 1 gRNA to at least 8 different gRNAs, at least 1 gRNA to at least 4 different gRNAs, at least 2 gRNA to at least 10 different gRNAs, at least 2 gRNA to at least 8 different gRNAs, at least 2 different gRNAs to at least 4 different gRNAs, at least 4 gRNA to at least 10 different gRNAs, or at least 4 different gRNAs to at least 8 different gRNAs.

3. TARGET GENES

The CRISPR/Cas9-based gene activation system may be designed to target and activate the expression of any target gene. The target gene may be an endogenous gene, a transgene, or a viral gene in a cell line. In some embodiments, the target region is located on a different chromosome as the target gene. In some embodiments, the CRISPR/Cas9-based gene activation system may include more than 1 gRNA. In some embodiments, the CRISPR/Cas9-based gene activation system may include more than 1 different gRNAs. In some embodiments, the different gRNAs bind to different target regions. For example, the different gRNAs may bind to target regions of different target genes and the expression of two or more target genes are activated.

In some embodiments, the CRISPR/Cas9-based gene activation system may activate between about one target gene to about ten target genes, about one target genes to about five target genes, about one target genes to about four target genes, about one target genes to about three target genes, about one target genes to about two target genes, about two target gene to about ten target genes, about two target genes to about five target genes, about two target genes to about four target genes, about two target genes to about three target genes, about three target genes to about ten target genes, about three target genes to about five target genes, or about three target genes to about four target genes. In some embodiments, the CRISPR/Cas9-based gene activation system may activate at least one target gene, at least two target genes, at least three target genes, at least four target genes, at least five target genes, or at least ten target genes. For example, the may target the hypersensitive site 2 (HS2) enhancer region of the human β-globin locus and activate downstream genes (HBE, HBG, HBD and HBB).

In some embodiments, the CRISPR/Cas9-based gene activation system induces the gene expression of a target gene by at least about 1 fold, at least about 2 fold, at least about 3 fold, at least about 4 fold, at least about 5 fold, at least about 6 fold, at least about 7 fold, at least about 8 fold, at least about 9 fold, at least about 10 fold, at least 15 fold, at least 20 fold, at least 30 fold, at least 40 fold, at least 50 fold, at least 60 fold, at least 70 fold, at least 80 fold, at least 90 fold, at least 100 fold, at least about 110 fold, at least 120 fold, at least 130 fold, at least 140 fold, at least 150 fold, at least 160 fold, at least 170 fold, at least 180 fold, at least 190 fold, at least 200 fold, at least about 300 fold, at least 400 fold, at least 500 fold, at least 600 fold, at least 700 fold, at least 800 fold, at least 900 fold, or at least 1000 fold compared to a control level of gene expression. A control level of gene expression of the target gene may be the level of gene expression of the target gene in a cell that is not treated with any CRISPR/Cas9-based gene activation system The target gene may be a mammalian gene. For example, the CRISPR/Cas9-based gene activation system may target a mammalian gene, such as IL1RN, MYOD1, OCT4, HBE, HBG, HBD, HBB, MYOCD (Myocardin), PAX7 (Paired box protein Pax-7), FGF1 (fibroblast growth factor-1) genes, such as FGF1A, FGF1B, and FGF1C. Other target genes include, but not limited to, Atf3, Axud1, Btg2, c-Fos, c-Jun, Cxcl1, Cxcl2, Edn1, Ereg, Fos, Gadd45b, Ier2, Ier3, Ifrd1, Il1b, Il6, Irf1, Junb, Lif, Nfkbia, Nfkbiz, Ptgs2, Slc25a25, Sqstm1, Tieg, Tnf, Tnfaip3, Zfp36, Birc2, Ccl2, Ccl20, Ccl7, Cebpd, Ch25h, CSF1, Cx3cl1, Cxcl10, Cxcl5, Gch, Icam1, Ifi47, Ifngr2, Mmp10, Nfkbie, Npal1, p21, Relb, Ripk2, Rnd1, S1pr3, Stx11, Tgtp, Tlr2, Tmem140, Tnfaip2, Tnfrsf6, Vcam1, 1110004C05Rik (GenBank accession number BC010291), Abca1, AI561871 (GenBank accession number BI143915), AI882074 (GenBank accession number BB730912), Arts1, AW049765 (GenBank accession number BC026642.1), C3, Casp4, Ccl5, Ccl9, Cdsn, Enpp2, Gbp2, H2-D1, H2-K, H2-L, Ifit1, Ii, Il13ra1, Il1rl1, Lcn2, Lhfpl2, LOC677168 (GenBank accession number AK019325), Mmp13, Mmp3, Mt2, Naf1, Ppicap, Prnd, Psmb10, Saa3, Serpina3g, Serpinf1, Sod3, Stat1, Tapbp, U90926 (GenBank accession number NM_020562), Ubd, A2AR (Adenosine A2A receptor), B7-H3 (also called CD276), B7-H4 (also called VTCN1), BTLA (B and T Lymphocyte Attenuator; also called CD272), CTLA-4 (Cytotoxic T-Lymphocyte-Associated protein 4; also called CD152), IDO (Indoleamine 2,3-dioxygenase) KIR (Killer-cell Immunoglobulin-like Receptor), LAG3 (Lymphocyte Activation Gene-3), PD-1 (Programmed Death 1 (PD-1) receptor), TIM-3 (T-cell Immunoglobulin domain and Mucin domain 3), and VISTA (V-domain Ig suppressor of T cell activation).

4. COMPOSITIONS FOR GENE ACTIVATION

The present invention is directed to a composition for activating gene expression of a target gene, target enhancer, or target regulatory element in a cell or subject. The composition may include the CRISPR/Cas9-based gene activation system, as disclosed above. The composition may also include a viral delivery system. For example, the viral delivery system may include an adeno-associated virus vector or a modified lentiviral vector.

Methods of introducing a nucleic acid into a host cell are known in the art, and any known method can be used to introduce a nucleic acid (e.g., an expression construct) into a cell. Suitable methods include, include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery, and the like. In some embodiments, the composition may be delivered by mRNA delivery and ribonucleoprotein (RNP) complex delivery.

a) Constructs and Plasmids

The compositions, as described above, may comprise genetic constructs that encodes the CRISPR/Cas9-based gene activation system, as disclosed herein. The genetic construct, such as a plasmid or expression vector, may comprise a nucleic acid that encodes the CRISPR/Cas9-based gene activation system, such as the CRISPR/Cas9-based acetyltransferase and/or at least one of the gRNAs. The compositions, as described above, may comprise genetic constructs that encodes the modified AAV vector and a nucleic acid sequence that encodes the CRISPR/Cas9-based gene activation system, as disclosed herein. The genetic construct, such as a plasmid, may comprise a nucleic acid that encodes the CRISPR/Cas9-based gene activation system. The compositions, as described above, may comprise genetic constructs that encodes a modified lentiviral vector. The genetic construct, such as a plasmid, may comprise a nucleic acid that encodes the CRISPR/Cas9-based acetyltransferase and at least one sgRNA. The genetic construct may be present in the cell as a functioning extrachromosomal molecule. The genetic construct may be a linear minichromosome including centromere, telomeres or plasmids or cosmids.

The genetic construct may also be part of a genome of a recombinant viral vector, including recombinant lentivirus, recombinant adenovirus, and recombinant adenovirus associated virus. The genetic construct may be part of the genetic material in attenuated live microorganisms or recombinant microbial vectors which live in cells. The genetic constructs may comprise regulatory elements for gene expression of the coding sequences of the nucleic acid. The regulatory elements may be a promoter, an enhancer, an initiation codon, a stop codon, or a polyadenylation signal.

The nucleic acid sequences may make up a genetic construct that may be a vector. The vector may be capable of expressing the fusion protein, such as the CRISPR/Cas9-based gene activation system, in the cell of a mammal. The vector may be recombinant. The vector may comprise heterologous nucleic acid encoding the fusion protein, such as the CRISPR/Cas9-based gene activation system. The vector may be a plasmid. The vector may be useful for transfecting cells with nucleic acid encoding the CRISPR/Cas9-based gene activation system, which the transformed host cell is cultured and maintained under conditions wherein expression of the CRISPR/Cas9-based gene activation system takes place.

Coding sequences may be optimized for stability and high levels of expression. In some instances, codons are selected to reduce secondary structure formation of the RNA such as that formed due to intramolecular bonding.

The vector may comprise heterologous nucleic acid encoding the CRISPR/Cas9-based gene activation system and may further comprise an initiation codon, which may be upstream of the CRISPR/Cas9-based gene activation system coding sequence, and a stop codon, which may be downstream of the CRISPR/Cas9-based gene activation system coding sequence. The initiation and termination codon may be in frame with the CRISPR/Cas9-based gene activation system coding sequence. The vector may also comprise a promoter that is operably linked to the CRISPR/Cas9-based gene activation system coding sequence. The CRISPR/Cas9-based gene activation system may be under the light-inducible or chemically inducible control to enable the dynamic control of gene activation in space and time. The promoter operably linked to the CRISPR/Cas9-based gene activation system coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human ubiquitin C (hUbC), human actin, human myosin, human hemoglobin, human muscle creatine, or human metalothionein. The promoter may also be a tissue specific promoter, such as a muscle or skin specific promoter, natural or synthetic. Examples of such promoters are described in US Patent Application Publication No. US20040175727, the contents of which are incorporated herein in its entirety.

The vector may also comprise a polyadenylation signal, which may be downstream of the CRISPR/Cas9-based gene activation system. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 vector (Invitrogen, San Diego, CA).

The vector may also comprise an enhancer upstream of the CRISPR/Cas9-based gene activation system, i.e., the CRISPR/Cas9-based acetyltransferase coding sequence or sgRNAs. The enhancer may be necessary for DNA expression. The enhancer may be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737, the contents of each are fully incorporated by reference. The vector may also comprise a mammalian origin of replication in order to maintain the vector extrachromosomally and produce multiple copies of the vector in a cell. The vector may also comprise a regulatory sequence, which may be well suited for gene expression in a mammalian or human cell into which the vector is administered. The vector may also comprise a reporter gene, such as green fluorescent protein ("GFP") and/or a selectable marker, such as hygromycin ("Hygro").

The vector may be expression vectors or systems to produce protein by routine techniques and readily available starting materials including Sambrook et al., Molecular Cloning and Laboratory Manual, Second Ed., Cold Spring Harbor (1989), which is incorporated fully by reference. In some embodiments the vector may comprise the nucleic acid sequence encoding the CRISPR/Cas9-based gene activation system, including the nucleic acid sequence encoding the CRISPR/Cas9-based acetyltransferase and the nucleic acid sequence encoding the at least one gRNA comprising the nucleic acid sequence of at least one of SEQ ID NOs: 23-73, 188-223, or 224-254.

b) Combinations

The CRISPR/Cas9-based gene activation system composition may be combined with orthogonal dCas9s, TALEs, and zinc finger proteins to facilitate studies of independent targeting of particular effector functions to distinct loci. In some embodiments, the CRISPR/Cas9-based gene activation system composition may be multiplexed with various activators, repressors, and epigenetic modifiers to precisely control cell phenotype or decipher complex networks of gene regulation.

5. METHODS OF USE

Potential applications of the CRISPR/Cas9-based gene activation system are diverse across many areas of science and biotechnology. The CRISPR/Cas9-based gene activation system may be used to activate gene expression of a target gene or target a target enhancer or target regulatory element. The CRISPR/Cas9-based gene activation system may be used to transdifferentiate a cell and/or activate genes related to cell and gene therapy, genetic reprogramming, and regenerative medicine. The CRISPR/Cas9-based gene activation system may be used to reprogram cell lineage specification. Activation of endogenous genes encoding the key regulators of cell fate, rather than forced overexpression of these factors, may potentially lead to more rapid, efficient, stable, or specific methods for genetic reprogramming and transdifferentiation. The CRISPR/Cas9-based gene activation system could provide a greater diversity of transcriptional activators to complement other tools for modulating mammalian gene expression. The CRISPR/Cas9-based gene activation system may be used to compensate for genetic defects, suppress angiogenesis, inactivate oncogenes, activate silenced tumor suppressors, regenerate tissue or reprogram genes.

6. METHODS OF ACTIVATING GENE EXPRESSION

The present disclosure provides a mechanism for activating the expression of target genes based on targeting a histone acetyltransferase to a target region via a CRISPR/Cas9-based gene activation system, as described above. The CRISPR/Cas9-based gene activation system may activate silenced genes. The CRISPR/Cas9-based gene activation system target regions upstream of the TSS of the target gene and substantially induced gene expression of the target gene. The polynucleotide encoding the CRISPR/Cas9-based gene activation system can also be transfected directly to cells.

The method may include administering to a cell or subject a CRISPR/Cas9-based gene activation system, compositions of CRISPR/Cas9-based gene activation system, or one or more polynucleotides or vectors encoding said CRISPR/Cas9-based gene activation system, as described above. The method may include administering a CRISPR/Cas9-based gene activation system, compositions of CRISPR/Cas9-based gene activation system, or one or more polynucleotides or vectors encoding said CRISPR/Cas9-based gene activation system, as described above, to a mammalian cell or subject.

7. PHARMACEUTICAL COMPOSITIONS

The CRISPR/Cas9-based gene activation system may be in a pharmaceutical composition. The pharmaceutical composition may comprise about 1 ng to about 10 mg of DNA encoding the CRISPR/Cas9-based gene activation system. The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity may include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The pharmaceutical composition containing the CRISPR/Cas9-based gene activation system may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the pharmaceutical composition containing the CRISPR/Cas9-based gene activation system at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA vector encoding the CRISPR/Cas9-based gene activation system may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

8. METHODS OF DELIVERY

Provided herein is a method for delivering the pharmaceutical formulations of the CRISPR/Cas9-based gene activation system for providing genetic constructs and/or proteins of the CRISPR/Cas9-based gene activation system. The delivery of the CRISPR/Cas9-based gene activation system may be the transfection or electroporation of the CRISPR/Cas9-based gene activation system as one or more nucleic acid molecules that is expressed in the cell and delivered to the surface of the cell. The CRISPR/Cas9-based gene activation system protein may be delivered to the cell. The nucleic acid molecules may be electroporated using BioRad Gene Pulser Xcell or Amaxa Nucleofector IIb devices or other electroporation device. Several different buffers may be used, including BioRad electroporation solution, Sigma phosphate-buffered saline product #D8537 (PBS), Invitrogen OptiMEM I (OM), or Amaxa Nucleofector solution V (N.V.). Transfections may include a transfection reagent, such as Lipofectamine 2000.

The vector encoding a CRISPR/Cas9-based gene activation system protein may be delivered to the mammal by DNA injection (also referred to as DNA vaccination) with and without in vivo electroporation, liposome mediated, nanoparticle facilitated, and/or recombinant vectors. The recombinant vector may be delivered by any viral mode. The viral mode may be recombinant lentivirus, recombinant adenovirus, and/or recombinant adeno-associated virus.

The nucleotide encoding a CRISPR/Cas9-based gene activation system protein may be introduced into a cell to induce gene expression of the target gene. For example, one or more nucleotide sequences encoding the CRISPR/Cas9-based gene activation system directed towards a target gene may be introduced into a mammalian cell. Upon delivery of the CRISPR/Cas9-based gene activation system to the cell, and thereupon the vector into the cells of the mammal, the transfected cells will express the CRISPR/Cas9-based gene activation system. The CRISPR/Cas9-based gene activation system may be administered to a mammal to induce or modulate gene expression of the target gene in a mammal. The mammal may be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

9. ROUTES OF ADMINISTRATION

The CRISPR/Cas9-based gene activation system and compositions thereof may be administered to a subject by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian may readily determine the dosing regimen and route of administration that is most appropriate for a particular animal. The CRISPR/Cas9-based gene activation system and compositions thereof may be administered by traditional syringes, needleless injection devices, "microprojectile bombardment gone guns", or other physical methods such as electroporation ("EP"), "hydrodynamic method", or ultrasound. The composition may be delivered to the mammal by several technologies including DNA injection (also referred to as DNA vaccination) with and without in vivo electroporation, liposome mediated, nanoparticle facilitated, recombinant vectors such as recombinant lentivirus, recombinant adenovirus, and recombinant adenovirus associated virus.

10. CELL TYPES

The CRISPR/Cas9-based gene activation system may be used with any type of cell. In some embodiments, the cell is a bacterial cell, a fungal cell, an archaea cell, a plant cell or an animal cell. In some embodiments, the cell may be an ENCODE cell line, including but not limited to, GM12878, K562, H1 human embryonic stem cells, HeLa-S3, HepG2, HUVEC, SK-N-SH, IMR90, A549, MCF7, HMEC or LHCM, CD14+, CD20+, primary heart or liver cells, differentiated H1 cells, 8988T, Adult_CD4_naive, Adult_CD4_Th0, Adult_CD4_Th1, AG04449, AG04450, AG09309, AG09319, AG10803, AoAF, AoSMC, BC_Adipose_UHN00001, BC_Adrenal_Gland_H12803N, BC_Bladder_01-11002, BC_Brain_H11058N, BC_Breast_02-03015, BC_Colon 01-11002, BC_Colon_H12817N, BC_Esophagus_01-11002, BC_Esophagus_H12817N, BC_Jejunum_H12817N, BC_Kidney_01-11002, BC_Kidney_H12817N, BC_Left_Ventricle_N41, BC_Leukocyte_UHN00204, BC_Liver_01-11002, BC_Lung_01-11002, BC_Lung_H12817N, BC_Pancreas_H12817N, BC_Penis_H12817N, BC_Pericardium_H12529N, BC Placenta UHN00189, BC_Prostate_Gland_H12817N, BC_Rectum_N29, BC_Skeletal_Muscle_01-11002, BC_Skeletal_Muscle_H12817N, BC_Skin_01-11002, BC_Small_Intestine_01-11002, BC_Spleen_H12817N, BC_Stomach_01-11002, BC_Stomach_H12817N, BC_Testis_N30, BC_Uterus_BN0765, BE2_C, BG02ES, BG02ES-EBD, BJ, bone_marrow_HS27a, bone_marrow_HS5, bone_marrow_MSC, Breast_OC, Caco-2, CD20+_RO01778, CD20+_RO01794, CD34+_Mobilized, CD4+_Naive_Wb11970640, CD4+_Naive_Wb78495824, Cerebellum_OC, Cerebrum_frontal_OC, Chorion, CLL, CMK, Colo829, Colon_BC, Colon_OC, Cord_CD4_naive, Cord_CD4_Th0, Cord_CD4_Th1, Decidua, Dnd41, ECC-1, Endometrium_OC, Esophagus_BC, Fibrobl, Fibrobl_GM03348, FibroP, FibroP_AG08395, FibroP_AG08396, FibroP_AG20443, Frontal_cortex_OC, GC_B_cell, Gliobla, GM04503, GM04504, GM06990, GM08714, GM10248, GM10266, GM10847, GM12801, GM12812, GM12813, GM12864, GM12865, GM12866, GM12867, GM12868, GM12869, GM12870, GM12871, GM12872, GM12873, GM12874, GM12875, GM12878-XiMat, GM12891, GM12892, GM13976, GM13977, GM15510, GM18505, GM18507, GM18526, GM18951, GM19099, GM19193, GM19238, GM19239, GM19240, GM20000, H0287, H1-neurons, H7-hESC, H9ES, H9ES-AFP−, H9ES-AFP+, H9ES-CM, H9ES-E, H9ES-EB, H9ES-EBD, HAc, HAEpiC, HA-h, HAL, HAoAF, HAoAF_6090101.11, HAoAF_6111301.9, HAoEC, HAoEC_7071706.1, HAoEC_8061102.1, HA-sp, HBMEC, HBVP, HBVSMC, HCF, HCFaa, HCH, HCH_0011308.2P, HCH_8100808.2, HCM, HConF, HCPEpiC, HCT-116, Heart_OC, Heart_STL003, HEEpiC, HEK293, HEK293T, HEK293-T-REx, Hepatocytes, HFDPC, HFDPC_0100503.2, HFDPC_0102703.3, HFF, HFF-Myc, HFL11W, HFL24W, HGF, HHSEC, HIPEpiC, HL-60, HMEpC, HMEpC_6022801.3, HMF, hMNC-CB, hMNC- CB_8072802.6, hMNC-CB_9111701.6, hMNC-PB, hMNC-PB_0022330.9, hMNC-PB_0082430.9, hMSC-AT, hMSC-AT_0102604.12, hMSC-AT_9061601.12, hMSC-BM, hMSC-BM_0050602.11, hMSC-BM_0051105.11, hMSC-UC, hMSC-UC_0052501.7, hMSC-UC_0081101.7, HMVEC-dAd, HMVEC-dBl-Ad, HMVEC-dBl-Neo, HMVEC-dLy-Ad, HMVEC-dLy-Neo, HMVEC-dNeo, HMVEC-LBl, HMVEC-LLy, HNPCEpiC, HOB, HOB_0090202.1, HOB_0091301, HPAEC, HPAEpiC, HPAF, HPC-PL, HPC-PL_0032601.13, HPC-PL_0101504.13, HPDE6-E6E7, HPdLF, HPF, HPIEpC, HPIEpC_9012801.2, HPIEpC_9041503.2, HRCEpiC, HRE, HRGEC, HRPEpiC, HSaVEC, HSaVEC_0022202.16, HSaVEC_9100101.15, HSMM, HSMM_emb, HSMM_FSHD, HSMMtube, HSMMtube_emb, HSMMtube_FSHD, HT-1080, HTR8svn, Huh-7, Huh-7.5, HVMF, HVMF_6091203.3, HVMF_6100401.3, HWP, HWP_0092205, HWP_8120201.5, iPS, iPS_CWRU1, iPS_hFib2_iPS4, iPS_hFib2_iPS5, iPS_NIHi11, iPS_NIHi7, Ishikawa, Jurkat, Kidney_BC, Kidney_OC, LHCN-M2, LHSR, Liver_OC, Liver_STL004, Liver_STL011, LNCaP, Loucy, Lung_BC, Lung_OC, Lymphoblastoid_cell_line, M059J, MCF10A-Er-Src, MCF-7, MDA-MB-231, Medullo, Medullo_D341, Mel_2183, Melano, Monocytes-CD14+, Monocytes-CD14+_RO01746, Monocytes-CD14+_RO01826, MRT_A204, MRT_G401, MRT_TTC549, Myometr, Naive_B_cell, NB4, NH-A, NHBE, NHBE_RA, NHDF, NHDF_0060801.3, NHDF_7071701.2, NHDF-Ad, NHDF-neo, NHEK, NHEM.f_M2, NHEM.f_M2_5071302.2, NHEM.f_M2_6022001, NHEM_M2, NHEM_M2_7011001.2, NHEM_M2_7012303, NHLF, NT2-D1, Olf_neurosphere, Osteobl, ovcar-3, PANC-1, Pancreas_OC, PanIsletD, PanIslets, PBDE, PBDEFetal, PBMC, PFSK-1, pHTE, Pons_OC, PrEC, ProgFib, Prostate, Prostate_OC, Psoas_muscle_OC, Raji, RCC_7860, RPMI-7951, RPTEC, RWPE1, SAEC, SH-SY5Y, Skeletal_Muscle_BC, SkMC, SKMC, SkMC_8121902.17, SkMC_9011302, SK-N-MC, SK-N-SH_RA, Small_intestine_OC, Spleen_OC, Stellate, Stomach_BC, T_cells_CD4+, T-47D, T98G, TBEC, Th1, Th1_Wb33676984, Th1_Wb54553204, Th17, Th2, Th2_Wb33676984, Th2_Wb54553204, Treg_Wb78495824, Treg_Wb83319432, U2OS, U87, UCH-1, Urothelia, WERI-Rb-1, and WI-38.

11. KITS

Provided herein is a kit, which may be used to activate gene expression of a target gene. The kit comprises a composition for activating gene expression, as described above, and instructions for using said composition. Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

The composition for activating gene expression may include a modified AAV vector and a nucleotide sequence encoding a CRISPR/Cas9-based gene activation system, as described above. The CRISPR/Cas9-based gene activation system may include CRISPR/Cas9-based acetyltransferase, as described above, that specifically binds and targets a cis-regulatory region or trans-regulatory region of a target gene. The CRISPR/Cas9-based acetyltransferase, as described above, may be included in the kit to specifically bind and target a particular regulatory region of the target gene.

12. EXAMPLES

The foregoing may be better understood by reference to the following examples, which are presented for purposes of illustration and are not intended to limit the scope of the invention.

Example 1

Methods and Materials—Activator

Cell lines and transfection. HEK293T cells were procured from the American Tissue Collection Center (ATCC, Manassas VA) through the Duke University Cell Culture Facility. Cells were cultured in Dulbecco's modified Eagle's medium (DMEM) supplemented with 10% FBS and 1% penicillin/streptomycin and maintained at 37° C. and 5% $CO_2$. Transfections were performed in 24-well plates using 375 ng of respective dCas9 expression vector and 125 ng of equimolar pooled or individual gRNA expression vectors mixed with Lipofectamine 2000 (Life Technologies, cat. #11668019) as per manufacturer's instruction. For ChIP-qPCR experiments, HEK293T cells were transfected in 15 cm dishes with Lipofectamine 2000 and 30 µg of respective dCas9 expression vector and 10 µg of equimolar pooled gRNA expression vectors as per manufacturer's instruction.

Plasmid constructs. pcDNA-dCas9$^{VP64}$ (dCas9$^{VP64}$; Addgene, plasmid #47107) was used (Perez-Pinera, P. et al, *Nature methods* 10:973-976 (2013)). An HA epitope tag was added to dCas9 (no effector) by removing the VP64 effector domain from dCas9$^{VP64}$ via AscI/PacI restriction sites and using isothermal assembly (Gibson et al. Nat. Methods 6:343-345 (2009)) to include an annealed set of oligos containing the appropriate sequence as per manufacturers instruction (NEB cat. #2611). pcDNA-dCas9$^{FLp300}$ (dCas9$^{FLp300}$) was created by amplifying full-length p300 from pcDNA3.1-p300 (Addgene, plasmid #23252) (Chen et al. EMBO J. 21:6539-6548 (2002)) in two separate fragments and cloning these fragments into the dCas9$^{VP64}$ backbone via isothermal assembly. A substitution in the full-length p300 protein (L553M), located outside of the HAT Core region, was identified in dCas9$^{FLp300}$ and in the precursor pcDNA3.1-p300 during sequence validation. pcDNA-dCas9$^{p300\ Core}$ (dCas9$^{p300\ Core}$) was generated by first amplifying amino acids 1048-1664 of human p300 from cDNA and then subcloning the resulting amplicon into pCR-Blunt (pCR-Blunt$^{p300\ Core}$) (Life Technologies cat. #K2700). An AscI site, HA-epitope tag, and a PmeI site were added by PCR amplification of the p300 Core from pCR-Blunt$^{p300\ Core}$ and subsequently this amplicon was cloned into pCR-Blunt (pCR-Blunt$^{p300\ Core+HA}$) (Life Technologies cat. #K2700). The HA-tagged p300 Core was cloned from pCR-Blunt$^{p300\ Core+HA}$ into the dCas9$^{VP64}$ backbone via shared AscI/PmeI restriction sites. pcDNA-dCas9$^{p300\ Core\ (D1399Y)}$ (dCas9$^{p300\ Core\ (D1399Y)}$) was generated by amplification of the p300 Core from dCas9$^{p300\ Core}$ in overlapping fragments with primer sets including the specified nucleic acid mutations, with a subsequent round of linkage PCR and cloning into the dCas9$^{p300\ Core}$ backbone using shared AscI/PmeI restriction sites. All PCR amplifications were carried out using Q5 high-fidelity DNA polymerase (NEB cat. #M0491). Protein sequences of all dCas9 constructs are shown in FIGS. 15A-15J.

IL1RN, MYOD, and OCT4 promoter gRNA protospacers have been described previously (Perez-Pinera, P. et al, *Nature methods* 10:973-976 (2013); Hu, J. et al., *Nucleic Acids Res* 42:4375-4390 (2014)). *Neisseria meningitidis* dCas9$^{VP64}$ (Nm-dCas9$^{VP64}$) was obtained from Addgene (plasmid #48676). Nm-dCas9$^{p300\ Core}$ was created by amplifying the HA-tagged p300 Core from dCas9$^{p300\ Core}$ with primers to facilitate subcloning into the AleI/AgeI-digested Nm-dCas9$^{VP64}$ backbone using isothermal assembly (NEB cat. #2611). IL1RN TALE$^{p300\ Core}$ TALEs were generated by subcloning the HA-tagged p300 Core domain from dCas9$^{p300\ Core}$ into previously published (Perez-Pinera, P. et al, *Nature methods* 10:973-976 (2013)) IL1RN TALE$^{VP64}$ constructs via shared AscI/PmeI restriction sites. IL1RN TALE target sites are shown in Table 1.

TABLE 1

IL1RN TAL effector information.

| Name | Target Site | SEQ ID NO | Location (GRCh37/hg19 assembly) |
|---|---|---|---|
| IL1RN TALE$^{VP64}$ A | GGGCTCCTCCTTGTACT | 15 | chr2: 113875431-113875447 |
| IL1RN TALE$^{VP64}$ B | ACGCAGATAAGAACCAGT | 16 | chr2: 113875291-113875308 |
| IL1RN TALE$^{VP64}$ C | GGCATCAAGTCAGCCAT | 17 | chr2: 113875356-113875372 |
| IL1RN TALE$^{VP64}$ D | AGCCTGAGTCACCCTCCT | 18 | chr2: 113875321-113875338 |
| IL1RN TALE$^{p300\ Core}$ A | GGGCTCCTCCTTGTACT | 19 | chr2: 113875431-113875447 |
| IL1RN TALE$^{p300\ Core}$ B | ACGCAGATAAGAACCAGT | 20 | chr2: 113875291-113875308 |
| IL1RN TALE$^{p300\ Core}$ C | GGCATCAAGTCAGCCAT | 21 | chr2: 113875356-113875372 |
| IL1RN TALE$^{p300\ Core}$ D | AGCCTGAGTCACCCTCCT | 22 | chr2: 113875321-113875338 |

ICAM1 ZF$^{VP64}$ and ICAM1 ZF$^{p300\ Core}$ were constructed by subcloning the ICAM1 ZF from pMX-CD54-31Opt-VP64[54] into dCas9$^{VP64}$ and dCas9$^{p300\ Core}$ backbones, respectively, using isothermal assembly (NEB cat. #2611). Protein sequences of ICAM1 ZF constructs are shown in FIG. 16. Transfection efficiency was routinely above 90% as assayed by co-transfection of PL-SIN-EF1α-EGFP (Addgene plasmid #21320) and gRNA empty vector in all experiments. All *Streptococcus pyogenes* gRNAs were annealed and cloned into pZdonor-pSPgRNA (Addgene plasmid #47108) for expression (Cong, L. et al., *Science* 339:819-823 (2013)) with slight modifications using NEB BbsI and T4 ligase (Cat. #s R0539 and M0202). Nm-dCas9 gRNA oligos were rationally designed using published PAM requirements (Esvelt, K. M. et al., *Nature Methods* 10:1116-1121 (2013)), and then cloned into pZDonor-Nm-Cas9-gRNA-hU6 (Addgene, plasmid #61366) via BbsI sites. Plasmids are available through Addgene (Table 2).

TABLE 2

Referenced plasmids in this study available at Addgene.

| Plasmid Name | Addgene Plasmid # |
|---|---|
| pcDNA-dCas9$^{VP64}$ (SEQ ID NO: 139) | 47107 |
| pcDNA-dCas9-HA (SEQ ID NO: 138) | 61355 |
| pcDNA3.1-p300 | 23252 |
| pcDNA-dCas9$^{FLp300}$ (SEQ ID NO: 140) | 61356 |
| pcDNA-dCas9$^{p300\ Core}$ (SEQ ID NO: 141) | 61357 |
| pcDNA-dCas9$^{p300\ Core\ (D1399Y)}$ (SEQ ID NO: 142) | 61358 |

TABLE 2-continued

Referenced plasmids in this study available at Addgene.

| Plasmid Name | Addgene Plasmid # |
|---|---|
| pcDNA-dCas9$^{p300\ Core\ (1645/1646\ RR/EE)}$ (SEQ ID NO: 143) | 61359 |
| pcDNA-dCas9$^{p300\ Core\ (C1204R)}$ (SEQ ID NO: 144) | 61361 |
| pcDNA-dCas9$^{p300\ Core\ (Y1467F)}$ (SEQ ID NO: 145) | 61362 |
| pcDNA-dCas9$^{p300\ Core\ (1396/1397\ SY/WW)}$ (SEQ ID NO: 146) | 61363 |
| pcDNA-dCas9$^{p300\ Core\ (H1415A/E1423A/Y1424A/L1428S/Y1430A/H1434A)}$ (SEQ ID NO: 147) | 61364 |
| pZdonor-pSPgRNA | 47108 |
| pcDNA3.1-300(HAT-) | 23254 |
| pcDNA3.3-Nm-dCas9$^{VP64}$ (SEQ ID NO: 148) | 48676 |
| pcDNA3.3-Nm-dCas9$^{p300\ Core}$ (SEQ ID NO: 149) | 61365 |
| pZDonor-NmCas9-gRNA-hU6 | 61366 |
| PL-SIN-EF1α-EGFP | 21320 |

All gRNA protospacer targets are listed in Tables 3 and 4.

TABLE 3 gRNA information.

| Target Location | Protospacer Sequence (5'-3') | SEQ ID NO | Genomic Location (GRCh37/hg19 Assembly) |
|---|---|---|---|
| IL1RN Promoter A | TGTACTCTCTGAGGTGCTC | 23 | chr2: 113875442-113875460 |
| IL1RN Promoter B | ACGCAGATAAGAACCAGTT | 24 | chr2: 113875291-113875309 |
| IL1RN Promoter C | CATCAAGTCAGCCATCAGC | 25 | chr2: 113875358-113875376 |
| IL1RN Promoter D | GAGTCACCCTCCTGGAAAC | 26 | chr2: 113875326-113875344 |
| MYOD Promoter A | CCTGGGCTCCGGGGCGTTT | 27 | chr11: 17741056-17741074 |
| MYOD Promoter B | GGCCCCTGCGGCCACCCCG | 28 | chr11: 17740969-17740987 |
| MYOD Promoter C | CTCCCTCCCTGCCCGGTAG | 29 | chr11: 17740897-17740915 |
| MYOD Promoter D | AGGTTTGGAAAGGGCGTGC | 30 | chr11: 17740837-17740855 |
| OCT4 Promoter A | ACTCCACTGCACTCCAGTCT | 31 | chr6: 31138711-31138730 |
| OCT4 Promoter B | TCTGTGGGGACCTGCACTG | 32 | chr6: 31138643-31138662 |
| OCT4 Promoter C | GGGGCGCCAGTTGTGTCTCC | 33 | chr6: 31138613-31138632 |
| OCT4 Promoter D | ACACCATTGCCACCACCATT | 34 | chr6: 31138574-31138593 |
| MYOD DRR A | TGTTTTCAGCTTCCAAACT | 35 | chr11: 17736528-17736546 |
| MYOD DRR B | CATGAAGACAGCAGAAGCC | 36 | chr11: 17736311-17736329 |
| MYOD DRR C | GGCCCACATTCCTTTCCAG | 37 | chr11: 17736158-17736176 |
| MYOD DRR D | GGCTGGATTGGGTTTCCAG | 38 | chr11: 17736065-17736083 |
| MYOD CE A | CAACTGAGTCCTGAGGTTT | 39 | chr11: 17721347-17721365 |
| MYOD CE B | CTCACAGCACAGCCAGTGT | 40 | chr11: 17721257-17721275 |
| MYOD CE C | CAGCAGCTGGTCACAAAGC | 41 | chr11: 17721200-17721218 |
| MYOD CE D | CTTCCTATAAACTTCTGAG | 42 | chr11: 17721139-17721157 |

TABLE 3-continued gRNA information.

| Target Location | Protospacer Sequence (5'-3') | SEQ ID NO | Genomic Location (GRCh37/hg19 Assembly) |
|---|---|---|---|
| OCT4 PE A | AGTGATAAGACACCCGCTTT | 43 | chr6: 31139524-31139543 |
| OCT4 PE B | CAGACATCTAATACCACGGT | 44 | chr6: 31139604-31139623 |
| OCT4 PE C | AGGGAGAACGGGGCCTACCG | 45 | chr6: 31139620-31139639 |
| OCT4 PE D | ACTTCAGGTTCAAAGAAGCC | 46 | chr6: 31139725-31139744 |
| OCT4 PE E | TTTTCCCCACCCAGGGCCTA | 47 | chr6: 31139671-31139690 |
| OCT4 PE F | CCCTGGGTGGGGAAAACCAG | 48 | chr6: 31139675-31139694 |
| OCT4 DE A | GGAGGAACATGCTTCGGAAC | 49 | chr6: 31140809-31140828 |
| OCT4 DE B | GTGCCGTGATGGTTCTGTCC | 50 | chr6: 31140864-31140883 |
| OCT4 DE C | GGTCTGCCGGAAGGTCTACA | 51 | chr6: 31140707-31140726 |
| OCT4 DE D | TCGGCCTTTAACTGCCCAAA | 52 | chr6: 31140757-31140776 |
| OCT4 DE E | GCATGACAAAGGTGCCGTGA | 53 | chr6: 31140875-31140894 |
| OCT4 DE F | CCTGCCTTTTGGGCAGTTAA | 54 | chr6: 31140764-31140783 |
| HS2 A | AATATGTCACATTCTGTCTC | 55 | chr11: 5301800-5301819 |
| HS2 B | GGACTATGGGAGGTCACTAA | 56 | chr11: 5302108-5302127 |
| HS2 C | GAAGGTTACACAGAACCAGA | 57 | chr11: 5302033-5302052 |
| HS2 D | GCCCTGTAAGCATCCTGCTG | 58 | chr11: 5301898-5301917 |

TABLE 4

| Target Location | Protospacer Sequence (5'-3') | SEQ ID NO | Genomic Location (GRCh37/hg19 Assembly) |
|---|---|---|---|
| HBG Promoter A | CCACTGCTAACTGAAAGAGA | 59 | chr11: 5271570-5271589 |
| HBG Promoter B | AGCCACAGTTTCAGCGCAGT | 60 | chr11: 5271692-5271711 |
| HBG Promoter C | CTGTTTCATCTTAGAAAAAT | 61 | chr11: 5271793-5271812 |
| HBG Promoter D | GAATGTTCTTTGGCAGGTAC | 62 | chr11: 5271942-5271961 |
| HBG Promoter E | CGCACATCTTATGTCTTAGA | 63 | chr11: 5272021-5272040 |
| HBE Promoter A | CTTAAGAGAGCTAGAACTGG | 64 | chr11: 5291618-5291637 |
| HBE Promoter B | TCCCAAAGTACAGTACCTTG | 65 | chr11: 5291758-5291777 |
| HBE Promoter C | TCCCTAGAGAGGACAGACAG | 66 | chr11: 5291785-5291804 |
| HBE Promoter D | TCATAGAGAAATGAAAAGAG | 67 | chr11: 5291840-5291859 |
| HBE Promoter E | ATAATATACCCTGACTCCTA | 68 | chr11: 5292038-5292057 |
| HS2 A | AGGCCACCTGCAAGATAAAT | 69 | chr11: 5301662-5301681 |
| HS2 B | TGTTGTTATCAATTGCCATA | 70 | chr11: 5301708-5301727 |
| HS2 C | ATCCCTTCCAGCATCCTCAT | 71 | chr11: 5302187-5302206 |
| HS2 D | GTGCTTCAAAACCATTTGCT | 72 | chr11: 5302245-5302264 |
| HS2 E | GATACATGTTTTATTCTTAT | 73 | chr11: 5302306-5302325 |

Western Blotting. 20 µg of protein was loaded for SDS PAGE and transferred onto a nitrocellulose membrane for western blots. Primary antibodies (α-FLAG; Sigma-Aldrich cat. #F7425 and α-GAPDH; Cell Signaling Technology cat. #14C10) were used at a 1:1000 dilution in TBST+500 Milk. Secondary α-Rabbit HRP (Sigma-Aldrich cat. #A6154) was used at a 1:5000 dilution in TBST+500 Milk. Membranes were exposed after addition of ECL (Bio-Rad cat. #170-5060).

Quantitative reverse-transcription PCR. RNA was isolated from transfected cells using the RNeasy Plus mini kit (Qiagen cat. #74136) and 500 ng of purified RNA was used as template for cDNA synthesis (Life Technologies, cat. #11754). Real-time PCR was performed using PerfeCTa SYBR Green FastMix (Quanta Biosciences, cat. #95072) and a CFX96 Real-Time PCR Detection System with a C1000 Thermal Cycler (Bio-Rad). Baselines were subtracted using the baseline subtraction curve fit analysis mode and thresholds were automatically calculated using the Bio-Rad CFX Manager software version 2.1. Results are expressed as fold change above control mock transfected cells (No DNA) after normalization to GAPDH expression using the ΔΔCt method (Schmittgen et al., *Nat. Protoc.* 3:1101-1108 (2008)). All qPCR primers and conditions are listed in Table 5.

TABLE 5

Quantitative reverse transcription PCR and ChIP-qPCR primers and conditions.

| Target | Primer (5'-3') | SEQ ID NO | Reverse Primer (5'-3') | SEQ ID NO | Cycling Parameters |
|---|---|---|---|---|---|
| GAPDH | CAATGACCCCTTCATTGACC | 74 | TTGATTTTGGAGGGATCTCG | 75 | 95° C. 30 sec<br>95° C. 5 sec<br>53° C. 20 sec 45X |
| IL1RN | GGAATCCATGGAGGGAAGAT | 76 | TGTTCTCGCTCAGGTCAGTG | 77 | 95° C. 30 sec<br>95° C. 5 sec<br>58° C. 20 sec 45X |
| MYOD | TCCCTCTTTCACGGTCTCAC | 78 | AACACCCGACTGCTGTATCC | 79 | 95° C. 30 sec<br>95° C. 5 sec<br>53° C. 20 sec 45X |
| OCT4 | CGAAAGAAAAGCGAACCAGTATCGAGAAC | 80 | CGTTGTGCATAGTCGCTGCTTGATCGC | 81 | 95° C. 30 sec<br>95° C. 5 sec<br>53° C. 20 sec 45X |
| HBB | GCACGTGGATCCTGAGAACT | 82 | ATTGGACAGCAAGAAAGCGAG | 83 | 95° C. 30 sec<br>95° C. 5 sec<br>58° C. 20 sec 45X |
| HBD | GCACGTGGATCCTGAGAACT | 84 | CAGGAAACAGTCCAGGATCTCA | 85 | 95° C. 30 sec<br>95° C. 5 sec<br>58° C. 20 sec 45X |
| HBG | GCTGAGTGAACTGCACTGTGA | 86 | GAATTCTTTGCCGAAATGGA | 87 | 95° C. 30 sec<br>95° C. 5 sec<br>58° C. 20 sec 45X |
| HBE | TCACTAGCAAGCTCTCAGGC | 88 | AACAACGAGGAGTCTGCCC | 89 | 95° C. 30 sec<br>95° C. 5 sec<br>62° C. 20 sec 45X |
| ICAM1 | GCAGACAGTGACCATCTACAGCTT | 90 | CAATCCCTCTCGTCCAGTCG | 91 | 95° C. 30 sec<br>95° C. 5 sec<br>58° C. 20 sec 45X |
| HS2 ChIP Region 1 | TGCTTGGACTATGGGAGGTC | 92 | GCAGGTGCTTCAAAACCATT | 93 | 95° C. 30 sec<br>95° C. 5 sec<br>60° C. 20 sec 45X |
| HS2 ChIP Region 2 | TCAGGTGGTCAGCTTCTCCT | 94 | AAGCAAACCTTCTGGCTCAA | 95 | 95° C. 30 sec<br>95° C. 5 sec<br>60° C. 20 sec 45X |
| HS2 ChIP Region 3 | CCACACAGGTGAACCCTTTT | 96 | GGACACATGCTCACATACGG | 97 | 95° C. 30 sec<br>95° C. 5 sec<br>60° C. 20 sec 45X |
| HBE ChIP Region 1 | ATTCGATCCATGTGCCTGA | 98 | CAATGCTGGAATTTGTGGAA | 99 | 95° C. 30 sec<br>95° C. 5 sec<br>60° C. 20 sec 45X |
| HBE ChIP Region 2 | GGGGTGATTCCCTAGAGAGG | 100 | AAGCAGGACAGACAGGCAAG | 101 | 95° C. 30 sec<br>95° C. 5 sec<br>60° C. 20 sec 45X |

TABLE 5-continued

Quantitative reverse transcription PCR and ChIP-qPCR primers and conditions.

| Target | Primer (5'-3') | SEQ ID NO | Reverse Primer (5'-3') | SEQ ID NO | Cycling Parameters | |
|---|---|---|---|---|---|---|
| HBE ChIP Region 3 | GAGGGTCAGCAGTGA TGGAT | 102 | TGGAAAAGGAGAATG GGAGA | 103 | 95° C. 30 sec<br>95° C. 5 sec<br>60° C. 20 sec | 45X |
| HBG1/2 ChIP Region 1 | TGGTCAAGTTTGCCTT GTCA | 104 | GGAATGACTGAATCG GAACAA | 105 | 95° C. 30 sec<br>95° C. 5 sec<br>60° C. 20 sec | 45X |
| HBG1/2 ChIP Region 2 | CCTCCAGCATCTTCCA CATT | 106 | GAAGCACCCTTCAGC AGTTC | 107 | 95° C. 30 sec<br>95° C. 5 sec<br>60° C. 20 sec | 45X |
| HBG1/2 ChIP Region 3 | CCACAGTTTCAGCGCA GTAATA | 108 | ATCAGCCAGCACACA CACTT | 109 | 95° C. 30 sec<br>95° C. 5 sec<br>60° C. 20 sec | 45X |
| IL1RN ChIP Region 1 | CCCTGTCAGGAGGGAC AGAT | 110 | GGCTCACCGGAAGCA TGAAT | 111 | 95° C. 30 sec<br>95° C. 5 sec<br>60° C. 20 sec | 45X |
| IL1RN ChIP Region 2 | AAGCTACAAGCAGGTT CGCT | 112 | AATAACAGGGTCCAT CCCGC | 113 | 95° C. 30 sec<br>95° C. 5 sec<br>60° C. 20 sec | 45X |
| IL1RN ChIP Region 3 | TGTTCCCTCCACCTGG AATA | 114 | GGGAAAATCCAAAGC AGGAT | 115 | 95° C. 30 sec<br>95° C. 5 sec<br>60° C. 20 sec | 45X |
| IL1RN ChIP Region 4 | TCCTAGGTCCCTCAAA AGCA | 116 | GTCCCCAACGCTCTA ACAAA | 117 | 95° C. 30 sec<br>95° C. 5 sec<br>60° C. 20 sec | 45X |
| IL1RN ChIP Region 5 | GTTAGAGCGTTGGGGA CCTT | 118 | CACATGCAGAGAACT GAGCTG | 119 | 95° C. 30 sec<br>95° C. 5 sec<br>60° C. 20 sec | 45X |
| IL1RN ChIP Region 6 | GTTGGGGTAAGCACG AAGG | 120 | TTTCCAGGAGGGTGA CTCAG | 121 | 95° C. 30 sec<br>95° C. 5 sec<br>60° C. 20 sec | 45X |
| IL1RN ChIP Region 7 | TTCTCTGCATGTGACC TCCC | 122 | ACACACTCACAGAGG GTTGG | 123 | 95° C. 30 sec<br>95° C. 5 sec<br>60° C. 20 sec | 45X |
| IL1RN ChIP Region 8 | TGAGTCACCCTCCTGG AAAC | 124 | CTCCTTCCAGAGCAC CTCAG | 125 | 95° C. 30 sec<br>95° C. 5 sec<br>60° C. 20 sec | 45X |
| IL1RN ChIP Region 9 | GCTGGGCTCCTCCTTG TACT | 126 | GCTGCTGCCCATAAA GTAGC | 127 | 95° C. 30 sec<br>95° C. 5 sec<br>60° C. 20 sec | 45X |
| IL1RN ChIP Region 10 | GGACTGTGGCCCAGGT ACT | 128 | GGCCTCATAGGACAG GAGGT | 129 | 95° C. 30 sec<br>95° C. 5 sec<br>60° C. 20 sec | 45X |
| IL1RN ChIP Region 11 | TTATGGGCAGCAGCTC AGTT | 130 | GACATTTTCCTGGAC GCTTG | 131 | 95° C. 30 sec<br>95° C. 5 sec<br>60° C. 20 sec | 45X |
| IL1RN ChIP Region 12 | CCCTCCCCATGGCTTT AGGT | 132 | AGCTCCATGCGCTTG ACATT | 133 | 95° C. 30 sec<br>95° C. 5 sec<br>60° C. 20 sec | 45X |
| IL1RN ChIP Region 13 | AGCGTCCAGGAAAAT GTCAA | 134 | ATGACCCTCACACTC CAAGG | 135 | 95° C. 30 sec<br>95° C. 5 sec<br>60° C. 20 sec | 45X |

TABLE 5-continued

Quantitative reverse transcription PCR and ChIP-qPCR primers and conditions.

| Target | Primer (5'-3') | SEQ ID NO | Reverse Primer (5'-3') | SEQ ID NO | Cycling Parameters |
|---|---|---|---|---|---|
| Upstream, β-actin ChIP NEG CTRL | GTTGGGTGCTCCAGCT TTTA | 136 | CCTCAAAACTCCTGG ACTCG | 137 | 95° C. 30 sec  45X<br>95° C.  5 sec<br>60° C. 20 sec |

RNA-seq. RNA-seq was performed using three replicates per experimental condition. RNA was isolated from transfected cells using the RNeasy Plus mini kit (Qiagen cat. #74136) and 1 µg of purified mRNA was used as template for cDNA synthesis and library construction using the PrepX RNA-Seq Library Kit (Wafergen Biosystems, cat. #400039). Libraries were prepared using the Apollo 324 liquid handling platform, as per manufacturer's instruction. Indexed libraries were validated for quality and size distribution using the Tapestation 2200 (Agilent) and quantified by qPCR using the KAPA Library Quantification Kit (KAPA Biosystems; KK4835) prior to multiplex pooling and sequencing at the Duke University Genome Sequencing Shared Resource facility. Libraries were pooled and then 50 bp single-end reads were sequenced on a Hiseq 2500 (Illumina), de-multiplexed and then aligned to the HG19 transcriptome using Bowtie 2 (Langmead et al. Nat. Methods 9:357-359 (2012)). Transcript abundance was calculated using the SAMtools (Li et al. Bioinformatics 25:2078:2079 (2009)) suite and differential expression was determined in R using the DESeq2 analysis package. Multiple hypothesis correction was performed using the method of Benjamini and Hochberg with a FDR of <5%. RNA-seq data is deposited in the NCBI's Gene Expression Omnibus and is accessible through GEO Series accession number GSE66742.

ChIP-qPCR. HEK293T cells were co-transfected with four HS2 enhancer gRNA constructs and indicated dCas9 fusion expression vectors in 15 cm plates in biological triplicate for each condition tested. Cells were cross-linked with 1% Formaldehyde (final concentration; Sigma F8775-25ML) for 10 min at RT and then the reaction was stopped by the addition of glycine to a final concentration of 125 mM. From each plate ~2.5e7 cells were used for H3K27ac ChIP-enrichment. Chromatin was sheared to a median fragment size of 250 bp using a Bioruptor XL (Diagenode). H3K27ac enrichment was performed by incubation with 5 µg of Abcam ab4729 and 200 µl of sheep anti-rabbit IgG magnetic beads (Life Technologies 11203D) for 16 hrs at 4° C. Cross-links were reversed via overnight incubation at 65° C. with sodium dodecyl sulfate, and DNA was purified using MinElute DNA purification columns (Qiagen). 10 ng of DNA was used for subsequent qPCR reactions using a CFX96 Real-Time PCR Detection System with a C1000 Thermal Cycler (Bio-Rad). Baselines were subtracted using the baseline subtraction curve fit analysis mode and thresholds were automatically calculated using the Bio-Rad CFX Manager software version 2.1. Results are expressed as fold change above cells co-transfected with dCas9 and four HS2 gRNAs after normalization to β-actin enrichment using the ΔΔCt method (Schmittgen et al., Nat. Protoc. 3:1101-1108 (2008)). All ChIP-qPCR primers and conditions are listed in Table 5.

Example 2

A dCas9 Fusion to the p300 HAT Domain Activates Target Genes

The full-length p300 protein was fused to dCas9 ($dCas9^{FLp300}$; FIGS. 1A-1B) and assayed for its capacity for transactivation by transient co-transfection of human HEK293T cells with four gRNAs targeting the endogenous promoters of IL1RN, MYOD1 (MYOD), and POU5F1/OCT4 (OCT4) (FIG. 1C). A combination of four gRNAs targeting each promoter was used. $dCas9^{FLp300}$ was well expressed and induced modest activation above background compared to the canonical dCas9 activator fused to the VP64 acidic activation domain ($dCas9^{VP64}$) (FIGS. 1A-1C). The full-length p300 protein is a promiscuous acetyltransferase which interacts with a multitude of endogenous proteins, largely via its termini. In order to mitigate these interactions the contiguous region of full-length p300 (2414 aa) solely required for inherent HAT activity (amino acids 1048-1664), known as the p300 HAT core domain (p300 Core) was isolated. When fused to the C-terminus of dCas9 ($dCas9^{p300\ Core}$, FIGS. 1A-1B) the p300 Core domain induced high levels of transcription from endogenous gRNA-targeted promoters (FIG. 1C). When targeted to the IL1RN and MYOD promoters, the $dCas9p^{300\ Core}$ fusion displayed significantly higher levels of transactivation than $dCas9^{VP64}$ (P-value 0.01924 and 0.0324 respectively; FIGS. 1A-1C). These dCas9-effector fusion proteins were expressed at similar levels (FIG. 1B, FIGS. 7A-7C) indicating that the observed differences were due to differences to transactivation capacity. Additionally, no changes to target gene expression were observed when the effector fusions were transfected without gRNAs (FIG. 8). For FIG. 8, dCas9 fusion proteins were transiently co-transfected with an empty gRNA vector backbone and mRNA expression of IL1RN, MYOD, and OCT4 was assayed as in the main text. Red dashed line indicates background expression level from No DNA-transfected cells. n=2 independent experiments, error bars: s.e.m., no significant activation was observed for any target gene assayed.

Figures 7A, 7B:
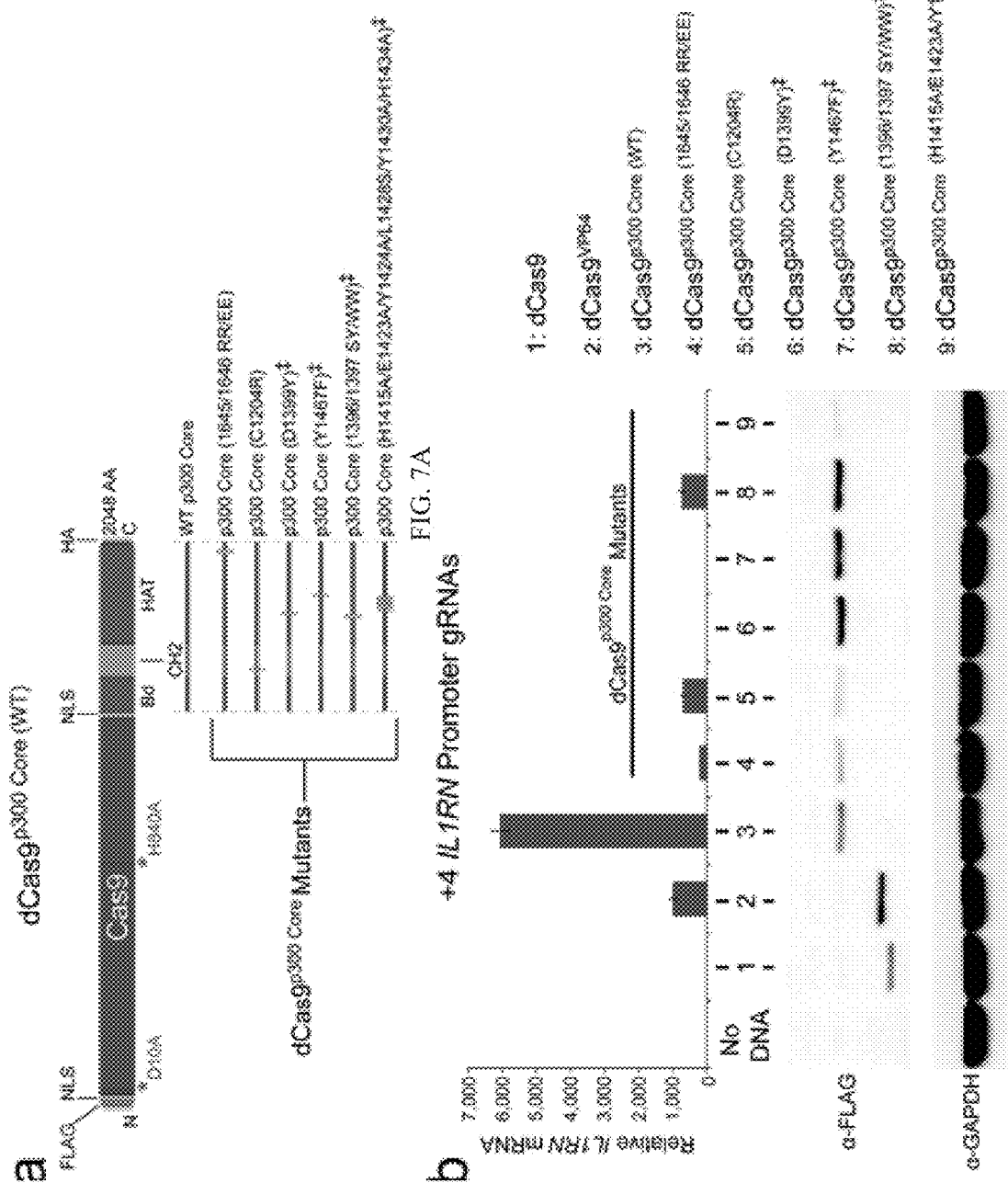
Figure 8:
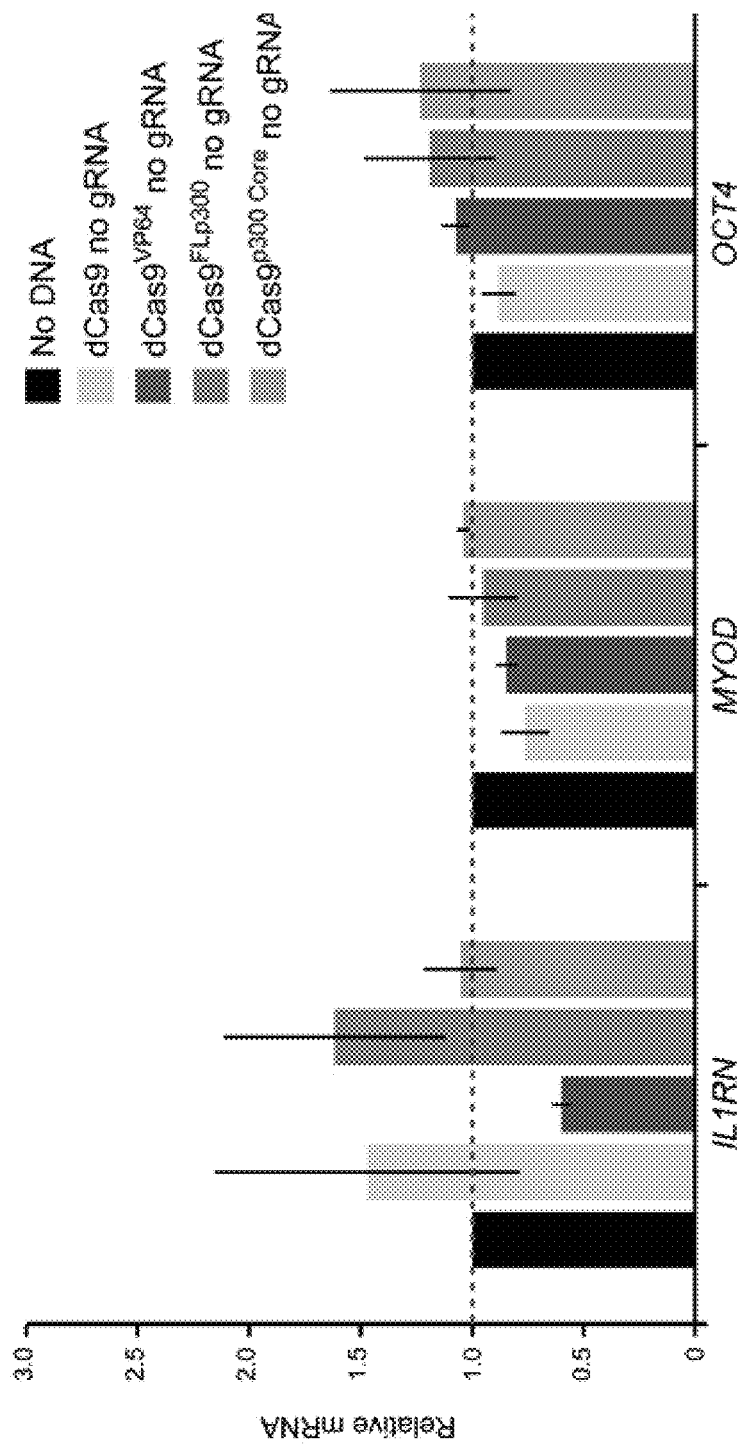
FIG. 8 shows target gene activation is unaffected by overexpression of synthetic dCas9 fusion proteins.
Figure 9A:
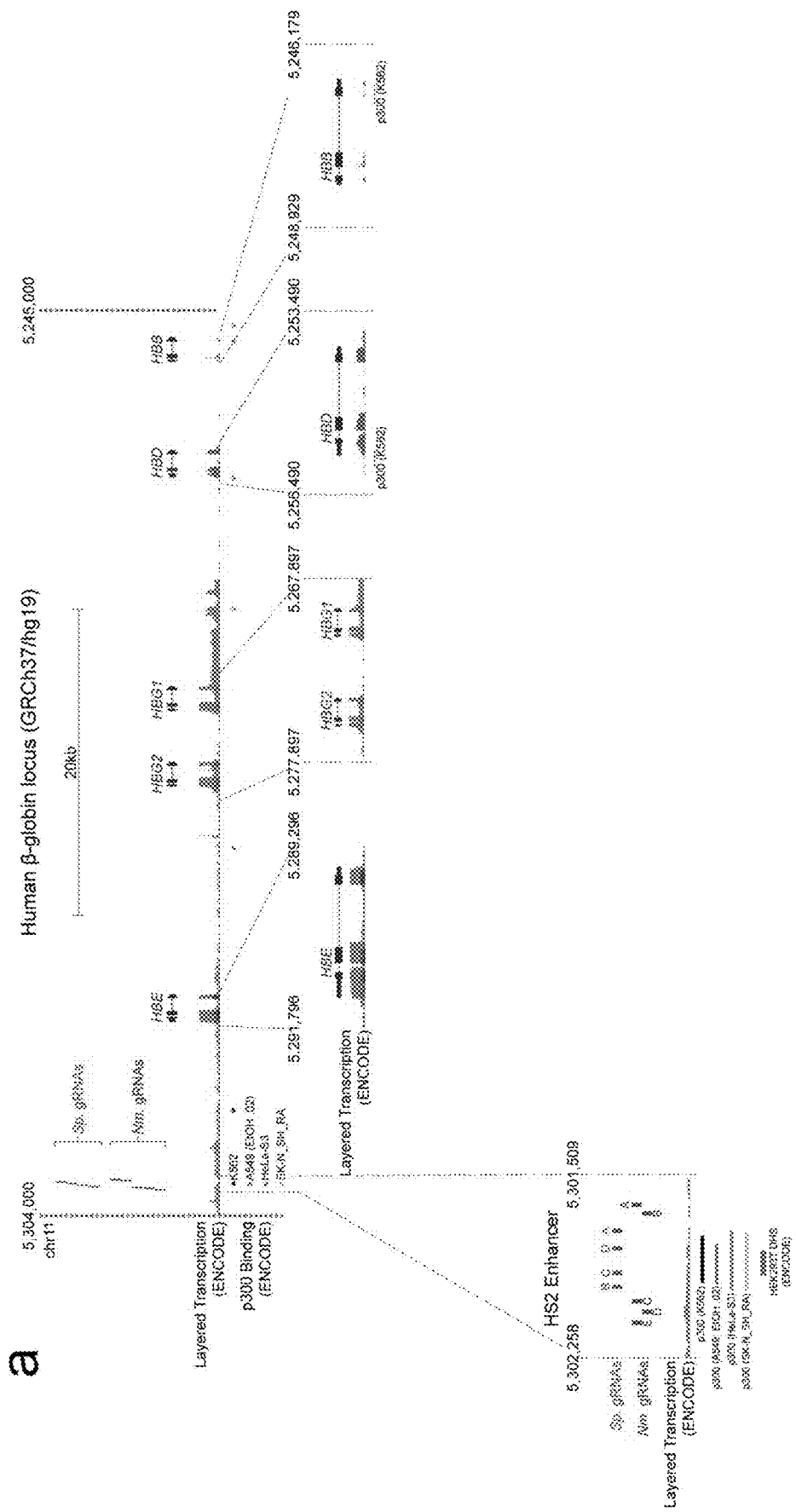
FIGS. 9A-9E show a comparison of Sp. dCas9 and Nm. dCas9 gene induction from the HS2 enhancer with individual and pooled gRNAs.
Figures 9B, 9C, 9D, 9E:
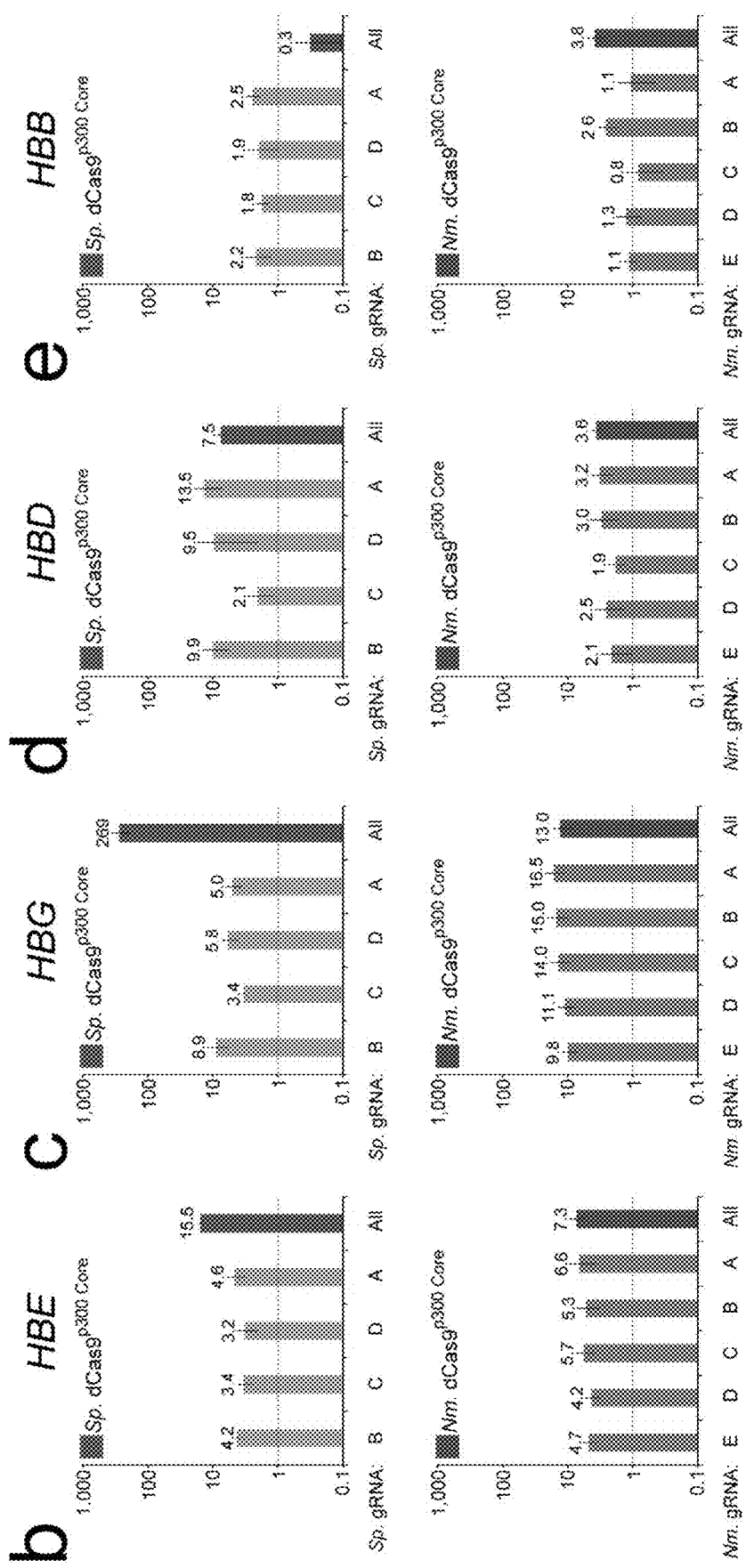

To ensure that the p300 Core acetyltransferase activity was responsible for gene transactivation using the $dCas9^{p300\ Core}$ fusion, a panel of $dCas9^{p300\ Core}$ HAT-domain mutant fusion proteins was screened (FIGS. 7A-7C). A single inactivating amino acid substitution within the HAT core domain (WT residue D1399 of full-length p300) of $dCas9^{p300\ Core}$ ($dCas9^{p300\ Core\ (D1399Y)}$ (FIG. 1A) abolished the transactivation capacity of the fusion protein (FIG. 1C), demonstrating that intact p300 Core acetyltransferase activity was required for $dCas9^{p300\ Core}$-mediated transactivation.

Example 3 dCas9$^{p300\ Core}$ Activates Genes from Proximal and Distal Enhancers

As p300 plays a role and is localized at endogenous enhancers, the dCas9$^{p300\ Core}$ may effectively induce transcription from distal regulatory regions with appropriately targeted gRNAs. The distal regulatory region (DRR) and core enhancer (CE) of the human MYOD locus was targeted through co-transfection of four gRNAs targeted to each region and either dCas9$^{VP64}$ or dCas9$^{p300\ Core}$ (FIG. 2A). Compared to a mock-transfected control, dCas9$^{VP64}$ did not show any induction when targeted to the MYOD DRR or CE region. In contrast, dCas9$^{p300\ Core}$ induced significant transcription when targeted to either MYOD regulatory element with corresponding gRNAs (P-value 0.0115 and 0.0009 for the CE and DRR regions respectively). The upstream proximal (PE) and distal (DE) enhancer regions of the human OCT4 gene were also targeted by co-transfection of six gRNAs and either dCas9$^{VP64}$ or dCas9$^{p300\ Core}$ (FIG. 2B). dCas9$^{p300\ Core}$ induced significant transcription from these regions (P-value≤0.0001 and P-value≤0.003 for the DE and PE, respectively), whereas dCas9$^{VP64}$ was unable to activate OCT4 above background levels when targeted to either the PE or DE regions.

The well-characterized mammalian β-globin locus control region (LCR) orchestrates transcription of the downstream hemoglobin genes; hemoglobin epsilon 1 (HBE, from ~11 kb), hemoglobin gamma 1 and 2 (HBG, from ~30 kb), hemoglobin delta (HBD, from ~46 kb), and hemoglobin beta (HBB, from ~54 kb) (FIG. 2C). DNase hypersensitive sites within the β-globin LCR serve as docking sites for transcriptional and chromatin modifiers, including p300, which coordinate distal target gene expression. Four gRNAs targeting the DNase hypersensitive site 2 within the LCR enhancer region (HS2 enhancer) were generated. These four HS2-targeted gRNAs were co-transfected with dCas9, dCas9$^{VP64}$, dCas9$^{p300\ Core}$, or dCas9$^{p300\ Core\ (D1399Y)}$, and the resulting mRNA production from HBE, HBG, HBD, and HBB was assayed (FIG. 2C). dCas9, dCas9$^{VP64}$, and dCas9$^{p300\ Core\ (D1399Y)}$ were unable to transactivate any downstream genes when targeted to the HS2 enhancer. In contrast, targeting of dCas9$^{p300\ Core}$ to the HS2 enhancer led to significant expression of the downstream HBE, HBG, and HBD genes (P-value≤0.0001, 0.0056, and 0.0003 between dCas9$^{p300\ Core}$ and mock-transfected cells for HBE, HBG, and HBD respectively). Overall, HBD and HBE appeared relatively less responsive to synthetic p300 Core-mediated activation from the HS2 enhancer; a finding consistent with lower rates of general transcription from these two genes across several cell lines (FIGS. 9A-9E).

Nevertheless, with the exception of the most distal HBB gene, dCas9$^{p300\ Core}$ exhibited a capacity to activate transcription from downstream genes when targeted to all characterized enhancer regions assayed, a capability not observed for dCas9$^{VP64}$. Together, these results demonstrate that dCas9$^{p300\ Core}$ is a potent programmable transcription factor that can be used to regulate gene expression from a variety of promoter-proximal and promoter-distal locations.

Example 4

Gene Activation by dCas9$^{p300\ Core}$ is Highly Specific

Figure 3B:
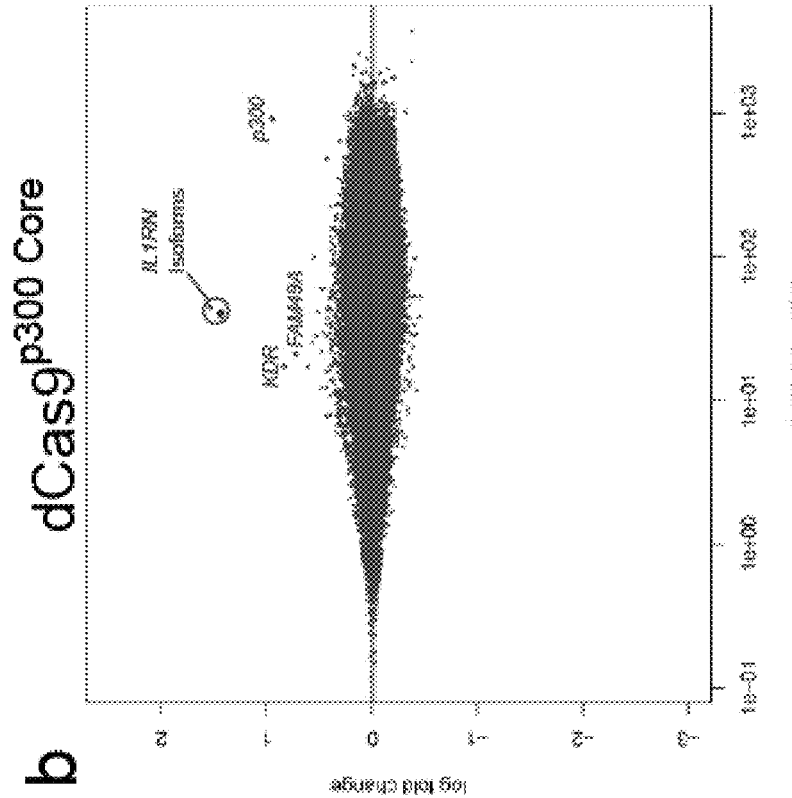
FIGS. 3A-3C show that dCas9$^{p300\ Core}$ targeted transcriptional activation is specific and robust.
Figure 3A:
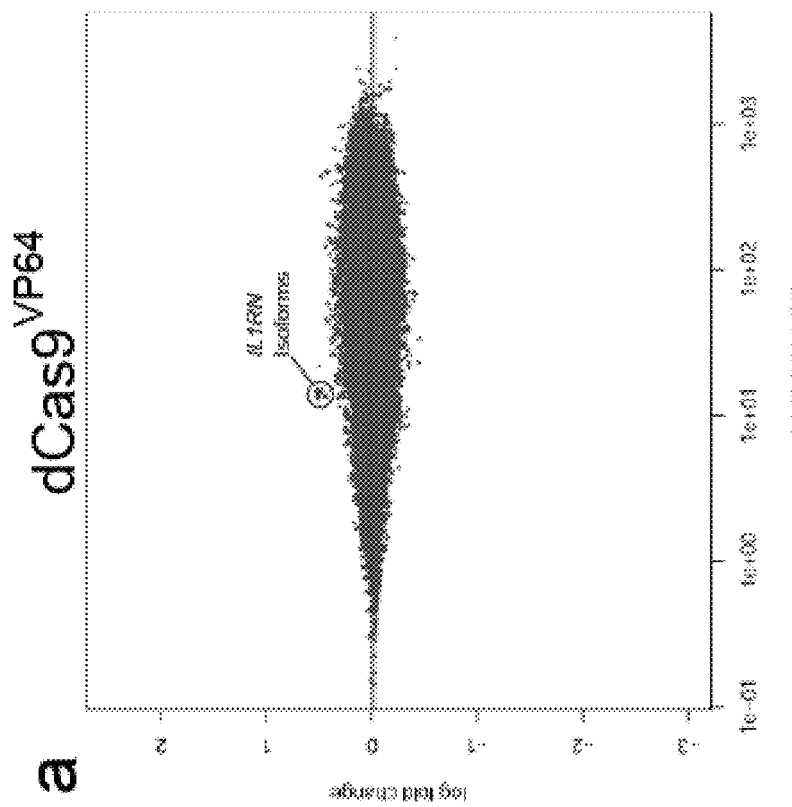
Figure 3C:
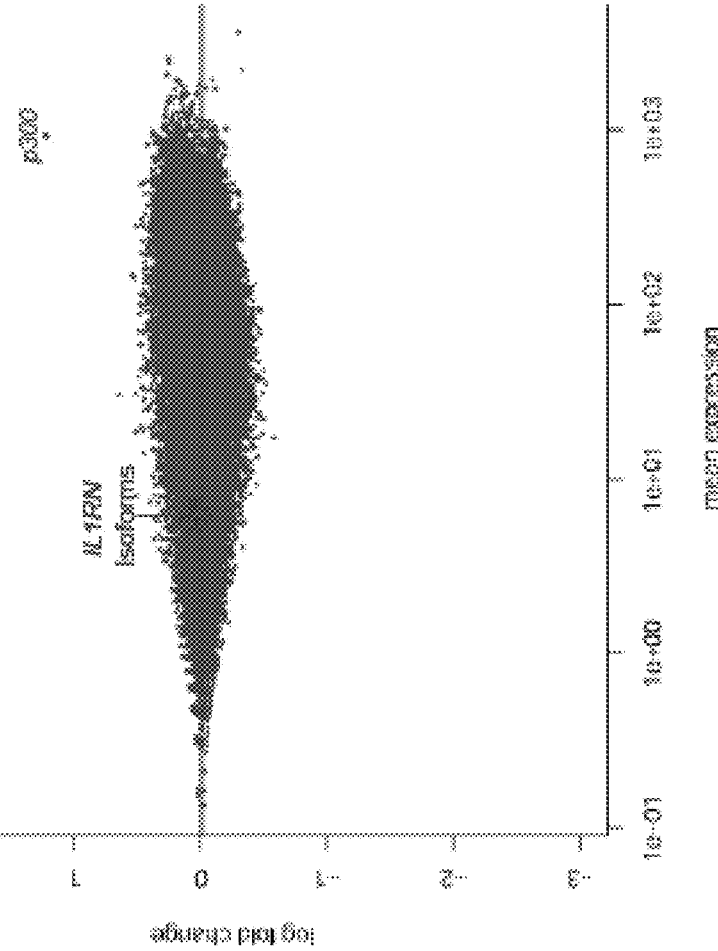

Recent reports indicate that dCas9 may have widespread off-target binding events in mammalian cells in combination with some gRNAs, which could potentially lead to off-target changes in gene expression. In order to assess the transcriptional specificity of the dCas9$^{p300\ Core}$ fusion protein, transcriptome was performed profiling by RNA-seq in cells co-transfected with four IL1RN-targeted gRNAs and either dCas9, dCas9$^{VP64}$, dCas9$^{p300\ Core}$, or dCas9$^{p300\ Core\ (D1399Y)}$. Genome-wide transcriptional changes were compared between dCas9 with no fused effector domain and either dCas9$^{VP64}$, dCas9$^{p300\ Core}$, or dCas9$^{p300\ Core\ (D1399Y)}$ (FIGS. 3A-3C). While both dCas9$^{VP64}$ and dCas9$^{p300\ Core}$ upregulated all four IL1RN isoforms, only the effects of dCas9$^{p300\ Core}$ reached genome-wide significance (FIGS. 3A-3B, Table 6; P-value $1.0 \times 10^{-3}$-$5.3 \times 10^{-4}$ for dCas9$^{VP64}$; P-value $1.8 \times 10^{-17}$-$1.5 \times 10^{-19}$ for dCas9$^{p300\ Core}$)

TABLE 6

Ten most enriched mRNAs for dCas9 IL1RN-targeted RNA-seq experiments

| | Refseq ID | Gene | Base Mean | log2 Fold Change | lfcSE | stat | pvalue | padj |
|---|---|---|---|---|---|---|---|---|
| | | dCas9$^{VP64}$ + 4 IL1RN gRNAs compared to dCas9 + 4 IL1RN gRNAs | | | | | | |
| 1 | NM_173842 | IL1RN (transcript variant 1) | 14.764 | 0.529 | 0.152 | 3.48 | 0.000494857 | 0.99992134 |
| 2 | NM_173843 | IL1RN (transcript variant 4) | 13.606 | 0.517 | 0.149 | 3.47 | 0.000530109 | 0.99992134 |
| 3 | NR_073102 | ZNF551 | 21.505 | 0.505 | 0.159 | 3.17 | 0.00152863 | 0.99992134 |
| 4 | NM_000577 | IL1RN (transcript variant 3) | 14.890 | 0.497 | 0.152 | 3.28 | 0.001039353 | 0.99992134 |
| 5 | NM_001077441 | BCLAF1 (transcript variant 3) | 437.814 | 0.482 | 0.153 | 3.14 | 0.001665925 | 0.99992134 |
| 6 | NM_173841 | IL1RN (transcript variant 2) | 13.711 | 0.448 | 0.15 | 3.00 | 0.002716294 | 0.99992134 |
| 7 | NM_001268 | RCBTB2 | 46.265 | 0.440 | 0.167 | 2.64 | 0.008335513 | 0.99992134 |
| 8 | NM_000922 | PDE3B | 143.947 | 0.439 | 0.167 | 2.63 | 0.008471891 | 0.99992134 |
| 9 | NM_001077440 | BCLAF1 (transcript variant 2) | 463.743 | 0.439 | 0.156 | 2.82 | 0.004790762 | 0.99992134 |
| 10 | NM_014739 | BCLAF1 (transcript variant 1) | 474.598 | 0.432 | 0.158 | 2.74 | 0.006232218 | 0.99992134 |
| | | dCas9$^{p300\ Core}$ + 4 IL1RN gRNAs compared to dCas9 + 4 IL1RN gRNAs | | | | | | |
| 1 | NM_173843 | IL1RN (transcript variant 4) | 45.517 | 1.548 | 0.171 | 9.04 | 1.52E−19 | 5.24E−15 |
| 2 | NM_173841 | IL1RN (transcript variant 2) | 40.690 | 1.457 | 0.171 | 8.50 | 1.83E−17 | 3.16E−13 |
| 3 | NM_173842 | IL1RN (transcript variant 1) | 39.568 | 1.448 | 0.171 | 8.45 | 2.88E−17 | 3.30E−13 |
| 4 | NM_000577 | IL1RN (transcript variant 3) | 41.821 | 1.437 | 0.171 | 8.39 | 4.88E−17 | 4.20E−13 |
| 5 | NM_001429 | p300 | 928.435 | 0.955 | 0.171 | 5.57 | 2.50E−08 | 0.000171838 |
| 6 | NM_002253 | KDR | 17.477 | 0.842 | 0.163 | 5.17 | 2.36E−07 | 0.00135472 |
| 7 | NM_030797 | FAM49A | 21.286 | 0.736 | 0.166 | 4.44 | 8.91E−06 | 0.043823927 |

TABLE 6-continued

Ten most enriched mRNAs for dCas9 IL1RN-targeted RNA-seq experiments

| Refseq ID | Gene | Base Mean | log2 Fold Change | lfcSE | stat | pvalue | padj |
|---|---|---|---|---|---|---|---|
| 8 NM_012074 | DPF3 | 17.111 | 0.609 | 0.164 | 3.72 | 0.000202676 | 0.871938986 |
| 9 NM_031476 | CRISPLD2 | 25.148 | 0.569 | 0.167 | 3.41 | 0.000653132 | 0.999954424 |
| 10 NM_007365 | PADI2 | 99.012 | 0.554 | 0.162 | 3.41 | 0.000641145 | 0.999954424 |
| dCas9$^{p300\ Core\ (D1399Y)}$ + 4 IL1RN gRNAs compared to dCas9 + 4 IL1RN gRNAs | | | | | | | |
| 1 NM_001429 | p300 | 935.659 | 1.234 | 0.198 | 6.24 | 4.36E−10 | 1.49E−05 |
| 2 NM_001270493 | SREK1 (transcript variant 4) | 30.118 | 0.651 | 0.203 | 3.20 | 0.001388089 | 0.999938051 |
| 3 NM_001079802 | FKTN (transcript variant 1) | 148.558 | 0.546 | 0.203 | 2.69 | 0.007212168 | 0.999938051 |
| 4 NM_000922 | PDE3B | 140.122 | 0.535 | 0.201 | 2.66 | 0.007805491 | 0.999938051 |
| 5 NM_206937 | LIG4 (transcript variant 2) | 30.589 | 0.521 | 0.203 | 2.56 | 0.010513626 | 0.999938051 |
| 6 NM_001136116 | ZNF879 | 18.421 | 0.520 | 0.201 | 2.59 | 0.009600802 | 0.999938051 |
| 7 NM_018374 | TMEM106B (transcript variant 1) | 280.758 | 0.516 | 0.196 | 2.64 | 0.008329592 | 0.999938051 |
| 8 NM_019863 | F8 (transcript variant 2) | 8.048 | 0.515 | 0.178 | 2.89 | 0.003827553 | 0.999938051 |
| 9 NM_001193349 | MEF2C (transcript variant 5) | 18.934 | 0.510 | 0.202 | 2.53 | 0.011492452 | 0.999938051 |
| 10 NM_183245 | INVS (transcript variant 2) | 38.545 | 0.497 | 0.203 | 2.45 | 0.014125973 | 0.999938051 |

In contrast, dCas9$^{p300\ Core\ (D1399Y)}$ did not significantly induce any IL1RN expression (FIG. 3C; P-value>0.5 for all 4 IL1RN isoforms). Comparative analysis to dCas9 revealed limited dCas9$^{p300\ Core}$ off-target gene induction, with only two transcripts induced significantly above background at a false discovery rate (FDR)<5%: KDR (FDR=1.4×10$^{-3}$); and FAM49A (FDR=0.04) (FIG. 3B, Table 6). Increased expression of p300 mRNA was observed in cells transfected with dCas9$^{p300\ Core}$ and dCas9$^{p300\ Core\ (D1399Y)}$. This finding is most likely explained by RNA-seq reads mapping to mRNA from the transiently transfected p300 core fusion domains. Thus the dCas9$^{p300\ Core}$ fusion displayed high genome-wide targeted transcriptional specificity and robust gene induction of all four targeted IL1RN isoforms.

Example 5 dCas9$^{p300}$ Core Acetylates H3K27 at Enhancers and Promoters

Figure 4A:
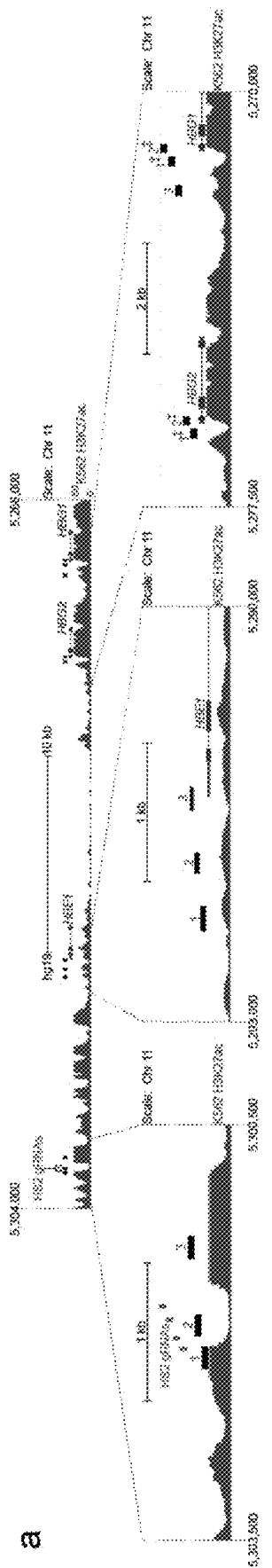
FIGS. 4A-4D show that dCas9$^{p300\ Core}$ fusion protein acetylates chromatin at a targeted enhancer and corresponding downstream genes.
Figures 4B, 4C:
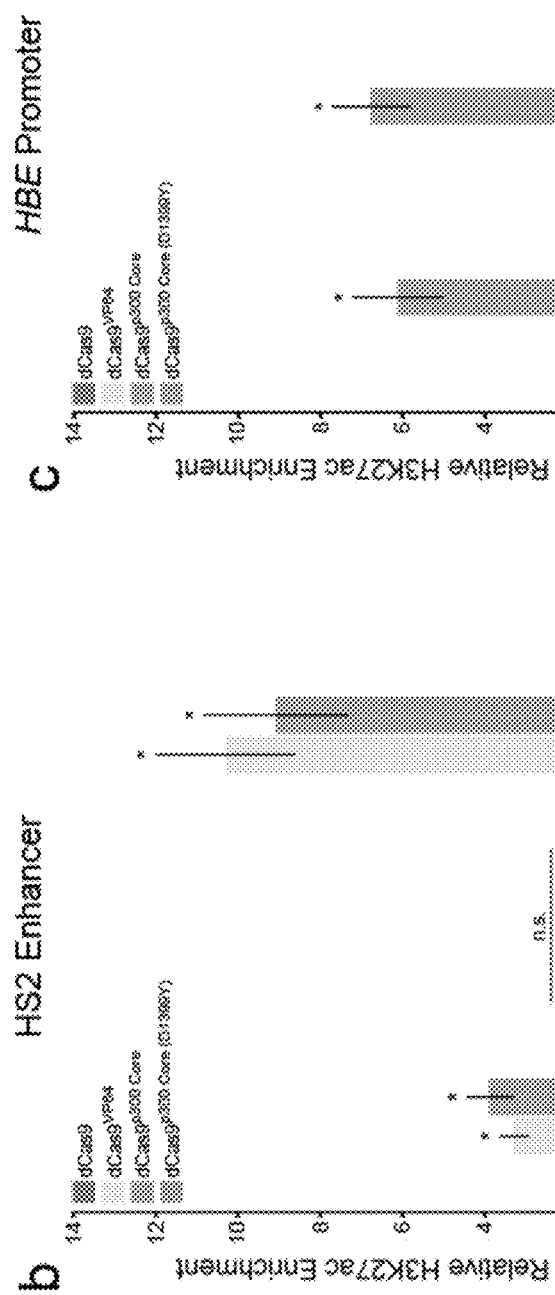

Activity of regulatory elements correlates with covalent histone modifications such as acetylation and methylation. Of those histone modifications, acetylation of lysine 27 on histone H3 (H3K27ac) is one of the most widely documented indicators of enhancer activity. Acetylation of H3K27 is catalyzed by p300 and is also correlated with endogenous p300 binding profiles. Therefore H3K27ac enrichment was used as a measurement of relative dCas9$^{p300\ Core}$-mediated acetylation at the genomic target site. To quantify targeted H3K27 acetylation by dCas9$^{p300\ Core}$ chromatin immuno-precipitation was performed with an anti-H3K27ac antibody followed by quantitative PCR (ChIP-qPCR) in HEK293T cells co-transfected with four HS2 enhancer-targeted gRNAs and either dCas9, dCas9$^{VP64}$, dCas9$^{p300\ Core}$ or dCas9$^{p300\ Core\ (D1399Y)}$ (FIGS. 4A-4D). Three amplicons were analyzed at or around the target site in the HS2 enhancer or within the promoter regions of the HBE and HBG genes (FIG. 4A). Notably, H3K27ac is enriched in each of these regions in the human K562 erythroid cell line that has a high level of globin gene expression (FIG. 4A). Significant H3K27ac enrichment was observed at the HS2 enhancer target locus compared to treatment with dCas9 in both the dCas9$^{VP64}$ (P-value 0.0056 for ChIP Region 1 and P-value 0.0029 for ChIP Region 3) and dCas9$^{p300\ Core}$ (P-value 0.0013 for ChIP Region 1 and P-value 0.0069 for ChIP Region 3) co-transfected samples (FIG. 4B).

Figure 10:
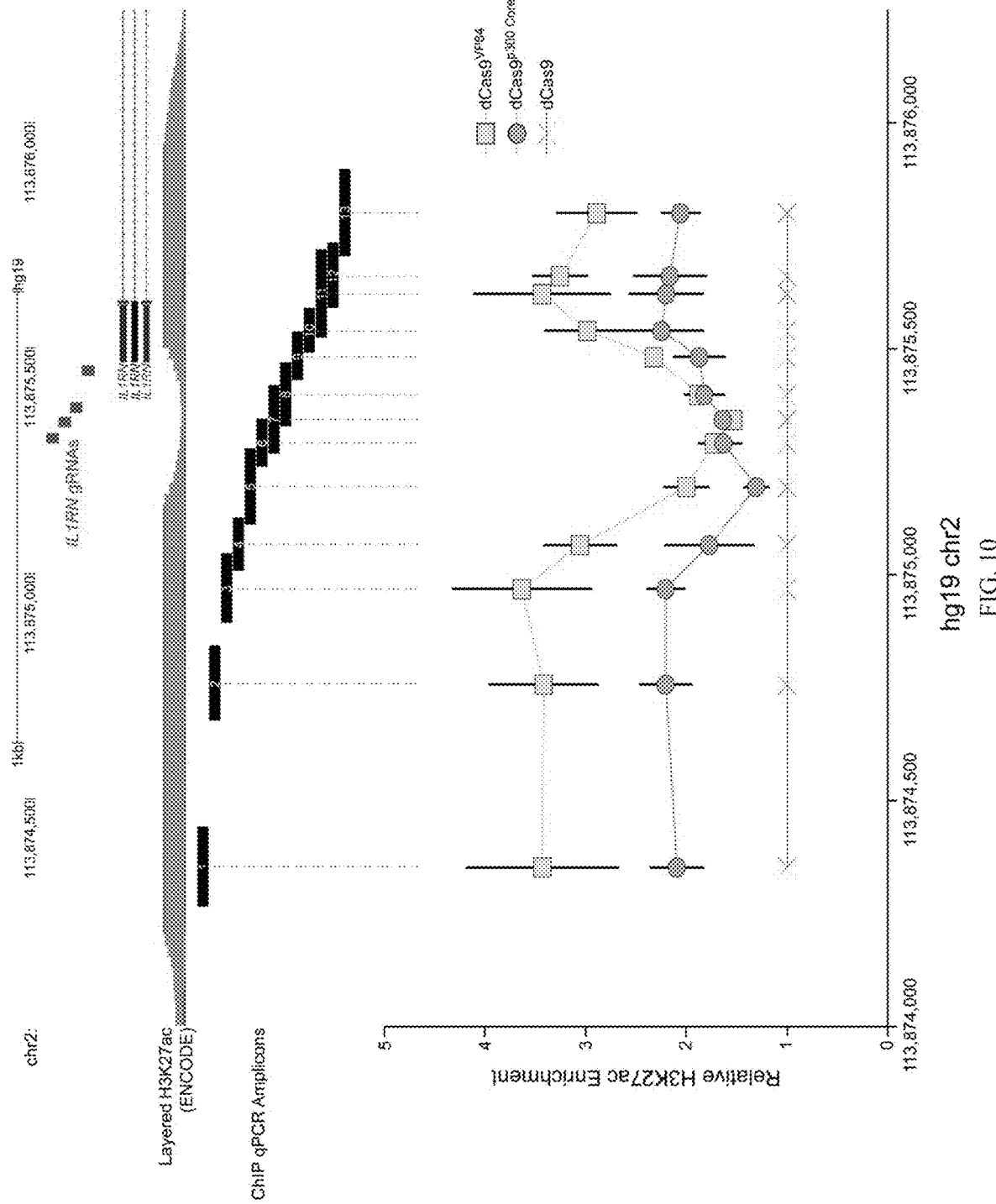
FIG. 10 shows that dCas9$^{VP64}$ and dCas9$^{p300\ Core}$ induce H3K27ac enrichment at IL1RN gRNA-targeted chromatin.

A similar trend of H3K27ac enrichment was also observed when targeting the IL1RN promoter with dCas9$^{VP64}$ or dCas9$^{p300\ Core}$ (FIG. 10). FIG. 10 shows the IL1RN locus on GRCh37/hg19 along with IL1RN gRNA target sites. In addition, layered ENCODE H3K27ac enrichment from seven cell lines (GM12878, H1-hESC, HSMM, HUVEC, K562, NHEK, and NHLF) is indicated with the vertical range setting set to 50. Tiled IL1RN ChIP qPCR amplicons (1-13) are also shown in corresponding locations on GRCh37/hg19. H3K27ac enrichment for dCas9$^{VP64}$ and dCas9$^{p300\ Core}$ co-transfected with four IL1RN-targeted gRNAs and normalized to dCas9 co-transfected with four IL1RN gRNAs is indicated for each ChIP qPCR locus assayed. 5 ng of ChIP-prepared DNA was used for each reaction (n=3 independent experiments, error bars: s.e.m.).

Figure 4D:
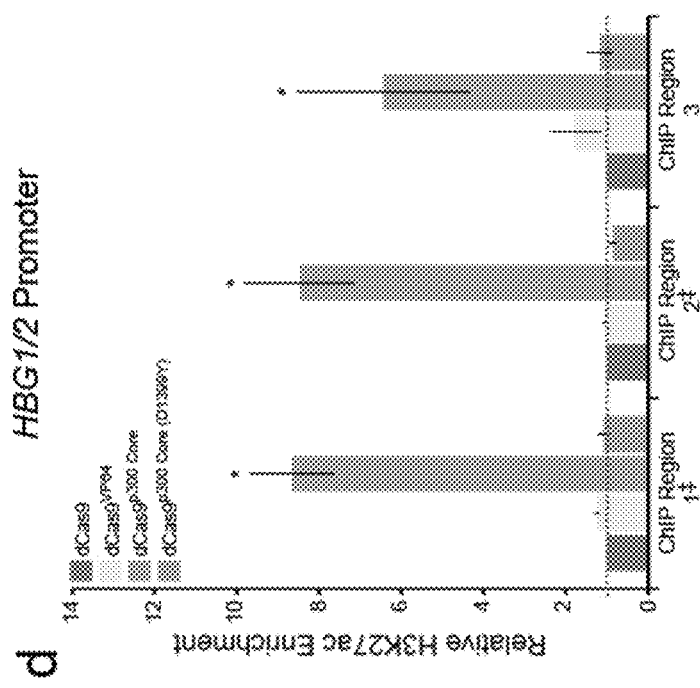

In contrast to these increases in H3K27ac at the target sites by both dCas9$^{VP64}$ or dCas9$^{p300\ Core}$, robust enrichment in H3K27ac at the HS2-regulated HBE and HBG promoters was observed only with dCas9$^{p300\ Core}$ treatment (FIGS. 4C-4D). Together these results demonstrate that dCas9$^{p300\ Core}$ uniquely catalyzes H3K27ac enrichment at gRNA-targeted loci and at enhancer-targeted distal promoters. Therefore the acetylation established by dCas9$^{p300\ Core}$ at HS2 may catalyze enhancer activity in a manner distinct from direct recruitment of preinitiation complex components by dCas9$^{VP64}$, as indicated by the distal activation of the HBE, HBG, and HBD genes from the HS2 enhancer by dCas9$^{p300\ Core}$ but not by dCas9$^{VP64}$ (FIG. 2C, FIGS. 9A-9E).

Example 6 dCas9$^{p300\ Core}$ Activates Genes with a Single gRNA

Figures 5A, 5B:
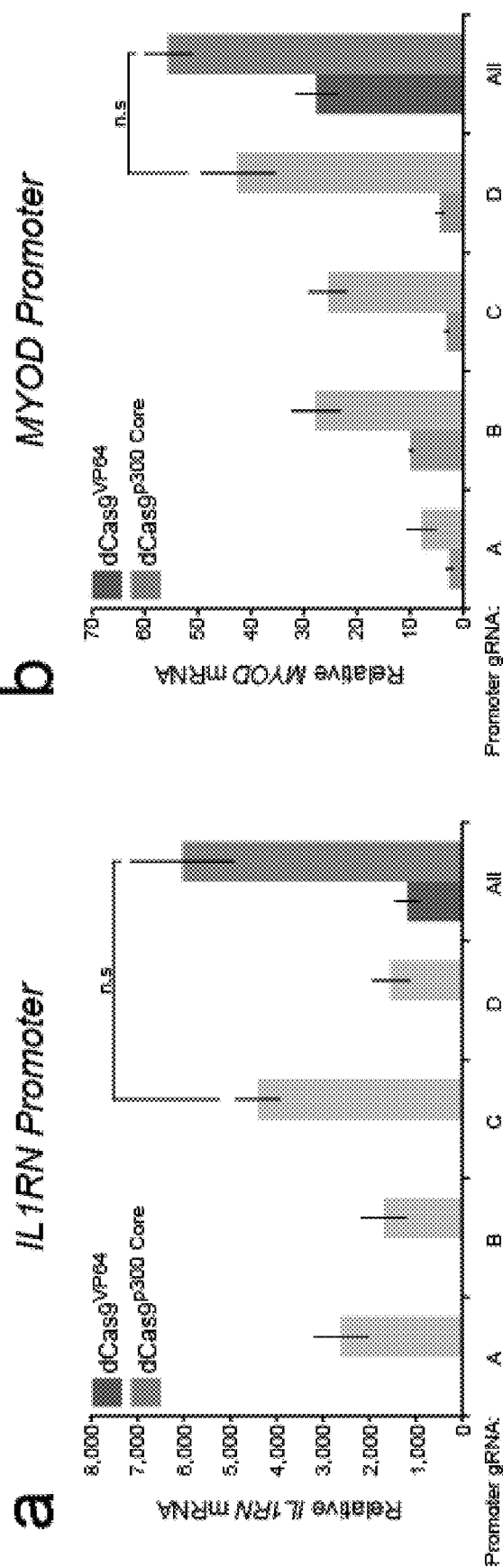
Figure 5D:
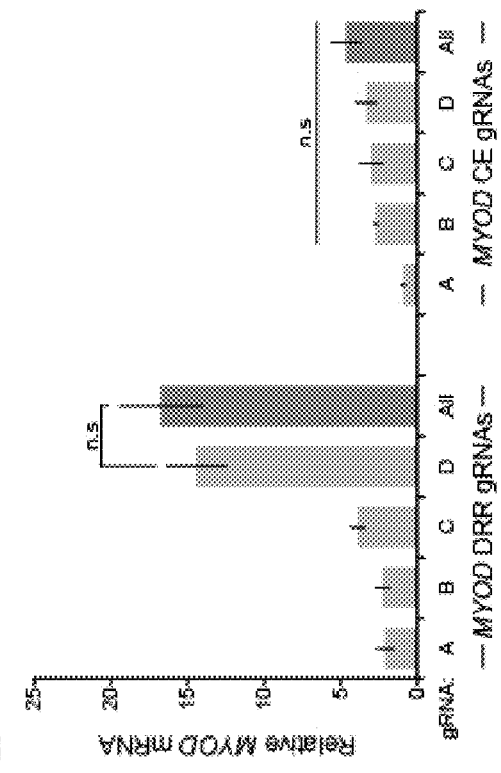
Figure 5C:
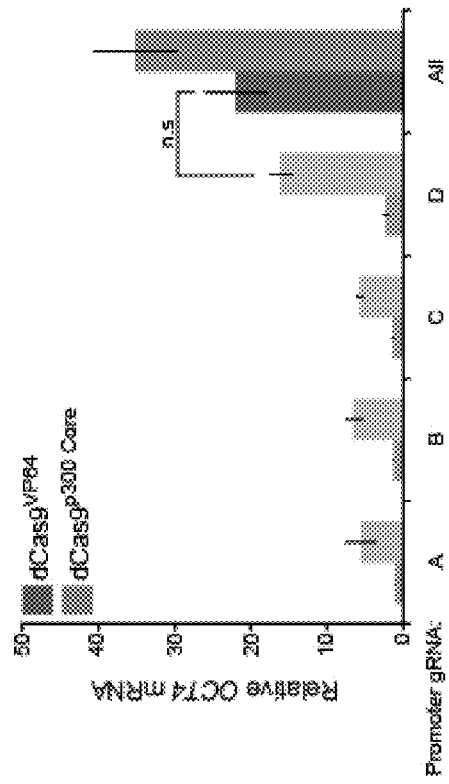

Robust transactivation using dCas9-effector fusion proteins currently relies upon the application of multiple gRNAs, multiple effector domains, or both. Transcriptional activation could be simplified with the use of single gRNAs in tandem with a single dCas9-effector fusion. This would also facilitate multiplexing distinct target genes and the incorporation of additional functionalities into the system. The transactivation potential of dCas9$^{p300\ Core}$ with single gRNAs was compared to that of dCas9$^{p300\ Core}$ with four pooled gRNAs targeting the IL1RN, MYOD and OCT4 promoters (FIGS. 5A-5B). Substantial activation was observed upon co-transfection of the dCas9$^{p300\ Core}$ and a single gRNA at each promoter tested. For the IL1RN and MYOD promoters, there was no significant difference between the pooled gRNAs and the best individual gRNA (FIGS. 5A-5B; IL1RN gRNA "C", P-value 0.78; MYOD gRNA "D", P-value 0.26). Although activation of the OCT4 promoter produced additive effects when four gRNAs were pooled with dCas9$^{p300\ Core}$ the most potent single gRNA (gRNA "D") induced a statistically comparable amount of gene expression to that observed upon co-transfection of dCas9$^{VP64}$ with an equimolar pool of all four promoter gRNAs (P-value 0.73; FIG. 5C). Compared to dCas9$^{p300\ Core}$, levels of gene activation with dCas9$^{VP64}$ and single gRNAs were substantially lower. Also, in contrast to dCas9$^{p300\ Core}$, dCas9$^{VP64}$ demonstrated synergistic effects with combinations of gRNAs in every case (FIGS. 5A-5C).

Based on the transactivation ability of dCas9$^{p300\ Core}$ at enhancer regions and with single gRNAs at promoter regions, it was hypothesized that dCas9$^{p300\ Core}$ might also be able to transactivate enhancers via a single targeted gRNA. The MYOD (DRR and CE), OCT4 (PE and DE), and HS2 enhancer regions were tested with equimolar concentrations of pools or single gRNAs (FIGS. 5D-5G). For both MYOD enhancer regions, co-transfection of dCas9$^{p300\ Core}$ and a single enhancer-targeting gRNA was sufficient to activate gene expression to levels similar to cells co-transfected with dCas9$^{p300\ Core}$ and the four pooled enhancer gRNAs (FIG. 5D). Similarly, OCT4 gene expression was activated from the PE via dCas9$^{p300\ Core}$ localization with a single gRNA to similar levels as dCas9$^{p300\ Core}$ localized with a pool of six PE-targeted gRNAs (FIG. 5E). dCas9$^{p300\ Core}$-mediated induction of OCT4 from the DE (FIG. 5E) and HBE and HBG genes from the HS2 enhancer (FIGS. 5F-5G) showed increased expression with the pooled gRNAs relative to single gRNAs. Nevertheless, there was activation of target gene expression above control for several single gRNAs at these enhancers (FIGS. 5E-5G).

Example 7

The p300 HAT Domain is Portable to Other DNA-Binding Proteins

Figures 6A, 6B:
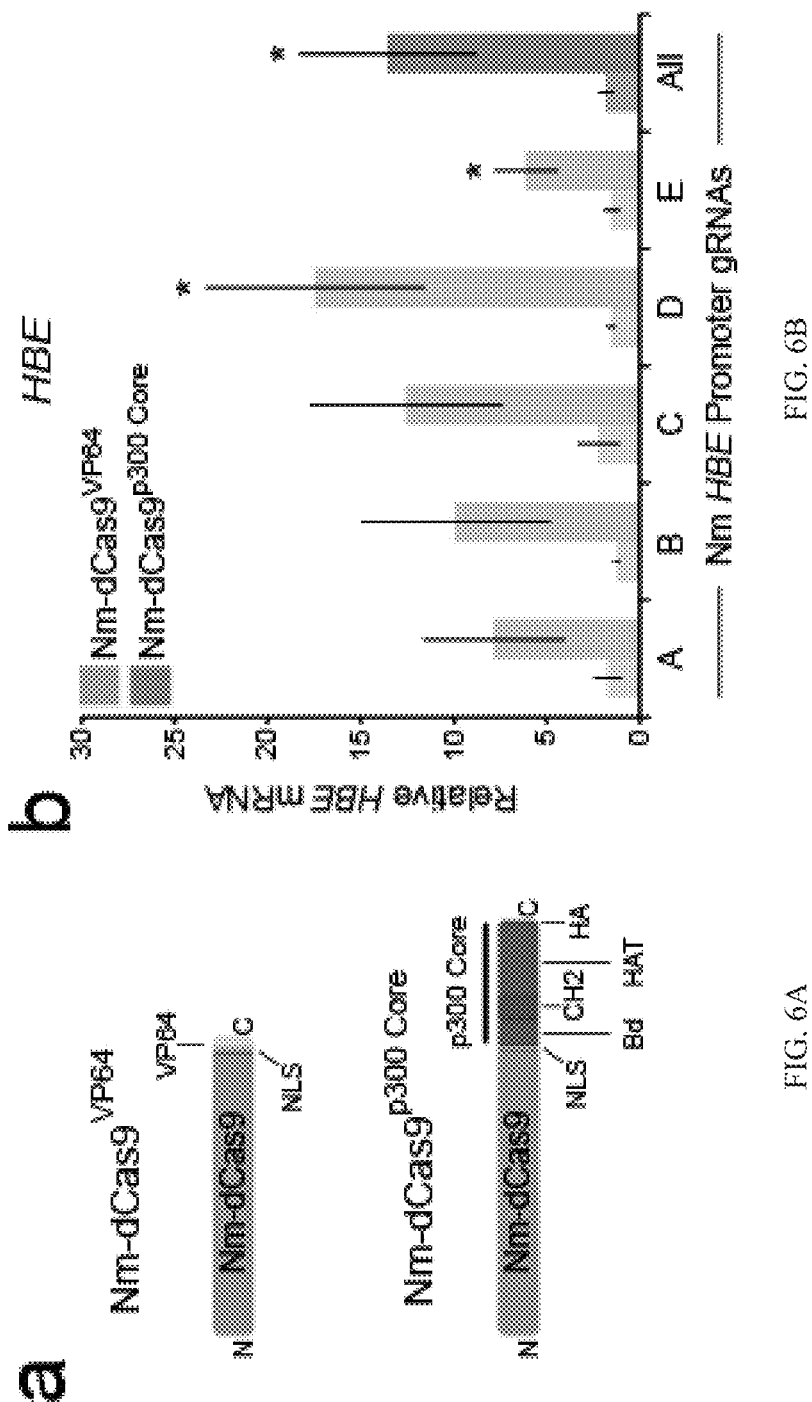
Figures 6C, 6D:
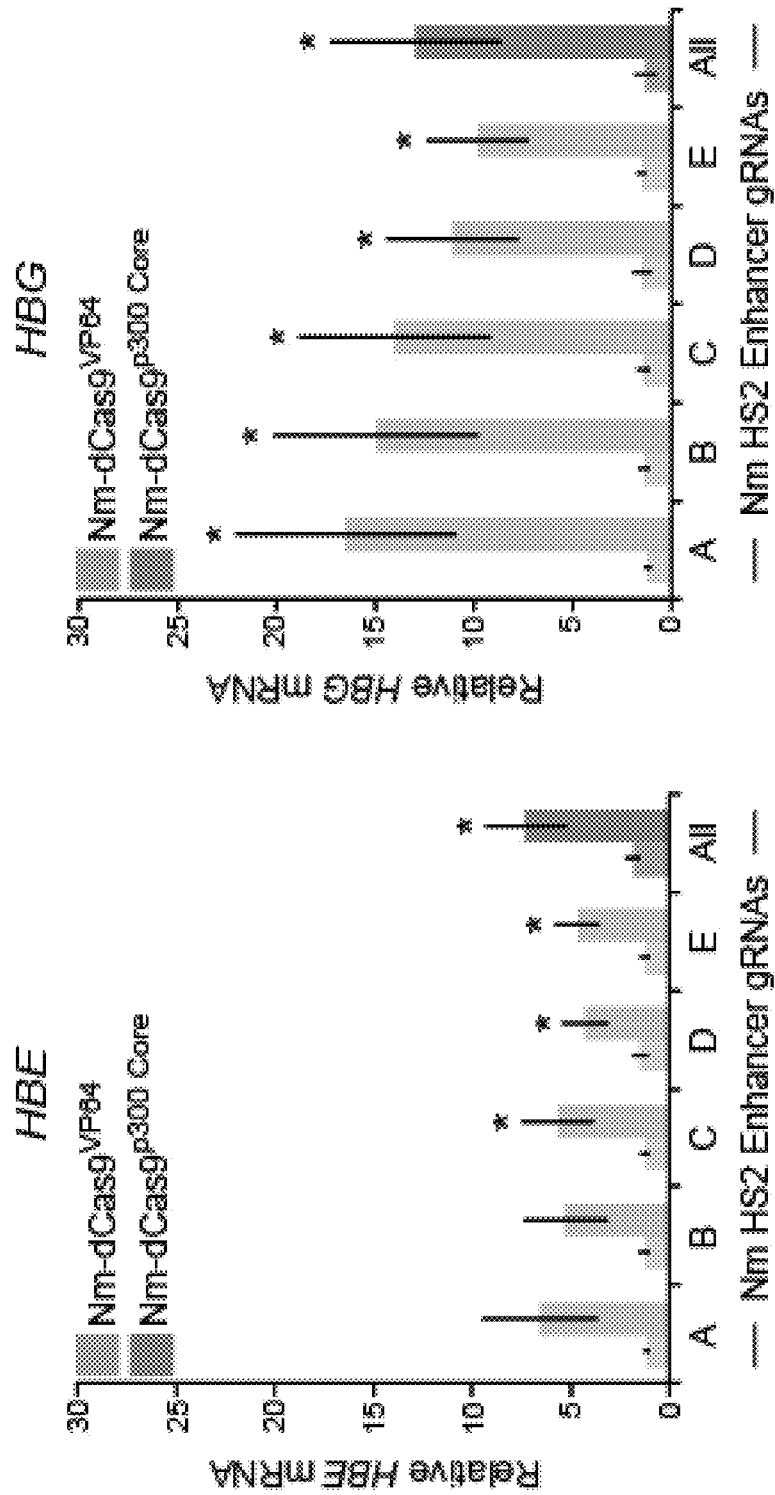
Figures 11A, 11B, 11C:
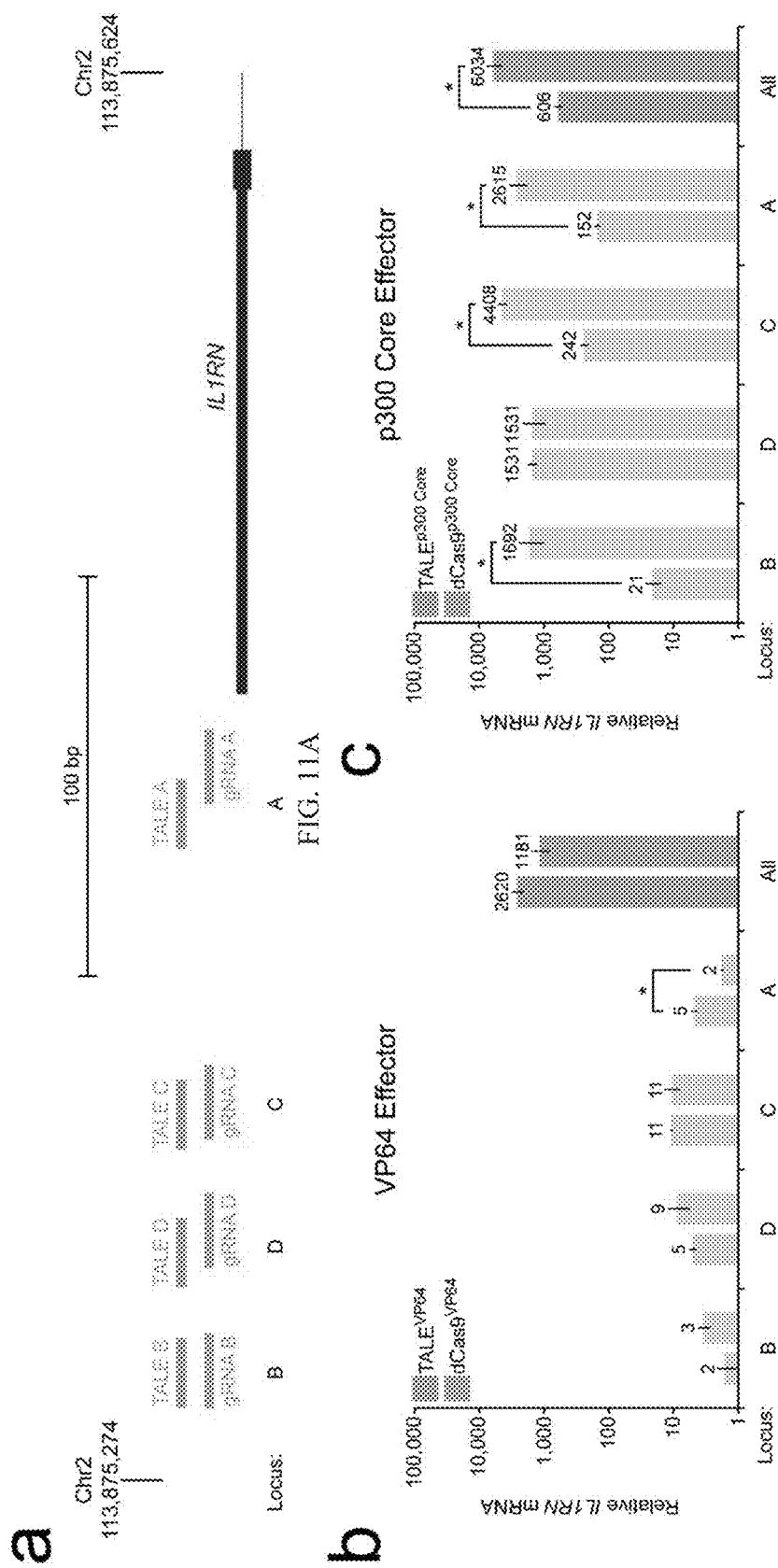
FIGS. 11A-11C show a direct comparison of VP64 and p300 Core effector domains between TALE and dCas9 programmable DNA binding proteins.
Figures 13A, 13B:
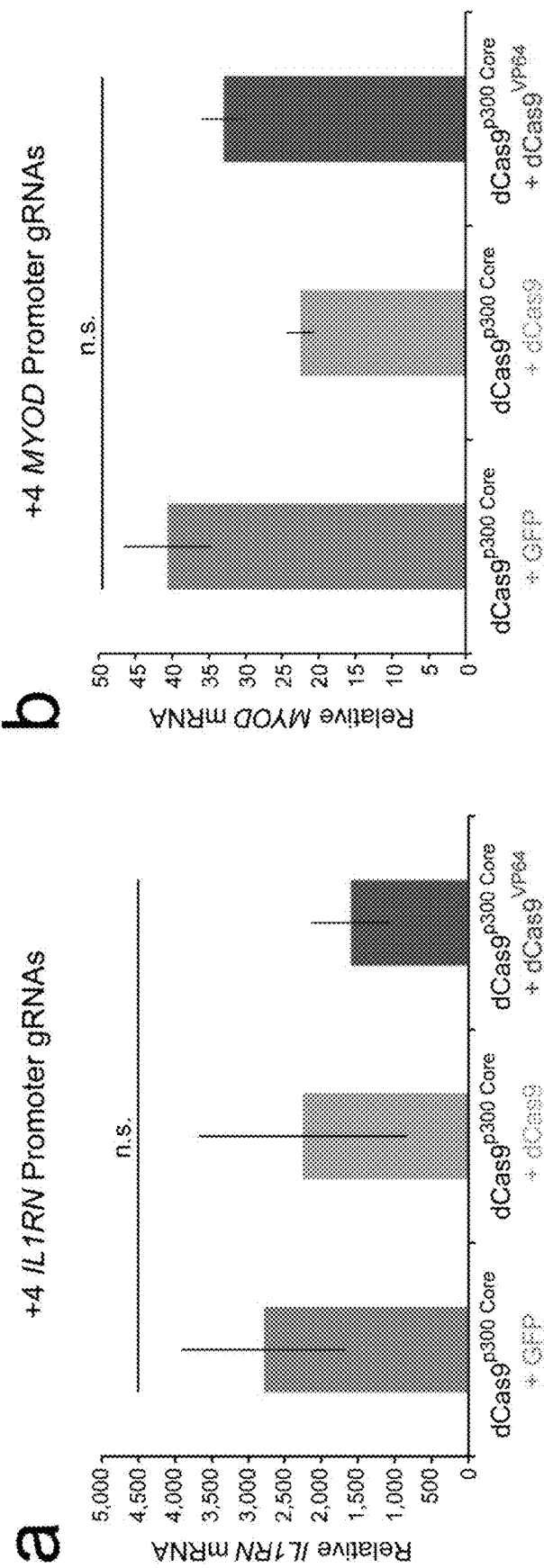
FIGS. 13A-13B show that dCas9$^{p300\ Core}$ and dCas9$^{VP64}$ do not display synergy in transactivation.

The dCas9/gRNA system from *Streptococcus pyogenes* has been widely adopted due to its robust, versatile, and easily programmable properties. However, several other programmable DNA-binding proteins are also under development for various applications and may be preferable for particular applications, including orthogonal dCas9 systems from other species, TALEs, and zinc finger proteins. To determine if the p300 Core HAT domain was portable to these other systems, fusions were created to dCas9 from *Neisseria meningitidis* (Nm-dCas9), four different TALEs targeting the IL1RN promoter, and a zinc finger protein targeting ICAM1 (FIGS. 6A-6H). Co-transfection of Nm-dCas9$^{p300\ Core}$ and five Nm-gRNAs targeted to the HBE or the HBG promoters led to significant gene induction compared to mock-transfected controls (P-value 0.038 and 0.0141 for HBE and HBG respectively) (FIG. 6B). When co-transfected with five Nm-gRNAs targeted to the HS2 enhancer, Nm-dCas9$^{p300\ Core}$ also significantly activated the distal HBE and HBG, globin genes compared to mock-transfected controls (p=0.0192 and p=0.0393, respectively) (FIGS. 6C-6D). Similar to dCas9$^{p300\ Core}$ Nm-dCas9$^{p300\ Core}$ activated gene expression from promoters and the HS2 enhancer via a single gRNA. Nm-dCas9$^{VP64}$ displayed negligible capacity to transactivate HBE or HBG regardless of localization to promoter regions or to the HS2 enhancer either with single or multiple gRNAs (FIGS. 6B-6D). Transfection of the expression plasmids for a combination of four TALE$^{p300\ Core}$ fusion proteins targeted to the IL1RN promoter (IL1RN TALE$^{p300\ Core}$) also activated downstream gene expression, although to a lesser extent than four corresponding TALE$^{VP64}$ fusions (IL1RN TALE$^{VP64}$) (FIGS. 6E-6F). However, single p300 Core effectors were much more potent than single VP64 domains when fused to IL1RN TALEs. Interestingly, dCas9$^{p300\ Core}$ directed to any single binding site generated comparable IL1RN expression relative to single or pooled IL1RN TALE effectors and direct comparisons suggest that dCas9 may be a more robust activator than TALEs when fused to the larger p300 Core fusion domain (FIGS. 11A-11C). The p300 Core effector domain did not display synergy with either additional gRNAs or TALEs (see FIGS. 5A-5G, 6A-6H, 9A-9E, and 11A-11C) or in combination with VP64 (see FIGS. 13A-13B). The underlying chromatin context of the dCas9p300 Core target loci is shown in FIGS. 14A-14E.

Figure 6H:
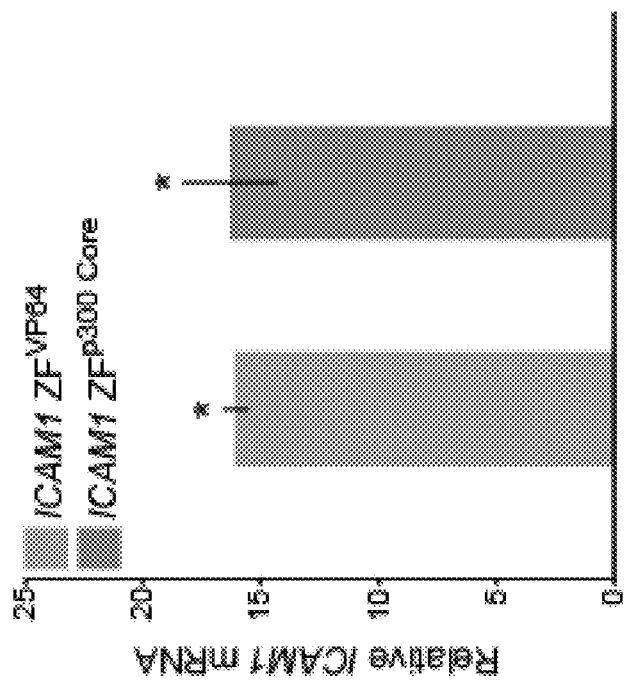
Figure 6G:
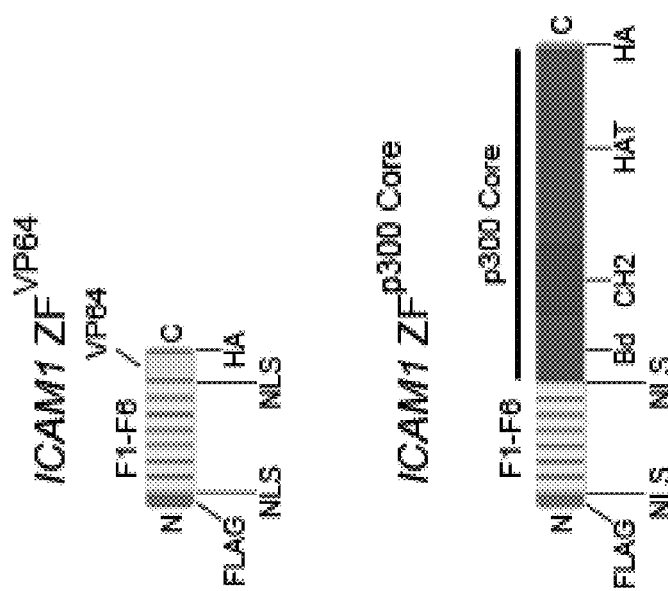
Figures 12A, 12B:
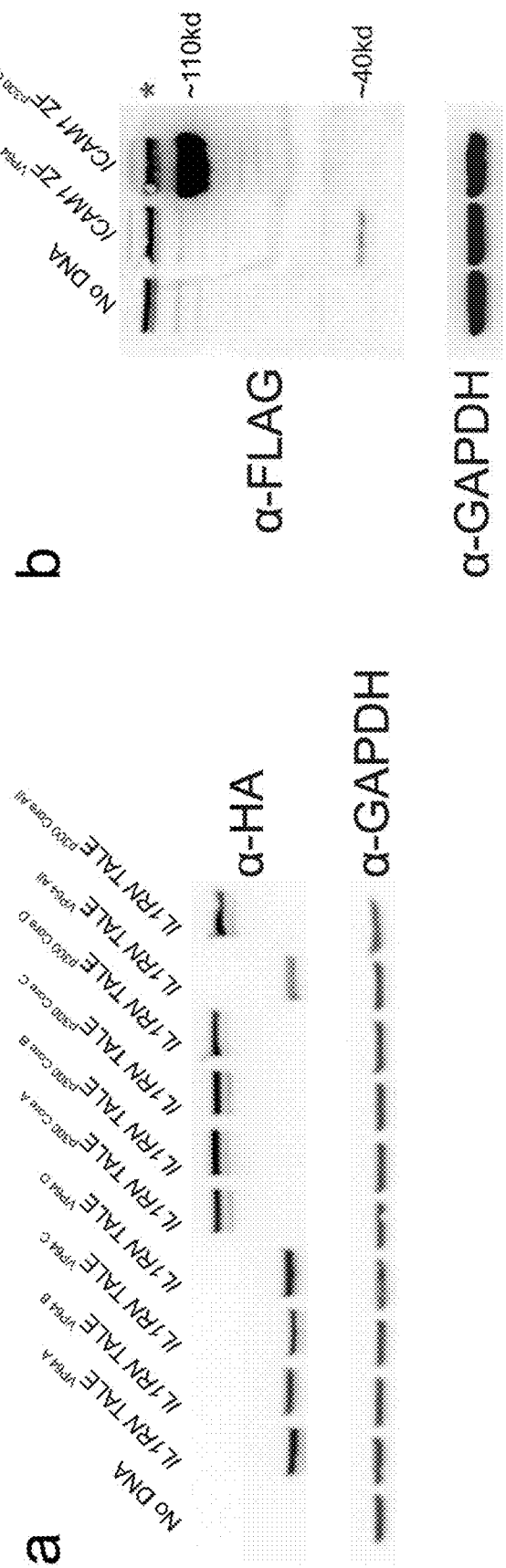
FIGS. 12A-12B show TALE and ZF fusion protein expression.

The ZF$^{p300\ Core}$ fusion targeted to the ICAM1 promoter (ICAM1 ZF$^{p300\ Core}$) also activated its target gene relative to control and at a similar level as ZF$^{VP64}$ (ICAM1 ZF$^{VP64}$) (FIGS. 6G-6H). The versatility of the p300 Core fusion with multiple targeting domains is evidence that this is a robust approach for targeted acetylation and gene regulation. The various p300 core fusion proteins were expressed well, as determined by western blot (FIGS. 12A-12B), but differences in p300 Core activity between different fusion proteins could be attributable to binding affinity or protein folding.

Example 8

Myocardin 36 gRNAs were designed to span −2000 bp to +250 bp (coordinates relative to TSS) region of the MYOCD gene (Table 7).

TABLE 7

Myocd gRNAs Information

| Target Name | gRNA Name | Protospacer (N20) | SEQ ID NO | PAM | SEQ ID NO | +/− | Length | Coordinates Relative to TSS |
|---|---|---|---|---|---|---|---|---|
| Myocd | Cr1 | cctggtcttcaatgagaaga | 152 | NGG | 188 | − | 20 | −1991 −1971 |
| Myocd | Cr2 | gattaggacatgaacatggg | 153 | NGG | 189 | − | 20 | −1897 −1877 |
| Myocd | Cr3 | cctcttctacattaacctta | 154 | NGG | 190 | − | 20 | −1771 −1751 |

TABLE 7-continued

Myocd gRNAs Information

| Target Name | gRNA Name | Protospacer (N20) | SEQ ID NO | PAM | SEQ ID NO | +/- | Length | Coordinates Relative to TSS | |
|---|---|---|---|---|---|---|---|---|---|
| Myocd | Cr4  | tttttgaagccagcaatcgt | 155 | NGG | 191 | - | 20 | -1693 | -1673 |
| Myocd | Cr5  | cgttagtttctggaggctct | 156 | NGG | 192 | - | 20 | -1597 | -1577 |
| Myocd | Cr6  | acaaattaccacgaatgtag | 157 | NGG | 193 | - | 20 | -1480 | -1460 |
| Myocd | Cr7  | tggcctgggcgcctgtctat | 158 | NGG | 194 | - | 20 | -1395 | -1375 |
| Myocd | Cr8  | attttgtaaataaggtcttc | 159 | NGG | 195 | - | 20 | -1297 | -1277 |
| Myocd | Cr9  | agcaacaggggatggggcag | 160 | NGG | 196 | + | 20 | -1221 | -1201 |
| Myocd | Cr10 | aggactcgtagtatgcaggc | 161 | NGG | 197 | + | 20 | -1120 | -1100 |
| Myocd | Cr11 | ctgagccaccaactatttaa | 162 | NGG | 198 | + | 20 | -1005 | -985 |
| Myocd | Cr12 | ctgagccaccaactatttaa | 163 | NGG | 199 | + | 20 | -945 | -925 |
| Myocd | Cr13 | actctgggtcggttacggaa | 164 | NGG | 200 | + | 20 | -907 | -887 |
| Myocd | Cr14 | gggctgggcttagcttggga | 165 | NGG | 201 | - | 20 | -837 | -817 |
| Myocd | Cr15 | atagggaggggctctggagc | 166 | NGG | 202 | - | 20 | -798 | -778 |
| Myocd | Cr16 | atgggaaaagatacctgagt | 167 | NGG | 203 | - | 20 | -751 | -731 |
| Myocd | Cr17 | tgggagcgttgtgtcgcagc | 168 | NGG | 204 | + | 20 | -713 | -693 |
| Myocd | Cr18 | tggaaaggcttcatttct   | 169 | NGG | 205 | - | 20 | -642 | -622 |
| Myocd | Cr19 | gtatctcgcagctccaatac | 170 | NGG | 206 | - | 20 | -594 | -574 |
| Myocd | Cr20 | acgcattccctcggtttga  | 171 | NGG | 207 | - | 20 | -544 | -524 |
| Myocd | Cr21 | tcggaagcttttcttctcag | 172 | NGG | 208 | + | 20 | -511 | -491 |
| Myocd | Cr22 | cgaaagggcgtgcgcgcccg | 173 | NGG | 209 | - | 20 | -449 | -429 |
| Myocd | Cr23 | ccggcgaaagggaagcggcc | 174 | NGG | 210 | - | 20 | -396 | -376 |
| Myocd | Cr24 | ggctgcgcacgcccatcccc | 175 | NGG | 211 | + | 20 | -352 | -332 |
| Myocd | Cr25 | ggggcttgcaggtggttcgc | 176 | NGG | 212 | - | 20 | -297 | -277 |
| Myocd | Cr26 | cgagctaaagagcggatgcc | 177 | NGG | 213 | - | 20 | -246 | -226 |
| Myocd | Cr27 | agagggcgggagcagggcca | 178 | NGG | 214 | - | 20 | -200 | -180 |
| Myocd | Cr28 | aaccggctcttaactctttg | 179 | NGG | 215 | - | 20 | -153 | -133 |
| Myocd | Cr29 | caggagcggcgagcgggtc  | 180 | NGG | 216 | - | 20 | -101 | -81 |
| Myocd | Cr30 | gggtatcagatggcaaagtt | 181 | NGG | 217 | + | 20 | -54 | -34 |
| Myocd | Cr31 | tcataggctgccggcgattg | 182 | NGG | 218 | - | 20 | 0 | 20 |
| Myocd | Cr32 | gaggttggccaggagcagcg | 183 | NGG | 219 | - | 20 | 47 | 67 |
| Myocd | Cr33 | aattagccccgcacggcgag | 184 | NGG | 220 | + | 20 | 100 | 120 |
| Myocd | Cr34 | tccctgggtaggagtacag  | 185 | NGG | 221 | - | 20 | 157 | 177 |
| Myocd | Cr35 | ggttgttagctgcggtcagc | 186 | NGG | 222 | + | 20 | 203 | 223 |
| Myocd | Cr36 | ggtggagaacaggggcgcc  | 187 | NGG | 223 | + | 20 | 246 | 266 |

Figure 17:
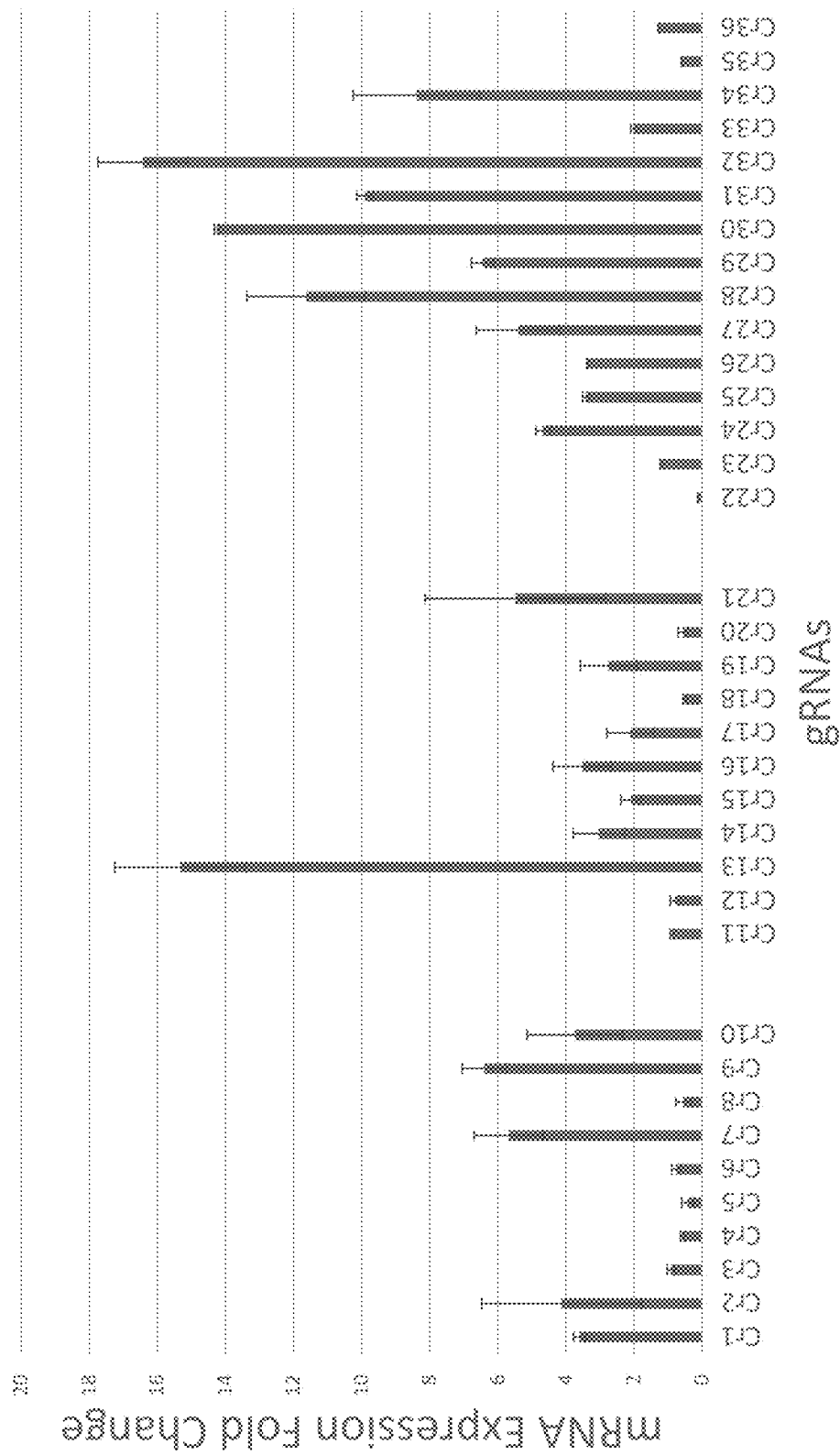
FIG. 17 shows gRNA design and screening.
Figure 18:
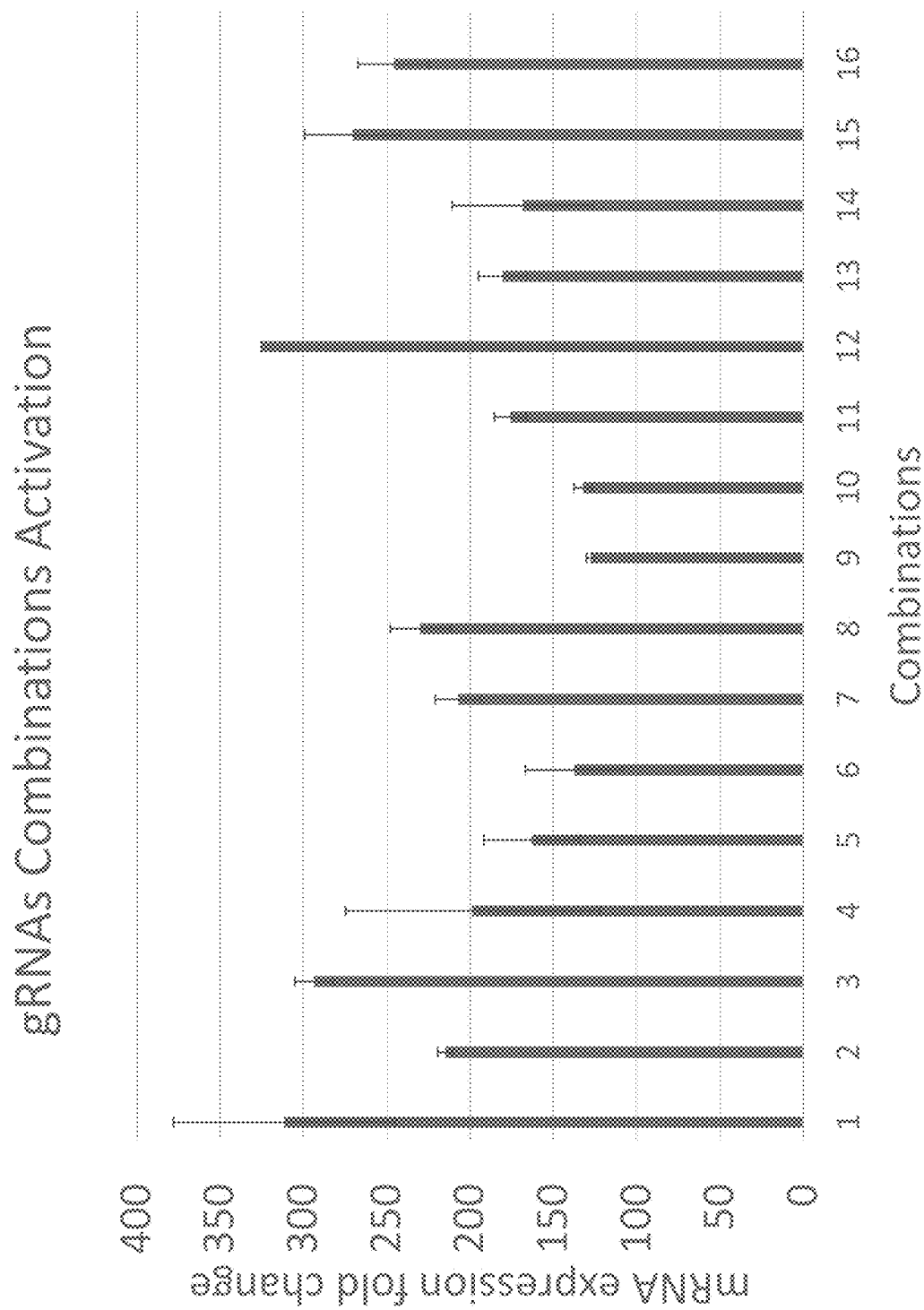
FIG. 18 shows gRNA combination activation.

The gRNAs were cloned into a spCas9 gRNA expression vector containing hU6 promoter and BbsI restriction site. The gRNAs were transiently co-transfected with dCas9$^{p300\ Core}$ into BTEK293T cells. The resulting mRNA production for myocardin was assayed in samples harvested three days post-transfection (FIG. 17). Combinations of Cr32, Cr13, Cr30, Cr28, Cr31, and Cr34 were analyzed with dCas9$^{p300\ Core}$ (Table 8; FIG. 18).

TABLE 8

| Condition | Cr32 | Cr13 | Cr30 | Cr28 | Cr31 | Cr34 |
|---|---|---|---|---|---|---|
| 1 | X | X | X | X | X | X |
| 2 | X | X | X | X | | |
| 3 | X | X | X | | X | |
| 4 | X | X | X | | | X |
| 5 | X | X | | X | X | |
| 6 | X | X | | | X | X |
| 7 | X | X | | X | | X |
| 8 | X | | X | X | X | |
| 9 | | X | X | X | | X |
| 10 | | X | | X | X | X |
| 11 | | X | X | X | X | X |
| 12 | X | | X | X | X | X |
| 13 | X | X | | X | X | X |
| 14 | X | X | X | | X | X |
| 15 | X | X | X | X | | X |
| 16 | X | X | X | X | X | |

Example 9

Figure 19:
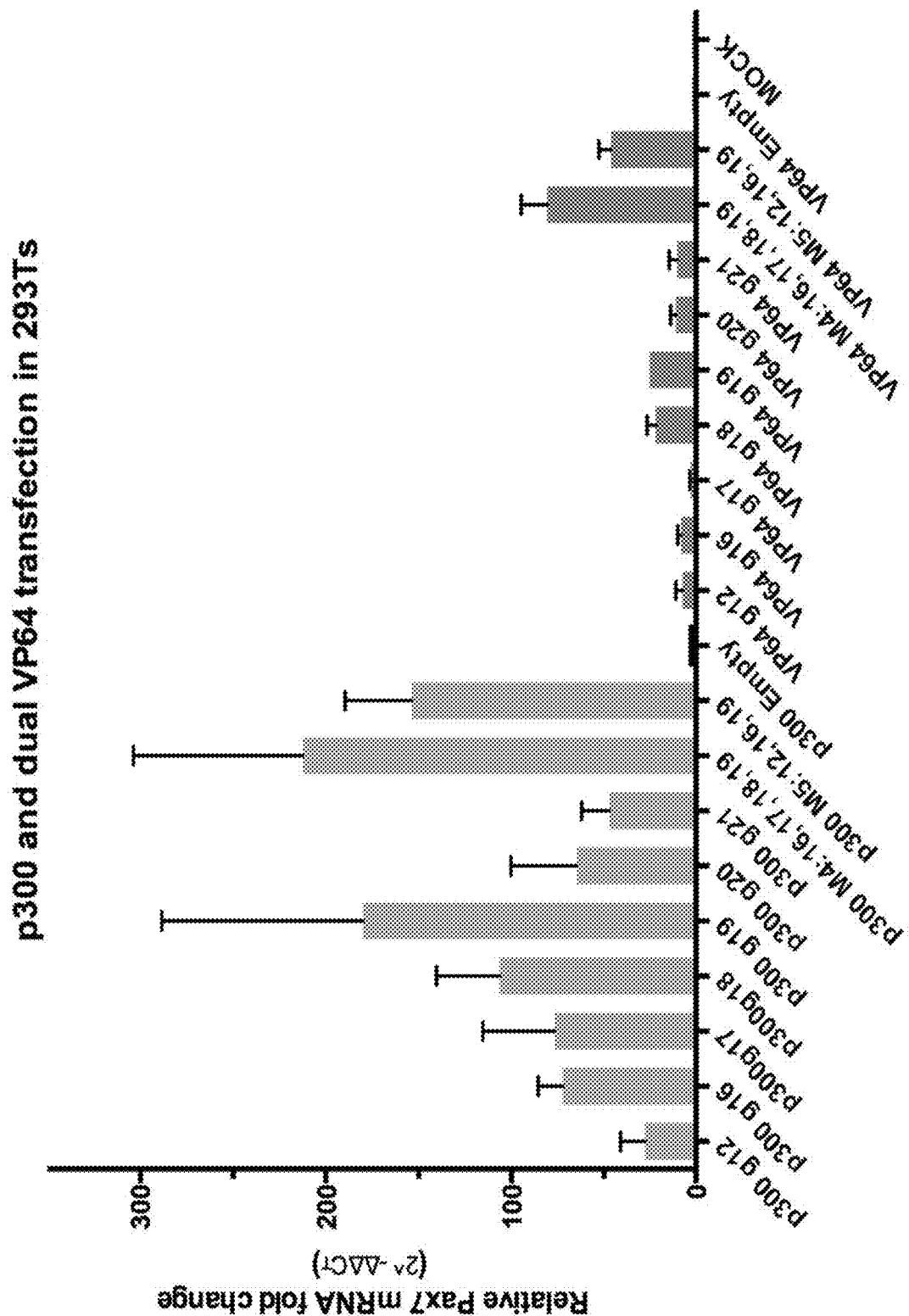
FIG. 19 shows Pax7 guide screening in 293 Ts.
Figure 20:
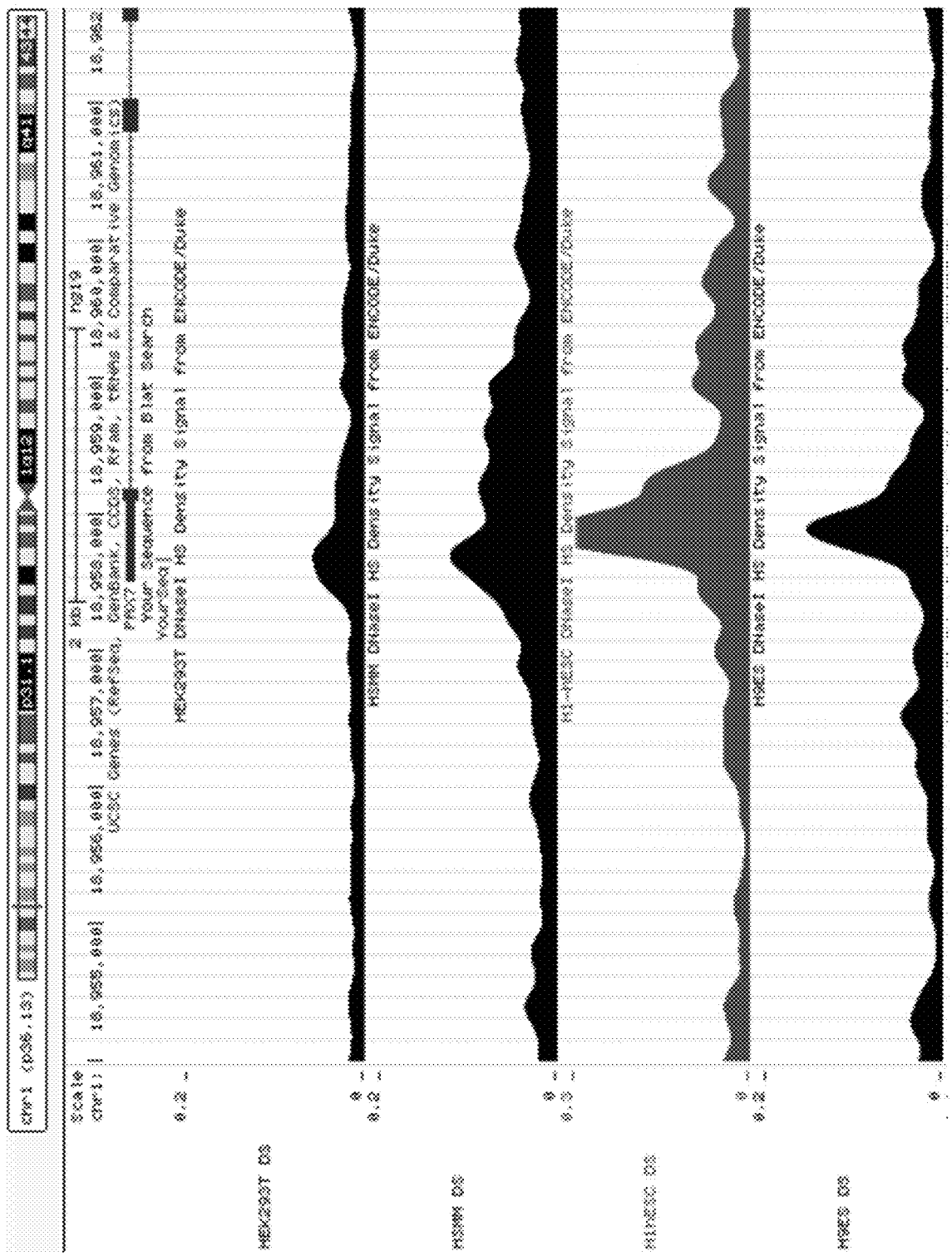
FIG. 20 shows that gRNA19 localizes to a DHS.

Pax7 gRNAs were designed to span the region surrounding the PAX7 gene (Table 9). The gRNAs were cloned into a spCas9 gRNA expression vector containing hU6 promoter and BbsI restriction site. The gRNAs were transiently co-transfected with dCas9$^{p300}$ $^{Core}$ or dCas9$^{VP64}$ into HEK293T cells. The resulting mRNA production for Pax7 was assayed in samples harvested three days post-transfection (FIG. 19). The gRNA19 ("g19") was used in further experiments and shown to localize to a DNase hypersensitive site (DHS) (FIG. 20).

TABLE 9

Pax7 gRNAs

| TSS Target position | Strand | Target name | Oligo in sense strand | SEQ ID NO |
|---|---|---|---|---|
| 138 | AS | JK12 | GGGGGCGCGAGTGATCAGCT | 224 |
| 27 | S | JK16 | CCCGGGTCTCCTAGGGGACG | 225 |
| +95 | S | JK17 | TGGTCCGGAGAAAGAAGGCG | 226 |
| +187 | S | JK18 | GTCTCCGGGCTCGGAAACTT | 227 |
| +223 | S | JK19 | AGCGCCAGAGCGCGAGAGCG | 228 |
| +273 | S | JK20 | CGATTCCGGCCGCGTTCCCC | 229 |
| +335 | AS | JK21 | GTTGTGCGGGCTGATGCGCC | 230 |

Example 10

Figure 21:
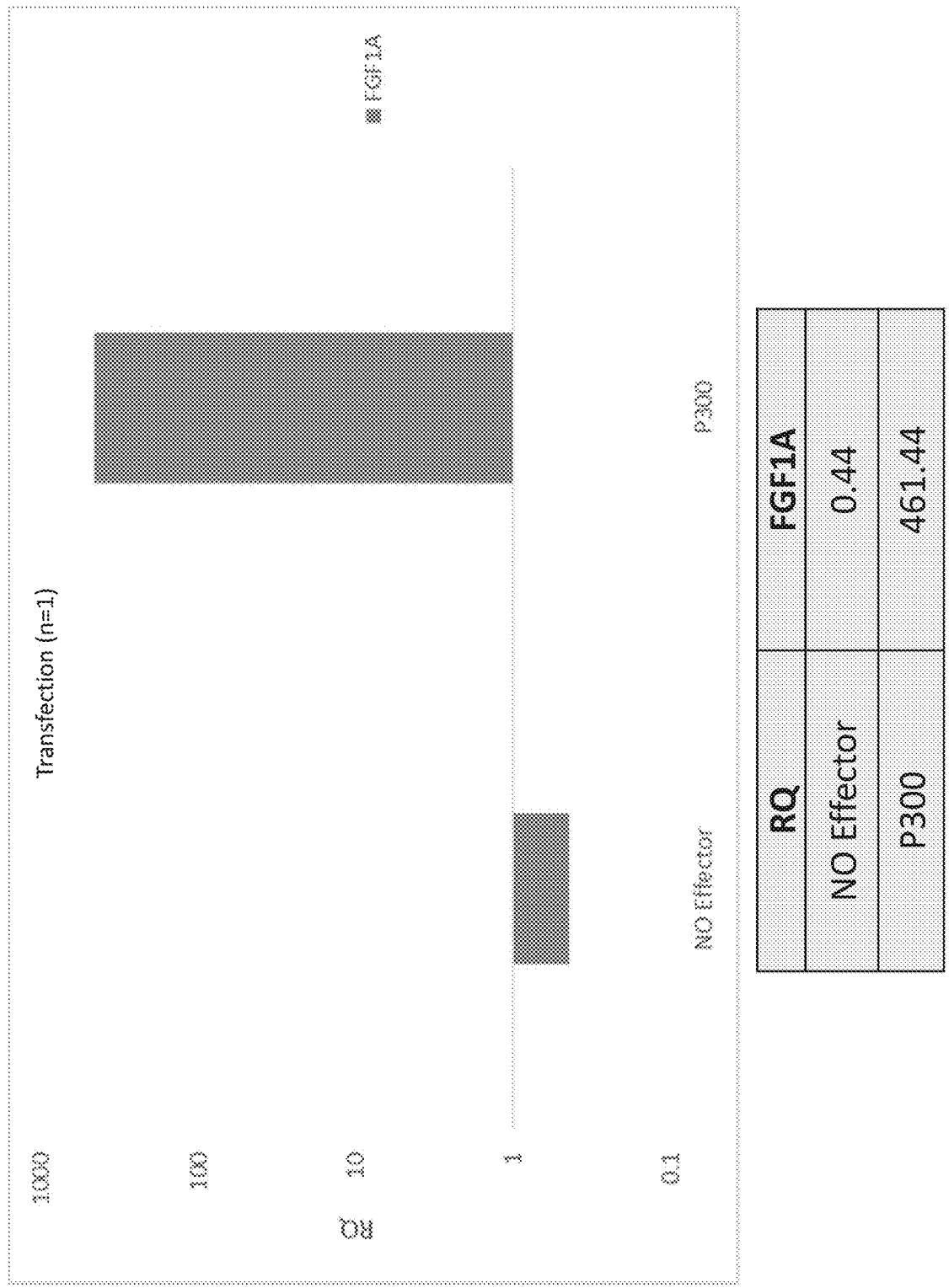
FIG. 21 shows the relative quantity of FGF1A mRNA in 293 Ts with or without dCas9$^{p300\ Core}$.
Figure 22:
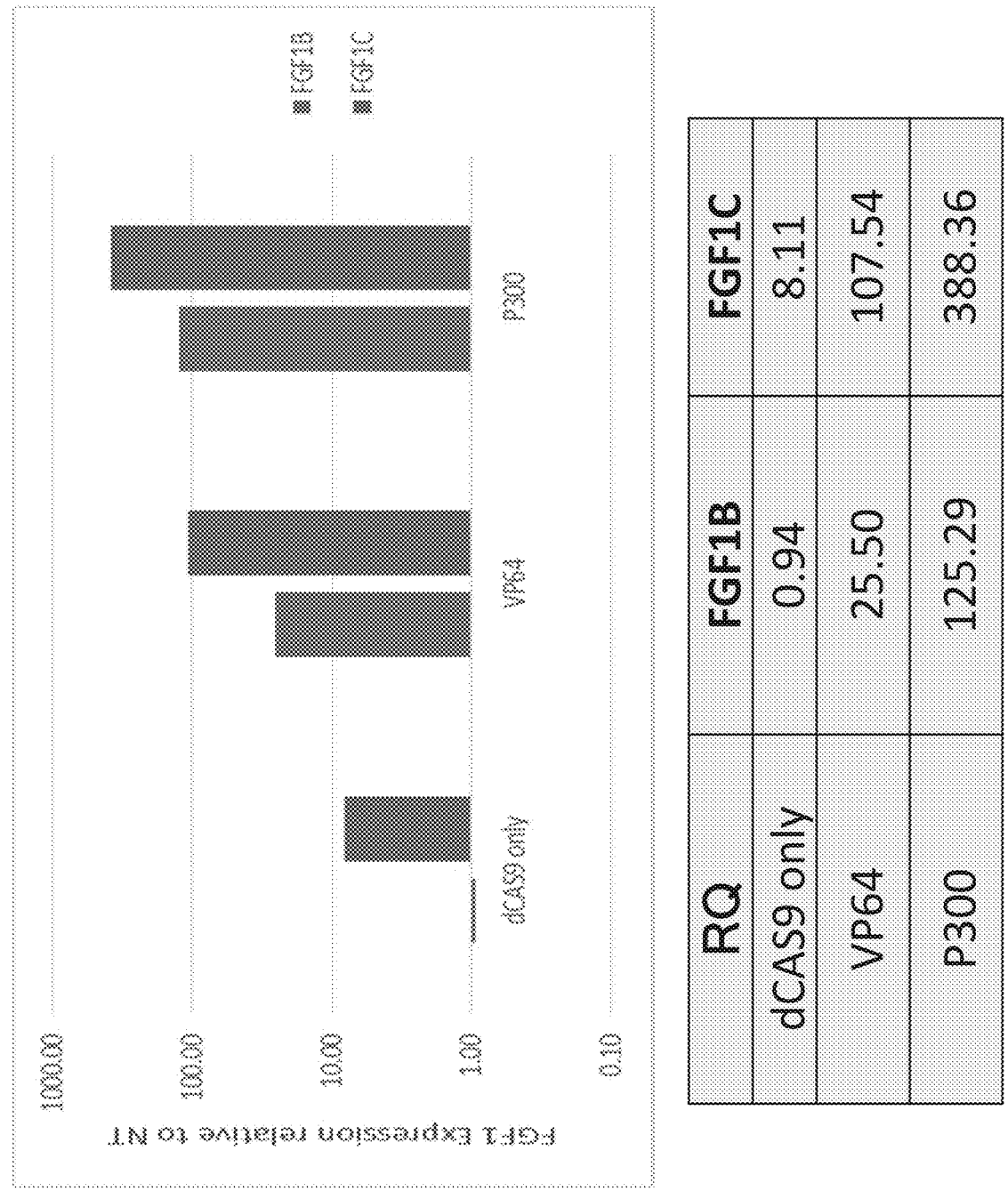
FIG. 22 shows expression levels of FGF1B and FGF1C in 293 Ts with dCas9$^{p300\ Core}$, dCas9$^{VP64}$, or dCas9 alone.
Figure 23:
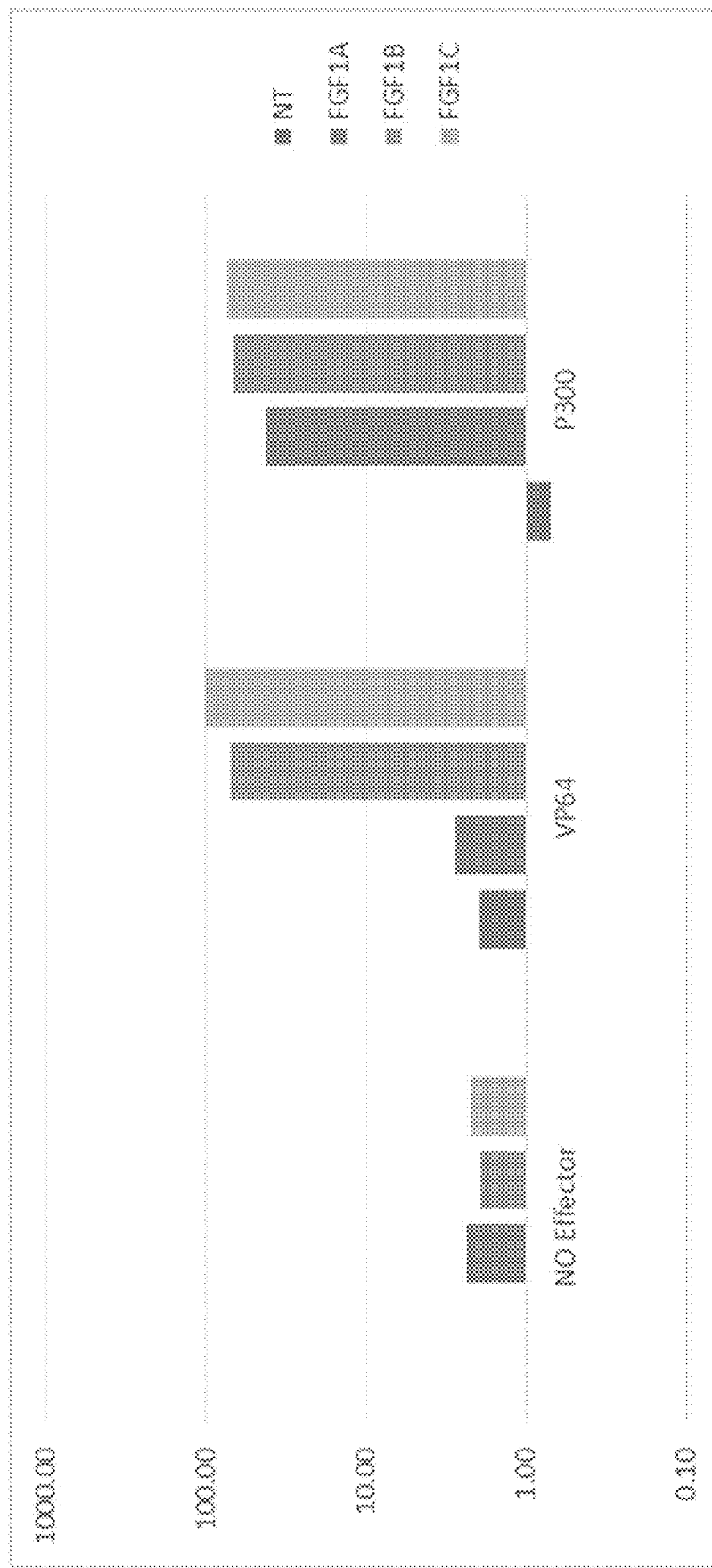
FIG. 23 shows expression levels of FGF1A, FGF1B, and FGF1C in 293 Ts with dCas9$^{p300\ Core}$ dCas9$^{VP64}$, or dCas9 alone.

FGF1 gRNAs were designed for the FGF1A, FGF1B, and FGF1C genes (Tables 10 and 11). The 25 nM of gRNAs were transiently co-transfected with dCas9$^{p300}$ $^{Core}$ or dCas9$^{VP64}$ into HEK293T cells. The resulting mRNA production for FGF1 expression was determined (FIGS. 21-23). In FIG. 23, the number of stable cell-lines transfected with the lentivirus vector was 2, except for FGF1A where n=1.

TABLE 10

| gRNA | Gene | Type | Name |
|---|---|---|---|
| 1 | FGF1A | F_7sk | 1FGF1AF_7sk |
| 2 | FGF1A | F_h1 | 2FGF1AF_h1 |
| 3 | FGF1A | F_hU6 | 3FGF1AF_hU6 |
| 4 | FGF1A | F_mU6 | 4FGF1AF_mU6 |
| 1 | FGF1A | R_7sk | 1FGF1AR_7sk |
| 2 | FGF1A | R_h1 | 2FGF1AR_h1 |
| 3 | FGF1A | R_hU6 | 3FGF1AR_hU6 |
| 4 | FGF1A | R_mU6 | 4FGF1AR_mU6 |
| 1 | FGF1B | F_7sk | 1FGF1BF_7sk |
| 2 | FGF1B | F_h1 | 2FGF1BF_h1 |
| 3 | FGF1B | F_hU6 | 3FGF1BF_hU6 |
| 4 | FGF1B | F_mU6 | 4FGF1BF_mU6 |
| 1 | FGF1B | R_7sk | 1FGF1BR_7sk |
| 2 | FGF1B | R_h1 | 2FGF1BR_h1 |
| 3 | FGF1B | R_hU6 | 3FGF1BR_hU6 |
| 4 | FGF1B | R_mU6 | 4FGF1BR_mU6 |
| 1 | FGF1C | F_7sk | 1FGF1CF_7sk |
| 2 | FGF1C | F_h1 | 2FGF1CF_h1 |
| 3 | FGF1C | F_hU6 | 3FGF1CF_hU6 |
| 4 | FGF1C | F_mU6 | 4FGF1CF_mU6 |
| 1 | FGF1C | R_7sk | 1FGF1CR_7sk |
| 2 | FGF1C | R_h1 | 2FGF1CR_h1 |
| 3 | FGF1C | R_hU6 | 3FGF1CR_hU6 |
| 4 | FGF1C | R_mU6 | 4FGF1CR_mU6 |

TABLE 11

FGF1 gRNAs Information

| gRNA | Final Sequence | SEQ ID NO | 1st addition | Sequence | SEQ ID NO | 2nd addition |
|---|---|---|---|---|---|---|
| 1 | CCTCGTGTGTTCCTGGGCCTGCTGC | 231 | CCTCG | TGTGTTCCTGGGCCTGCTGC | 255 | |
| 2 | TCCCATAAACAGGATTCTGCTCAGA | 232 | TCCCA | TAAACAGGATTCTGCTCAGA | 256 | |
| 3 | CACCGGCCAGATGACAGAACAGAAA | 233 | CACCG | GCCAGATGACAGAACAGAAA | 257 | |
| 4 | TTGTTTGAAAATGCCATTTGTAGGGCT | 234 | TTGTTTG | AAAATGCCATTTGTAGGGCT | 258 | |

TABLE 11-continued

FGF1 gRNAs Information

| gRNA | Final Sequence | SEQ ID NO | 1st addition | Sequence | SEQ ID NO | 2nd addition |
|---|---|---|---|---|---|---|
| 1 | AAACGCAGCAGGCCCAGGAACACAC | 235 | AAAC | GCAGCAGGCCCAGGAACACA | 259 | C |
| 2 | AAACTCTGAGCAGAATCCTGTTTAT | 236 | AAAC | TCTGAGCAGAATCCTGTTTA | 260 | T |
| 3 | AAACTTTCTGTTCTGTCATCTGGCC | 237 | AAAC | TTTCTGTTCTGTCATCTGGC | 261 | C |
| 4 | AAACAGCCCTACAAATGGCATTTTCAA | 238 | AAAC | AGCCCTACAAATGGCATTTT | 262 | CAA |
| 1 | CCTCGtctgcttctgccgaacctca | 239 | CCTCG | tctgcttctgccgaacctca | 263 | |
| 2 | TCCCAcctaaagagcttgtaggccg | 240 | TCCCA | cctaaagagcttgtaggccg | 264 | |
| 3 | CACCGagagctggctacccgtccct | 241 | CACCG | agagctggctacccgtccct | 265 | |
| 4 | TTGTTTGcggtccttgtttatcagtag | 242 | TTGTTTG | cggtccttgtttatcagtag | 266 | |
| 1 | AAACtgaggttcggcagaagcagac | 243 | AAAC | tgaggttcggcagaagcaga | 267 | C |
| 2 | AAACcggcctacaagctctttaggT | 244 | AAAC | cggcctacaagctctttagg | 268 | T |
| 3 | AAACagggacgggtagccagctctc | 245 | AAAC | agggacgggtagccagctct | 269 | C |
| 4 | AAACctactgataaacaaggaccgCAA | 246 | AAAC | ctactgataaacaaggaccg | 270 | CAA |
| 1 | CCTCGGAGCTGGCTACCCGTCCCTA | 247 | CCTCG | GAGCTGGCTACCCGTCCCTA | 271 | |
| 2 | TCCCACTTTGGCTGGGTTTAAACCA | 248 | TCCCA | CTTTGGCTGGGTTTAAACCA | 272 | |
| 3 | CACCGGTCAGCTCAGGGTTTTGGTA | 249 | CACCG | GTCAGCTCAGGGTTTTGGTA | 273 | |
| 4 | TTGTTTGGAGTTAGCTCCCCGACCCAG | 250 | TTGTTTG | GAGTTAGCTCCCCGACCCAG | 274 | |
| 1 | AAACTAGGGACGGGTAGCCAGCTCC | 251 | AAAC | TAGGGACGGGTAGCCAGCTC | 275 | C |
| 2 | AAACTGGTTTAAACCCAGCCAAAGT | 252 | AAAC | TGGTTTAAACCCAGCCAAAG | 276 | T |
| 3 | AAACTACCAAAACCCTGAGCTGACC | 253 | AAAC | TACCAAAACCCTGAGCTGAC | 277 | C |
| 4 | AAACCTGGGTCGGGGAGCTAACTCCAA | 254 | AAAC | CTGGGTCGGGGAGCTAACTC | 278 | CAA |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. A fusion protein comprising two heterologous polypeptide domains, wherein the first polypeptide domain comprises a Clustered Regularly Interspaced Short Palindromic Repeats associated (Cas) protein and the second polypeptide domain comprises a peptide having histone acetyltransferase activity.

Clause 2. The fusion protein of clause 1, wherein the fusion protein activates transcription of a target gene.

Clause 3. The fusion protein of clause 1 or 2, wherein the Cas protein comprises Cas9.

Clause 4. The fusion protein of clause 3, wherein the Cas9 comprises at least one amino acid mutation which knocks out nuclease activity of Cas9.

Clause 5. The fusion protein of clause 4, wherein the Cas protein comprises SEQ ID NO: 1 or SEQ ID NO: 10.

Clause 6. The fusion protein of any one of clauses 1-5, wherein the second polypeptide domain comprises a histone acetyltransferase effector domain.

Clause 7. The fusion protein of clause 6, wherein the histone acetyltransferase effector domain is a p300 histone acetyltransferase effector domain.

Clause 8. The fusion protein of any one of clauses 1-7, wherein the second polypeptide domain comprises SEQ ID NO: 2 or SEQ ID NO: 3.

Clause 9. The fusion protein of any one of clauses 1-8, wherein the first polypeptide domain comprises SEQ ID NO: 1 or SEQ ID NO: 10 and the second polypeptide domain comprises SEQ ID NO: 2 or SEQ ID NO. 3.

Clause 10. The fusion protein of any one of clauses 1-9, wherein the first polypeptide domain comprises SEQ ID NO: 1 and the second polypeptide domain comprises SEQ ID NO. 3, or the first polypeptide domain comprises SEQ ID NO: 10 and the second polypeptide domain comprises SEQ ID NO. 3.

Clause 11. The fusion protein of any one of clauses 1-10, further comprising a linker connecting the first polypeptide domain to the second polypeptide domain.

Clause 12. The fusion protein of any one of clauses 1-11, wherein the fusion protein comprises an amino acid sequence of SEQ ID NO: 140, 141, or 149.

Clause 13. A DNA targeting system comprising the fusion protein of any one of clauses 1-12 and at least one guide RNA (gRNA).

Clause 14. The DNA targeting system of clause 13, wherein the at least one gRNA comprises a 12-22 base pair complementary polynucleotide sequence of the target DNA sequence followed by a protospacer-adjacent motif.

Clause 15. The DNA targeting system of clause 13 or 14, wherein the at least one gRNA targets a target region, the target region comprises a target enhancer, target regulatory element, a cis-regulatory region of a target gene, or a trans-regulatory region of a target gene.

Clause 16. The DNA targeting system of clause 15, wherein the target region is a distal or proximal cis-regulatory region of the target gene.

Clause 17. The DNA targeting system of clause 15 or 16, wherein the target region is an enhancer region or a promoter region of the target gene.

Clause 18. The DNA targeting system of any one of clauses 15-17, wherein the target gene is an endogenous gene or a transgene.

Clause 19. The DNA targeting system of clause 15, wherein the target region comprises a target enhancer or a target regulatory element.

Clause 20. The DNA targeting system of clause 19, wherein the target enhancer or target regulatory element control the gene expression of more than one target gene.

Clause 21. The DNA targeting system of any one of clauses 15-20, wherein the DNA targeting system comprises between one and ten different gRNAs.

Clause 22. The DNA targeting system of any one of clauses 15-21, wherein the DNA targeting system comprises one gRNA.

Clause 23. The DNA targeting system of any one of clauses 15-22, wherein the target region is located on the same chromosome as the target gene.

Clause 24. The DNA targeting system of clause 23, wherein the target region is located about 1 base pair to about 100,000 base pairs upstream of a transcription start site of the target gene.

Clause 25. The DNA targeting system of clause 24, wherein the target region is located about 1000 base pairs to about 50,000 base pairs upstream of the transcription start site of the target gene.

Clause 26. The DNA targeting system of any one of clauses 15-22, wherein the target region is located on a different chromosome as the target gene.

Clause 27. The DNA targeting system of any one of clauses 15-28, wherein the different gRNAs bind to different target regions.

Clause 28. The DNA targeting system of clause 27, wherein the different gRNAs bind to target regions of different target genes.

Clause 29. The DNA targeting system of clause 27, wherein the expression of two or more target genes are activated.

Clause 30. The DNA targeting system of any one of clauses 15-29, wherein the target gene is selected from the group consisting of IL1RN, MYOD1, OCT4, HBE, HBG, HBD, HBB, MYOCD, PAX7, FGF1A, FGF1B, and FGF1C.

Clause 31. The DNA targeting system of clause 30, wherein the target region is at least one of HS2 enhancer of the human β-globin locus, distal regulatory region (DRR) of the MYOD gene, core enhancer (CE) of the MYOD gene, proximal (PE) enhancer region of the OCT4 gene, or distal (DE) enhancer region of the OCT4 gene.

Clause 32. The DNA targeting system of any one of clauses 13-31, wherein the gRNA comprises at least one of SEQ ID NOs: 23-73, 188-223, or 224-254.

Clause 33. An isolated polynucleotide encoding the fusion protein of any one of clauses 1-12 or the DNA targeting system of any one of clauses 13-32.

Clause 34. A vector comprising the isolated polynucleotide of clause 33.

Clause 35. A cell comprising the isolated polynucleotide of clause 33 or the vector of clause 34.

Clause 36. A kit comprising the fusion protein of any one of clauses 1-12, the DNA targeting system of clauses 13-32, the isolated polynucleotide of clause 33, the vector of clause 34, or the cell of clause 35.

Clause 37. A method of activating gene expression of a target gene in a cell, the method comprising contacting the cell with the fusion protein of any one of clauses 1-12, the DNA targeting system of clauses 13-32, the isolated polynucleotide of clause 33, or the vector of clause 34.

Clause 38. A method of activating gene expression of a target gene in a cell, the method comprising contacting the cell with a polynucleotide encoding a DNA targeting system, wherein the DNA targeting system comprises the fusion protein of any one of clauses 1-12 and at least one guide RNA (gRNA).

Clause 39. The method of clause 38, wherein the at least one gRNA comprises a 12-22 base pair complementary polynucleotide sequence of the target DNA sequence followed by a protospacer-adjacent motif.

Clause 40. The method of clause 38 or 39, wherein the at least one gRNA targets a target region, the target region is a cis-regulatory region or a trans-regulatory region of a target gene.

Clause 41. The method of clause 40, wherein the target region is a distal or proximal cis-regulatory region of the target gene.

Clause 42. The method of clause 40 or 41, wherein the target region is an enhancer region or a promoter region of the target gene.

Clause 43. The method of clause 40-42, wherein the target gene is an endogenous gene or a transgene.

Clause 44. The method of clause 43, wherein the DNA targeting system comprises between one and ten different gRNAs.

Clause 45. The method of clause 43, wherein the DNA targeting system comprises one gRNA.

Clause 46. The method of clause 40-45, wherein the target region is located on the same chromosome as the target gene.

Clause 47. The method of clause 46, wherein the target region is located about 1 base pair to about 100,000 base pairs upstream of a transcription start site of the target gene.

Clause 48. The method of clause 46, wherein the target region is located about 1000 base pairs to about 50,000 base pairs upstream of the transcription start site of the target gene.

Clause 49. The method of clause 40-45, wherein the target region is located on a different chromosome as the target gene.

Clause 50. The method of clause 40-45, wherein the different gRNAs bind to different target regions.

Clause 51. The method of clause 50, wherein the different gRNAs bind to target regions of different target genes.

Clause 52. The method of clause 51, wherein the expression of two or more target genes are activated.

Clause 53. The method of clause 40-52, wherein the target gene is selected from the group consisting of IL1RN, MYOD1, OCT4, HBE, HBG, HBD, HBB, MYOCD, PAX7, FGF1A, FGF1B, and FGF1C.

Clause 54. The method of clause 53, wherein the target region is at least one of HS2 enhancer of the human β-globin locus, distal regulatory region (DRR) of the MYOD gene, core enhancer (CE) of the MYOD gene, proximal (PE) enhancer region of the OCT4 gene, or distal (DE) enhancer region of the OCT4 gene.

Clause 55. The method of clause 37-54, wherein the gRNA comprises at least one of SEQ ID NOs: 23-73, 188-223, or 224-254.

Clause 56. The method of any one of clauses 37-55, wherein the DNA targeting system is delivered to the cell virally or non-virally.

Clause 57. The method of any one of clauses 37-56, wherein the cell is a mammalian cell.

---

APPENDIX

```
Sequences
Streptococcus pyogenes Cas 9 (with D10A, H849A) (SEQ ID NO: 1)
MDKKYSIGLAIGTNSVGWAVITDEYKVPSKKFKVLGNTDRHSIKKNLIGALLFDSGETA
EATRLKRTARRRYTRRKNRICYLQEIFSNEMAKVDDSFFHRLEESFLVEEDKKHERHPIF
GNIVDEVAYHEKYPTIYHLRKKLVDSTDKADLRLIYLALAHMIKFRGHFLIEGDLNPDNS
DVDKLFIQLVQTYNQLFEENPINASGVDAKAILSARLSKSRRLENLIAQLPGEKKNGLFG
NLIALSLGLTPNFKSNFDLAEDAKLQLSKDTYDDDLDNLLAQIGDQYADLFLAAKNLSD
AILLSDILRVNTEITKAPLSASMIKRYDEHHQDLTLLKALVRQQLPEKYKEIFFDQSKNGY
AGYIDGGASQEEFYKFIKPILEKMDGTEELLVKLNREDLLRKQRTFDNGSIPHQIHLGEL
HAILRRQEDFYPFLKDNREKIEKILTFRIPYYVGPLARGNSRFAWMTRKSEETITPWNFEE
VVDKGASAQSFIERMTNFDKNLPNEKVLPKHSLLYEYFTVYNELTKVKYVTEGMRKPA
FLSGEQKKAIVDLLFKTNRKVTVKQLKEDYFKKIECFDSVEISGVEDRFNASLGTYHDLL
KIIKDKDFLDNEENEDILEDIVLTLTLFEDREMIEERLKTYAHLFDDKVMKQLKRRRYTG
WGRLSRKLINGIRDKQSGKTILDFLKSDGFANRNFMQLIHDDSLTFKEDIQKAQVSGQG
DSLHEHIANLAGSPAIKKGILQTVKVVDELVKVMGRHKPENIVIEMARENQTTQKGQKN
SRERMKRIEEGIKELGSQILKEHPVENTQLQNEKLYLYYLQNGRDMYVDQELDINRLSD
YDVDAIVPQSFLKDDSIDNKVLTRSDKNRGKSDNVPSEEVVKKMKNYWRQLLNAKLIT
QRKFDNLTKAERGGLSELDKAGFIKRQLVETRQITKHVAQILDSRMNTKYDENDKLIRE
VKVITLKSKLVSDFRKDFQFYKVREINNYHHAHDAYLNAVVGTALIKKYPKLESEFVYG
DYKVYDVRKMIAKSEQEIGKATAKYFFYSNIMNFFKTEITLANGEIRKRPLIETNGETGEI
VWDKGRDFATVRKVLSMPQVNIVKKTEVQTGGFSKESILPKRNSDKLIARKKDWDPKK
YGGFDSPTVAYSVLVVAKVEKGKSKKLKSVKELLGITIMERSSFEKNPIDFLEAKGYKE
VKKDLIIKLPKYSLFELENGRKRMLASAGELQKGNELALPSKYVNFLYLASHYEKLKGS
PEDNEQKQLFVEQHKHYLDEIIEQISEFSKRVILADANLDKVLSAYNKHRDKPIREQAENI
IHLFTLTNLGAPAAFKYFDTTIDRKRYTSTKEVLDATLIHQSITGLYETRIDLSQLGGD Human p300 (with L553M mutation) (SEQ ID NO: 2)
MAENVVEPGPPSAKRPKLSSPALSASASDGTDFGSLFDLEHDLPDELINSTELGLTNGGDI
NQLQTSLGMVQDAASKHKQLSELLRSGSSPNLNMGVGGPGQVMASQAQQSSPGLGLIN
SMVKSPMTQAGLTSPNMGMGTSGPNQGPTQSTGMMNSPVNQPAMGMNTGMNAGMN
PGMLAAGNGQGIMPNQVMNGSIGAGRGRQNMQYPNPGMGSAGNLLTEPLQQGSPQM
GGQTGLRGPQPLKMGMMNNPNPYGSPYTQNPGQQIGASGLGLQIQTKTVLSNNLSPFA
MDKKAVPGGGMPNMGQQPAPQVQQPGLVTPVAQGMGSGAHTADPEKRKLIQQQLVL
LLHAHKCQRREQANGEVRQCNLPHCRTMKNVLNHMTHCQSGKSCQVAHCASSRQIISH
WKNCTRHDCPVCLPLKNAGDKRNQQPILTGAPVGLGNPSSLGVGQQSAPNLSTVSQIDP
SSIERAYAALGLPYQVNQMPTQPQVQAKNQQNQQPGQSPQGMRPMSNMSASPMGVNG
GVGVQTPSLLSDSMLHSAINSQNPMMSENASVPSMGPMPTAAQPSTTGIRKQWHEDITQ
DLRNHLVHKLVQAIFPTPDPAALKDRRMENLVAYARKVEGDMYESANNRAEYYHLLA
EKIYKIQKELEEKRRTRLQKQNMLPNAAGMVPVSMNPGPNMGQPQPGMTSNGPLPDPS
MIRGSVPNQMMPRITPQSGLNQFGQMSMAQPPIVPRQTPPLQHHGQLAQPGALNPPMG
YGPRMQQPSNQGQFLPQTQFPSQGMNVTNIPLAPSSGQAPVSQAQMSSSSCPVNSPIMPP
GSQGSHIHCPQLPQPALHQNSPSPVPSRTPTPHHTPPSIGAQQPPATTIPAPVPTPPAMPPG
PQSQALHPPPRQTPTPPTTQLPQQVQPSLPAAPSADQPQQQPRSQQSTAASVPTPTAPLLP
PQPATPLSQPAVSIEGQVSNPPSTSSTEVNSQAIAEKQPSQEVKMEAKMEVDQPEPADTQ
PEDISESKVEDCKMESTETEERSTELKTEIKEEEDQPSTSATQSSPAPGQSKKKIFKPEELR
QALMPTLEALYRQDPESLPFRQPVDPQLLGIPDYFDIVKSPMDLSTIKRKLDTGQYQEPW
QYVDDIWLMFNNAWLYNRKTSRVYKYCSKLSEVFEQEIDPVMQSLGYCCGRKLEFSPQ
TLCCYGKQLCTIPRDATYYSYQNRYHFCEKCFNEIQGESVSLGDDPSQPQTTINKEQFSK
RKNDTLDPELFVECTECGRKMHQICVLHHEIIWPAGFVCDGCLKKSARTRKENKFSAKR
LPSTRLGTFLENRVNDFLRRQNHPESGEVTVRVVHASDKTVEVKPGMKARFVDSGEMA
ESFPYRTKALFAFEEIDGVDLCFFGMHVQEYGSDCPPPNQRRVYISYLDSVHFFRPKCLR
TAVYHEILIGYLEYVKKLGYTTGHIWACPPSEGDDYIFHCHPPDQKIPKPKRLQEWYKK
```

APPENDIX

MLDKAVSERIVHDYKDIFKQATEDRLTSAKELPYFEGDFWPNVLEESIKELEQEEEERKR
EENTSNESTDVTKGDSKNAKKKNNKKTSKNKSSLSRGNKKKPGMPNVSNDLSQKLYAT
MEKHKEVFFVIRLIAGPAANSLPPIVDPDPLIPCDLMDGRDAFLTLARDKHLEFSSLRRA
QWSTMCMLVELHTQSQDRFVYTCNECKHHVETRWHCTVCEDYDLCITCYNTKNHDHK
MEKLGLGLDDESNNQQAAATQSPGDSRRLSIQRCIQSLVHACQCRNANCSLPSCQKMK
RVVQHTKGCKRKTNGGCPICKQLIALCCYHAKHCQENKCPVPFCLNIKQKLRQQQLQH
RLQQAQMLRRRMASMQRTGVVGQQQGLPSPTPATPTTPTGQQPTTPQTPQPTSQPQPTP
PNSMPPYLPRTQAAGPVSQGKAAGQVTPPTPPQTAQPPLPGPPPAAVEMAMQIQRAAET
QRQMAHVQIFQRPIQHQMPPMTPMAPMGMNPPPMTRGPSGHLEPGMGPTGMQQQPPW
SQGGLPQPQQLQSGMPRPAMMSVAQHGQPLNMAPQPGLGQVGISPLKGTVSQQALQ
NLLRTLRSPSSPLQQQQVLSILHANPQLLAAFIKQRAAKYANSNPQPIPGQPGMPQGQPG
LQPPTMPGQQGVHSNPAMQNMNPMQAGVQRAGLPQQQPQQQLQPPMGGMSPQAQQ
MNMNHNTMPSQFRDILRRQQMMQQQQQQGAGPGIGPGMANHNQFQQPQGVGYPPQQ
QQRMQHHMQQMQQGNMGQIGQLPQALGAEAGASLQAYQQRLLQQQMGSPVQPNPM
SPQQHMLPNQAQSPHLQGQQIPNSLSNQVRSPQPVPSPRPQSQPPHSSPSPRMQPQPSPH
HVSPQTSSPHPGLVAAQANPMEQGHFASPDQNSMLSQLASNPGMANLHGASATDLGLS
TDNSDLNSNLSQSTLDIH p300 Core Effector (aa 1048-1664 of SEQ ID NO: 2) (SEQ ID NO: 3)
IFKPEELRQALMPTLEALYRQDPESLPFRQPVDPQLLGIPDYFDIVKSPMDLSTIKRKLDT
GQYQEPWQYVDDIWLMFNNAWLYNRKTSRVYKYCSKLSEVFEQEIDPVMQSLGYCCG
RKLEFSPQTLCCYGKQLCTIPRDATYYSYQNRYHFCEKCFNEIQGESVSLGDDPSQPQTT
INKEQFSKRKNDTLDPELFVECTECGRKMHQICVLHHEIIWPAGFVCDGCLKKSARTRK
ENKFSAKRLPSTRLGTFLENRVNDFLRRQNHPESGEVTVRVVHASDKTVEVKPGMKAR
FVDSGEMAESFPYRTKALFAFEEIDGVDLCFFGMHVQEYGSDCPPPNQRRVYISYLDSV
HFFRPKCLRTAVYHEILIGYLEYVKKLGYTTGHIWACPPSEGDDYIFHCHPPDQKIPKPK
RLQEWYKKMLDKAVSERIVHDYKDIFKQATEDRLTSAKELPYFEGDFWPNVLEESIKEL
EQEEEERKREENTSNESTDVTKGDSKNAKKKNNKKTSKNKSSLSRGNKKKPGMPNVSN
DLSQKLYATMEKHKEVFFVIRLIAGPAANSLPPIVDPDPLIPCDLMDGRDAFLTLARDKH
LEFSSLRRAQWSTMCMLVELHTQSQD p300 Core Effector (aa 1048-1664 of SEQ ID NO: 2 with D1399Y
mutation) (SEQ ID NO: 4)
IFKPEELRQALMPTLEALYRQDPESLPFRQPVDPQLLGIPDYFDIVKSPMDLSTIKRKLDT
GQYQEPWQYVDDIWLMFNNAWLYNRKTSRVYKYCSKLSEVFEQEIDPVMQSLGYCCG
RKLEFSPQTLCCYGKQLCTIPRDATYYSYQNRYHFCEKCFNEIQGESVSLGDDPSQPQTT
INKEQFSKRKNDTLDPELFVECTECGRKMHQICVLHHEIIWPAGFVCDGCLKKSARTRK
ENKFSAKRLPSTRLGTFLENRVNDFLRRQNHPESGEVTVRVVHASDKTVEVKPGMKAR
FVDSGEMAESFPYRTKALFAFEEIDGVDLCFFGMHVQEYGSDCPPPNQRRVYISYLYSV
HFFRPKCLRTAVYHEILIGYLEYVKKLGYTTGHIWACPPSEGDDYIFHCHPPDQKIPKPK
RLQEWYKKMLDKAVSERIVHDYKDIFKQATEDRLTSAKELPYFEGDFWPNVLEESIKEL
EQEEEERKREENTSNESTDVTKGDSKNAKKKNNKKTSKNKSSLSRGNKKKPGMPNVSN
DLSQKLYATMEKHKEVFFVIRLIAGPAANSLPPIVDPDPLIPCDLMDGRDAFLTLARDKH
LEFSSLRRAQWSTMCMLVELHTQSQD p300 Core Effector (aa 1048-1664 of SEQ ID NO: 2 with 1645/1646
RR/EE mutations) (SEQ ID NO: 5)
IFKPEELRQALMPTLEALYRQDPESLPFRQPVDPQLLGIPDYFDIVKSPMDLSTIKRKLDT
GQYQEPWQYVDDIWLMFNNAWLYNRKTSRVYKYCSKLSEVFEQEIDPVMQSLGYCCG
RKLEFSPQTLCCYGKQLCTIPRDATYYSYQNRYHFCEKCFNEIQGESVSLGDDPSQPQTT
INKEQFSKRKNDTLDPELFVECTECGRKMHQICVLHHEIIWPAGFVCDGCLKKSARTRK
ENKFSAKRLPSTRLGTFLENRVNDFLRRQNHPESGEVTVRVVHASDKTVEVKPGMKAR
FVDSGEMAESFPYRTKALFAFEEIDGVDLCFFGMHVQEYGSDCPPPNQRRVYISYLDSV
HFFRPKCLRTAVYHEILIGYLEYVKKLGYTTGHIWACPPSEGDDYIFHCHPPDQKIPKPK
RLQEWYKKMLDKAVSERIVHDYKDIFKQATEDRLTSAKELPYFEGDFWPNVLEESIKEL
EQEEEERKREENTSNESTDVTKGDSKNAKKKNNKKTSKNKSSLSRGNKKKPGMPNVSN
DLSQKLYATMEKHKEVFFVIRLIAGPAANSLPPIVDPDPLIPCDLMDGRDAFLTLARDKH
LEFSSLEEAQWSTMCMLVELHTQSQD p300 Core Effector (aa 1048-1664 of SEQ ID NO: 2 with C1204R
mutation) (SEQ ID NO: 6)
IFKPEELRQALMPTLEALYRQDPESLPFRQPVDPQLLGIPDYFDIVKSPMDLSTIKRKLDT
GQYQEPWQYVDDIWLMFNNAWLYNRKTSRVYKYCSKLSEVFEQEIDPVMQSLGYCCG
RKLEFSPQTLCCYGKQLCTIPRDATYYSYQNRYHFCEKRFNEIQGESVSLGDDPSQPQTT
INKEQFSKRKNDTLDPELFVECTECGRKMHQICVLHHEIIWPAGFVCDGCLKKSARTRK
ENKFSAKRLPSTRLGTFLENRVNDFLRRQNHPESGEVTVRVVHASDKTVEVKPGMKAR
FVDSGEMAESFPYRTKALFAFEEIDGVDLCFFGMHVQEYGSDCPPPNQRRVYISYLDSV
HFFRPKCLRTAVYHEILIGYLEYVKKLGYTTGHIWACPPSEGDDYIFHCHPPDQKIPKPK
RLQEWYKKMLDKAVSERIVHDYKDIFKQATEDRLTSAKELPYFEGDFWPNVLEESIKEL
EQEEEERKREENTSNESTDVTKGDSKNAKKKNNKKTSKNKSSLSRGNKKKPGMPNVSN
DLSQKLYATMEKHKEVFFVIRLIAGPAANSLPPIVDPDPLIPCDLMDGRDAFLTLARDKH
LEFSSLRRAQWSTMCMLVELHTQSQD p300 Core Effector (aa 1048-1664 of SEQ ID NO: 2 with Y1467F
mutation) (SEQ ID NO: 7)
IFKPEELRQALMPTLEALYRQDPESLPFRQPVDPQLLGIPDYFDIVKSPMDLSTIKRKLDT
GQYQEPWQYVDDIWLMFNNAWLYNRKTSRVYKYCSKLSEVFEQEIDPVMQSLGYCCG

APPENDIX

RKLEFSPQTLCCYGKQLCTIPRDATYYSYQNRYHFCEKCFNEIQGESVSLGDDPSQPQTT
INKEQFSKRKNDTLDPELFVECTECGRKMHQICVLHHEIIWPAGFVCDGCLKKSARTRK
ENKFSAKRLPSTRLGTFLENRVNDFLRRQNHPESGEVTVRVVHASDKTVEVKPGMKAR
FVDSGEMAESFPYRTKALFAFEEIDGVDLCFFGMHVQEYGSDCPPPNQRRVYISYLDSV
HFFRPKCLRTAVYHEILIGYLEYVKKLGYTTGHIWACPPSEGDDYIFHCHPPDQKIPKPK
RLQEWFKKMLDKAVSERIVHDYKDIFKQATEDRLTSAKELPYFEGDFWPNVLEESIKEL
EQEEEERKREENTSNESTDVTKGDSKNAKKKNNKKTSKNKSSLSRGNKKKPGMPNVSN
DLSQKLYATMEKHKEVFFVIRLIAGPAANSLPPIVDPDPLIPCDLMDGRDAFLTLARDKH
LEFSSLRRAQWSTMCMLVELHTQSQD p300 Core Effector (aa 1048-1664 of SEQ ID NO: 2 with 1396/1397
SY/WW mutations) (SEQ ID NO: 8)
IFKPEELRQALMPTLEALYRQDPESLPFRQPVDPQLLGIPDYFDIVKSPMDLSTIKRKLDT
GQYQEPWQYVDDIWLMFNNAWLYNRKTSRVYKYCSKLSEVFEQEIDPVMQSLGYCCG
RKLEFSPQTLCCYGKQLCTIPRDATYYSYQNRYHFCEKCFNEIQGESVSLGDDPSQPQTT
INKEQFSKRKNDTLDPELFVECTECGRKMHQICVLHHEIIWPAGFVCDGCLKKSARTRK
ENKFSAKRLPSTRLGTFLENRVNDFLRRQNHPESGEVTVRVVHASDKTVEVKPGMKAR
FVDSGEMAESFPYRTKALFAFEEIDGVDLCFFGMHVQEYGSDCPPPNQRRVYIWWLDS
VHFFRPKCLRTAVYHEILIGYLEYVKKLGYTTGHIWACPPSEGDDYIFHCHPPDQKIPKP
KRLQEWYKKMLDKAVSERIVHDYKDIFKQATEDRLTSAKELPYFEGDFWPNVLEESIKE
LEQEEEERKREENTSNESTDVTKGDSKNAKKKNNKKTSKNKSSLSRGNKKKPGMPNVS
NDLSQKLYATMEKHKEVFFVIRLIAGPAANSLPPIVDPDPLIPCDLMDGRDAFLTLARDK
HLEFSSLRRAQWSTMCMLVELHTQSQD p300 Core Effector (aa 1048-1664 of SEQ ID NO: 2 with H1415A,
E1423A, Y1424A, L14285, Y1430A, and H1434A mutations)
(SEQ ID NO: 9)
IFKPEELRQALMPTLEALYRQDPESLPFRQPVDPQLLGIPDYFDIVKSPMDLSTIKRKLDT
GQYQEPWQYVDDIWLMFNNAWLYNRKTSRVYKYCSKLSEVFEQEIDPVMQSLGYCCG
RKLEFSPQTLCCYGKQLCTIPRDATYYSYQNRYHFCEKCFNEIQGESVSLGDDPSQPQTT
INKEQFSKRKNDTLDPELFVECTECGRKMHQICVLHHEIIWPAGFVCDGCLKKSARTRK
ENKFSAKRLPSTRLGTFLENRVNDFLRRQNHPESGEVTVRVVHASDKTVEVKPGMKAR
FVDSGEMAESFPYRTKALFAFEEIDGVDLCFFGMHVQEYGSDCPPPNQRRVYISYLDSV
HFFRPKCLRTAVYAEILIGYLAAVKKSGATTGAIWACPPSEGDDYIFHCHPPDQKIPKPK
RLQEWYKKMLDKAVSERIVHDYKDIFKQATEDRLTSAKELPYFEGDFWPNVLEESIKEL
EQEEEERKREENTSNESTDVTKGDSKNAKKKNNKKTSKNKSSLSRGNKKKPGMPNVSN
DLSQKLYATMEKHKEVFFVIRLIAGPAANSLPPIVDPDPLIPCDLMDGRDAFLTLARDKH
LEFSSLRRAQWSTMCMLVELHTQSQD

*Neisseria meningitidis* Cas9 (with D16A, D587A, H588A, and N611A
mutations) (SEQ ID NO: 10)
MAAFKPNPINYILGLAIGIASVGWAMVEIDEDENPICLIDLGVRVFERAEVPKTGDSLAM
ARRLARSVRRLTRRRAHRLLRARRLLKREGVLQAADFDENGLIKSLPNTPWQLRAAAL
DRKLTPLEWSAVLLHLIKHRGYLSQRKNEGETADKELGALLKGVADNAHALQTGDFRT
PAELALNKFEKESGHIRNQRGDYSHTFSRKDLQAELILLFEKQKEFGNPHVSGGLKEGIE
TLLMTQRPALSGDAVQKMLGHCTFEPAEPKAAKNTYTAERFIWLTKLNNLRILEQGSER
PLTDTERATLMDEPYRKSKLTYAQARKLLGLEDTAFFKGLRYGKDNAEASTLMEMKA
YHAISRALEKEGLKDKKSPLNLSPELQDEIGTAFSLFKTDEDITGRLKDRIQPEILEALLKH
ISFDKFVQISLKALRRIVPLMEQGKRYDEACAEIYGDHYGKKNTEEKIYLPPIPADEIRNP
VVLRALSQARKVINGVVRRYGSPARIHIETAREVGKSFKDRKEIEKRQEENRKDREKAA
AKFREYFPNFVGEPKSKDILKLRLYEQQHGKCLYSGKEINLGRLNEKGYVEIAAALPFSR
TWDDSFNNKVLVLGSEAQNKGNQTPYEYFNGKDNSREWQEFKARVETSRFPRSKKQRI
LLQKFDEDGFKERNLNDTRYVNRFLCQFVADRMRLTGKGKKRVFASNGQITNLLRGFW
GLRKVRAENDRHHALDAVVVACSTVAMQQKITRFVRYKEMNAFDGKTIDKETGEVLH
QKTHFPQPWEFFAQEVMIRVFGKPDGKPEFEEADTPEKLRTLLAEKLSSRPEAVHEYVTP
LFVSRAPNRKMSGQGHMETVKSAKRLDEGVSVLRVPLTQLKLKDLEKMVNREREPKL
YEALKARLEAHKDDPAKAFAEPFYKYDKAGNRTQQVKAVRVEQVQKTGVWVRNHNG
IADNATMVRVDVFEKGDKYYLVPIYSWQVAKGILPDRAVVQGKDEEDWQLIDDSFNFK
FSLHPNDLVEVITKKARMFGYFASCHRGTGNINIRIHDLDHKIGKNGILEGIGVKTALSFQ
KYQIDELGKEIRPCRLKKRPPVR 3X "Flag" Epitope (SEQ ID NO: 11)
DYKDHDGDYKDHDIDYKDDDDK Nuclear Localization Sequence (SEQ ID NO: 12)
PKKKRKVG HA Epitope (SEQ ID NO: 13)
YPYDVPDYAS VP64 Effector (SEQ ID NO: 14)
DALDDFDLDMLGSDALDDFDLDMLGSDALDDFDLDMLGSDALDDFDLDML

The invention claimed is:

1. A DNA targeting system comprising:
(1) a fusion protein comprising a first polypeptide domain and a second polypeptide domain, wherein the first polypeptide domain comprises a Clustered Regularly Interspaced Short Palindromic Repeats associated (Cas) protein comprising the sequence of SEQ ID NO: 1 and the second polypeptide domain comprises a peptide having histone acetyltransferase activity comprising the sequence of SEQ ID NO: 3, wherein the fusion protein activates transcription of a target gene; and
(2) at least one guide RNA (gRNA).

2. The DNA targeting system of claim 1, wherein the at least one gRNA targets a target region of the target gene.

3. The DNA targeting system of claim 2, wherein the target region comprises a target enhancer, target regulatory element, a cis-regulatory region of a target gene, or a trans-regulatory region of the target gene.

4. The DNA targeting system of claim 2, wherein the target region is a distal or proximal cis-regulatory region of the target gene.

5. The DNA targeting system of claim 2, wherein the target region is located on the same chromosome as the target gene.

6. The DNA targeting system of claim 5, wherein the target region is located about 1 base pair to about 100,000 base pairs upstream of a transcription start site of the target gene.

7. The DNA targeting system of claim 2, wherein the target region is located on a different chromosome as the target gene.

8. The DNA targeting system of claim 1, wherein the target gene is selected from the group consisting of IL1RN, MYOD1, OCT4, HBE, HBG, HBD, HBB, MYOCD, PAX7, FGF1A, FGF1B, and FGF1C.

9. The DNA targeting system of claim 1, wherein the gRNA comprises a polynucleotide encoded by a sequence selected from SEQ ID NO: 23-27.

10. A method of activating gene expression of a target gene in an isolated cell, the method comprising contacting the isolated cell with one or more polynucleotides encoding the DNA targeting system of claim 1.

11. The method of claim 10, wherein the DNA targeting system is delivered to the isolated cell virally or non-virally.

12. The method of claim 10, wherein the isolated cell is a mammalian cell.

* * * * *